United States Patent
Parham et al.

(10) Patent No.: US 10,636,979 B2
(45) Date of Patent: Apr. 28, 2020

(54) HETEROCYCLIC COMPOUNDS WITH DIBENZAZAPINE STRUCTURES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/539,202

(22) PCT Filed: Nov. 24, 2015

(86) PCT No.: PCT/EP2015/002359
§ 371 (c)(1),
(2) Date: Jun. 23, 2017

(87) PCT Pub. No.: WO2016/102039
PCT Pub. Date: Jun. 30, 2016

(65) Prior Publication Data
US 2018/0331301 A1    Nov. 15, 2018

(30) Foreign Application Priority Data
Dec. 23, 2014   (EP) .................................... 14004390

(51) Int. Cl.
| C07D 223/14 | (2006.01) |
| C07D 487/06 | (2006.01) |
| C09K 11/06 | (2006.01) |
| H01L 51/54 | (2006.01) |
| H01L 51/00 | (2006.01) |
| C07D 487/16 | (2006.01) |
| C07D 487/22 | (2006.01) |
| C07D 498/06 | (2006.01) |
| C07D 513/06 | (2006.01) |
| H01L 51/50 | (2006.01) |

(52) U.S. Cl.
CPC ........ *H01L 51/0072* (2013.01); *C07D 487/06* (2013.01); *C07D 487/16* (2013.01); *C07D 487/22* (2013.01); *C07D 498/06* (2013.01); *C07D 513/06* (2013.01); *H01L 51/0035* (2013.01); *H01L 51/5056* (2013.01); *H01L 51/5072* (2013.01); *H01L 51/5096* (2013.01); *Y02E 10/549* (2013.01)

(58) Field of Classification Search
CPC .... C07D 223/14; C07D 387/06; C09K 11/06; H01L 51/0072
USPC ............. 540/484; 257/40; 428/917; 313/501
See application file for complete search history.

(56) References Cited

U.S. PATENT DOCUMENTS 9,502,667 B2 * 11/2016 Saito .................... H01L 51/0072
2016/0163998 A1 * 6/2016 Saito .................... H01L 51/0072
257/40

FOREIGN PATENT DOCUMENTS

| EP | 2175005 A1 | 4/2010 |
| JP | 2014160813 A | 9/2014 |
| WO | WO-0033617 A1 | 6/2000 |
| WO | WO-2016052962 A1 | 4/2016 |

OTHER PUBLICATIONS

Atzrodt et al. Angew. Chem. Int. Ed. 2007, 46, 7744-7765.*
Hellwinkel et al. Chemische Berichte (1972), 105(3), 880-906; CA 76; 140477, 1972. CAPLUS Abstract provided.*
International Search Report for PCT/EP2015/002359 dated Feb. 22, 2016.
Written Opinion of the International Searching Authority for PCT/EP2015/002359 dated Feb. 22, 2016.
Office Action for JP2017534313 (Japanese counterpart application), dated Jul. 30, 2019 (in Japanese with English translation).

* cited by examiner

*Primary Examiner* — Venkataraman Balasubramanian

(74) *Attorney, Agent, or Firm* — Drinker Biddle & Reath LLP

(57) ABSTRACT

The present invention relates to heterocyclic compounds and electronic devices, in particular organic electroluminescent devices, containing these compounds.

19 Claims, No Drawings

HETEROCYCLIC COMPOUNDS WITH DIBENZAZAPINE STRUCTURES

CROSS-REFERENCE TO RELATED APPLICATIONS

This application is a national stage application (under 35 U.S.C. § 371) of PCT/EP2015/002359, filed Nov. 24, 2015, which claims benefit of European Application No. 14004390.2, filed Dec. 23, 2014, both of which are incorporated herein by reference in their entirety.

The present invention relates to heterocyclic compounds having dibenzazapine structures suitable for use in electronic devices. The present invention further relates to processes for preparation thereof and to electronic devices.

BACKGROUND OF THE INVENTION

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general layer structure which can be adjusted for the particular application:
  (1) substrate,
  (2) electrode, frequently metallic or inorganic, but also composed of organic or polymeric conductive materials,
  (3) charge injection layer(s) or interlayer(s), for example to compensate for unevenness in the electrode ("planarization layer"), frequently composed of a conductive doped polymer,
  (4) organic semiconductors,
  (5) possibly further charge transport, charge injection or charge blocker layers,
  (6) counterelectrode, materials as specified in (2),
  (7) encapsulation.

The above arrangement is the general structure of an organic electronic device, it being possible to combine various layers, such that the result in the simplest case is an arrangement composed of two electrodes with an organic layer in between. In this case, the organic layer fulfills all functions including the emission of light in the case of OLEDs. A system of this kind is described, for example, in WO 90/13148 A1, based on poly(p-phenylenes).

Electronic devices comprising compounds having dibenzazapine structures are known inter alia from the publication JP 2014-160813 A.

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

BRIEF SUMMARY OF THE INVENTION

It is therefore an object of the present invention to provide novel compounds which lead to electronic devices having improved properties. It is a particular object to provide hole transport materials, hole injection materials, hole blocker materials, electron injection materials, electron blocker materials and/or electron transport materials which exhibit improved properties in relation to efficiency, operating voltage and/or lifetime. Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of claim 1. Appropriate modifications to the compounds of the invention are protected in the dependent claims that refer back to claim 1.

DETAILED DESCRIPTION OF THE INVENTION

The invention thus provides a compound comprising at least one structure of the formula (I)

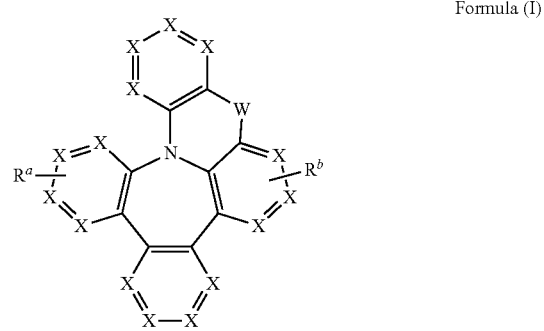

Formula (I)

where the symbols used are as follows:

X is the same or different at each instance and is N or $CR^1$, preferably $CR^1$, with the proviso that not more than two of the X groups in one cycle are N, or C is the attachment site of the $R^a$ and $R^b$ radical;

W is a bond, $NR^1$, $C(R^1)_2$, O, S or $B(R^1)$, $Si(R^1)_2$, C=O, C=C, C=$NR^1$, C=$C(R^1)_2$, S=O, $SO_2$, $P(R^1)$ and P(=O)$R^1$; preferably a bond, $NR^1$, $C(R^1)_2$, O or S;

$R^a$ is H, D, F, Cl, Br, I, $B(OR^1)_2$, CHO, C(=O)$R^1$, $CR^1$=$C(R^1)_2$, CN, C(=O)$OR^1$, C(=O)$N(R^1)_2$, $Si(R^1)_3$, $N(R^1)_2$, $NO_2$, P(=O)$(R^1)_2$, $OSO_2R^1$, $OR^1$,

S(=O)R$^1$, S(=O)$_2$R$^1$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^1$ radicals, where one or more nonadjacent CH$_2$ groups may be replaced by —R$^1$C=CR$^1$—, —C≡C—, Si(R$^1$)$_2$, C=O, C=S, C=NR$^1$, —C(=O)O—, —C(=O)NR$^1$—, NR$^1$, P(=O)(R$^1$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^1$ radicals, or an aryloxy or heteroaryloxy group which has 5 to 40 aromatic ring atoms and may be substituted by one or more R$^1$ radicals, or a combination of these systems;

R$^b$ is H, D, F, Cl, Br, I, B(OR$^1$)$_2$, CHO, C(=O)R$^1$, CR$^1$=C(R$^1$)$_2$, CN, C(=O)OR$^1$, C(=O)N(R$^1$)$_2$, Si(R$^1$)$_3$, N(R$^1$)$_2$, NO$_2$, P(=O)(R$^1$)$_2$, OSO$_2$R$^1$, OR$^1$, S(=O)R$^1$, S(=O)$_2$R$^1$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^1$ radicals, where one or more nonadjacent CH$_2$ groups may be replaced by —R$^1$C=CR$^1$—, —C≡C—, Si(R$^1$)$_2$, C=O, C=S, C=NR$^1$, —C(=O)O—, —C(=O)NR$^1$—, NR$^1$, P(=O)(R$^1$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^1$ radicals, or an aryloxy or heteroaryloxy group which has 5 to 40 aromatic ring atoms and may be substituted by one or more R$^1$ radicals, or a combination of these systems;

R$^1$ is the same or different at each instance and is H, D, F, Cl, Br, I, B(OR$^2$)$_2$, CHO, C(=O)R$^2$, CR$^2$=C(R$^2$)$_2$, CN, C(=O)OR$^2$, C(=O)N(R$^2$)$_2$, Si(R$^2$)$_3$, N(R$^2$)$_2$, NO$_2$, P(=O)(R$^2$)$_2$, OSO$_2$R$^2$, OR$^2$, S(=O)R$^2$, S(=O)$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^2$ radicals, or an aryloxy or heteroaryloxy group which has 5 to 40 aromatic ring atoms and may be substituted by one or more R$^2$ radicals, or a combination of these systems; at the same time, two or more adjacent R$^1$ substituents together may also form a mono- or polycyclic, aliphatic or aromatic ring system;

R$^2$ is the same or different at each instance and is H, D, F, Cl, Br, I, B(OR$^3$)$_2$, CHO, C(=O)R$^3$, CR$^3$=C(R$^3$)$_2$, CN, C(=O)OR$^3$, C(=O)N(R$^3$)$_2$, Si(R$^3$)$_3$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, Si(R$^2$)$_2$, Ge(R$^3$)$_2$, Sn(R$^3$)$_2$, C=O, C=S, C=Se, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more adjacent R$^2$ substituents together may also form a mono- or polycyclic, aliphatic or aromatic ring system;

R$^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent R$^3$ substituents together may also form a mono- or polycyclic, aliphatic or aromatic ring system;

with the proviso that at least one of the R$^a$ and/or R$^b$ radicals is an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more R$^1$ radicals.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

More particularly, the obligatory R$^a$ and/or R$^b$ radicals may include an aromatic and/or heteroaromatic group comprising at least two adjacent aromatic and/or heteroaromatic rings. Accordingly, the rings may be joined to one another via a bond, such that the R$^a$ and/or R$^b$ radicals may, for example, comprise a biphenyl group. In addition, the rings may be fused, such that, for example, two carbon atoms belong to the at least two aromatic or heteroaromatic rings, as is the case, for example, in a naphthyl group. In addition, the R$^a$ and/or R$^b$ radicals may also be adjacent to one another with one atom in between. For example, the R$^a$ and/or R$^b$ radicals may comprise a diarylamine compound, where at least two aryl groups are adjacent with a nitrogen atom in between. Preferably, aromatic and/or heteroaromatic groups having at least two adjacent aromatic and/or heteroaromatic rings comprise two aryl groups bonded or fused to one another via a bond. More preferably, aromatic and/or heteroaromatic groups having at least two adjacent aromatic and/or heteroaromatic rings comprise two aryl groups bonded to one another via a bond.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, the compounds of the invention may comprise structures of formula (II)

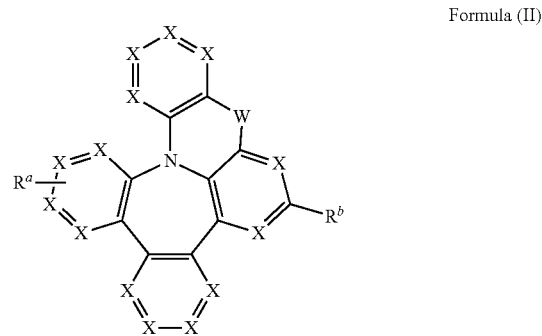

Formula (II)

where for the symbols used have the definition given above and the $R^b$ radical is an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more $R^1$ radicals.

In addition, the compounds of the invention may comprise structures of formula (III)

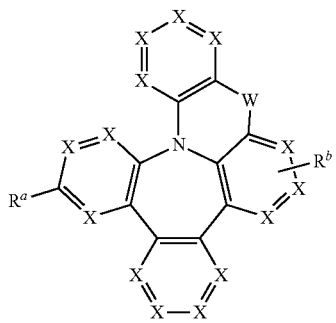

Formula (III)

where for the symbols used have the definition given above and the $R^a$ radical is an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more $R^1$ radicals.

Preferably, the compounds of the invention may comprise structures of formula (IV)

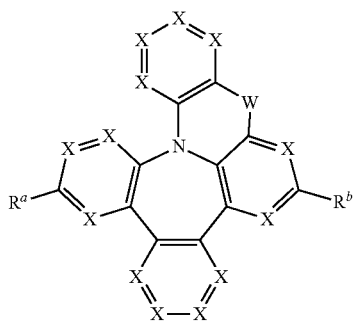

Formula (IV)

where for the symbols used have the definition given above and at least one of the $R^a$ and/or $R^b$ radicals is, and preferably both $R^a$ and $R^b$ radicals are, an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more $R^1$ radicals.

Preference is further given to compounds which are characterized in that at least one of the $R^a$ and/or $R^b$ radicals in the formulae (I), (II), (III) and/or (IV) is a hole transport group or an electron transport group.

In addition, compounds of formula (I) show surprising advantages where, in formulae (I), (II), (III) and/or (IV), not more than two X groups are N and preferably not more than one X group is N. Apart from the attachment sites of the $R^a$ and/or $R^b$ groups radicals in the formulae (I), (II) and/or (III) where X is C, preferably all X are a $CR^1$ group, where preferably not more than 4, more preferably not more than 3 and especially preferably not more than 2 of the $CR^1$ groups represented by X are not the CH group.

Particularly preferred compounds are those comprising structures of the formula (V)

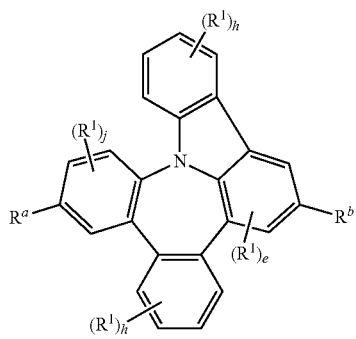

Formula (V)

in which $R^a$, $R^b$ and $R^1$ may assume the definitions detailed above, especially in relation to formula (I), e is 0, 1 or 2, preferably 0 or 1, more preferably 0, j is 0, 1, 2 or 3, preferably 0, 1 or 2, more preferably 0 or 1, h is 0, 1, 2, 3 or 4, preferably 0, 1 or 2, more preferably 0 or 1, where at least one of the $R^a$, $R^b$ radicals is a hole transport group and/or an electron transport group, where preferably each of the $R^a$ radicals and $R^b$ radical is a hole transport group and/or an electron transport group.

Very particular preference is further given to compounds comprising structures of the formula (VI)

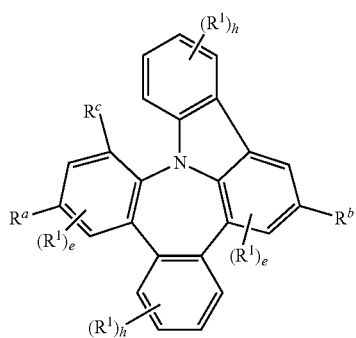

Formula (VI)

in which $R^a$, $R^b$ and $R^1$ may assume the definitions detailed above, especially in relation to formula (I), e is 0, 1 or 2, preferably 0 or 1, more preferably 0, h is 0, 1, 2, 3 or 4, preferably 0, 1 or 2, more preferably 0 or 1, where the $R^b$ radical is a hole transport group or an electron transport group and the $R^c$ radical is an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more $R^1$ radicals. More preferably, the $R^c$ radical in formula (VI) may be a hole transport group and/or an electron transport group.

Particularly preferred compounds are those comprising structures of the formula (VII)

Formula (VII)

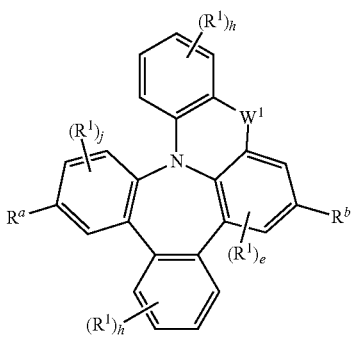

in which R$^a$, R$^b$ and R$^1$ may assume the definitions detailed above, especially in relation to formula (I), e is 0, 1 or 2, preferably 0 or 1, more preferably 0, j is 0, 1, 2 or 3, preferably 0, 1 or 2, more preferably 0 or 1, h is 0, 1, 2, 3 or 4, preferably 0, 1 or 2, more preferably 0 or 1, where at least one of the R$^a$, R$^b$ radicals is a hole transport group and/or an electron transport group and W$^1$ is NR$^1$, C(R$^1$)$_2$, O or S.

Very particular preference is further given to compounds comprising structures of the formula (VIII)

Formula (VIII)

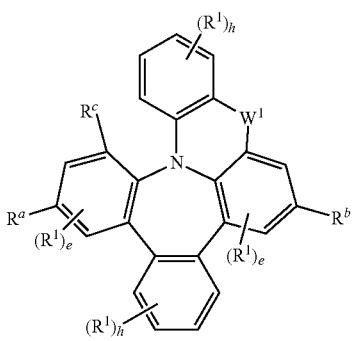

in which R$^a$, R$^b$ and R$^1$ may assume the definitions detailed above, especially in relation to formula (I), e is 0, 1 or 2, preferably 0 or 1, more preferably 0, h is 0, 1, 2, 3 or 4, preferably 0, 1 or 2, more preferably 0 or 1, where the R$^b$ radical is a hole transport group or an electron transport group and the R$^c$ radical is an aryl group which has 10 to 40 carbon atoms and comprises at least two rings, or a heteroaryl group which has 6 to 40 carbon atoms and comprises at least two rings, where each of the respective groups may be substituted by one or more R$^1$ radicals and Y$^1$ is NR$^1$, C(R$^1$)$_2$, O or S. More preferably, the R$^c$ radical in formula (VIII) may be a hole transport group and/or an electron transport group.

It may also be the case that the R$^b$ radical in a compound comprising structures of the formulae (I), (II), (III), (IV), (V), (VI), (VII) and/or (VIII) is a hole transport group and the R$^a$ radical in this structure of the identical formula selected from one of the formulae (I), (II), (III), (IV), (V), (VI), (VII) and/or (VIII) is a hole transport group.

It may further be the case that the R$^b$ radical in a compound comprising structures of the formulae (I), (II), (III), (IV), (V), (VI), (VII) and/or (VIII) is an electron transport group and the R$^a$ radical in this structure of the identical formula selected from one of the formulae (I), (II), (III), (IV), (V), (VI), (VII) and/or (VIII) is a hole transport group.

It may additionally be the case that the R$^b$ radical in a compound comprising structures of the formulae (I), (II), (III), (IV), (V), (VI), (VII) and/or (VIII) is a hole transport group and the R$^a$ radical in this structure of the identical formula selected from one of the formulae (I), (II), (III), (IV), (V), (VI), (VII) and/or (VIII) is an electron transport group.

It may furthermore be the case that the R$^b$ radical in a compound comprising structures of the formulae (I), (II), (III), (IV), (V), (VI), (VII) and/or (VIII) is an electron transport group and the R$^a$ radical in this structure of the identical formula selected from one of the formulae (I), (II), (III), (IV), (V), (VI), (VII) and/or (VIII) is an electron transport group.

In a particular embodiment of a compound of the invention, it may be the case that the sum total of the indices e, h and j in the structures of the formulae (V), (VI), (VII) and/or (VIII) in each case is preferably not more than 3, more preferably not more than 2 and especially preferably not more than 1.

Preference is given to compounds comprising structures of the formula (I) in which at least one R$^1$, R$^a$, R$^b$ and/or R$^c$ radical in the structures of formulae (I), (II), (III), (IV), (V), (VI), (VII) and/or (VIII) is a group selected from the formulae (R$^1$-1) to (R$^1$-72)

Formula (R$^1$-1)

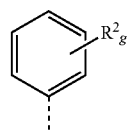

Formula (R$^1$-2)

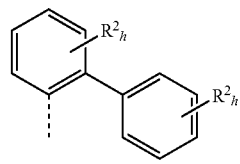

Formula (R$^1$-3)

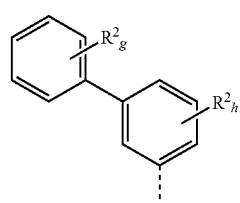

Formula (R$^1$-4)

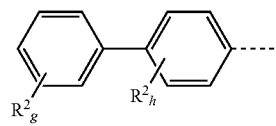

-continued
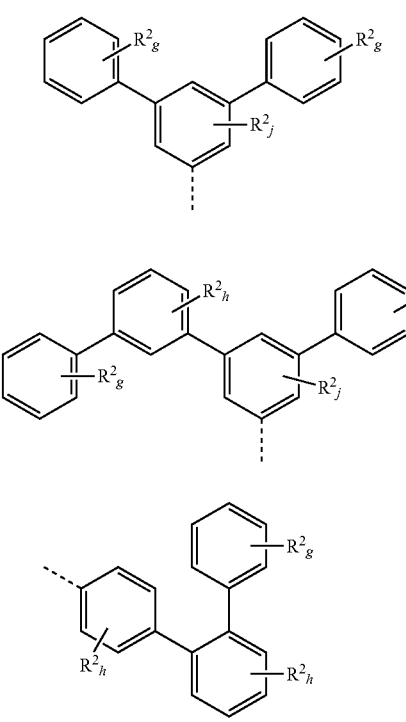
Formula (R¹-5)
Formula (R¹-6)
Formula (R¹-7)
Formula (R¹-8)
Formula (R¹-9)
Formula (R¹-10)
-continued
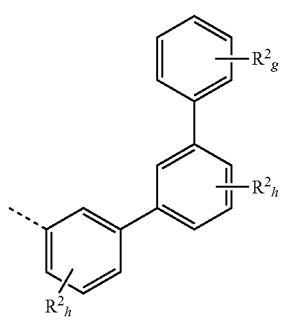
Formula (R¹-11)
Formula (R¹-12)
Formula (R¹-13)
Formula (R¹-14)
Formula (R¹-15)

Formula (R¹-16)
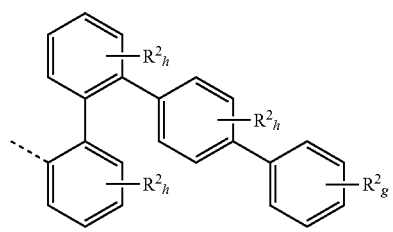
Formula (R¹-17)
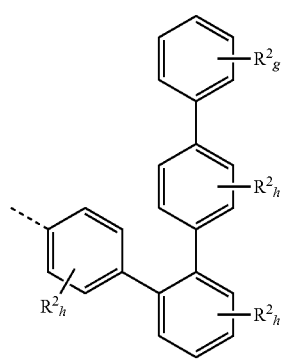
Formula (R¹-18)
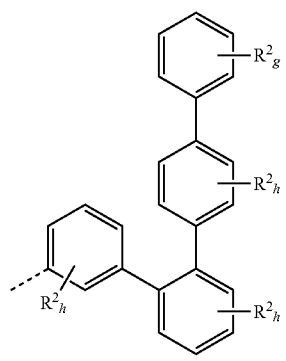
Formula (R¹-19)
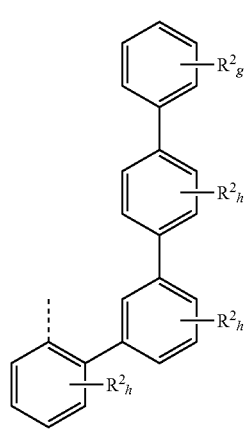
Formula (R¹-20)
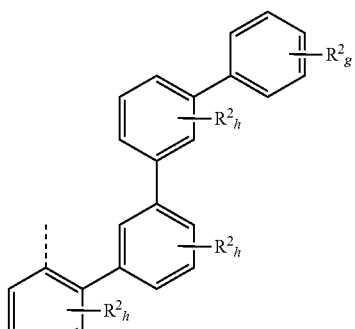
Formula (R¹-21)
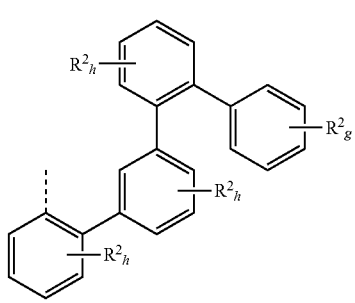
Formula (R¹-22)
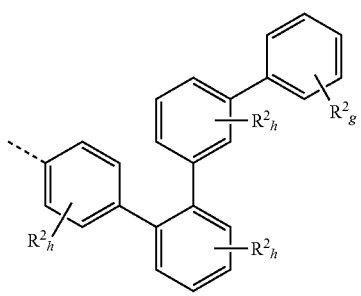
Formula (R¹-23)
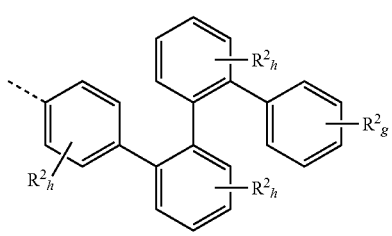
Formula (R¹-24)
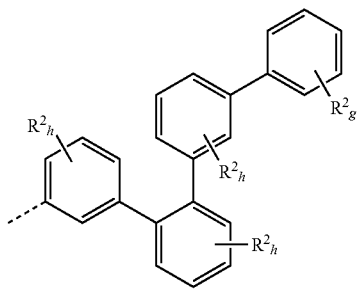

-continued
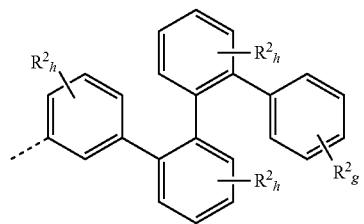
Formula (R¹-25)
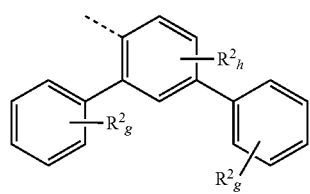
Formula (R¹-26)
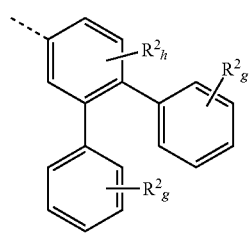
Formula (R¹-27)
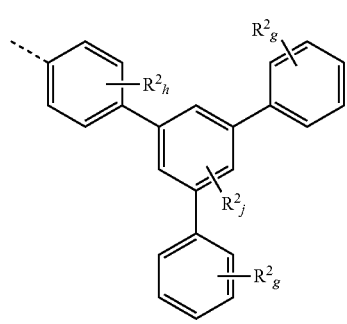
Formula (R¹-28)
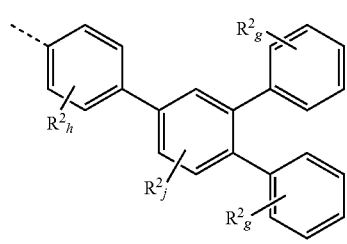
Formula (R¹-29)
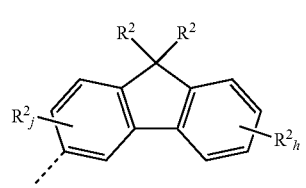
Formula (R¹-30)
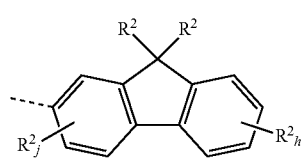
Formula (R¹-31)
-continued
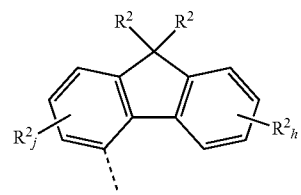
Formula (R¹-32)
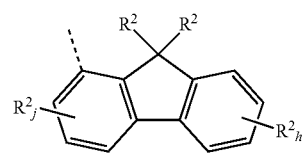
Formula (R¹-33)
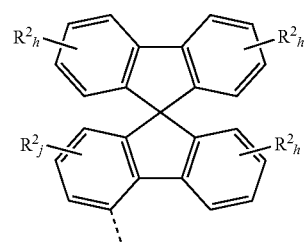
Formula (R¹-34)
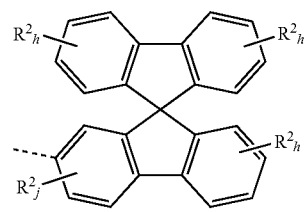
Formula (R¹-35)
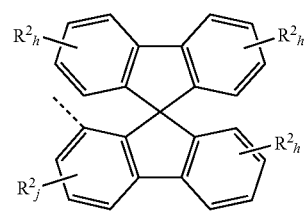
Formula (R¹-36)
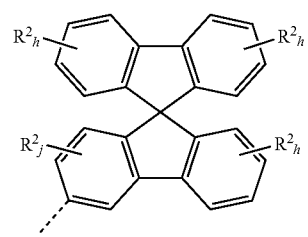
Formula (R¹-37)
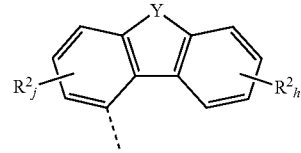
Formula (R¹-38)
Formula (R¹-39)

-continued

Formula (R¹-40)

Formula (R¹-41)

Formula (R¹-42)

Formula (R¹-43)

Formula (R¹-44)

Formula (R¹-45)

Formula (R¹-46)

-continued

Formula (R¹-47)

Formula (R¹-48)

Formula (R¹-49)

Formula (R¹-50)

Formula (R¹-51)

Formula (R¹-52)

Formula (R¹-53)
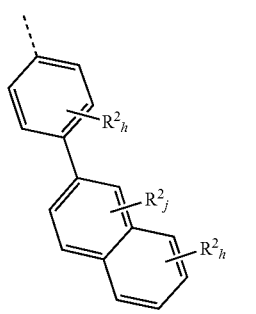
Formula (R¹-54)
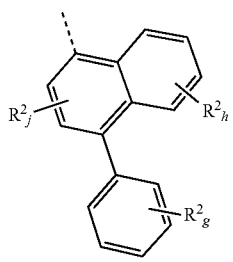
Formula (R¹-55)
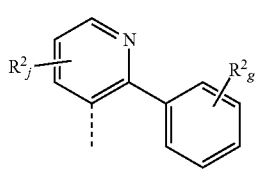
Formula (R¹-56)
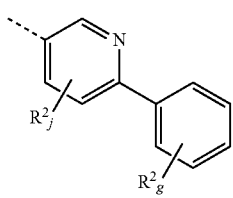
Formula (R¹-57)
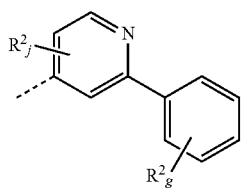
Formula (R¹-58)
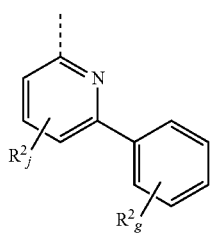
Formula (R¹-59)
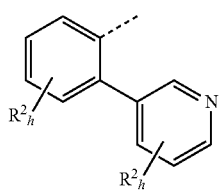
Formula (R¹-60)
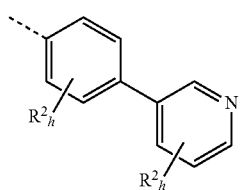
Formula (R¹-61)
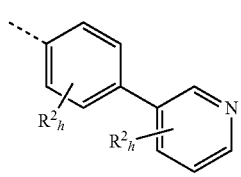
Formula (R¹-62)
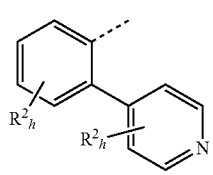
Formula (R¹-63)
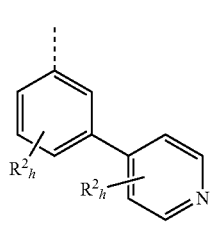
Formula (R¹-64)
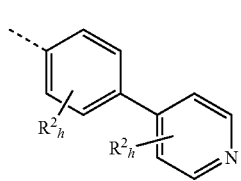
Formula (R¹-65)
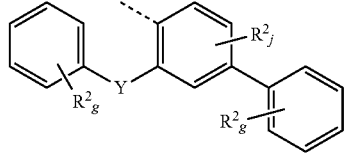
Formula (R¹-66)
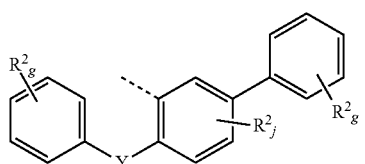
Formula (R¹-67)
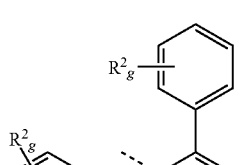
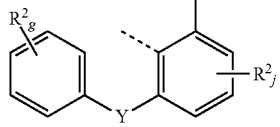

Formula (R¹-68)
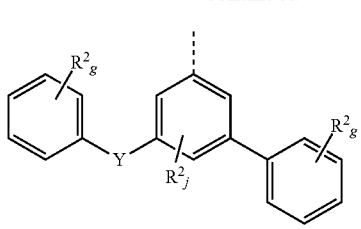

Formula (R¹-69)
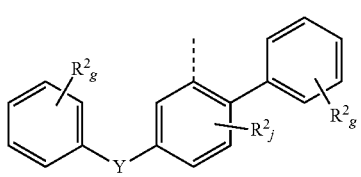

Formula (R¹-70)
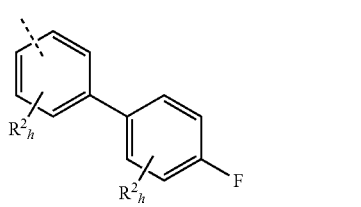

Formula (R¹-71)
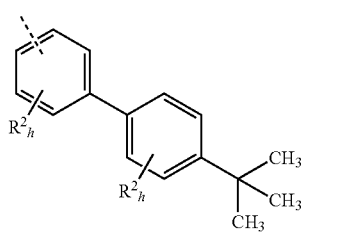

Formula (R¹-72)
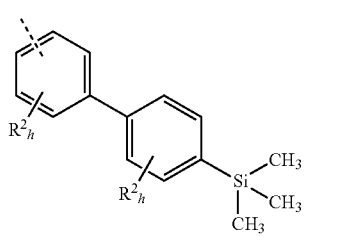

where the symbols used are as follows:
Y is O, S or NR², preferably O or S;
j independently at each instance is 0, 1, 2 or 3;
h independently at each instance is 0, 1, 2, 3 or 4;
g independently at each instance is 0, 1, 2, 3, 4 or 5;
the dotted bond marks the attachment position; and
R² may be as defined above.

It may preferably be the case that the sum total of the indices g, h and j in the structures of the formula (R¹-1) to (R¹-72) is not more than 3 in each case, preferably not more than 2 and more preferably not more than 1.

More preferably, the R¹, $R^a$, $R^b$ and/or $R^e$ group of formula (I), (II), (III), (IV), (V), (VI), (VII) and/or (VIII) may be an aromatic radical having 6 to 18 and preferably 6 to 12 carbon atoms.

The structure of formula (I) or of one of the preferred embodiments of this structure comprises at least one $R^a$ and/or $R^b$ group as detailed above. The nature of the functional group $R^a$ and/or $R^b$ affects the properties of the compound, these properties being adjustable over a wide range.

In this context, it should be emphasized that the compounds obtained generally have a significantly better profile of properties through the presence of the dibenzazapine structural element than comparable compounds according to the prior art. Particular preference is given especially to compounds comprising structures of the formula (I), or the preferred embodiments detailed above or hereinafter, which can be used as matrix material, as hole transport material or as electron transport material. For this purpose, compounds of the invention, especially the $R^a$, $R^b$ radicals in structures of the formulae (I), (II), (III), (IV), (V), (VI), (VII) and/or (VIII), are a hole transport group and/or an electron transport group.

In addition, at least one of the $R^a$, $R^b$ radicals in structures of the formulae (I), (II), (III), (IV), (V), (VI), (VII) and/or (VIII) may preferably be a pyridine, pyrimidine, pyrazine, pyridazine, triazine, dibenzofuran, dibenzothiophene, fluorene, spirobifluorene, anthracene or benzimidazole group. Compounds comprising structures of the formulae (I), (II), (III), (IV), (V), (VI), (VII) and/or (VIII) having at least one pyridine, pyrimidine, pyrazine, pyridazine, triazine, dibenzofuran, dibenzothiophene, fluorene, spirobifluorene, anthracene or benzimidazole group can be used advantageously as electron transport material (ETM).

It may preferably be the case that an electron transport comprises at least one structure selected from the group of triazines, pyrimidines, pyrazines, imidazoles, benzimidazoles and pyridines, particular preference being given to triazine structures.

It may further be the case that the electron transport group has at least one structure of the formulae (E-1) to (E-10)

Formula (E-1)
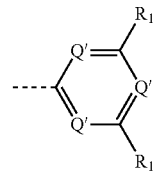

Formula (E-2)
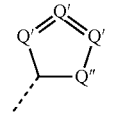

Formula (E-3)
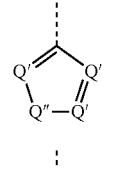

Formula (E-4)
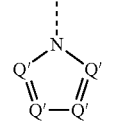

Formula (E-5)
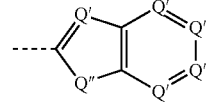

Formula (E-6)
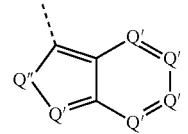

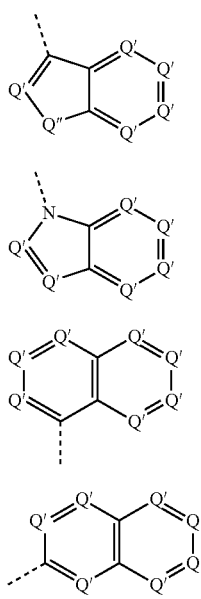

Formula (E-7)

Formula (E-8)

Formula (E-9)

Formula (E-10)

where the dotted bond marks the attachment position,
Q' is the same or different at each instance and is CR¹ or N, and
Q" is NR¹, O or S;
where at least one Q' is N and/or at least one Q" is NR' and R¹ is as defined in above.

It may more preferably be the case that the electron transport group has at least one structure of the formulae (E-11) to (E-23)

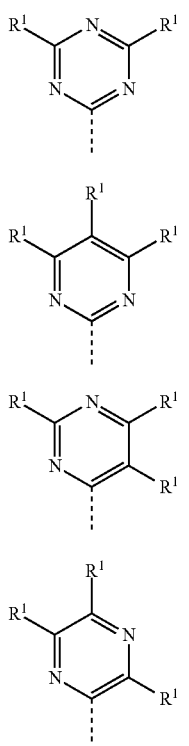

Formula (E-11)

Formula (E-12)

Formula (E-13)

Formula (E-14)

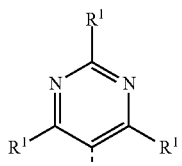

Formula (E-15)

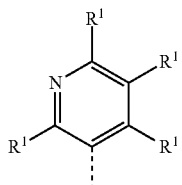

Formula (E-16)

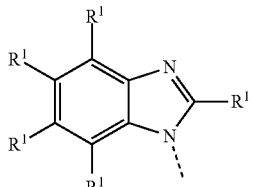

Formula (E-17)

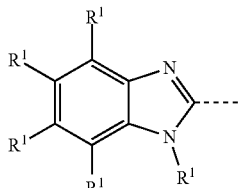

Formula (E-18)

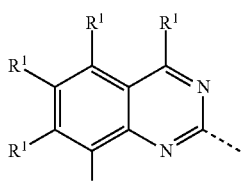

Formula (E-19)

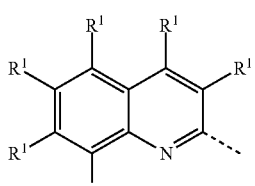

Formula (E-20)

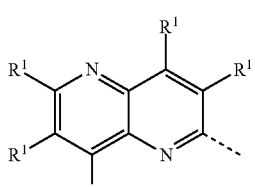

Formula (E-21)

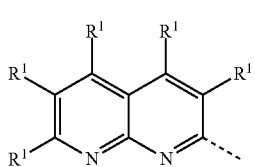

Formula (E-22)

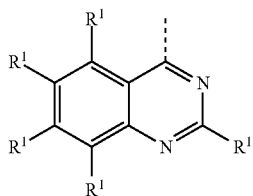

Formula (E-23)

where the dotted bond marks the attachment position and R¹ has the definition given above.

Preferably, for compounds having structures of formula (E-1) to formula (E-23), at least one and preferably at least two of the R¹ radicals are Ar$^a$, where Ar$^a$ is the same or different at each instance and is an aryl group having 6 to 40 carbon atoms or a heteroaryl group having 3 to 40 carbon atoms, each of which may be substituted by one or more R² radicals.

The R¹ substituents in the electron-transporting group E are preferably selected from the group consisting of H and an aromatic or heteroaromatic ring system which has 5 to 60 aromatic ring atoms and may be substituted in each case by one or more R² radicals, even more preferred groups being those of the formula (E-11), (E-17) and (E-18) and the most preferred group being that of the formula (E-11).

Examples of very particularly preferred electron-transporting groups E are the following groups which may be substituted by one or more independent R² radicals, where the dotted bonds indicate the attachment positions.

Formula (E-24)

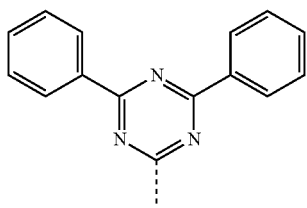

Formula (E-25)

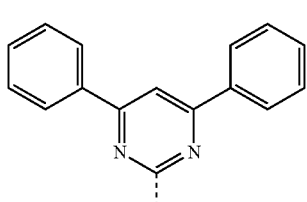

Formula (E-26)

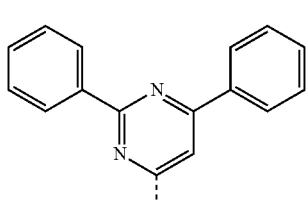

Formula (E-27)

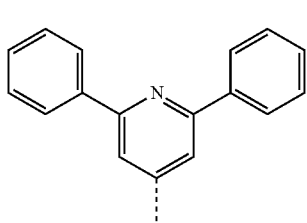

Formula (E-28)

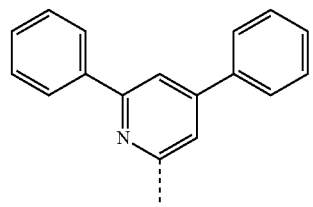

Formula (E-29)

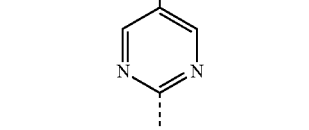

Formula (E-30)

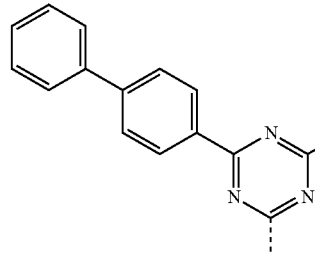

Formula (E-31)

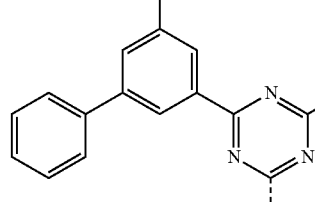

Formula (E-32)

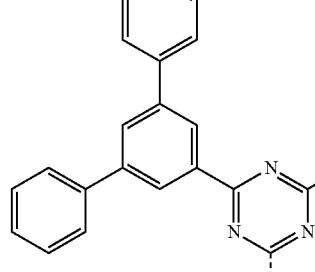

Formula (E-33)
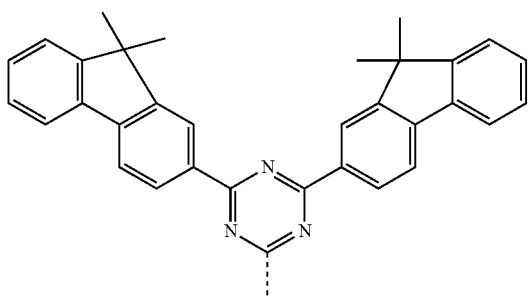

Formula (E-34)
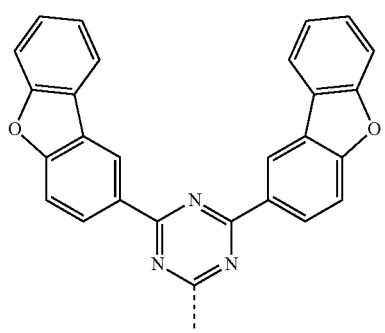

Formula (E-35)
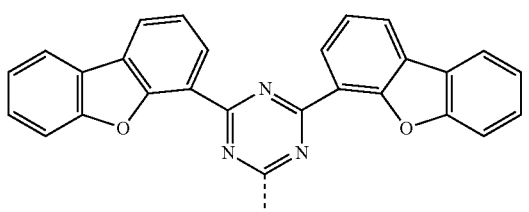

Formula (E-36)
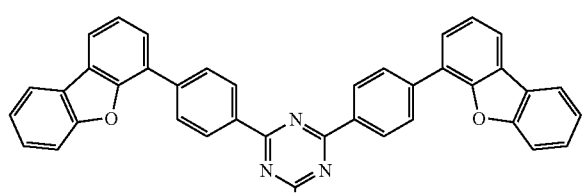

Formula (E-37)
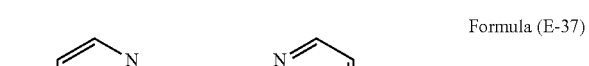

Formula (E-38)

Formula (E-39)
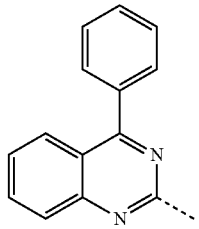

In a particular embodiment of the present invention, at least one of the $R^a$, $R^b$ radicals in structures of the formulae (I), (II), (III), (IV), (V), (VI), (VII) and/or (VIII) may preferably be a carbazole, indenocarbazole, indolocarbazole, arylamine or diarylamine group. Compounds of the formula (I) having at least one carbazole, indenocarbazole, indolocarbazole, arylamine or diarylamine group can be used with preference as matrix material.

It may preferably be the case that a hole transport group comprises at least one structure selected from the group of triarylamines, carbazoles, indenocarbazoles and indolocarbazoles.

It may further be the case that the hole transport group has at least one structure of the formulae (L-1) to (L-9)

Formula (L-1)
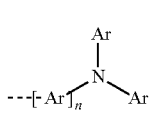

Formula (L-2)
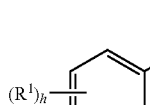

Formula (L-3)
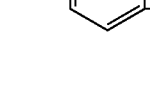

Formula (L-4)
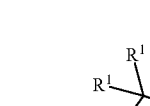

Formula (L-5)
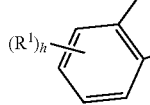

-continued

Formula (L-6)

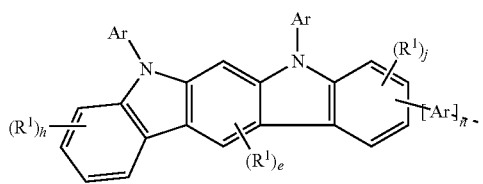

Formula (L-7)

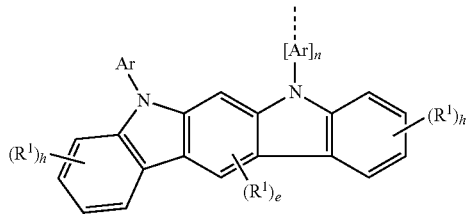

Formula (L-8)

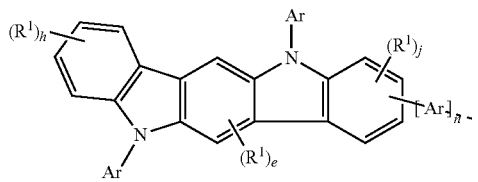

Formula (L-9)

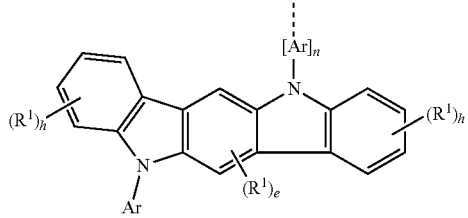

where the dotted bond marks the attachment position, e is 0, 1 or 2, j is 0, 1, 2 or 3, h is 0, 1, 2, 3 or 4, n is 0 or 1, Ar is an aryl group having 6 to 40 carbon atoms or a heteroaryl group having 3 to 40 carbon atoms which may be substituted by one or more $R^1$ radicals, and $R^1$ may assume the definition given above.

If a compound of the invention having one or more structures of formulae (I), (II), (III), (IV), (V), (VI), (VII) and/or (VIII) has both an electron transport group and a hole transport group, where more preferably at least one of the $R^a$ and/or $R^b$ radicals is an electron transport group and/or a hole transport group, these compounds can preferably be used as matrix material having both hole-conducting and electron-conducting properties.

Particular preference is given to compounds which are characterized in that at least one of the $R^a$, $R^b$ and/or $R^c$ groups in formulae (I), (II), (III), (IV) and/or (V) comprises a dibenzofuran and/or dibenzothiophene group, where preferably at least two of the $R^a$, $R^b$ and/or $R^c$ groups comprise a dibenzofuran and/or dibenzothiophene group, and more preferably at least one of the $R^a$, $R^b$ and/or $R^c$ groups in formulae (I), (II), (III), (IV), (V), (VI), (VII) and/or (VIII) is a dibenzofuran and/or dibenzothiophene group, where this group may be substituted by one or more $R^1$ radicals.

Preferably, the compound having structures of formula (I) or the embodiments detailed above and hereinafter may comprise $R^1$ radicals in which this $R^1$ radical is the same or different at each instance and is preferably selected from the group consisting of H, D, F, Br, I, CN, $Si(R^2)_3$, $B(OR^2)_2$, $C(=O)Ar^1$, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^2$ radicals, where one or more hydrogen atoms may be replaced by D or F, or an aromatic or heteroaromatic ring system which has 5 to 30 aromatic ring atoms and may be substituted in each case by one or more $R^2$ radicals; at the same time, two adjacent $R^1$ radicals together or $R^1$ radicals together with $R^2$ radicals may also form a mono- or polycyclic, aliphatic or aromatic ring system. More preferably, these $R^1$ radicals are the same or different at each instance and are selected from the group consisting of H, D, F, a straight-alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^2$ radicals; at the same time, two adjacent $R^1$ radicals together or $R^1$ radicals together with $R^2$ radicals may also form a mono- or polycyclic, aliphatic or aromatic ring system. More preferably, at least one of the $R^1$ radicals in formula (I) may be an aryl group or a heteroaryl group which has 6 to 18 carbon atoms and may be substituted by up to three $R^2$ radicals.

Preferably, the compound having structures of formula (I) or the embodiments detailed above and hereinafter may comprise $R^2$ radicals, where these $R^2$ radicals are the same or different at each instance and are preferably selected from the group consisting of H, D, F, Cl, Br, I, CHO, $C(=O)Ar^1$, $P(=O)(Ar^1)_2$, $S(=O)Ar^1$, $S(=O)_2Ar^1$, CN, $NO_2$, $Si(R^3)_3$, $B(OR^3)_2$, $OSO_2R^3$, a straight-chain alkyl, alkoxy or thioalkoxy group having 1 to 10 carbon atoms or a branched or cyclic alkyl, alkoxy or thioalkoxy group having 3 to 10 carbon atoms, each of which may be substituted by one or more $R^3$ radicals, where one or more nonadjacent $CH_2$ groups may be replaced by C≡C, $Si(R^3)_2$, $Ge(R^3)_2$, $Sn(R^3)_2$, C=O, C=S, C=Se, $P(=O)(R^3)$, SO, $SO_2$, O, S or $CONR^3$ and where one or more hydrogen atoms may be replaced by D, F, Cl, Br, I, CN or $NO_2$, or an aromatic or heteroaromatic ring system which has 5 to 24 aromatic ring atoms and may be substituted in each case by one or more $R^3$ radicals, or an aryloxy or heteroaryloxy group which has 5 to 24 aromatic ring atoms and may be substituted by one or more $R^3$ radicals, or a combination of these systems; at the same time, two or more adjacent $R^2$ substituents together may also form a mono- or polycyclic, aliphatic or aromatic ring system. More preferably, at least one of the $R^2$ radicals in formula (I) may be an aryl group or a heteroaryl group which has 6 to 18 carbon atoms and may be substituted by up to three $R^3$ radicals. Particularly preferred compounds include structures of the following formulae 1 to 70:

Formula 1
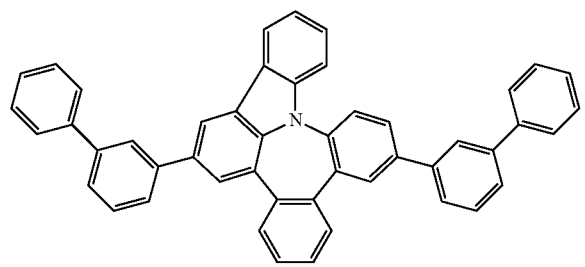
Formula 2
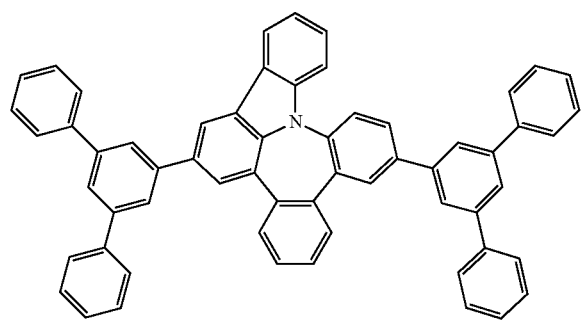
Formula 3
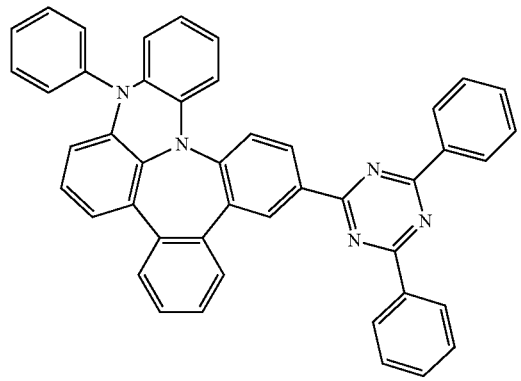
Formula 4
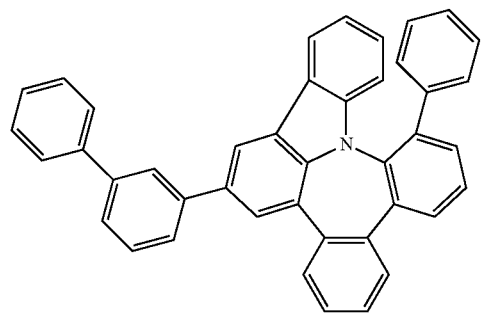
Formula 5
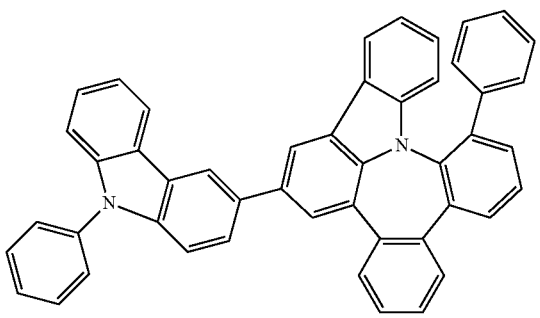
Formula 6
Formula 7
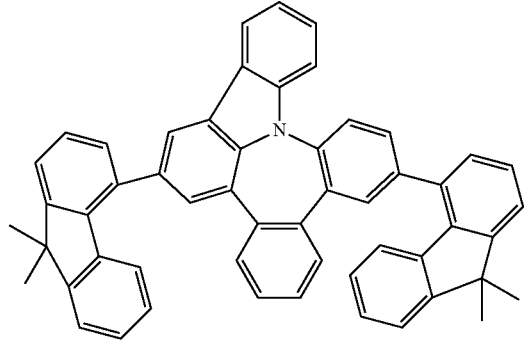
Formula 8
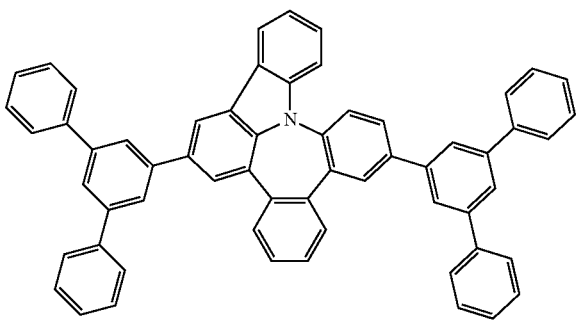

-continued
Formula 9
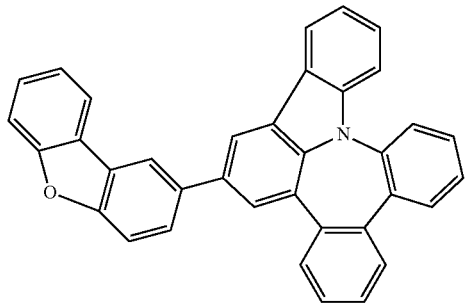
Formula 10
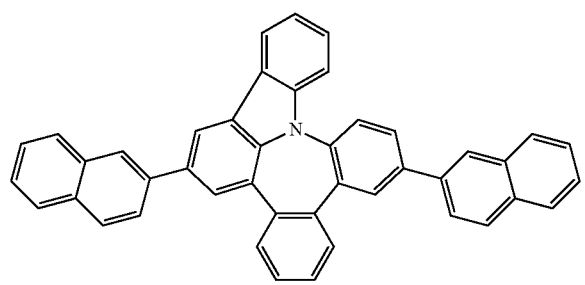
Formula 11
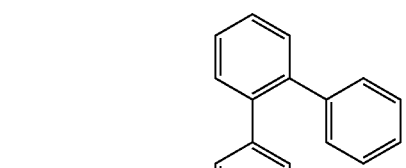
Formula 12
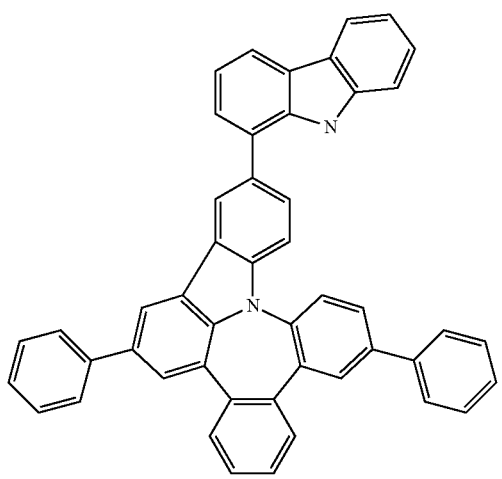
-continued
Formula 13
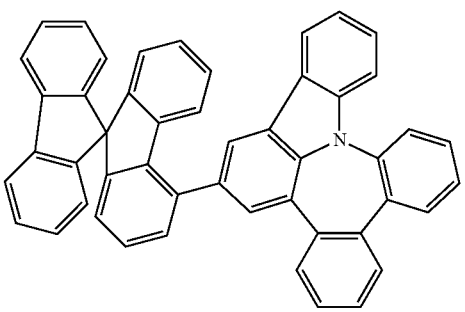
Formula 14
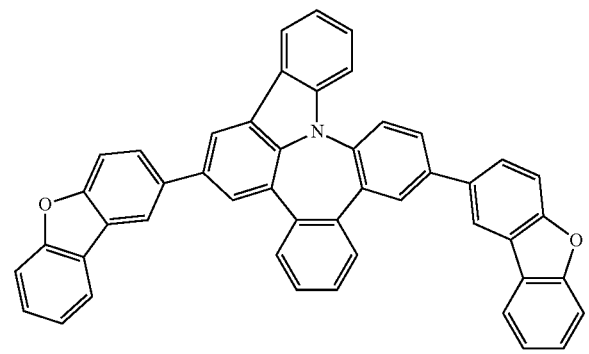
Formula 15
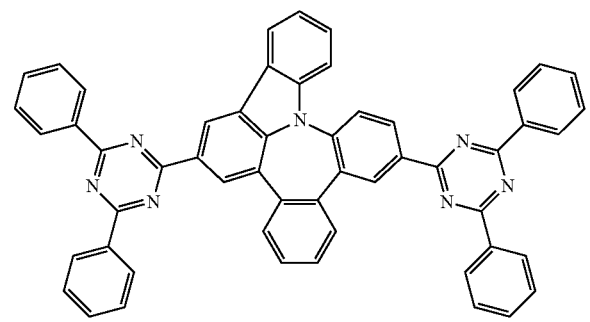
Formula 16
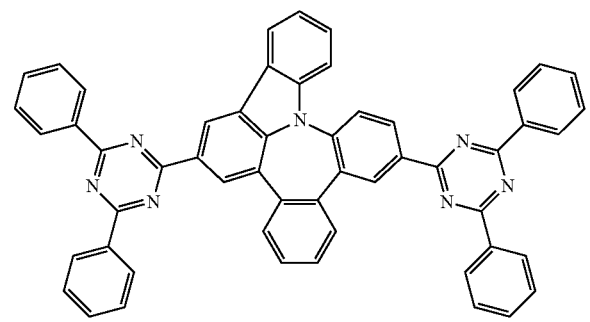

Formula 17
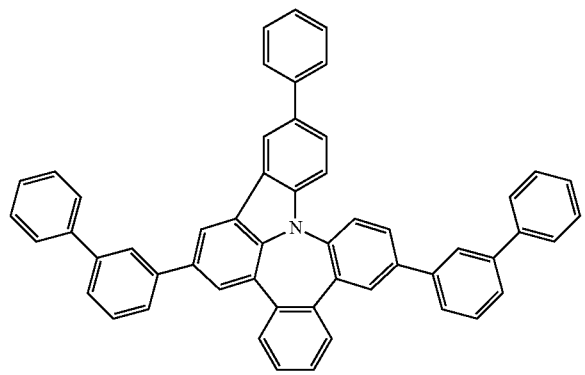
Formula 18
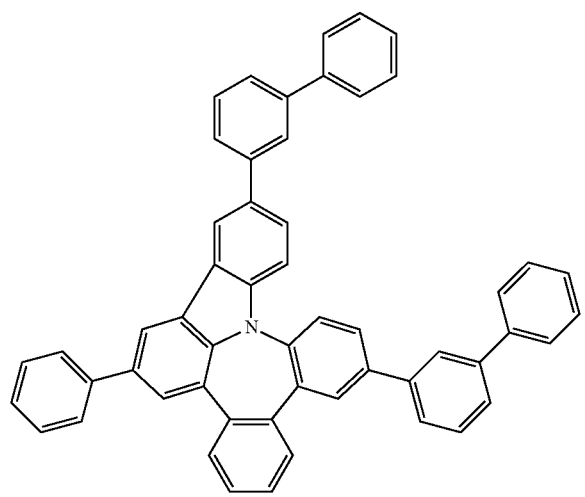
Formula 19
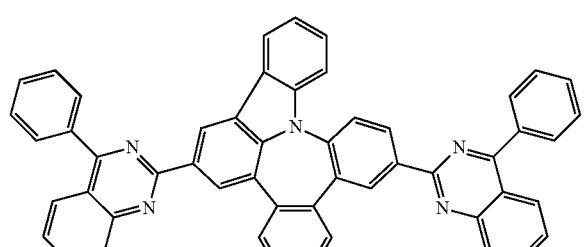
Formula 20
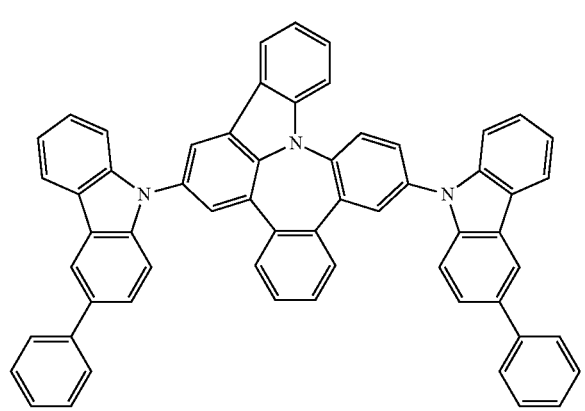
Formula 21
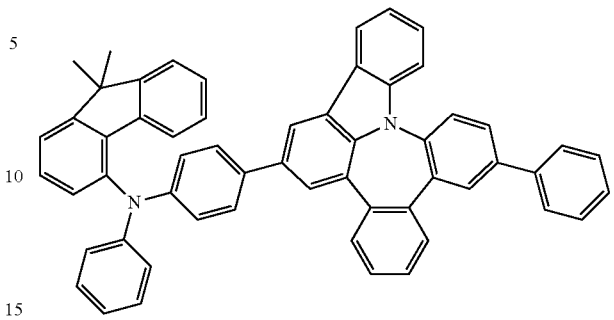
Formula 22
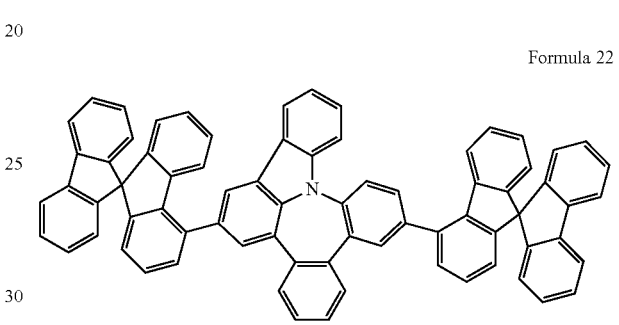
Formula 23
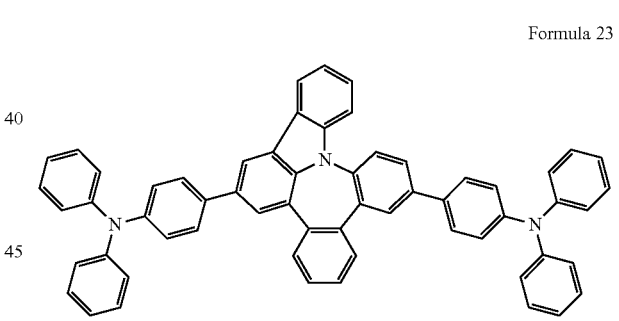
Formula 24
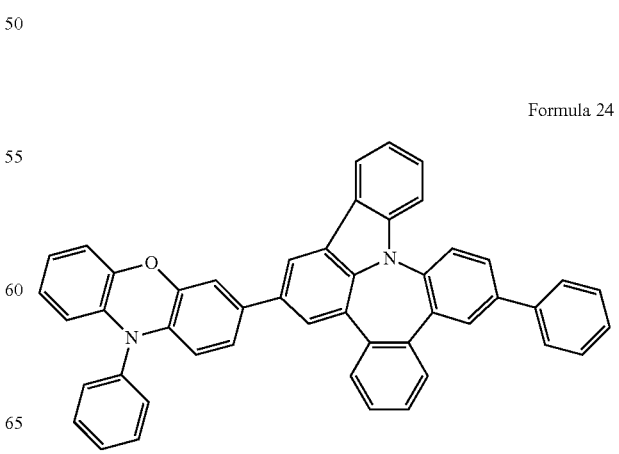

Formula 25
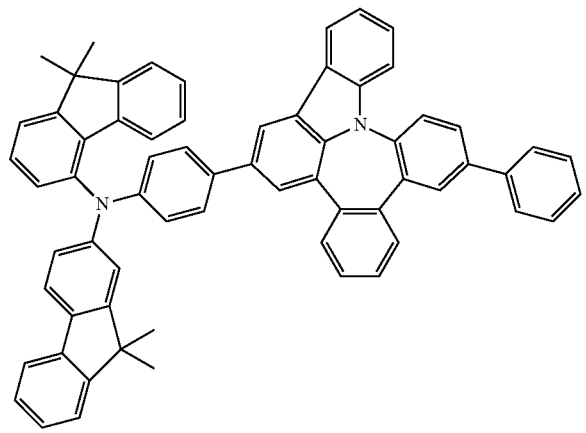
Formula 26
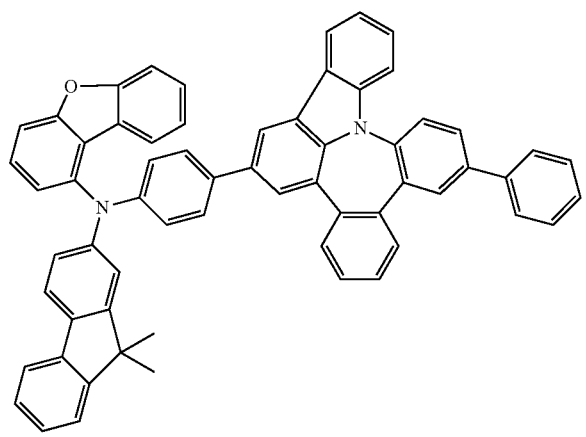
Formula 27
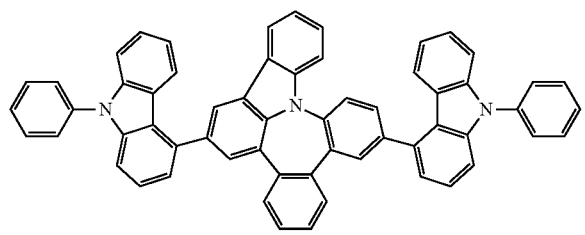
Formula 28
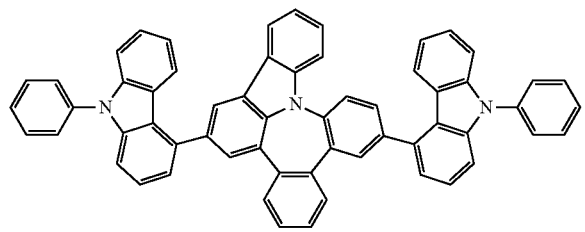
Formula 29
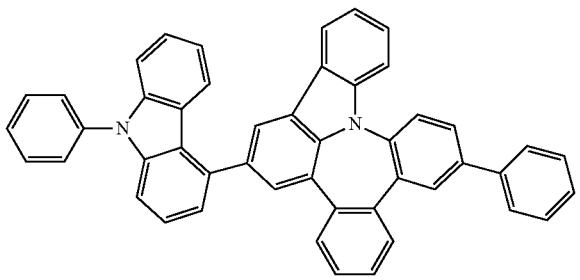
Formula 30
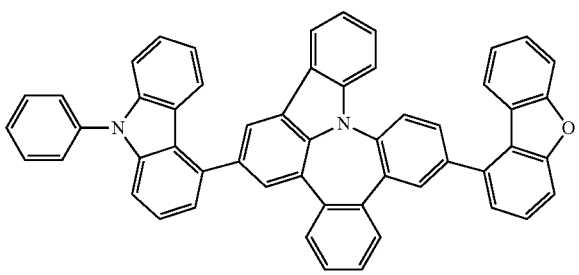
Formula 31
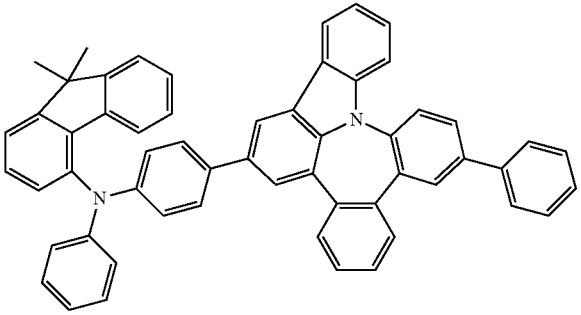
Formula 32
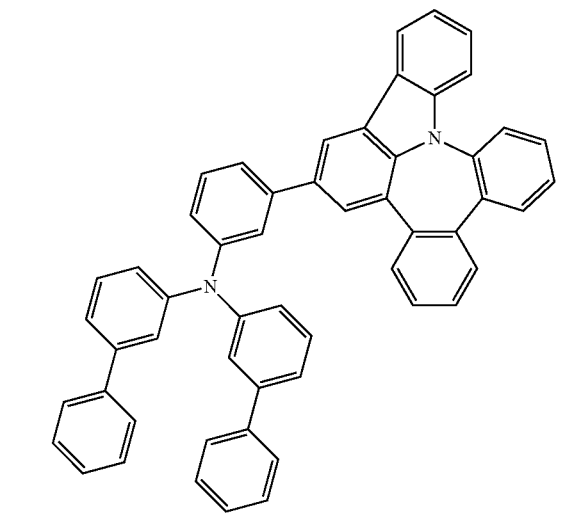

Formula 33
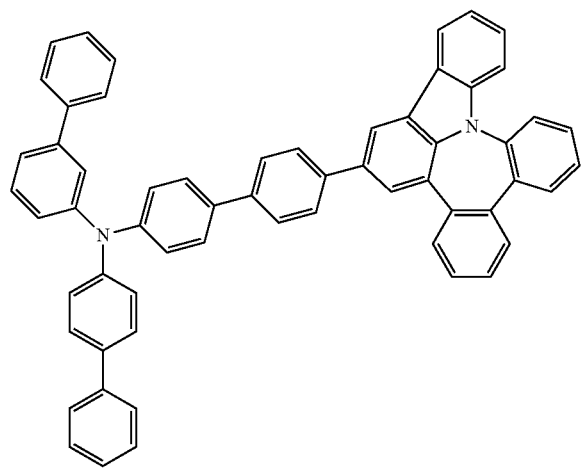
Formula 34
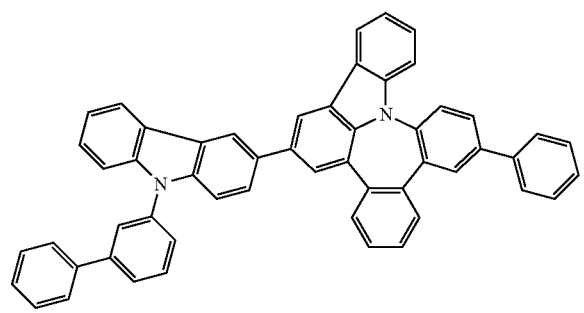
Formula 35
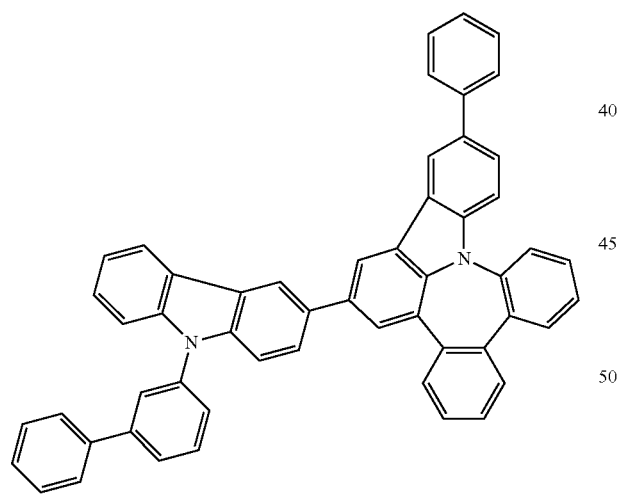
Formula 36
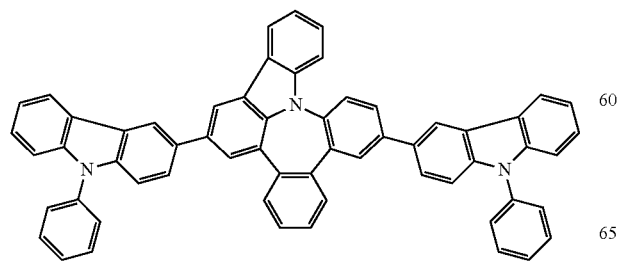
Formula 37
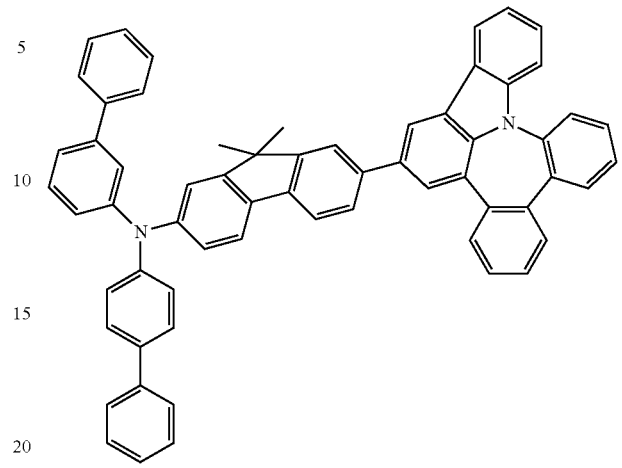
Formula 38
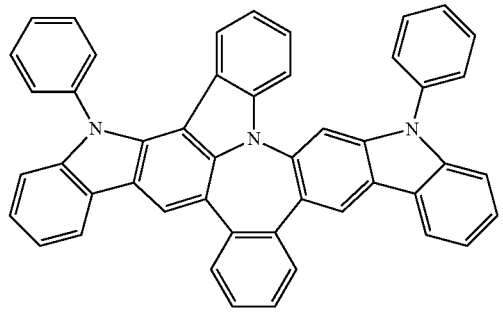
Formula 39
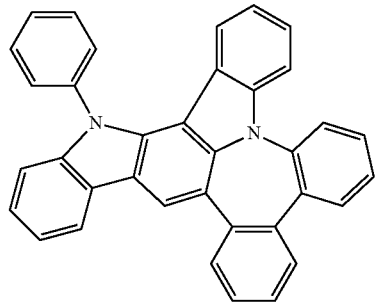
Formula 40
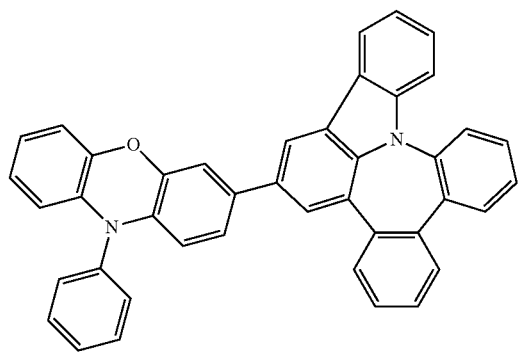

-continued
Formula 41
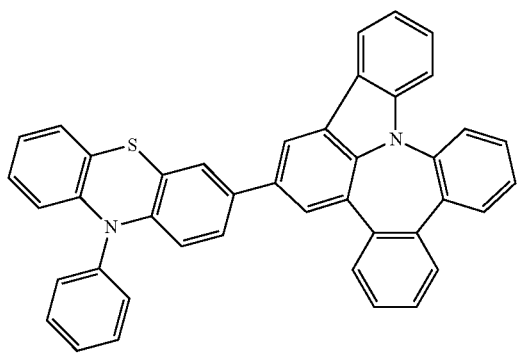
Formula 42
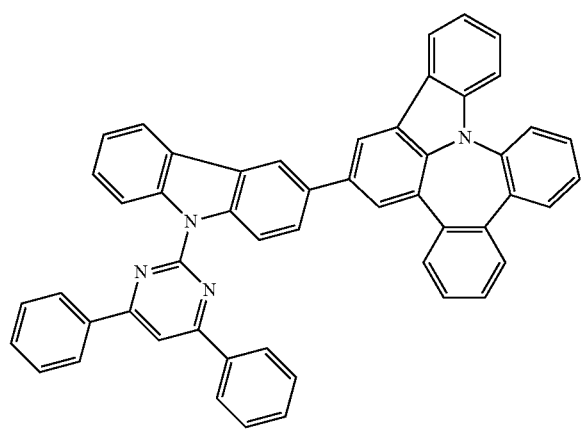
Formula 43
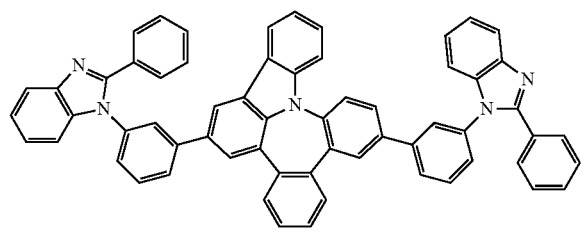
Formula 44
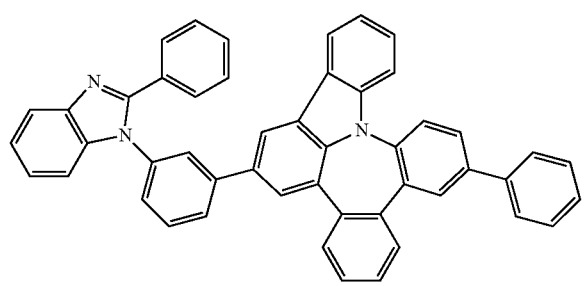
Formula 45
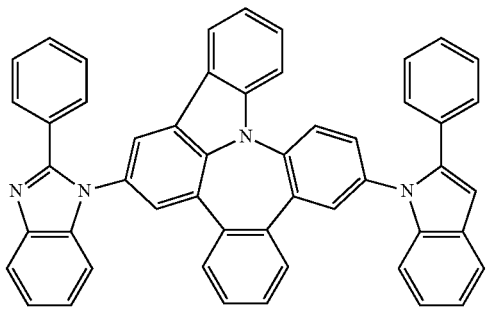
Formula 46
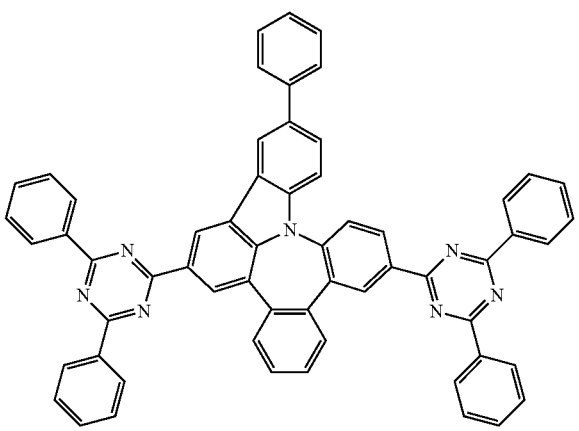
Formula 47
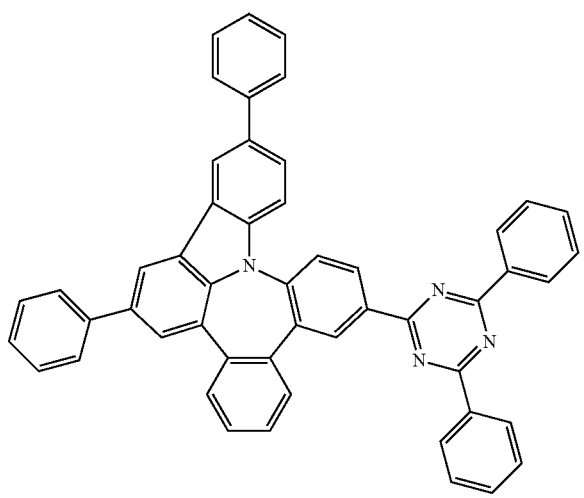

Formula 48
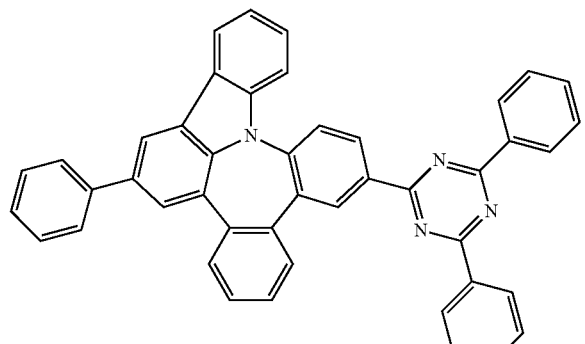
Formula 49
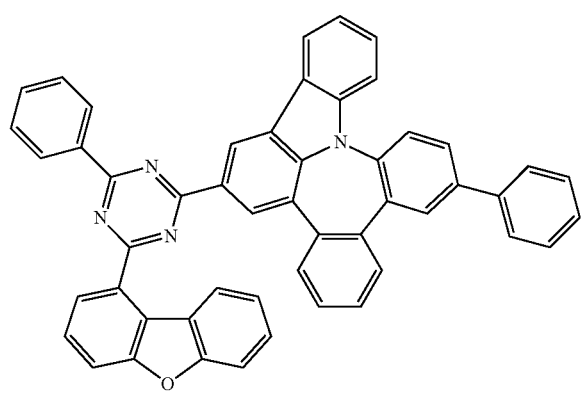
Formula 50
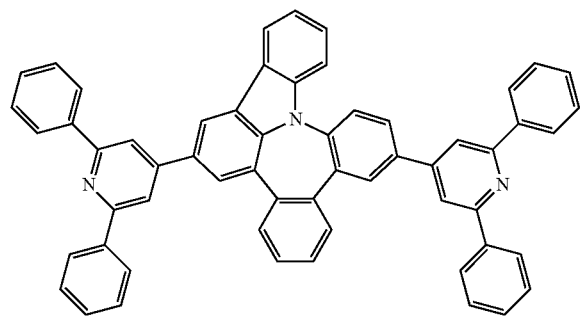
Formula 51
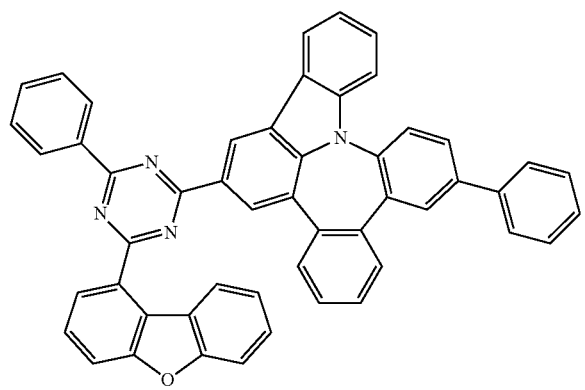
Formula 52
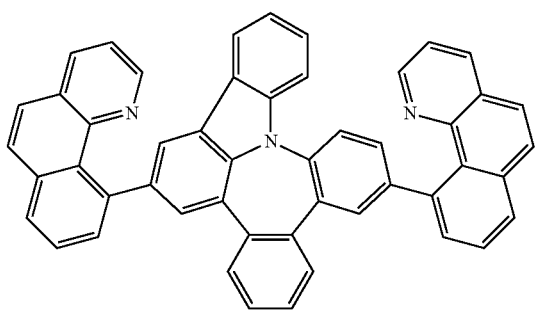
Formula 53
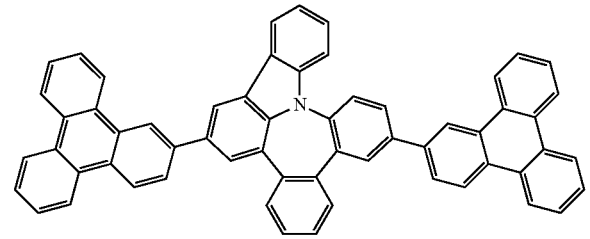
Formula 54
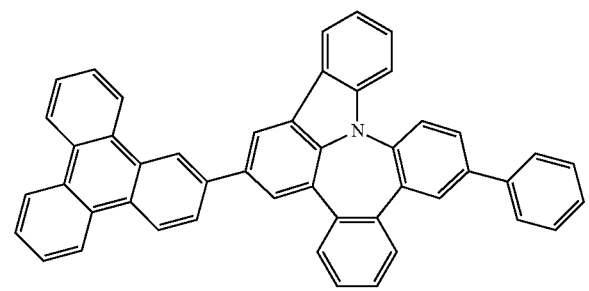
Formula 55
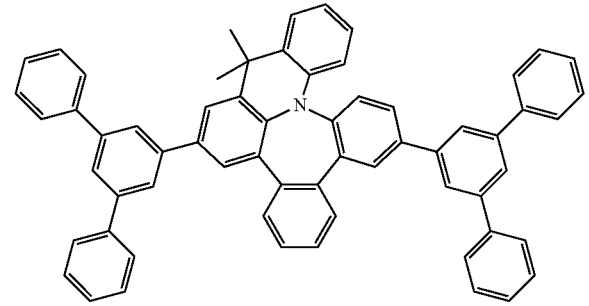

Formula 56
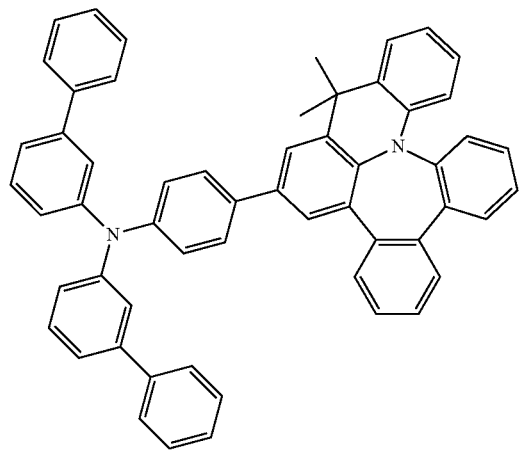
Formula 57
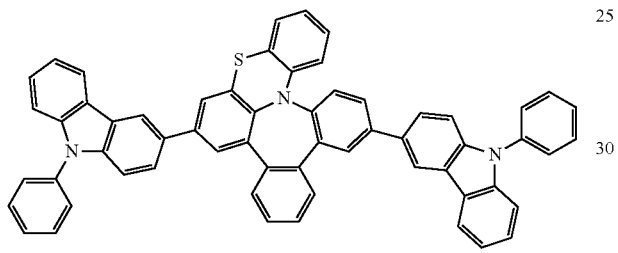
Formula 58
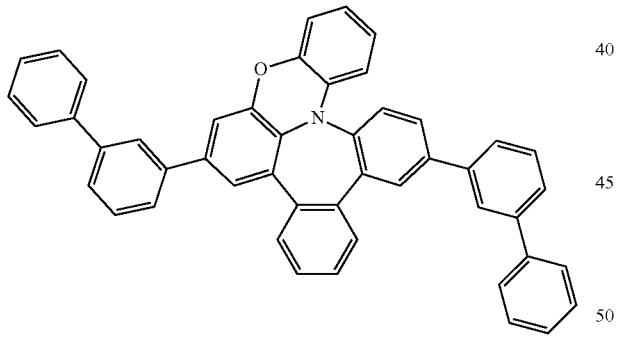
Formula 59
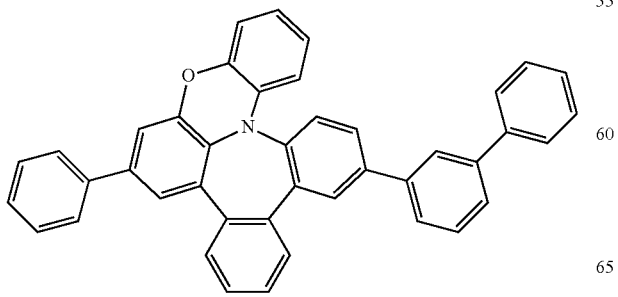
Formula 60
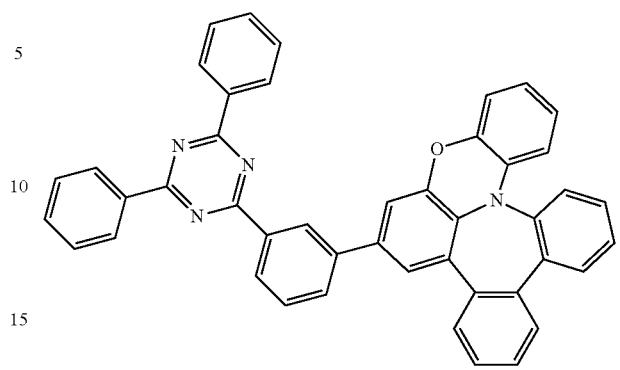
Formula 61
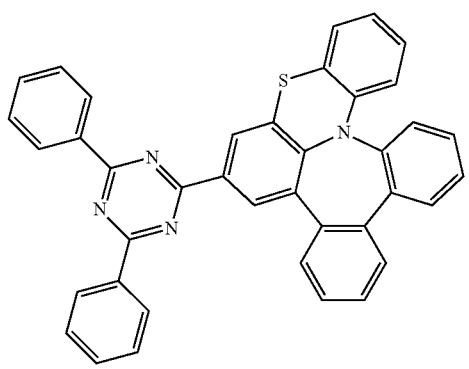
Formula 62
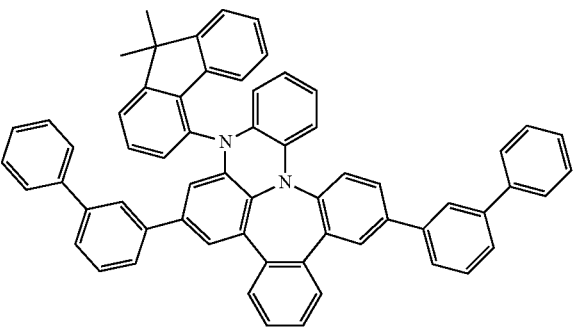
Formula 63
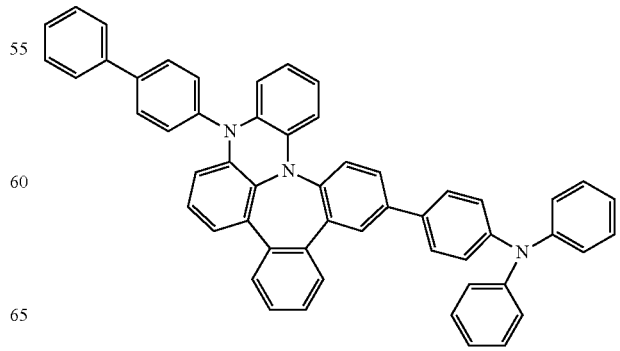

Formula 64
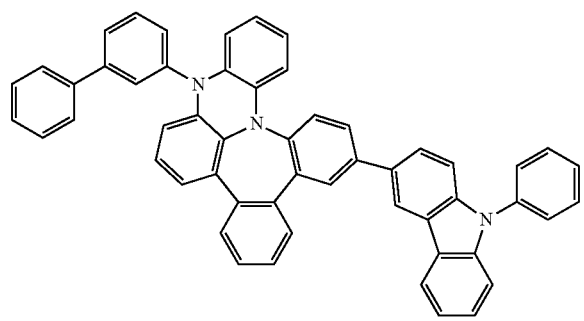
Formula 65
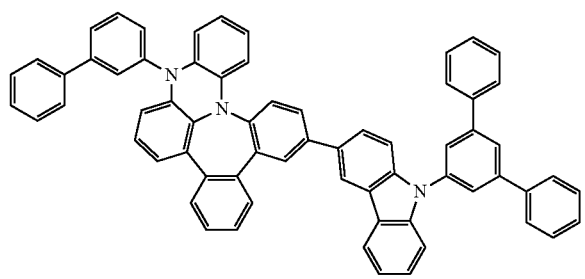
Formula 66
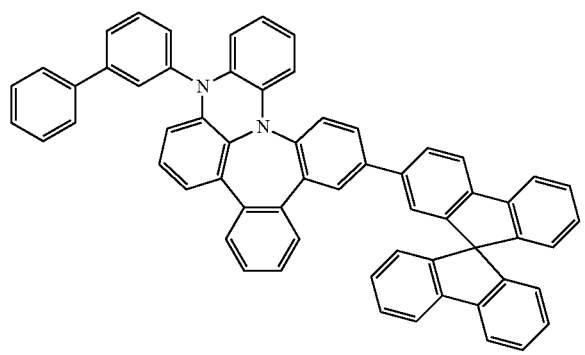
Formula 67
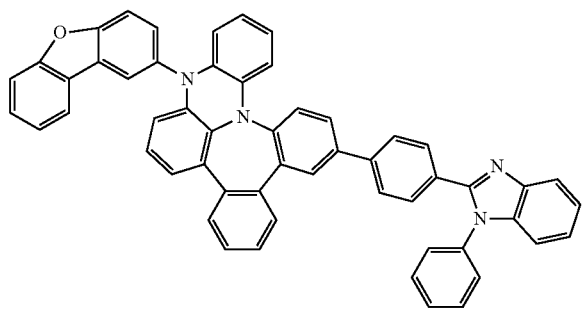
Formula 68
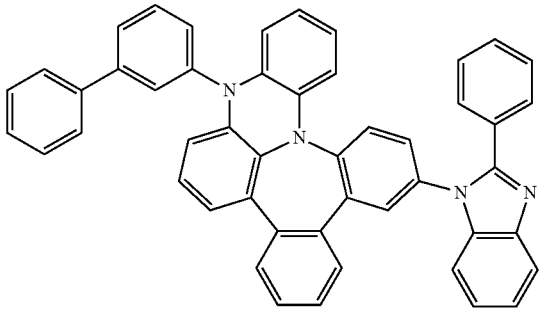
Formula 69
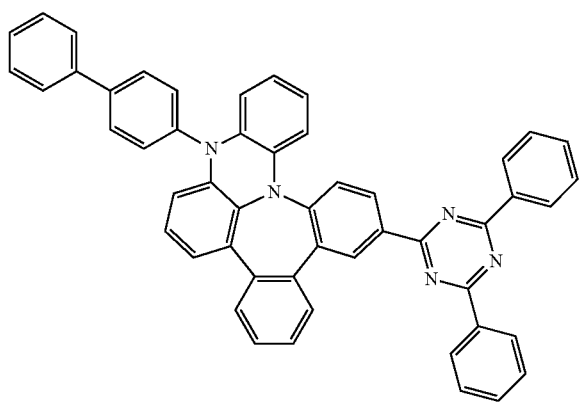
Formula 70
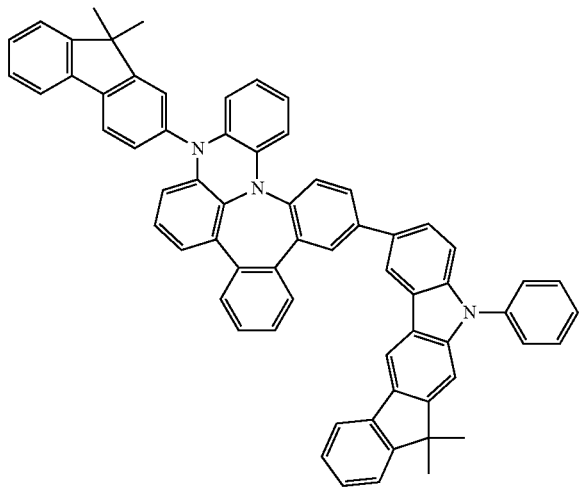
Formula 71
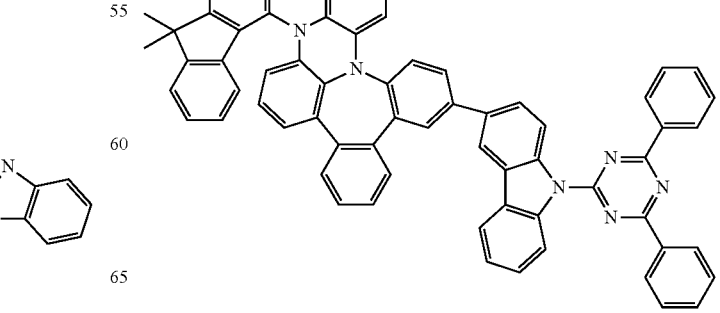

Formula 72
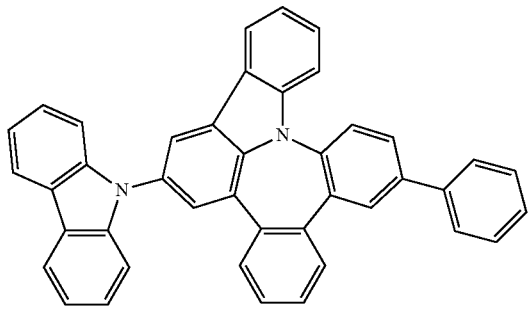
Formula 73
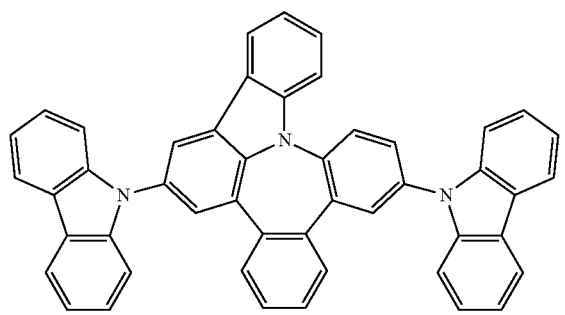
Formula 74
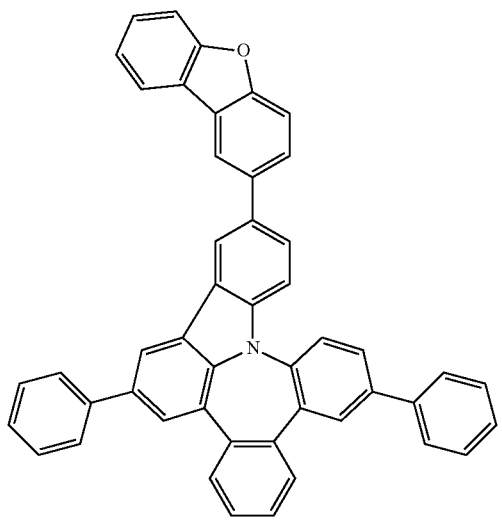
Formula 75
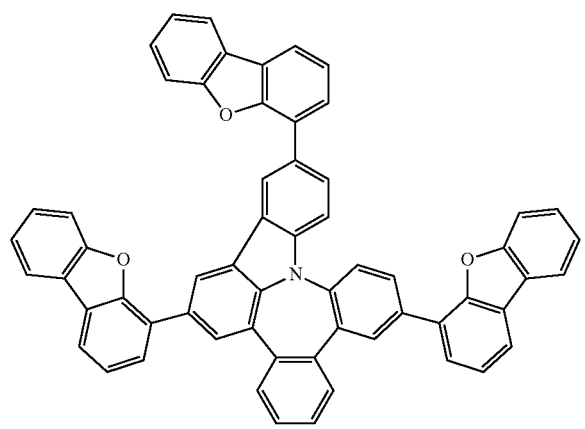
Formula 76
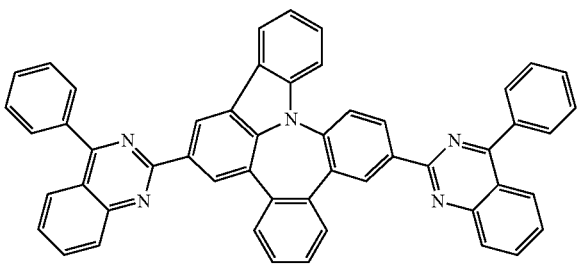
Formula 77
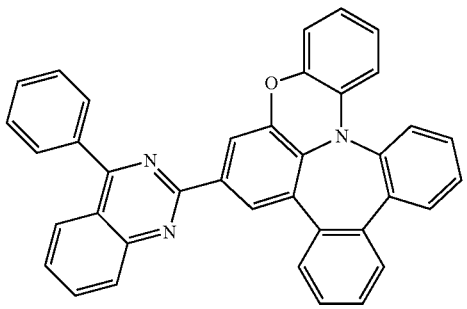
Formula 78
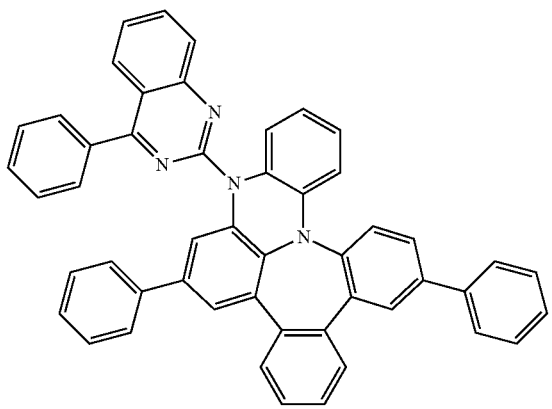
Formula 79
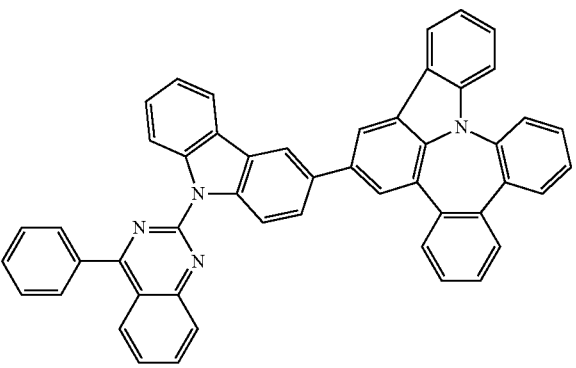

Formula 80

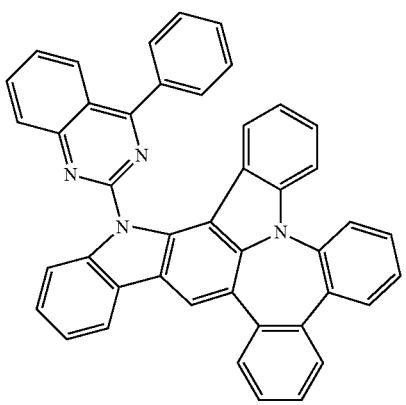

Preferred embodiments of compounds of the invention are recited specifically in the examples, these compounds being usable alone or in combination with further compounds for all purposes of the invention.

Provided that the conditions specified in Claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

The present invention therefore further provides a process for preparing the compounds comprising structures of formula (I), in which a ring closure reaction is conducted in a compound having an azapine structural element.

Compounds having an azapine structural element, for example 9H-tribenz[b,d,f]azapine, are in many cases commercially available, and the starting compounds detailed in the examples are obtainable by known processes, and so reference is made thereto.

These compounds can be reacted with further aryl compounds by known coupling reactions, the intermediate compounds obtained being subjected subsequently to a ring closure reaction in order to obtain the compounds of the invention which structures of the formulae (I), (II), (III), (IV), (V), (VI), (VII) and/or (VIII). In addition, the compounds obtained after a ring closure reaction can be converted in further reactions in order to obtain products of the invention.

The necessary conditions for this are known to those skilled in the art, and the specific details given in the examples will support the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

For example, according to scheme 1, proceeding from a 9H-tribenz[b,d,f]azapine compound, it is possible to prepare a reactive intermediate by a Buchwald coupling. The intermediate obtained can be subjected in a ring closure reaction by means of a catalyst, for example Pd(OAc)$_2$, in order to obtain a compound of the invention.

Scheme 1

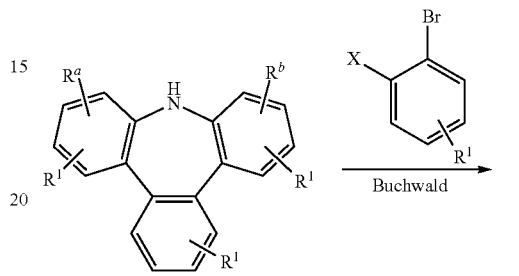

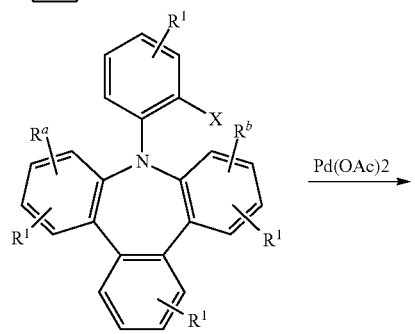

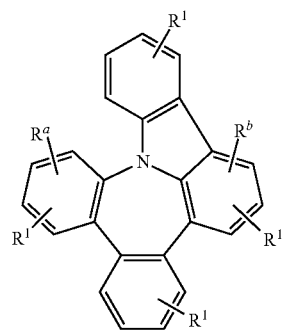

X = halogen or triflate, where the triflate can also be obtained in an intermediate reaction from an ether or a hydroxyl group.

In reactions according to scheme 2, proceeding from a reactant having an azapine structural element, a reaction is conducted with a fluoroaryl compound having a nitro group, for example using Cs$_2$CO$_3$. The intermediate compound obtained is first reduced in order to convert the nitro group of the intermediate compound to an amino group, for which it is possible to use SnCl$_2$, for example, as reducing agent. The intermediate having an amino group obtainable in this way can subsequently be converted to a compound of the invention via a ring closure reaction, for example by means of NaNO$_2$.

Scheme 2

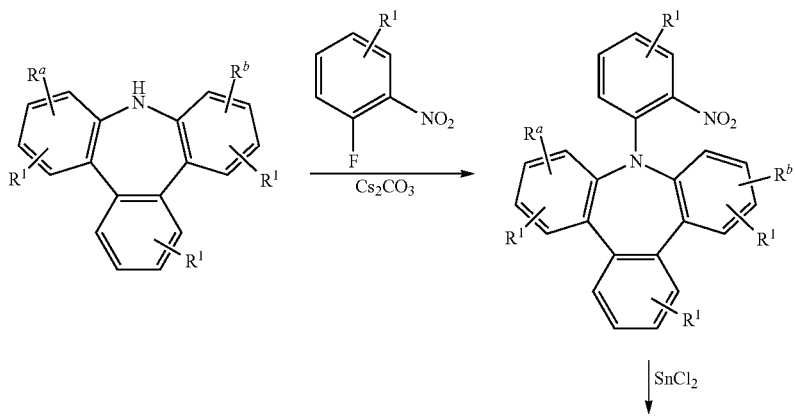

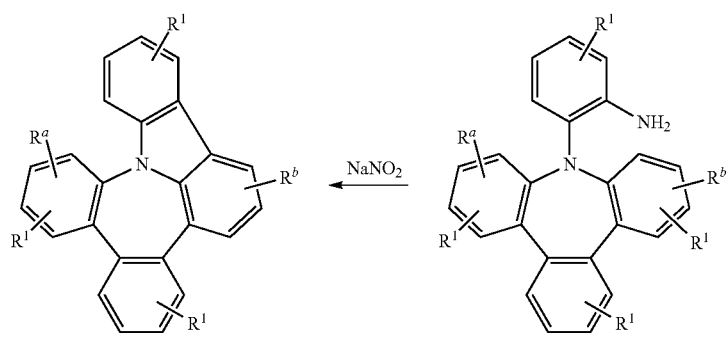

According to scheme 3, an azapine compound can be reacted with an aryl halide having an ester group. The ester group of the intermediate obtained can subsequently be reduced to an alcohol, for which it is possible to use an organometallic compound, for example, one example being methyllithium. The intermediate prepared can subsequently be subjected to a ring closure reaction, for which one usable reagent is an acid.

Scheme 3

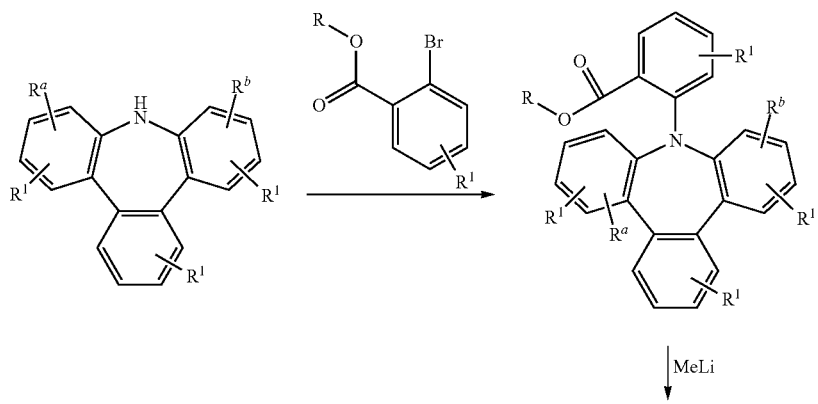

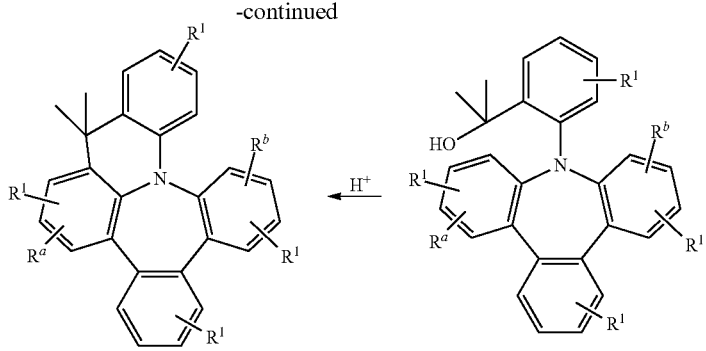

According to scheme 4, an azapine compound with a leaving group X adjacent to the nitrogen atom of the azapine compound can be converted in a Buchwald coupling, using an aryl compound having a nitro group and having a leaving group X in the ortho position to the nitro group for the purpose. The nitro group of the intermediate obtained can subsequently be reduced to an amino group, for which it is possible to use SnCl$_2$, for example. The intermediate prepared can subsequently be subjected to a ring closure reaction, and the ring closure can be brought about by a Buchwald coupling. This affords a diarylamino structure which can be converted in a further Buchwald coupling using an aryl compound having a leaving group X.

Scheme 4

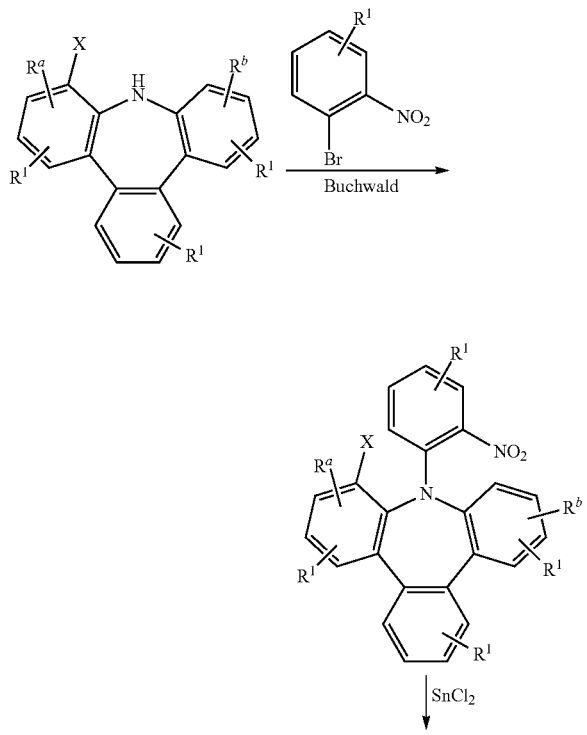

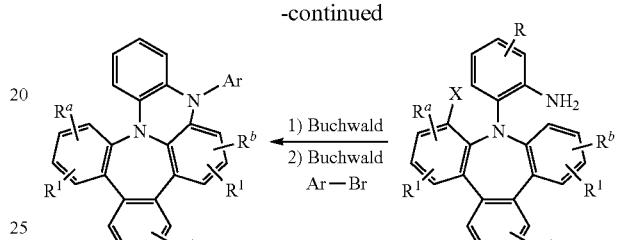

Ar = aryl compound
X = halogen or triflate, where the triflate can also be obtained in an intermediate reaction from an ether or a hydroxyl group.

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration soluble, in order to be able to process the compounds from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (I) or compounds of the invention, wherein one or more bonds of the compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound comprising one or more structures of the formula (I) or the preferred embodiments detailed above and hereinafter and having a molecular weight of preferably not more than 10 000 g/mol, more preferably not more than 5000 g/mol, particularly preferably not more than 4000 g/mol, especially preferably not more than 3000 g/mol, specifically preferably not more than 2000 g/mol and even more preferably not more than 1000 g/mol.

In addition, it is a feature of preferred compounds of the invention that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (I) or the preferred embodiments recited above and hereinafter and at least one further matrix material. According to a particular aspect of the present invention, the further matrix material has hole-transporting properties.

The present invention further provides a composition comprising at least one compound comprising at least one structure of formula (I) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

The present invention also relates to a composition comprising at least one compound comprising structures of formula (I) or the preferred embodiments recited above and hereinafter and at least one phosphorescent emitter, the term "phosphorescent emitters" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38 and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the devices of the invention.

Explicit examples of phosphorescent dopants are adduced in the following table:

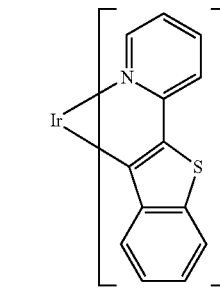

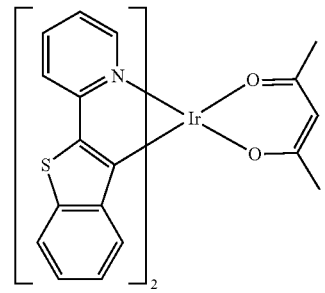

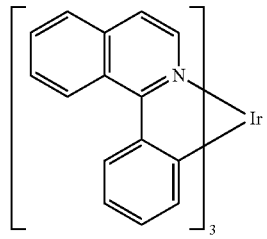

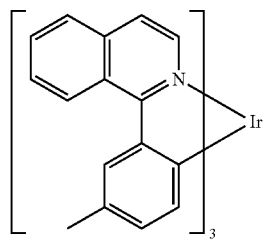

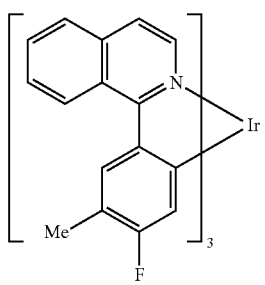
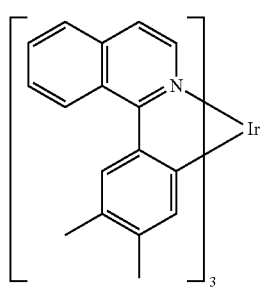
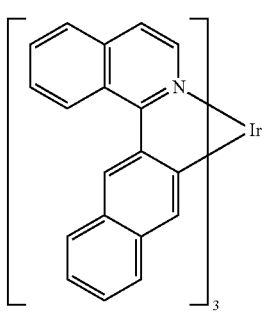
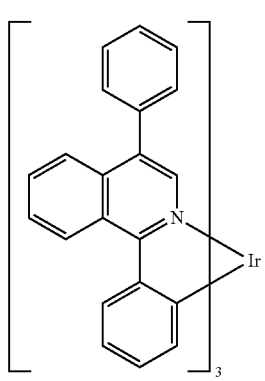
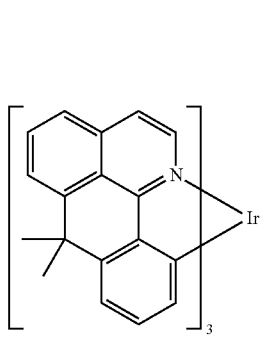
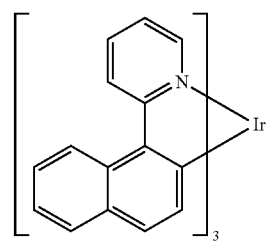
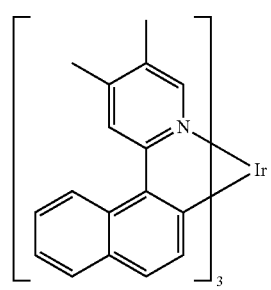
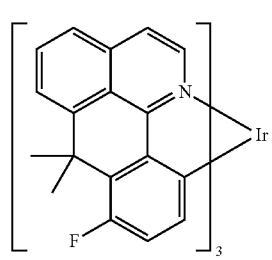
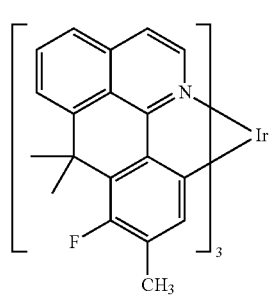
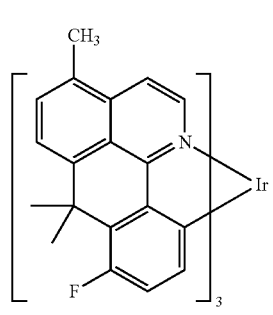

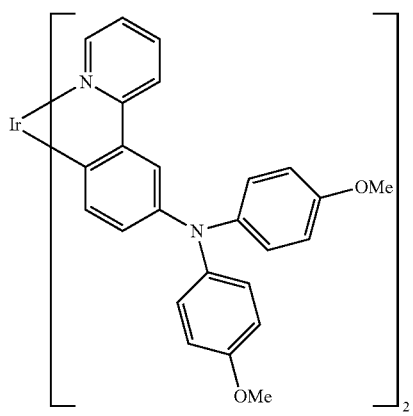
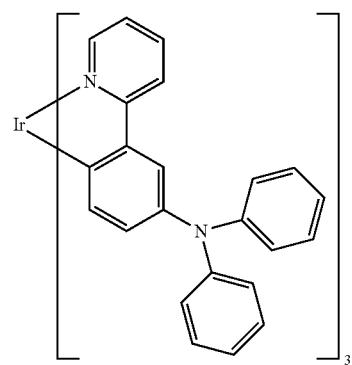
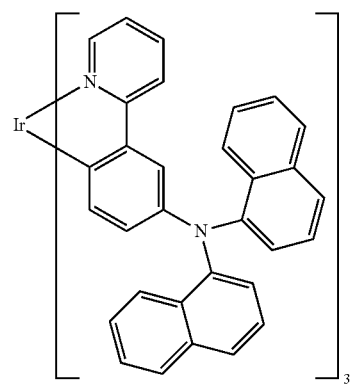
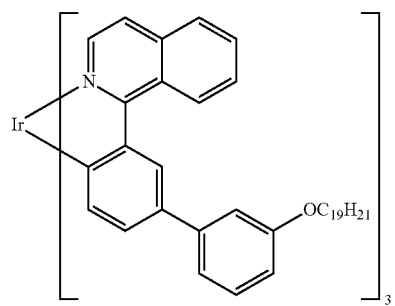
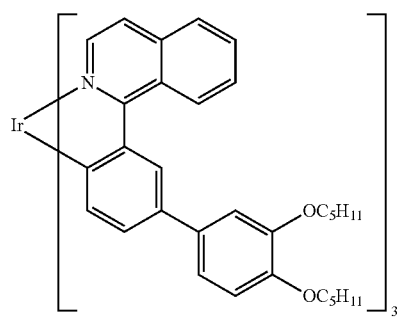
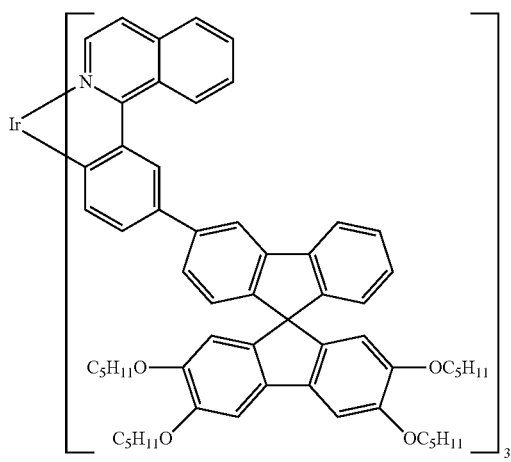
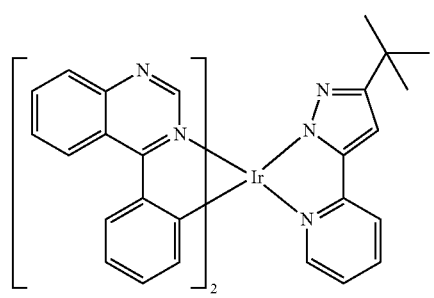
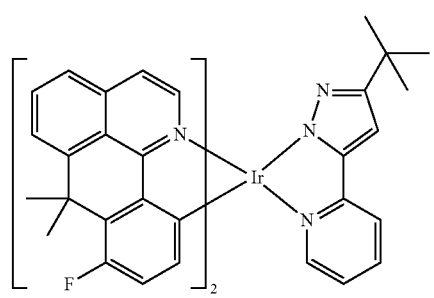

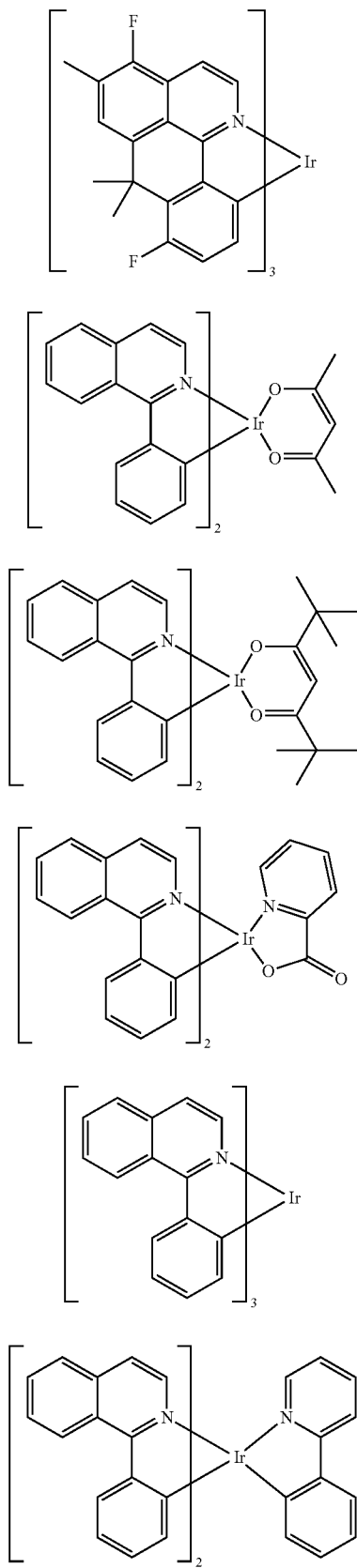
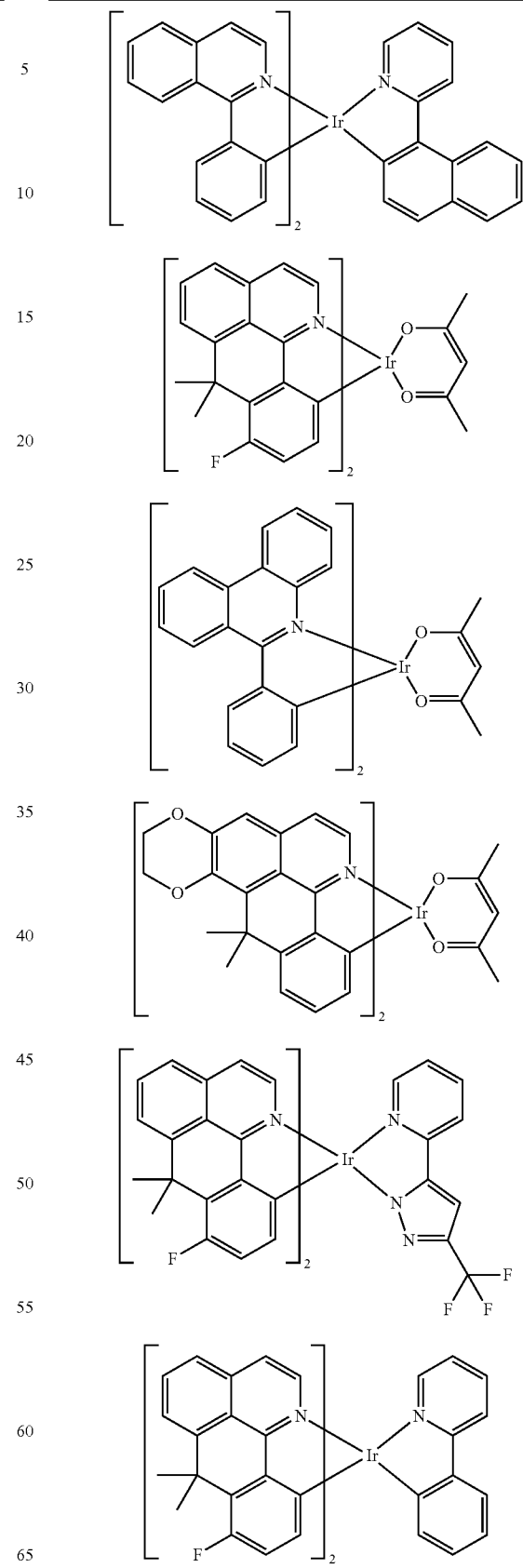

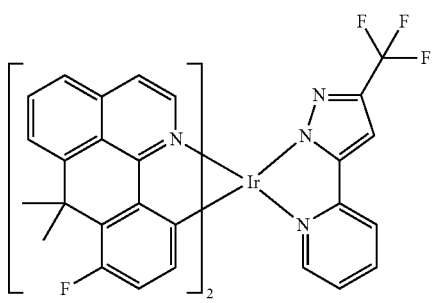
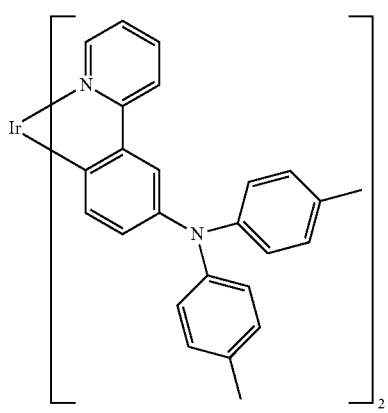
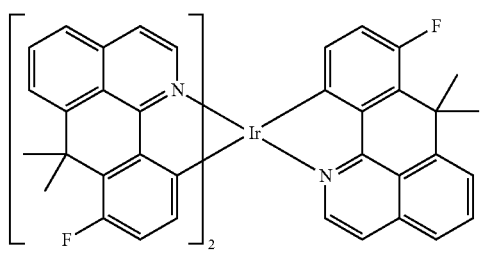
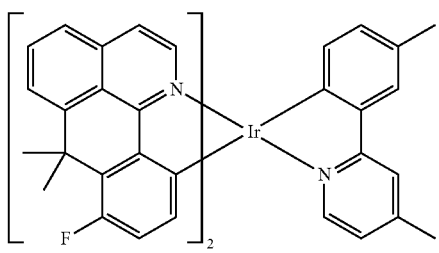
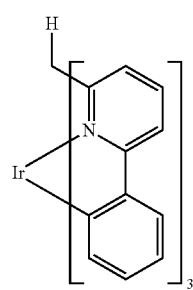
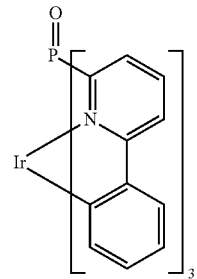
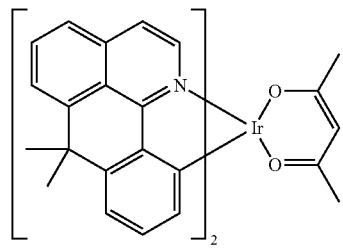
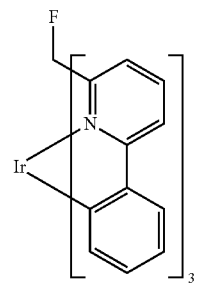
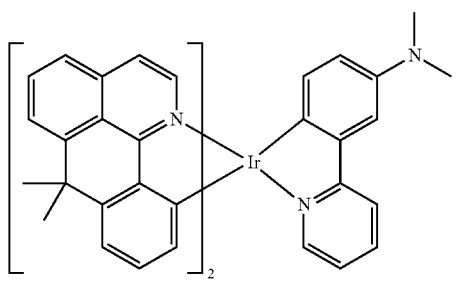
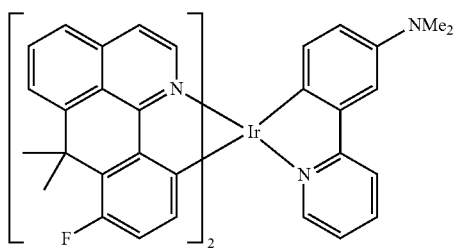
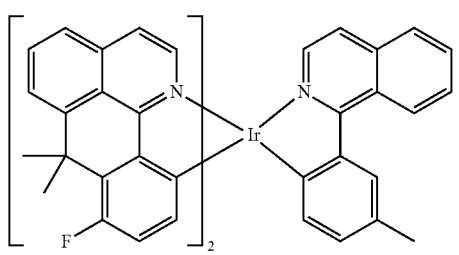

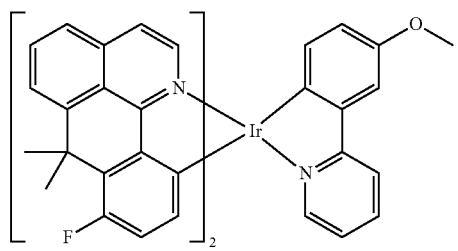
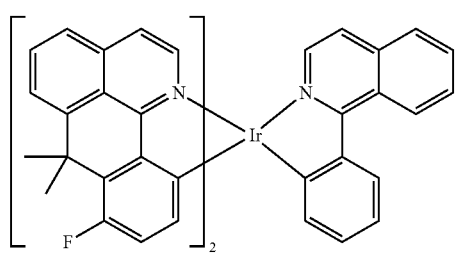
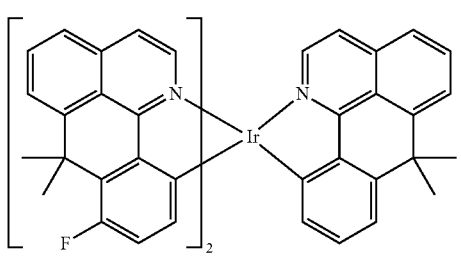
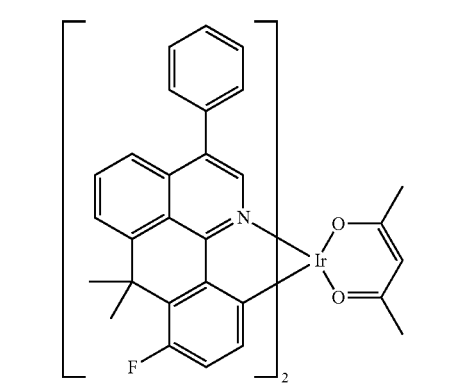
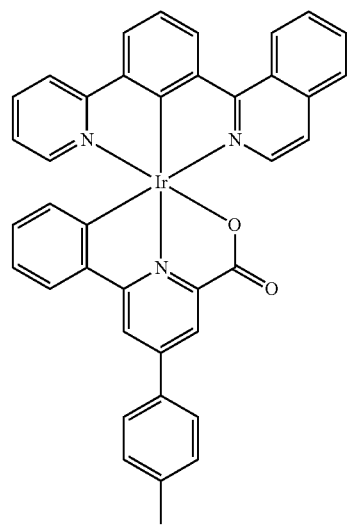

71
-continued
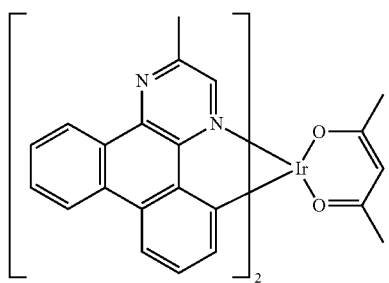
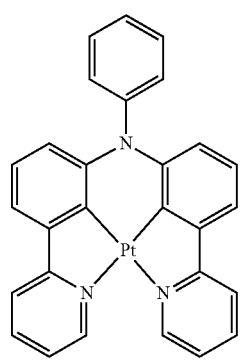
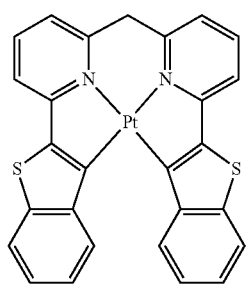
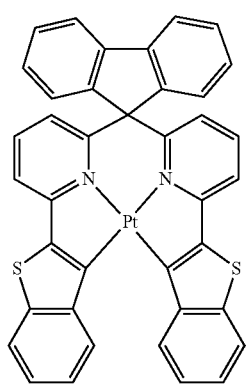
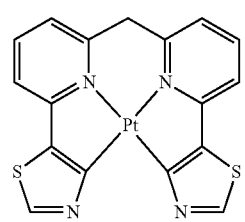
72
-continued
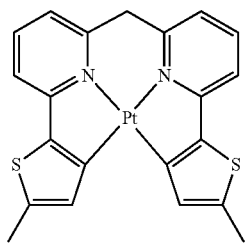
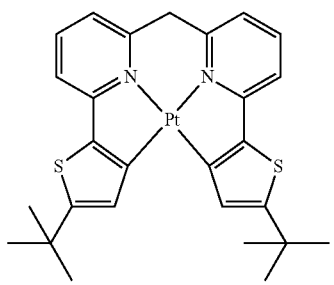
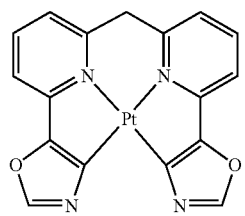
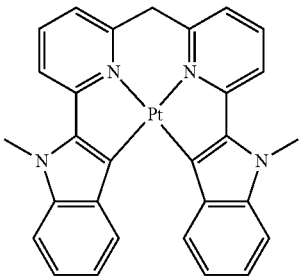
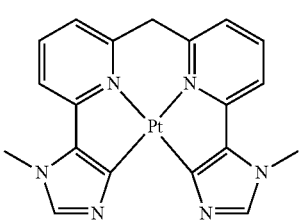

73
-continued
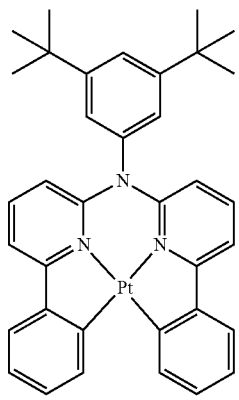
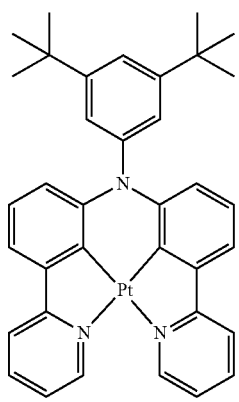
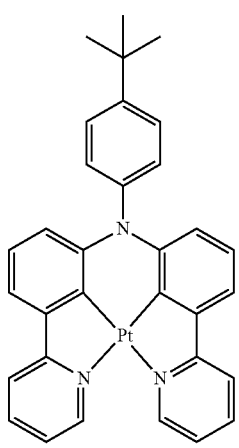
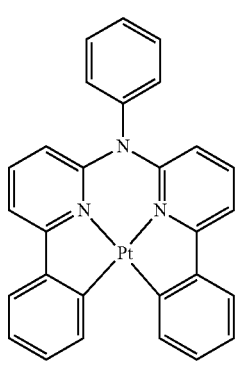
74
-continued
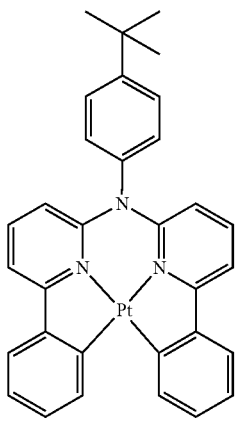
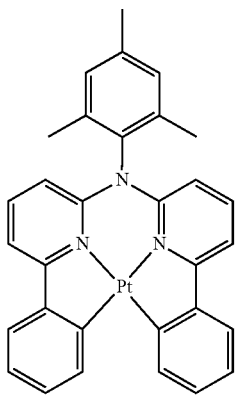
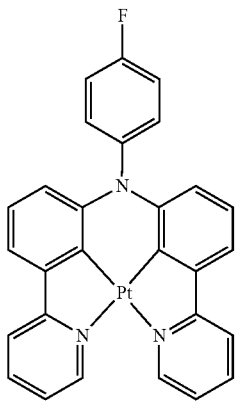

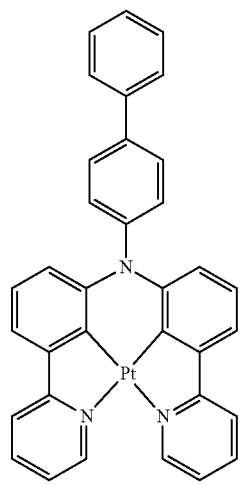
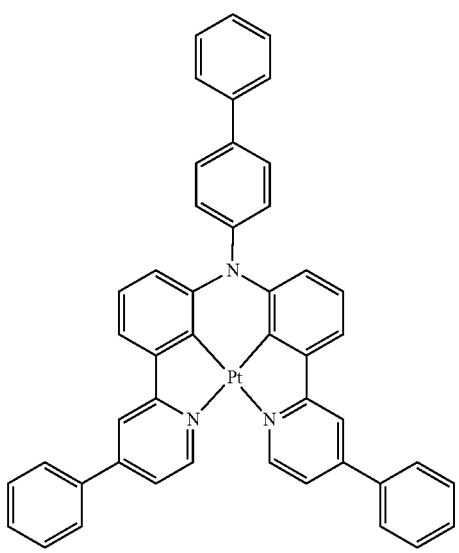
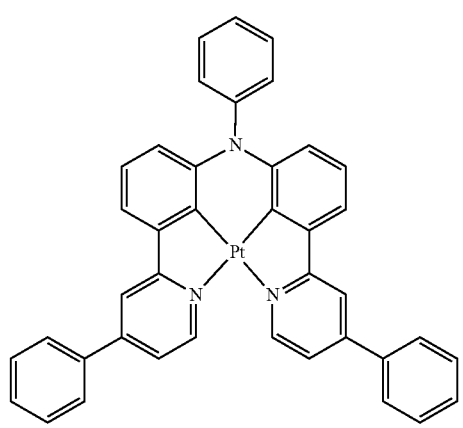
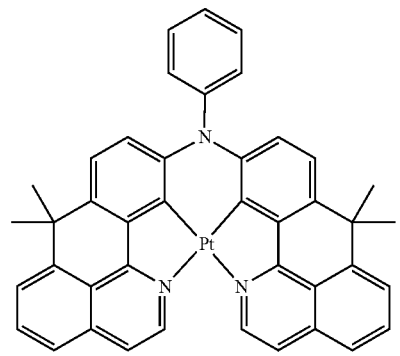
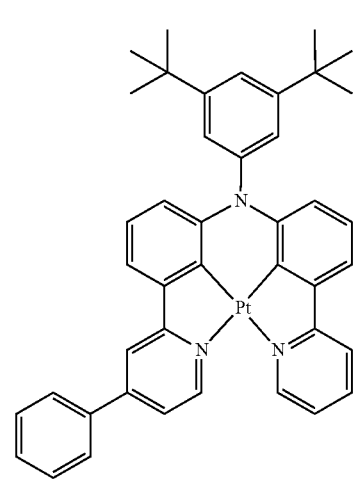
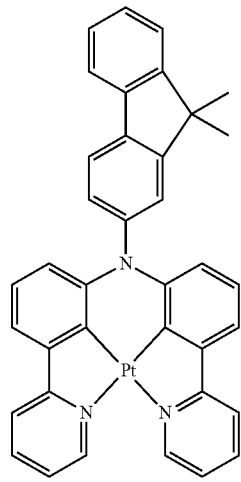

-continued
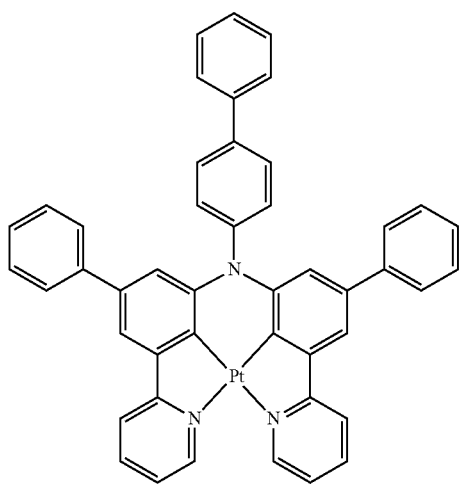
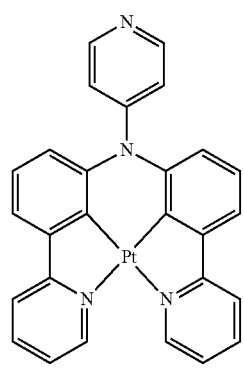
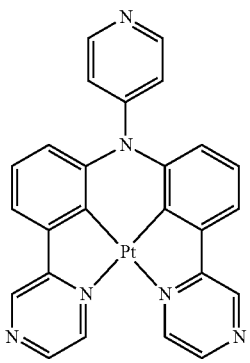
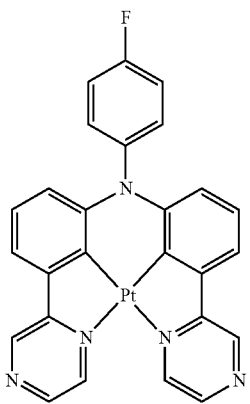
-continued
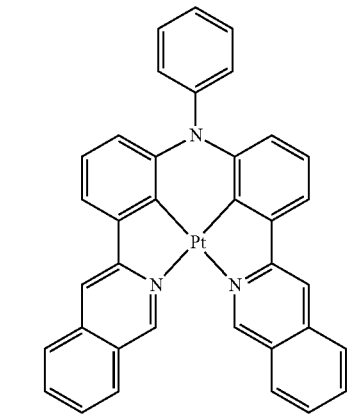
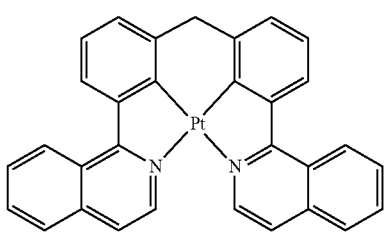
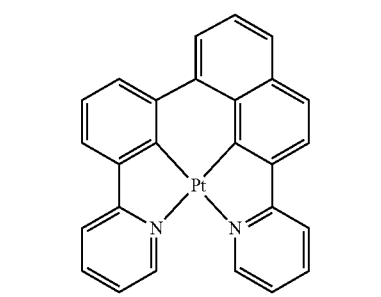
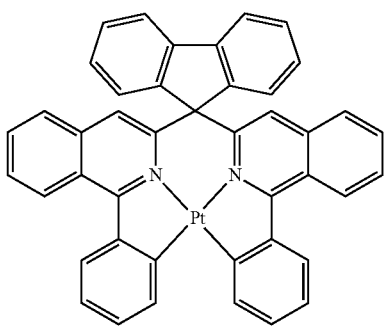
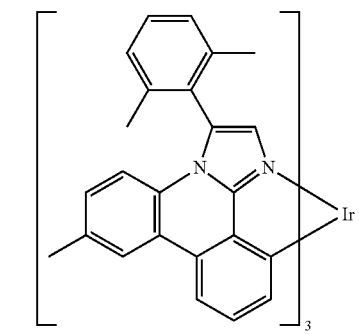

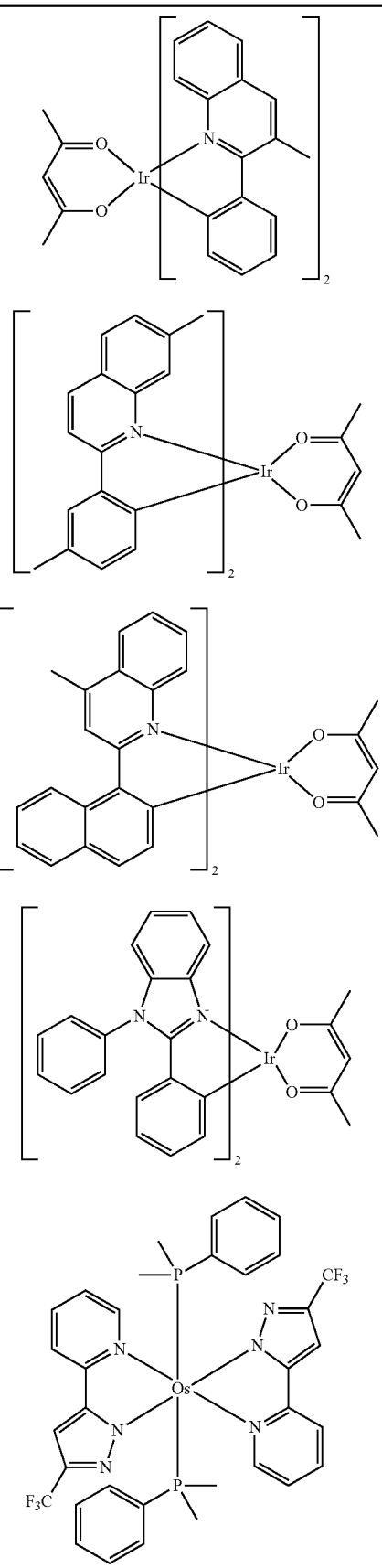
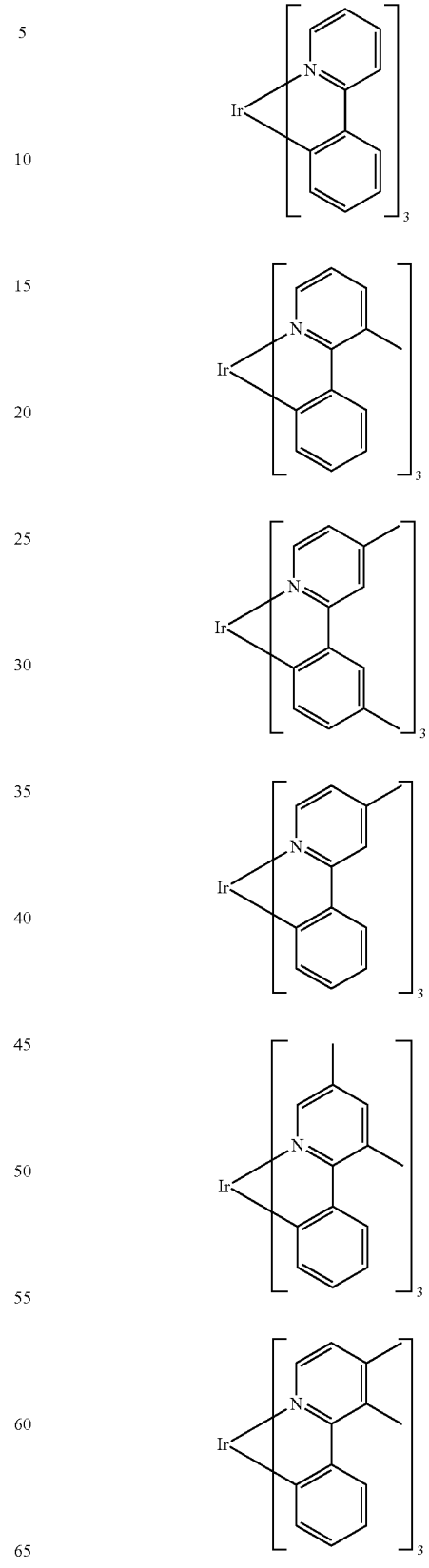

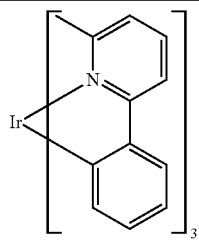
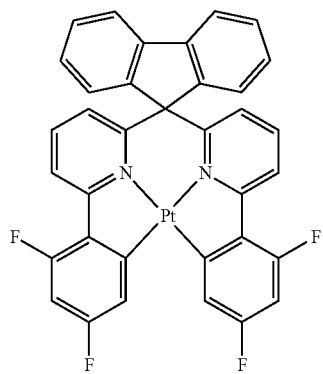
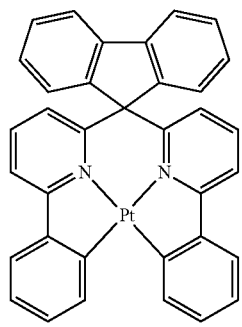
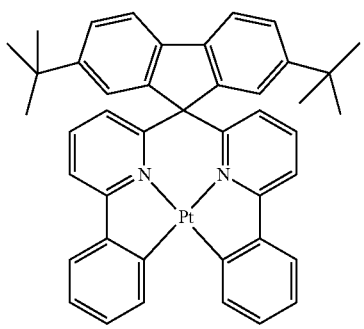
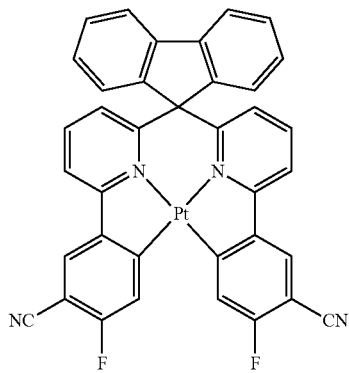
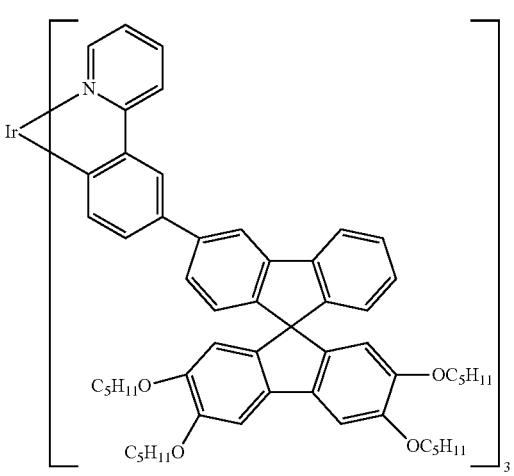
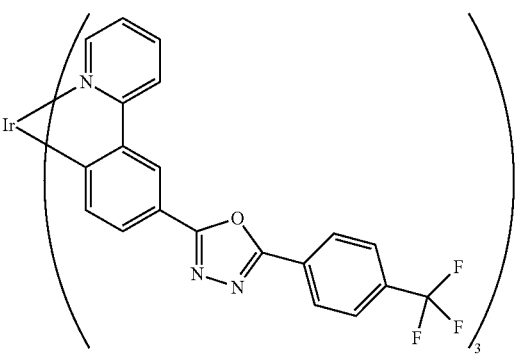
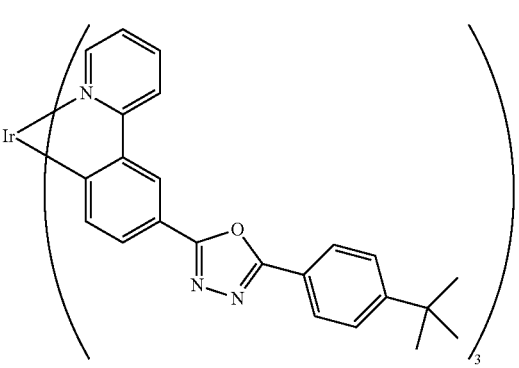
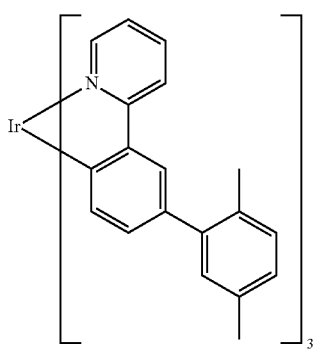

83
-continued
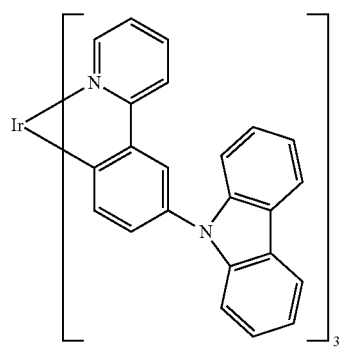
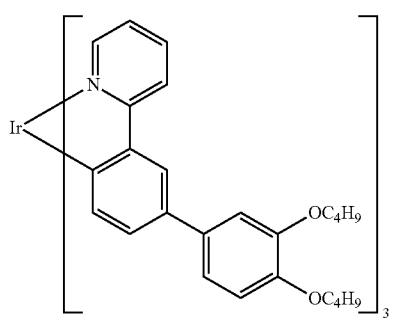
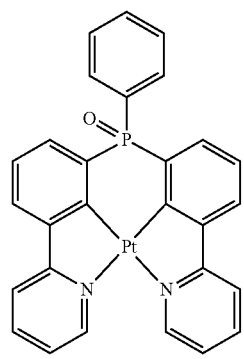
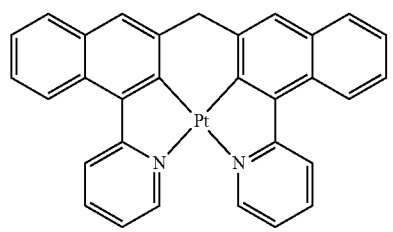
84
-continued
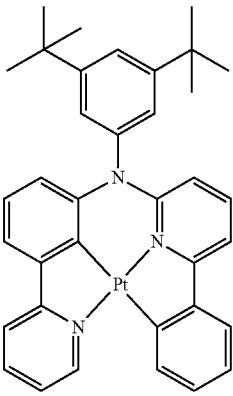
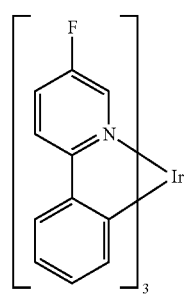
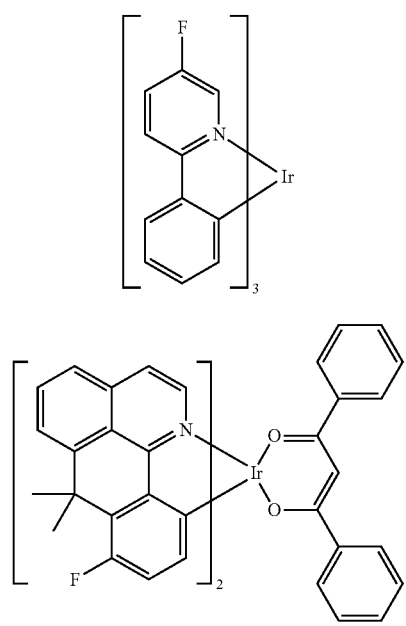
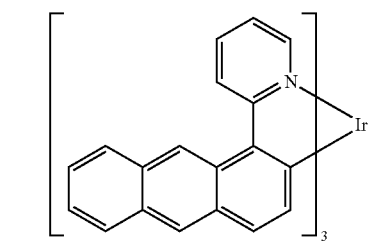
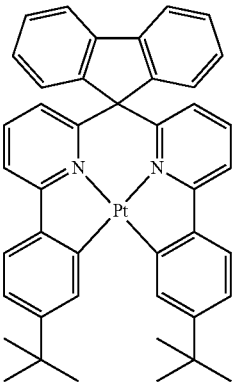

85
-continued
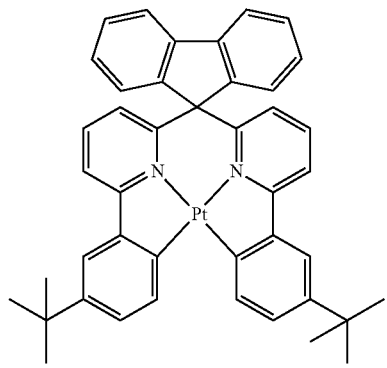
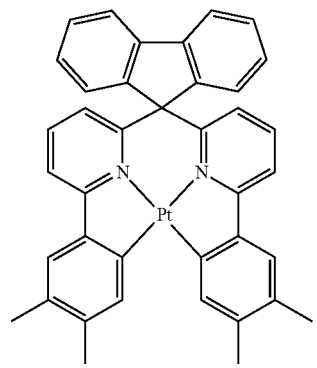
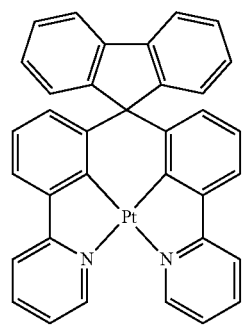
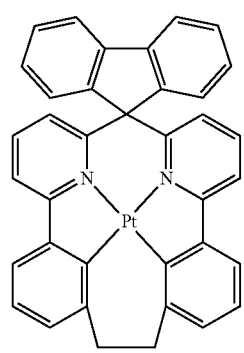
86
-continued
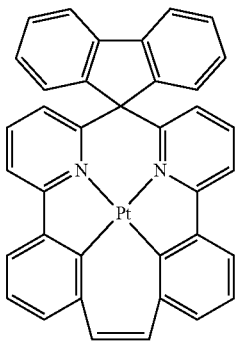
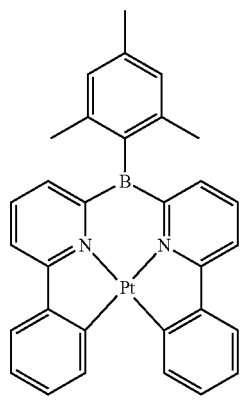
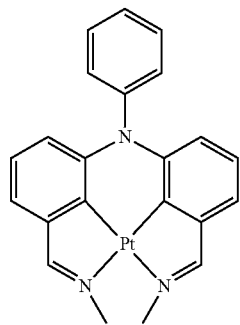
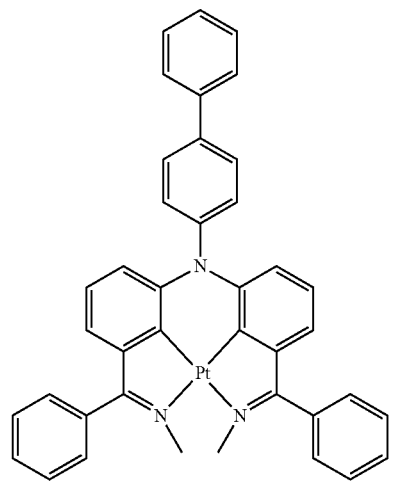

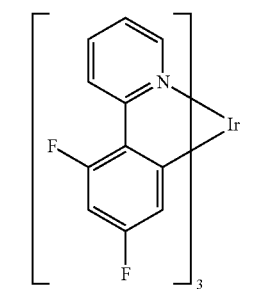
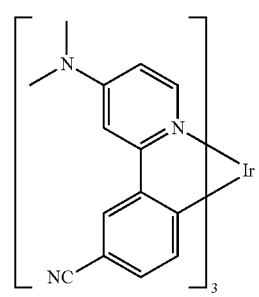
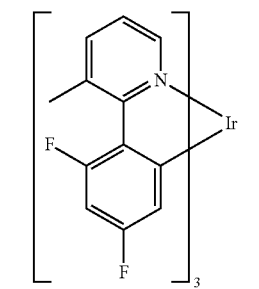
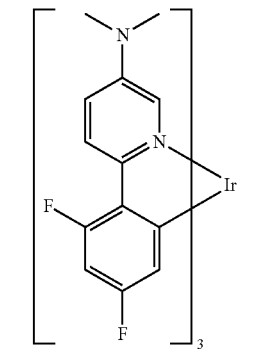
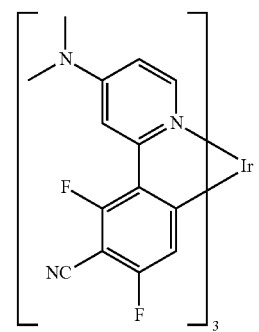
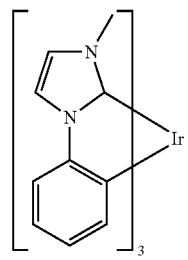
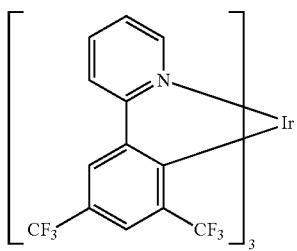
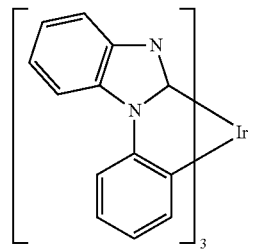
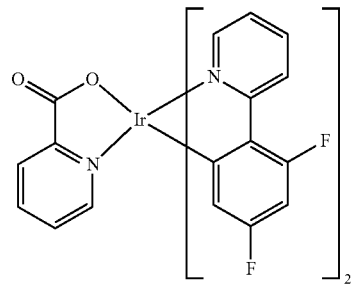
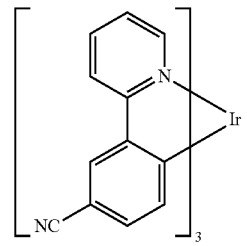
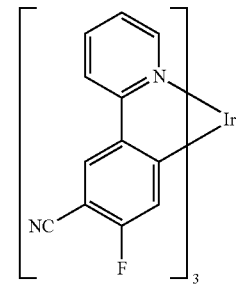

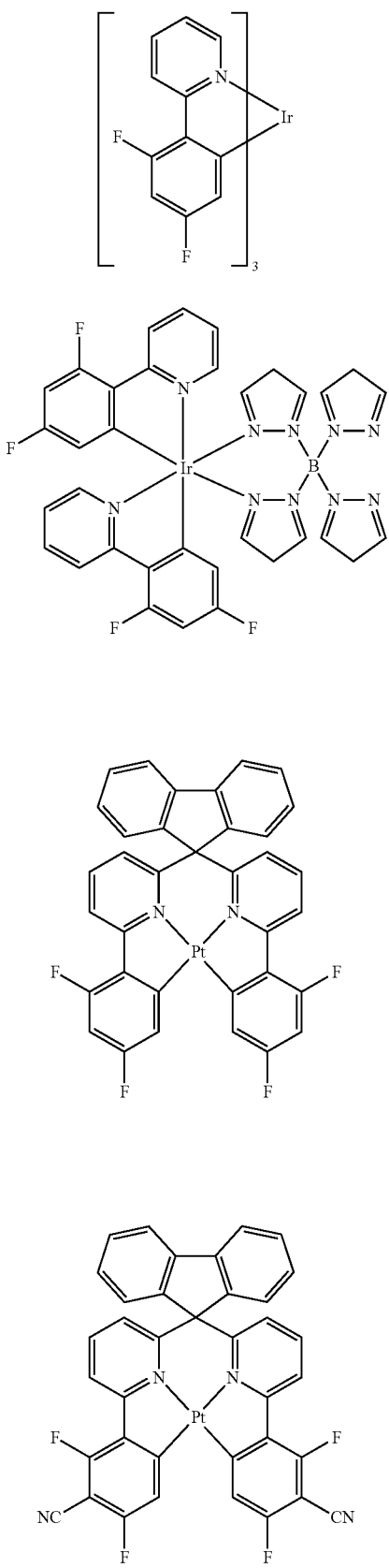
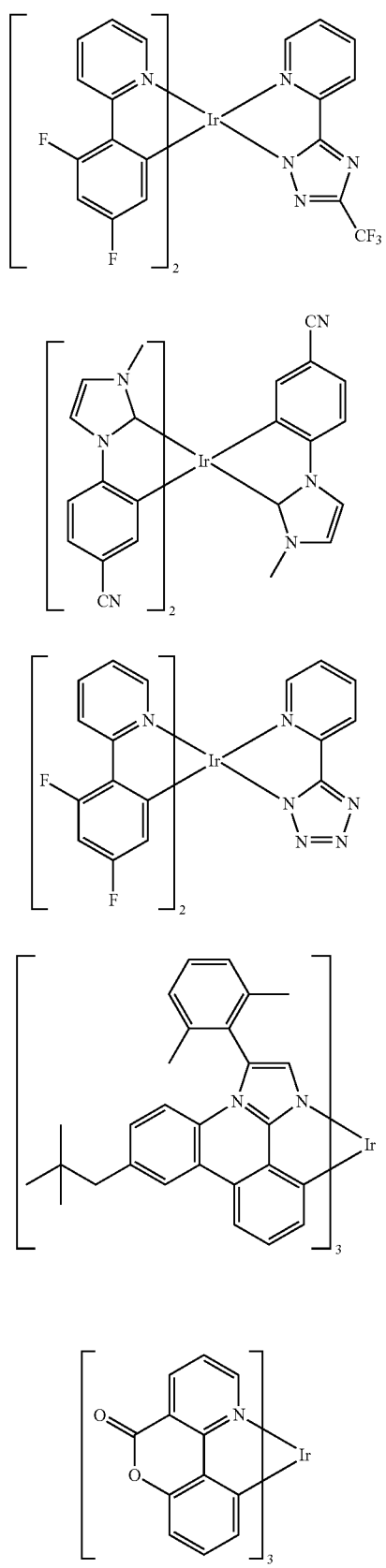

-continued

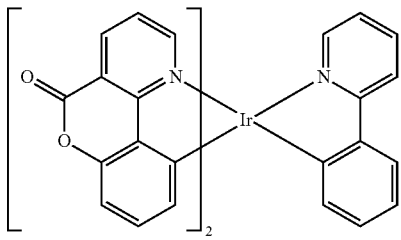

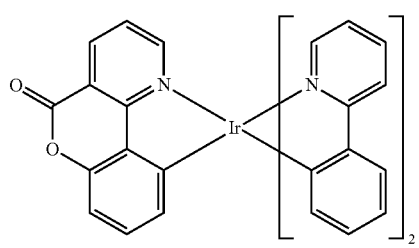

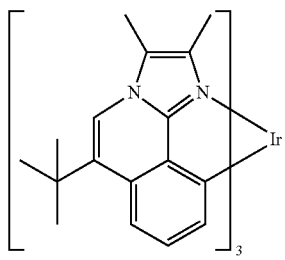

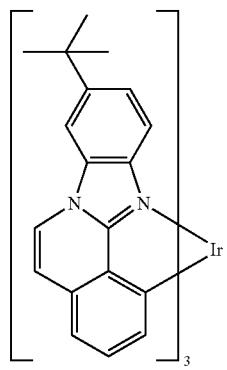

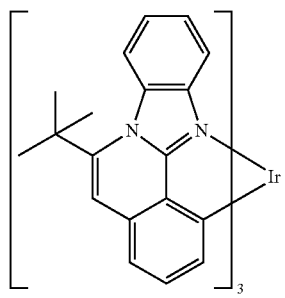

-continued

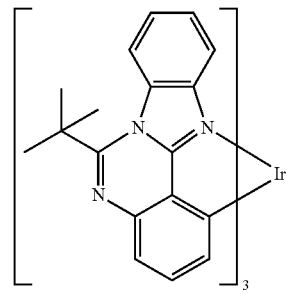

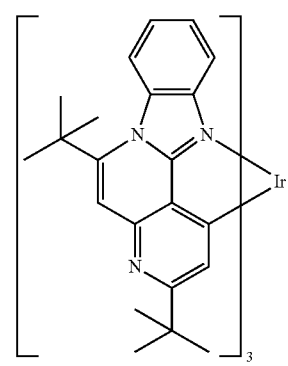

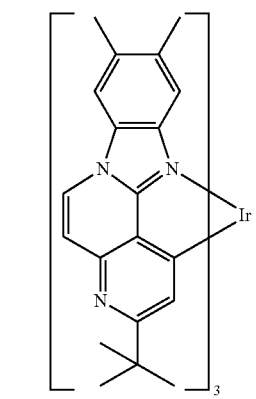

The above-described compound comprising structures of the formula (I) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs) and organic laser diodes (O-lasers), containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. An emitting layer comprises at least one emitting compound.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEC. In this case, the matrix material containing compound comprising structures of formula (I) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) or the preferred embodiments recited above and hereinafter are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapor deposition. For example, it is possible to apply an emitting layer comprising a compound of the invention comprising structures of formula (I) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) or the preferred embodiments recited above and hereinafter, especially as electron-conducting materials and/or as hole-conducting materials, have a very good lifetime.
2. Electronic devices, especially organic electroluminescent devices, comprising compounds, oligomers, polymers or dendrimers having structures of formula (I) or the preferred embodiments recited above and hereinafter, as electron-conducting materials and/or as hole-conducting materials, have an excellent efficiency. More particularly, efficiency is much higher compared to analogous compounds containing no structural unit of formula (I).
3. The compounds, oligomers, polymers or dendrimers of the invention having structures of formula (I) or the preferred embodiments recited above and hereinafter exhibit very high stability and lead to compounds having a very long lifetime.
4. With compounds, oligomers, polymers or dendrimers having structures of formula (I) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) or the preferred embodiments recited above and hereinafter in layers of electronic devices, especially organic electroluminescent devices, leads to a high mobility of the electron conductor structures and/or the hole conductor structures.
6. Compounds, oligomers, polymers or dendrimers having structures of formula (I) or the preferred embodiments recited above and hereinafter feature excellent thermal stability, and compounds having a molar mass of less than about 1200 g/mol have good sublimability.
7. Compounds, oligomers, polymers or dendrimers having structures of formula (I) or the preferred embodiments recited above and hereinafter have excellent glass film formation.
8. Compounds, oligomers, polymers or dendrimers having structures of formula (I) or the preferred embodiments recited above and hereinafter form very good films from solutions.
9. The compounds, oligomers, polymers or dendrimers comprising structures of formula (I) or the preferred embodiments recited above and hereinafter have a surprisingly high triplet level $T_1$, this being particularly true of compounds which are used as electron-conducting materials.

These abovementioned advantages are not accompanied by a deterioration in the further electronic properties.

The present invention further provides for the use of a compound of the invention and/or an oligomer, polymer or dendrimer of the invention in an electronic device as hole transport material, hole injection material, hole blocker material, electron injection material, electron blocker material and/or electron transport material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLE

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Preparation Examples a) 6,12-Dibromo-9H-9-azatribenz[b,d,f]azapine

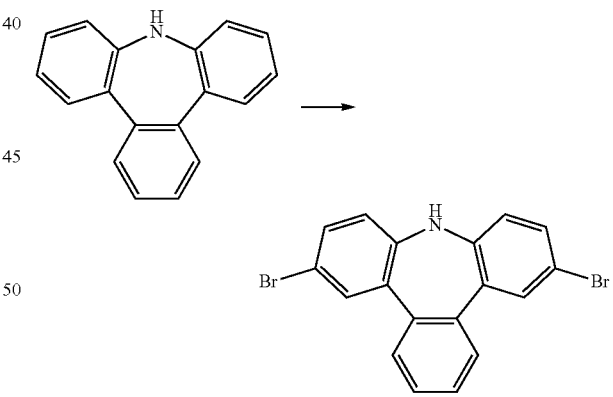

100 g (373.2 mmol) of 9H-tribenz[b,d,f]azapine are initially charged in 800 mL of DMF. Subsequently, 132.8 g (746.4 mmol) of NBS are added in portions and stirring is continued at this temperature for 4 h. Subsequently, 150 mL of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction. Yield: 122 g (295 mmol), 79% of theory, purity by $^1H$ NMR about 97%.

The following compounds are prepared in an analogous manner:

| | Reactant 1 | Product | Yield |
|---|---|---|---|
| a1 | 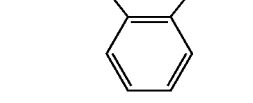 [163811-01-6] | 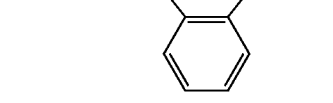 | 78% |
| a2 | 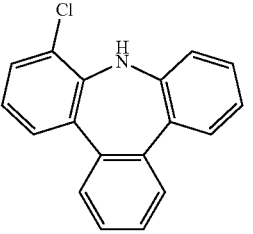 [163811-00-5] | 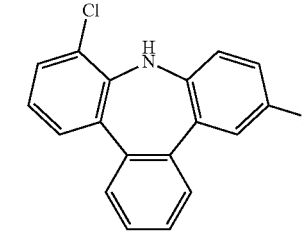 | 77% |
| a3 | 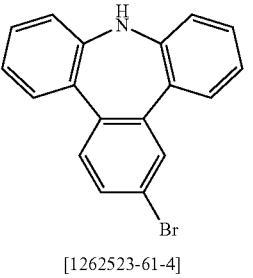 [1262523-61-4] | 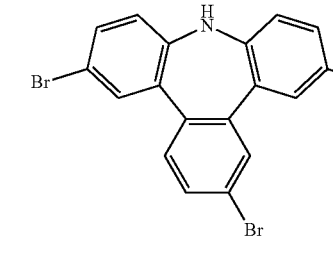 | 84% |
| a4 | 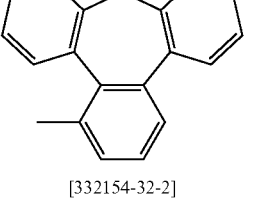 [332154-32-2] | 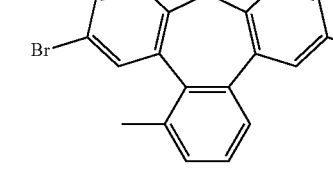 | 83% |
| a5 | 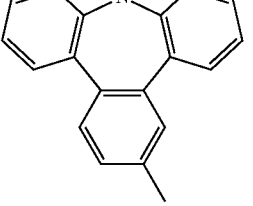 [204200-14-6] | 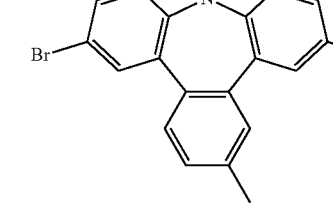 | 80% |

101 b) 6,12-Bis-(9,9-dimethyl-9H-fluoren-4-yl)-9H-9-azatribenzo[a,c,e]cycloheptene

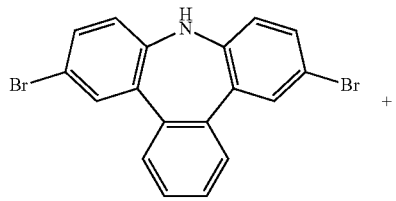

+

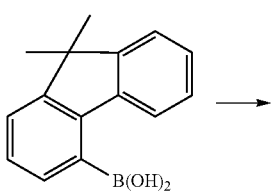

→

102

-continued

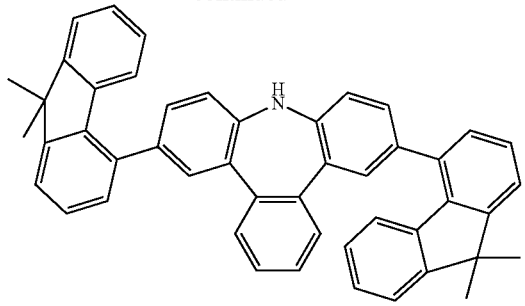

70.0 g (168 mmol) of 6,12-dibromo-9H-9-azatribenz[b,d,f]azapine, 71 g (343 mmol) of 9,9'-dimethylfluorene-4-boronic acid and 6.8 g (71 mmol) of $K_2CO_3$ are suspended in 200 mL of toluene, 250 mL of 1,4-dioxane and 150 mL of water. To this suspension are added 9.6 g (8.3 mmol) of tetrakis(triphenylphosphine)palladium(0). The reaction mixture is heated under reflux for 16 h. After cooling, the organic phase is removed, washed three times with 100 mL of water and then concentrated to dryness. The residue is subjected to hot extraction with toluene, recrystallized from toluene and finally sublimed under high vacuum. The yield is 61 g (98 mmol), 57% of theory, purity by $^1$H NMR about 98%.

The following compounds are prepared in an analogous manner:

| | Reactant 1 | Reactant 2 |
|---|---|---|
| b1 | ![structure] | ![structure] [1449431-83-7] |
| b2 | ![structure] | ![structure] [162607-19-4] |
| b3 | ![structure] | ![structure] [402936-15-6] |

| | 103 | 104 |
|---|---|---|
| b4 | 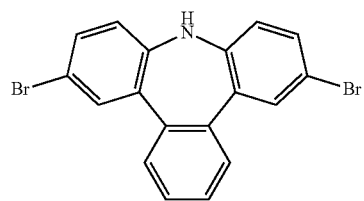 [SMILES: Clc1ccc2c(c1)-c1ccccc1-c1cc(Br)ccc1N2] | 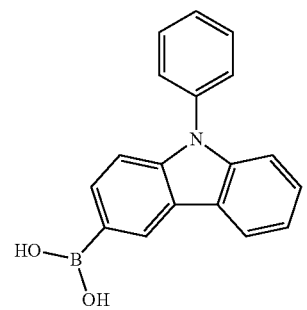<br>[854952-58-2] |
| b5 | 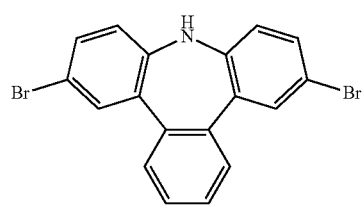 [SMILES: Clc1ccc2c(c1)-c1ccccc1-c1cc(Br)ccc1N2] | 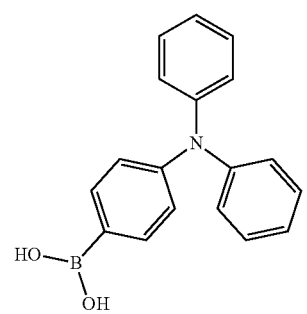<br>[201802-67-7] |
| b6 | 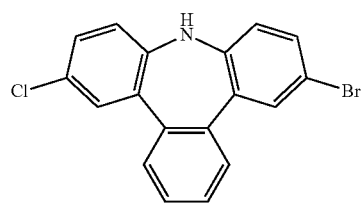 | 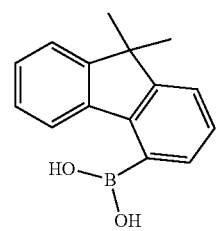<br>[1246022-50-3] |
| b7 | 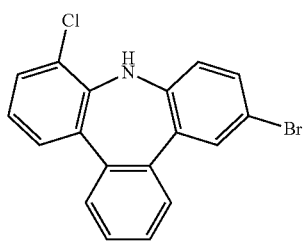 [SMILES: Clc1cccc2c1Nc1ccc(Br)cc1-c1ccccc1-2] | 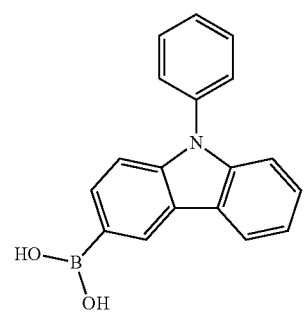<br>[854952-58-2] |
| b8 | 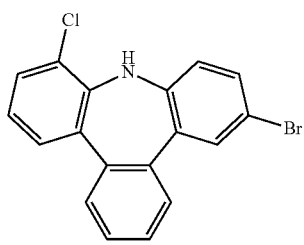 [SMILES: Clc1cccc2c1Nc1ccc(Br)cc1-c1ccccc1-2] | 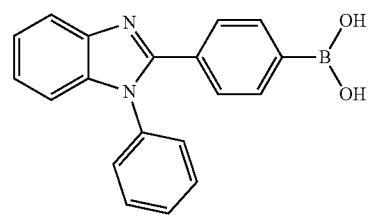<br>[952514-79-3] |

-continued
| | | | |
|---|---|---|---|
| b9 | 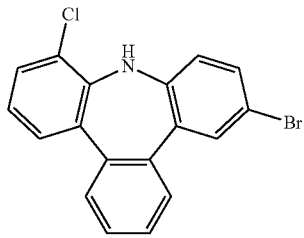 [SMILES: Clc1cccc2c1Nc1ccc(Br)cc1-c1ccccc1-2] | 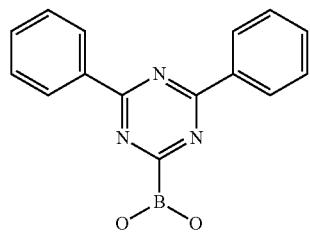[1251825-65-6] | |
| b10 | 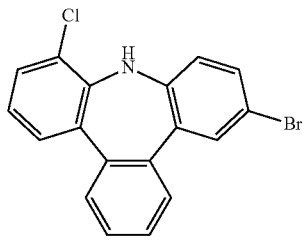 [SMILES: Clc1cccc2c1Nc1ccc(Br)cc1-c1ccccc1-2] | 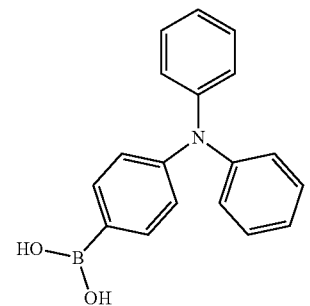[201802-67-7] | |
| b11 | 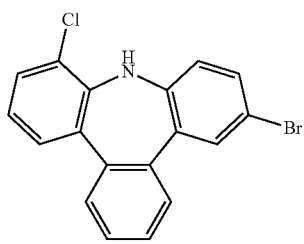 [SMILES: Clc1cccc2c1Nc1ccc(Br)cc1-c1ccccc1-2] | 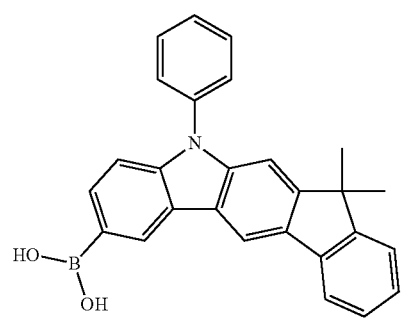[1376505-25-7] | |
| b12 | 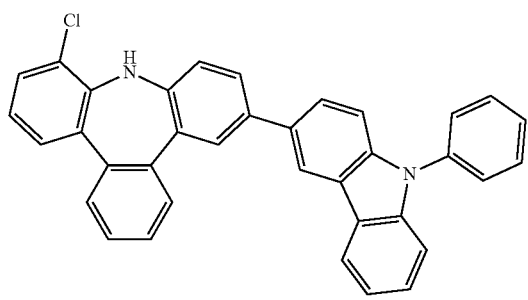 [SMILES: Clc1cccc2c1Nc1ccc(-c3ccc4c(c3)c3ccccc3n4-c3ccccc3)cc1-c1ccccc1-2] | 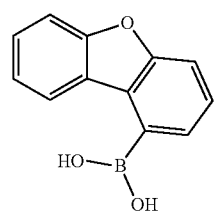[162607-19-4] | |
| b13 | 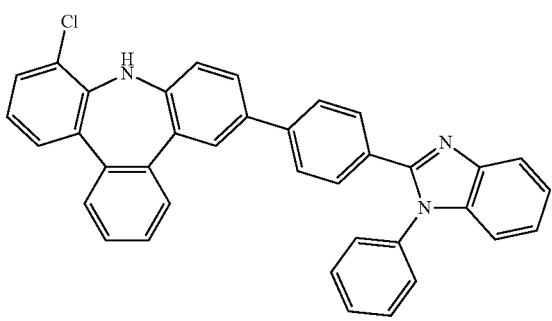 [SMILES: Clc1cccc2c1Nc1ccc(-c3ccc(-c4nc5ccccc5n4-c4ccccc4)cc3)cc1-c1ccccc1-2] | 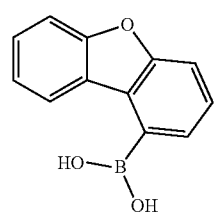[162607-19-4] | |

-continued
| | | |
|---|---|---|
| b14 | 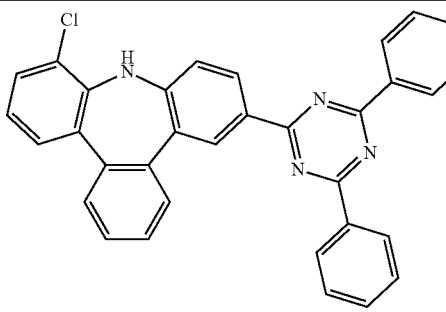 | 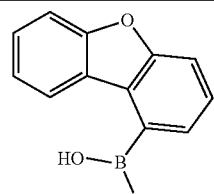
[162607-19-4] |
| b15 | 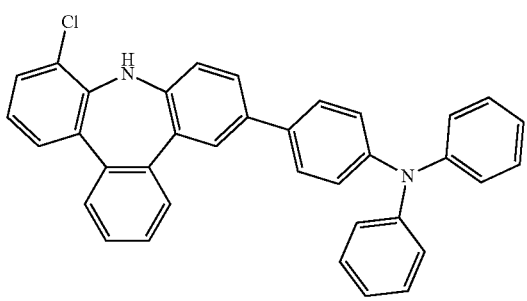 [SMILES: Clc1cccc2c1Nc1ccc(-c3ccc(N(c4ccccc4)c4ccccc4)cc3)cc1-c1ccccc1-2] | 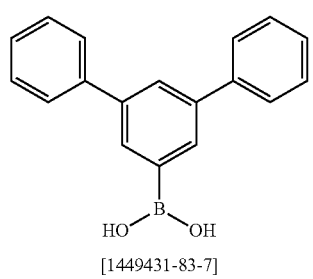 [SMILES: OB(O)c1cc(-c2ccccc2)cc(-c2ccccc2)c1]
[1449431-83-7] |
| b16 | 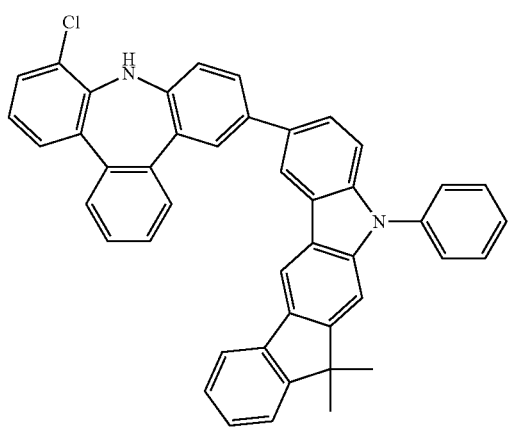 [SMILES: CC1(C)c2ccccc2-c2cc3c4cc(-c5ccc6c(c5)-c5ccccc5-c5cccc(Cl)c5N6)ccc4n(-c4ccccc4)c3cc21] | 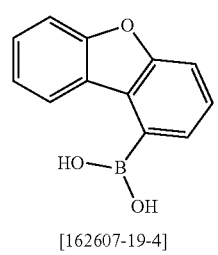 [SMILES: OB(O)c1cccc2oc3ccccc3c12]
[162607-19-4] |
| b18 | 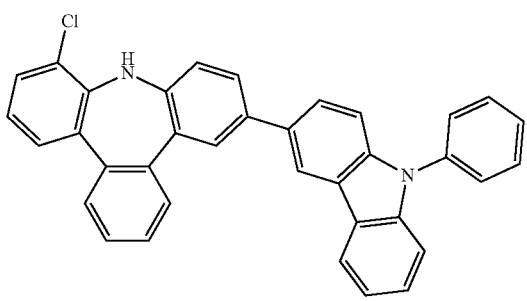 [SMILES: Clc1cccc2c1Nc1ccc(-c3ccc4c(c3)c3ccccc3n4-c3ccccc3)cc1-c1ccccc1-2] | 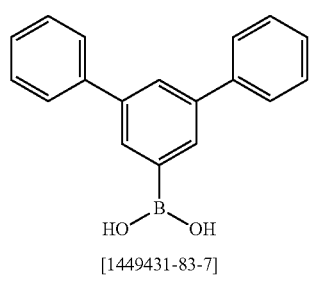 [SMILES: OB(O)c1cc(-c2ccccc2)cc(-c2ccccc2)c1]
[1449431-83-7] |
| b19 | 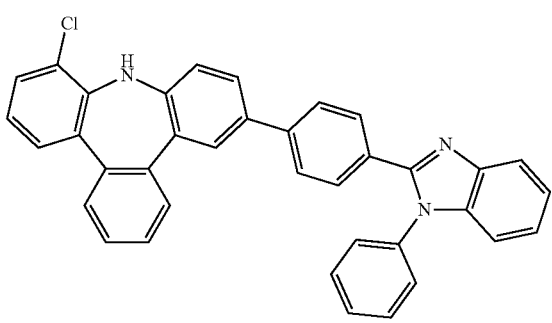 [SMILES: Clc1cccc2c1Nc1ccc(-c3ccc(-c4nc5ccccc5n4-c4ccccc4)cc3)cc1-c1ccccc1-2] | 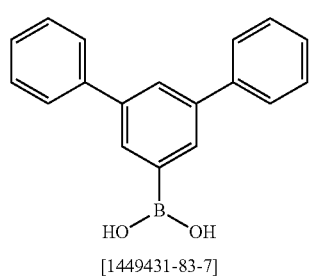 [SMILES: OB(O)c1cc(-c2ccccc2)cc(-c2ccccc2)c1]
[1449431-83-7] |

| | | |
|---|---|---|
| b20 | 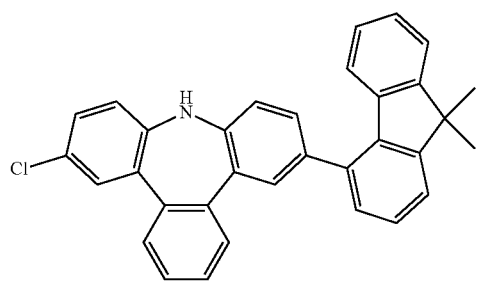 [SMILES: CC1(C)c2ccccc2-c2c(-c3ccc4c(c3)-c3ccccc3-c3cc(Cl)ccc3N4)cccc21] | 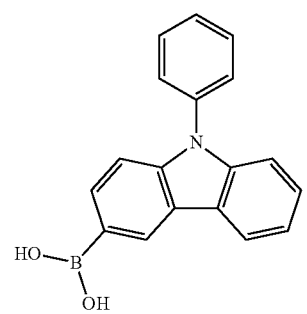<br>[854952-58-2] |
| b21 | 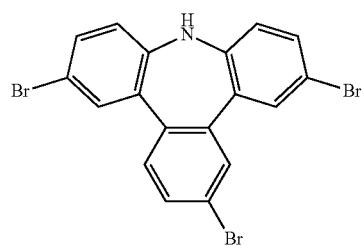 [SMILES: Brc1ccc2c(c1)-c1ccc(Br)cc1-c1cc(Br)ccc1N2] | 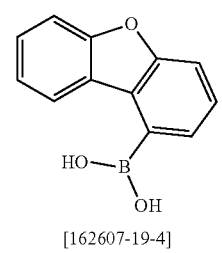 [SMILES: OB(O)c1cccc2oc3ccccc3c12]<br>[162607-19-4] |
| b22 | 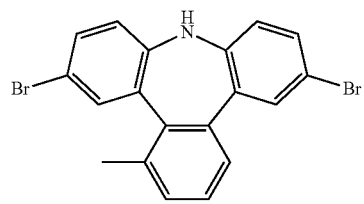 | 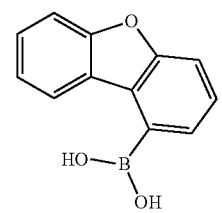<br>[162607-19-4] |
| b23 | 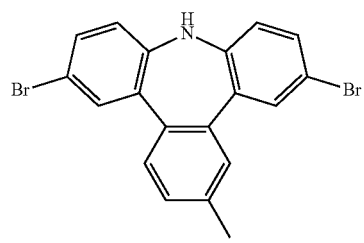 [SMILES: Cc1ccc2c(c1)-c1cc(Br)ccc1Nc1ccc(Br)cc1-2] | 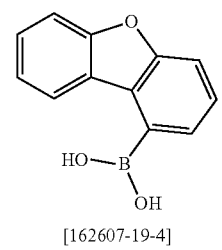 [SMILES: OB(O)c1cccc2oc3ccccc3c12]<br>[162607-19-4] |
| b24 | 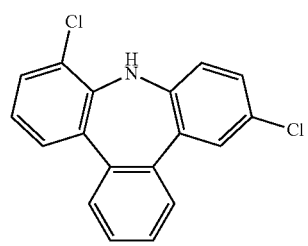<br>[163811-03-8] | 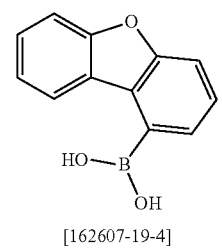 [SMILES: OB(O)c1cccc2oc3ccccc3c12]<br>[162607-19-4] |

| 111 | 112 |
|---|---|
| b25 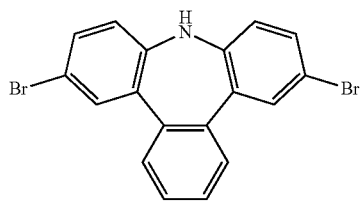 [SMILES: Clc1ccc2c(c1)-c1ccccc1-c1cc(Br)ccc1N2] | 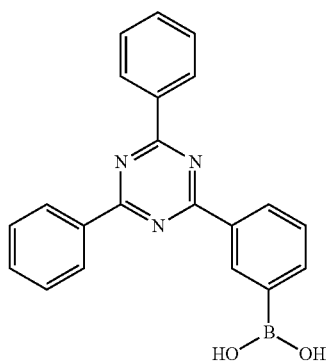 [1269508-31-7] |
| b26 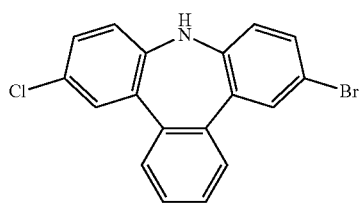 | 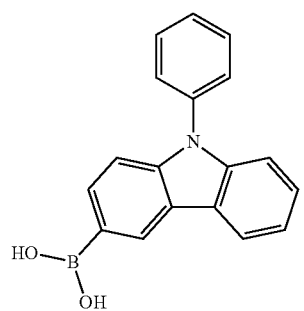 [854952-58-2] |
| b27 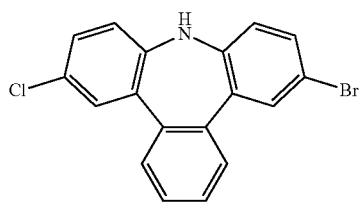 [SMILES: Clc1ccc2c(c1)-c1ccccc1-c1cc(Br)ccc1N2] | 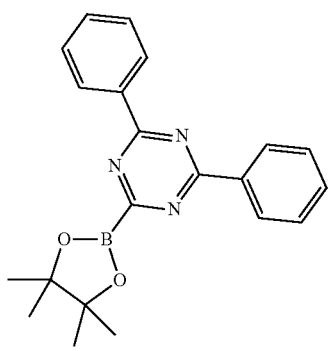 [1345345-08-5] |
| b28 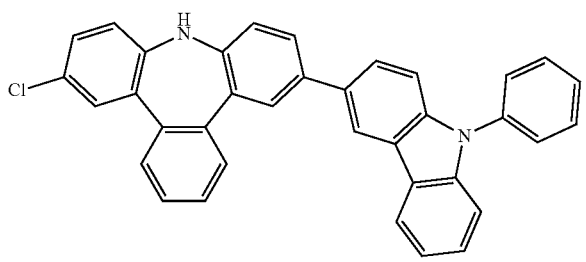 [SMILES: Clc1ccc2c(c1)-c1ccccc1-c1cc(-c3ccc4c(c3)c3ccccc3n4-c3ccccc3)ccc1N2] | 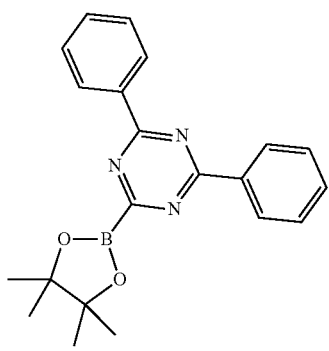 [1345345-08-5] |

-continued

| | Product | Yield |
|---|---|---|
| b1 | | 64% |
| b2 | | 78% |
| b3 | | 63% |
| b4 | | 78% |
| b5 | | 69% |

-continued
| | | |
|---|---|---|
| b6 | 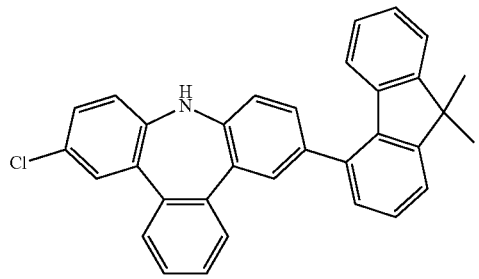 [SMILES: CC1(C)c2ccccc2-c2c(-c3ccc4c(c3)-c3ccccc3-c3cc(Cl)ccc3N4)cccc21] | 61% |
| b7 | 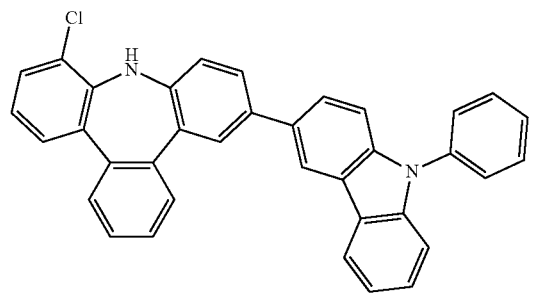 [SMILES: Clc1cccc2c1Nc1ccc(-c3ccc4c(c3)c3ccccc3n4-c3ccccc3)cc1-c1ccccc1-2] | 62% |
| b8 | 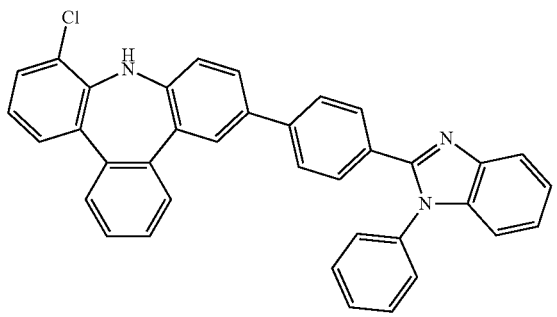 [SMILES: Clc1cccc2c1Nc1ccc(-c3ccc(-c4nc5ccccc5n4-c4ccccc4)cc3)cc1-c1ccccc1-2] | 58% |
| b9 | 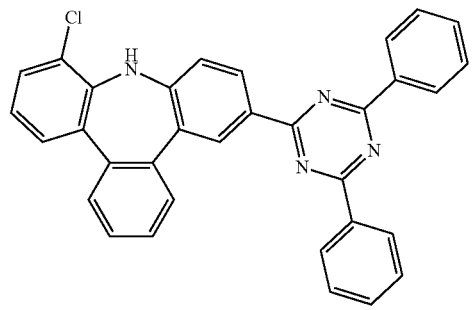 [SMILES: Clc1cccc2c1Nc1ccc(-c3nc(-c4ccccc4)nc(-c4ccccc4)n3)cc1-c1ccccc1-2] | 54% |
| b10 | 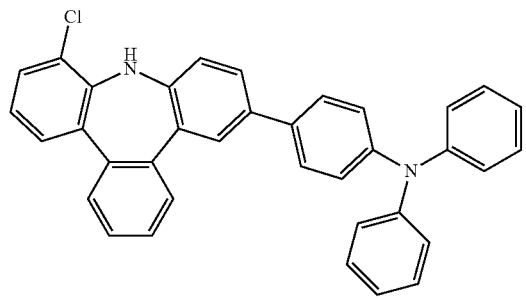 [SMILES: Clc1cccc2c1Nc1ccc(-c3ccc(N(c4ccccc4)c4ccccc4)cc3)cc1-c1ccccc1-2] | 59% |

| | | |
|---|---|---|
| b11 | 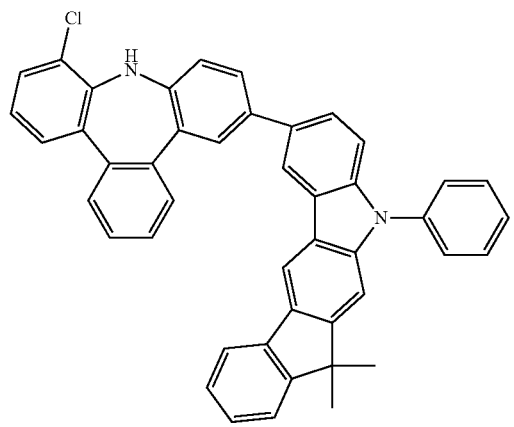 [SMILES: CC1(C)c2ccccc2-c2cc3c4cc(-c5ccc6c(c5)-c5ccccc5-c5cccc(Cl)c5N6)ccc4n(-c4ccccc4)c3cc21] | 62% |
| b12 | 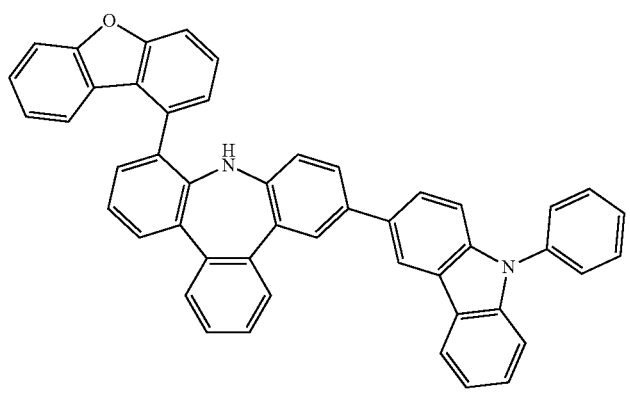 [SMILES: c1ccc(-n2c3ccccc3c3cc(-c4ccc5c(c4)-c4ccccc4-c4cccc(-c6cccc7oc8ccccc8c67)c4N5)ccc32)cc1] | 60% |
| b13 | 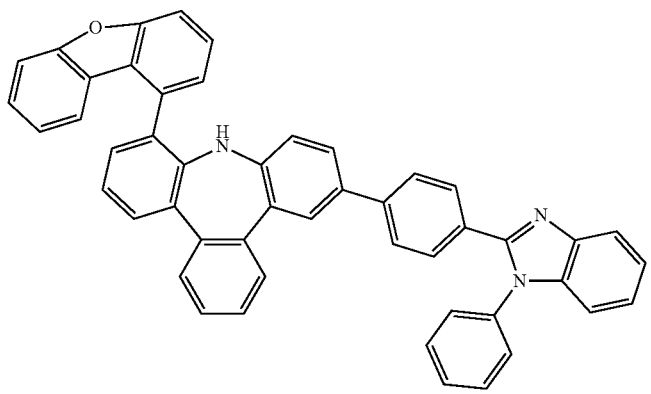 [SMILES: c1ccc(-n2c(-c3ccc(-c4ccc5c(c4)-c4ccccc4-c4cccc(-c6cccc7oc8ccccc8c67)c4N5)cc3)nc3ccccc32)cc1] | 81% |
| b14 | 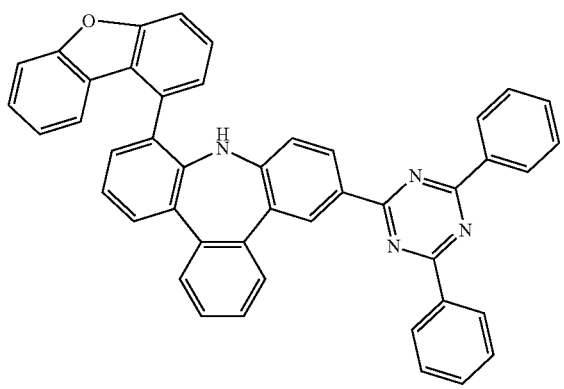 [SMILES: c1ccc(-c2nc(-c3ccccc3)nc(-c3ccc4c(c3)-c3ccccc3-c3cccc(-c5cccc6oc7ccccc7c56)c3N4)n2)cc1] | 89% |

| | | |
|---|---|---|
| b15 | 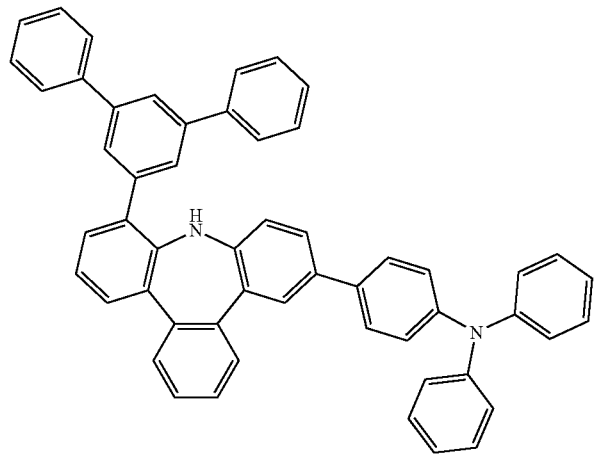 [SMILES: c1ccc(-c2cc(-c3ccccc3)cc(-c3cccc4c3Nc3ccc(-c5ccc(N(c6ccccc6)c6ccccc6)cc5)cc3-c3ccccc3-4)c2)cc1] | 87% |
| b16 | 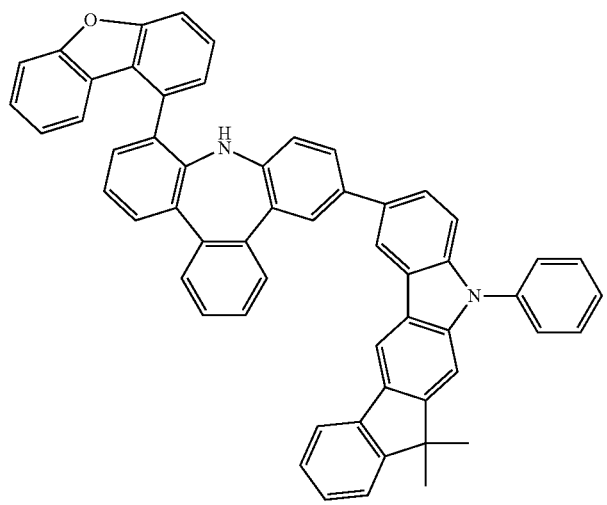 [SMILES: CC1(C)c2ccccc2-c2cc3c4cc(-c5ccc6c(c5)-c5ccccc5-c5cccc(-c7cccc8oc9ccccc9c78)c5N6)ccc4n(-c4ccccc4)c3cc21] | 88% |
| b18 | 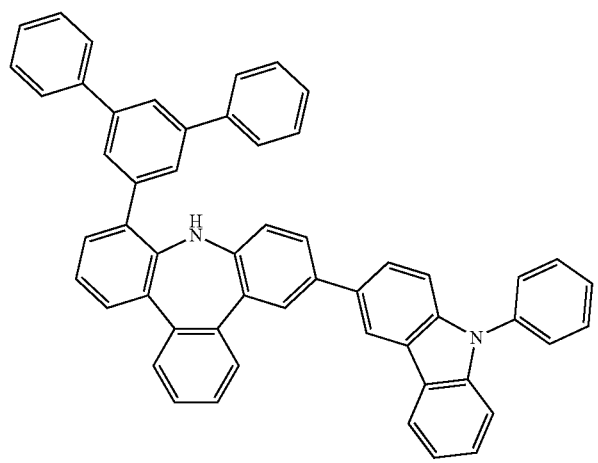 [SMILES: c1ccc(-c2cc(-c3ccccc3)cc(-c3cccc4c3Nc3ccc(-c5ccc6c(c5)c5ccccc5n6-c5ccccc5)cc3-c3ccccc3-4)c2)cc1] | 86% |

| b19 | 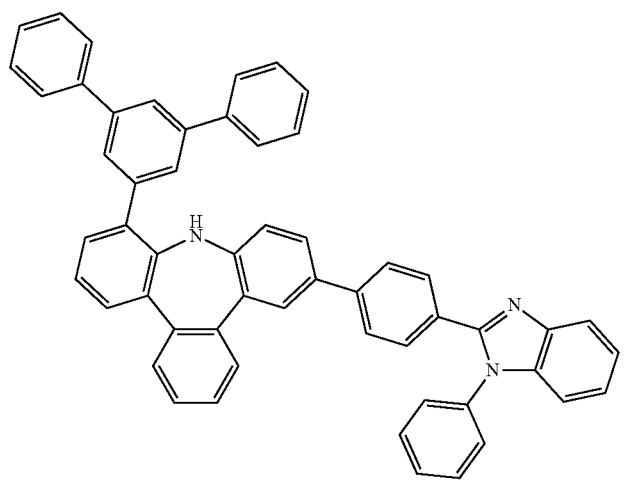 [SMILES: c1ccc(-c2cc(-c3ccccc3)cc(-c3cccc4c3Nc3ccc(-c5ccc(-c6nc7ccccc7n6-c6ccccc6)cc5)cc3-c3ccccc3-4)c2)cc1] | 78% |
| b20 | 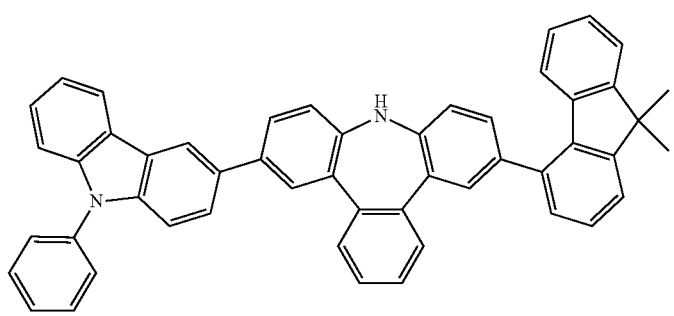 [SMILES: CC1(C)c2ccccc2-c2c(-c3ccc4c(c3)-c3ccccc3-c3cc(-c5ccc6c(c5)c5ccccc5n6-c5ccccc5)ccc3N4)cccc21] | 89% |
| b21 | 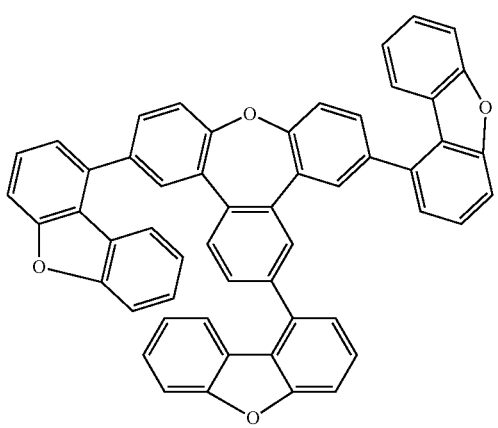 [SMILES: c1ccc2c(c1)oc1cccc(-c3ccc4c(c3)-c3ccc(-c5cccc6oc7ccccc7c56)cc3-c3cc(-c5cccc6oc7ccccc7c56)ccc3O4)c12] | 78% |
| b22 | 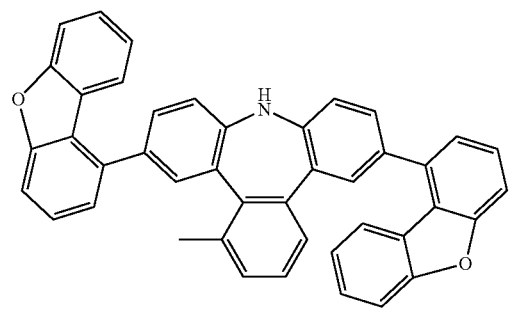 [SMILES: Cc1cccc2c1-c1cc(-c3cccc4oc5ccccc5c34)ccc1Nc1ccc(-c3cccc4oc5ccccc5c34)cc1-2] | 74% |

| | | |
|---|---|---|
| b23 | 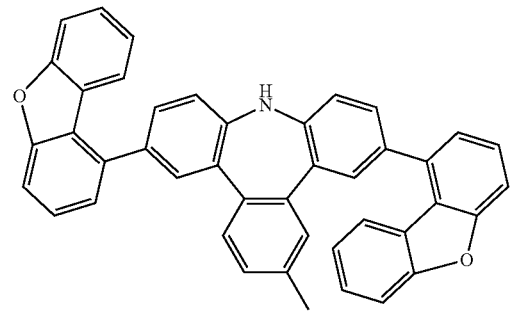 [SMILES: Cc1ccc2c(c1)-c1cc(-c3cccc4oc5ccccc5c34)ccc1Nc1ccc(-c3cccc4oc5ccccc5c34)cc1-2] | 73% |
| b24 | 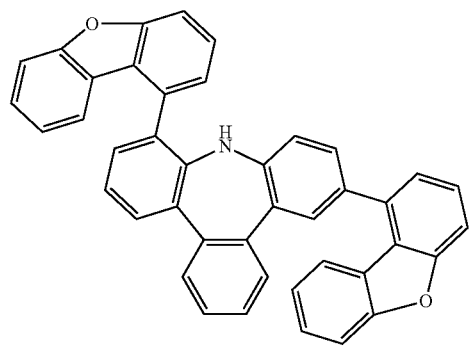 [SMILES: c1ccc2c(c1)-c1cc(-c3cccc4oc5ccccc5c34)ccc1Nc1c-2cccc1-c1cccc2oc3ccccc3c12] | 78% |
| b25 | 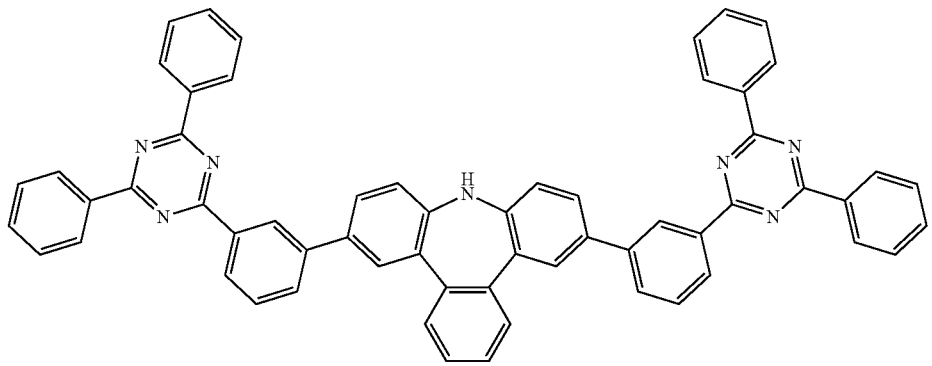 [SMILES: c1ccc(-c2nc(-c3ccccc3)nc(-c3cccc(-c4ccc5c(c4)-c4ccccc4-c4cc(-c6cccc(-c7nc(-c8ccccc8)nc(-c8ccccc8)n7)c6)ccc4N5)c3)n2)cc1] | 67% |
| b26 | 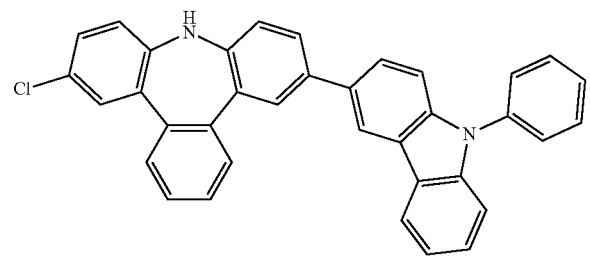 [SMILES: Clc1ccc2c(c1)-c1ccccc1-c1cc(-c3ccc4c(c3)c3ccccc3n4-c3ccccc3)ccc1N2] | 60% |
| b27 | 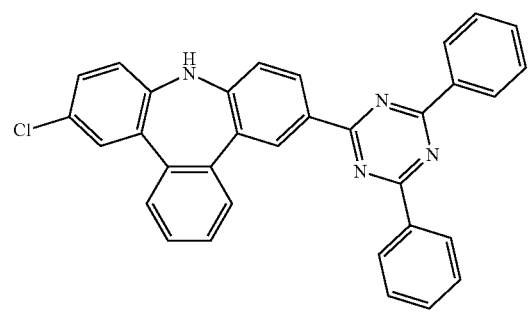 [SMILES: Clc1ccc2c(c1)-c1ccccc1-c1cc(-c3nc(-c4ccccc4)nc(-c4ccccc4)n3)ccc1N2] | 58% |

| b28 | 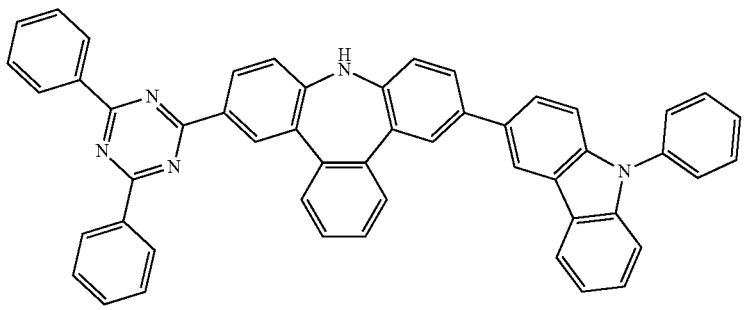 [SMILES: c1ccc(-c2nc(-c3ccccc3)nc(-c3ccc4c(c3)-c3ccccc3-c3cc(-c5ccc6c(c5)c5ccccc5n6-c5ccccc5)ccc3N4)n2)cc1] | 69% |

Synthesis of 6-carbazol-9-yl-12-(4,6-diphenyl[1,3,5]triazin-2-yl)-9H-9-azatribenzo[a,c,e]cycloheptene

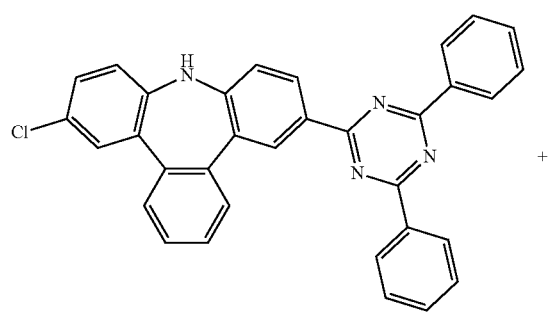

To 80 g (159.5 mmol) of 6-chloro-12-(4,6-diphenyl-[1,3,5]triazin-2-yl)-9H-9-azatribenzo[a,c,e]cycloheptene in 150 mL of di-n-butyl ether are added 67.7 g (145 mmol) of carbazole, and the solution is degassed. Subsequently added to the mixture are 10 g (0.158 mmol) of copper powder, 1.38 g (0.007 mmol) of copper iodide and 22 g (159.6 mmol) of K₂CO₃, and the mixture is stirred under protective gas at 144° C. for 4 days. The organic phase is dried over MgSO₄ and the solvent is removed under reduced pressure.

Yield: 32 g (50 mmol), 40% of theory.

c) 9-(2-Chlorophenyl)-6,12-bis-(9,9-dimethyl-9H-fluoren-4-yl)-9H-9-azatribenzo[a,c,e]cycloheptene

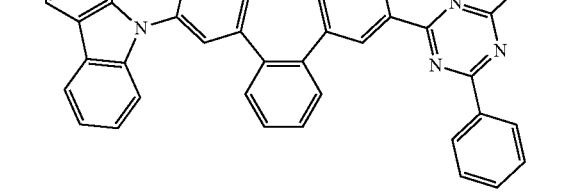

Under protective gas, 43.9 g (70 mmol) of 6,12-bis-(9,9-dimethyl-9H-fluoren-4-yl)-9H-9-azatribenzo[a,c,e]cycloheptene and 14 g (73 mmol) of 1-bromo-2-chlorobenzene, 8 g (84 mmol) of sodium tert-butoxide, 3.5 mL of tris-tert-butylphosphine (1 M in toluene) and 0.393 mg (1.7 mmol) palladium acetate are suspended in 300 mL of p-xylene. The reaction mixture is heated under reflux at 110° C. for 12 h. After cooling, the organic phase is removed, washed three times with 200 mL of water and then concentrated to dryness. The product is purified via column chromatography on silica gel with toluene/heptane (1:2). The yield is 45 g (61.6 mmol), 88% of theory, purity by ¹H NMR about 94%.

In an analogous manner, it is possible to obtain the following compounds

| Example | Reactant 1 | Reactant 2 |
|---|---|---|
| c1 | 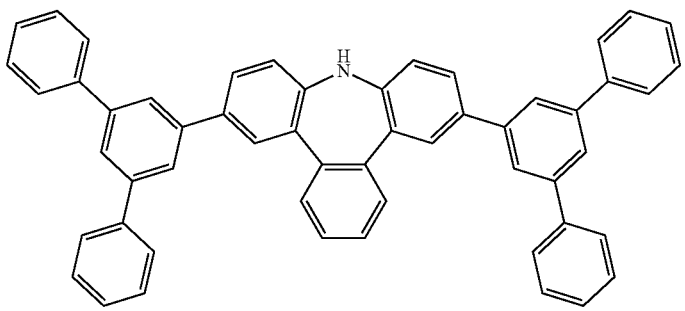 [SMILES: c1ccc(-c2cc(-c3ccccc3)cc(-c3ccc4c(c3)-c3ccccc3-c3cc(-c5cc(-c6ccccc6)cc(-c6ccccc6)c5)ccc3N4)c2)cc1] | 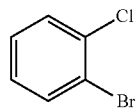 |
| c2 | 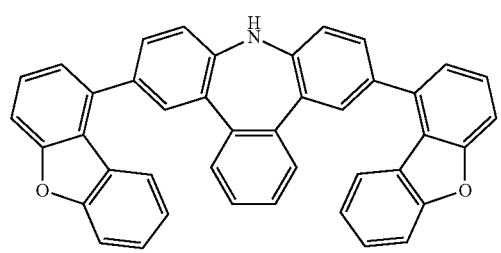 [SMILES: c1ccc2c(c1)-c1cc(-c3cccc4oc5ccccc5c34)ccc1Nc1ccc(-c3cccc4oc5ccccc5c34)cc1-2] | 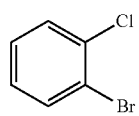 |
| c3 | 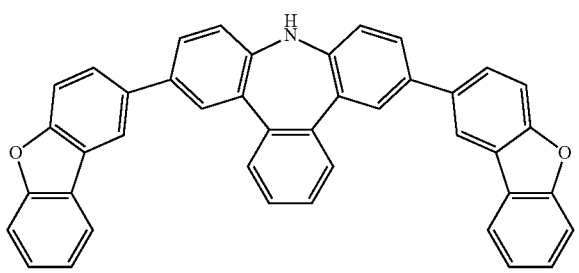 [SMILES: c1ccc2c(c1)-c1cc(-c3ccc4oc5ccccc5c4c3)ccc1Nc1ccc(-c3ccc4oc5ccccc5c4c3)cc1-2] | 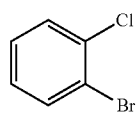 |
| c4 | 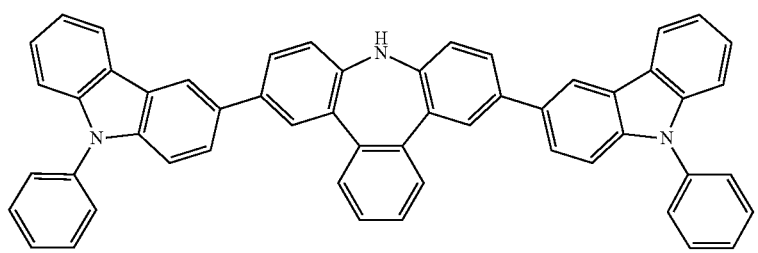 [SMILES: c1ccc(-n2c3ccccc3c3cc(-c4ccc5c(c4)-c4ccccc4-c4cc(-c6ccc7c(c6)c6ccccc6n7-c6ccccc6)ccc4N5)ccc32)cc1] | 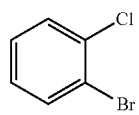 |
| c5 | 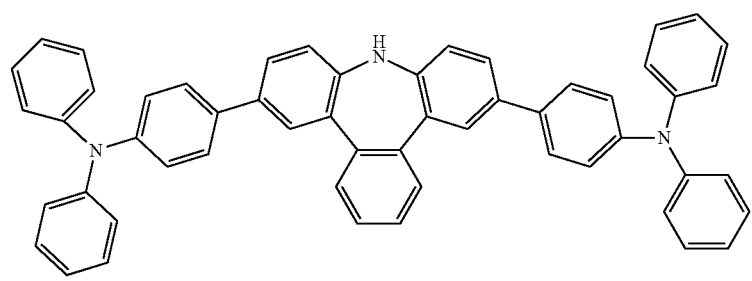 [SMILES: c1ccc(N(c2ccccc2)c2ccc(-c3ccc4c(c3)-c3ccccc3-c3cc(-c5ccc(N(c6ccccc6)c6ccccc6)cc5)ccc3N4)cc2)cc1] | 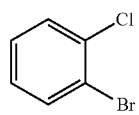 |

-continued
| c6 | 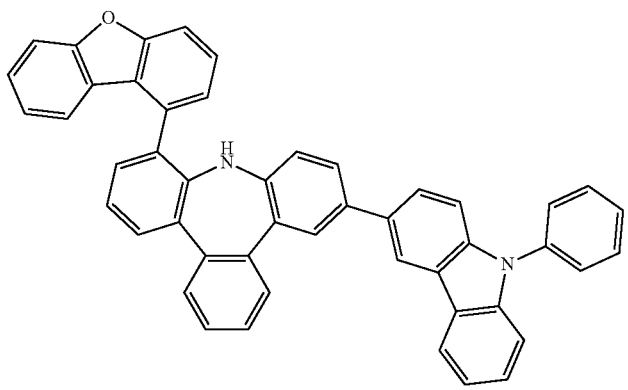 [SMILES: c1ccc(-n2c3ccccc3c3cc(-c4ccc5c(c4)-c4ccccc4-c4cccc(-c6cccc7oc8ccccc8c67)c4N5)ccc32)cc1] | 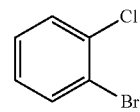 |
| c7 | 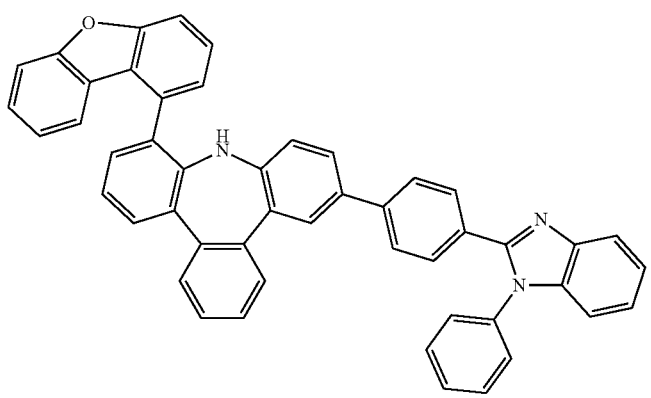 [SMILES: c1ccc(-n2c(-c3ccc(-c4ccc5c(c4)-c4ccccc4-c4cccc(-c6cccc7oc8ccccc8c67)c4N5)cc3)nc3ccccc32)cc1] | 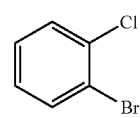 |
| c8 | 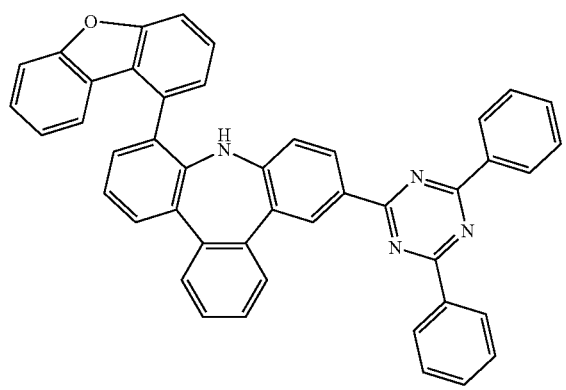 [SMILES: c1ccc(-c2nc(-c3ccccc3)nc(-c3ccc4c(c3)-c3ccccc3-c3cccc(-c5cccc6oc7ccccc7c56)c3N4)n2)cc1] | 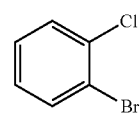 |
| c9 | 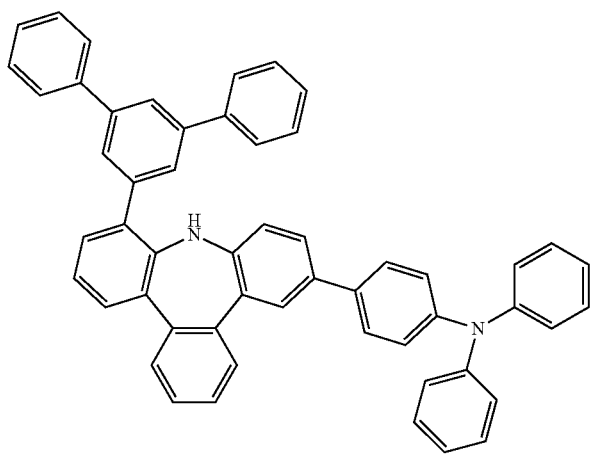 [SMILES: c1ccc(-c2cc(-c3ccccc3)cc(-c3cccc4c3Nc3ccc(-c5ccc(N(c6ccccc6)c6ccccc6)cc5)cc3-c3ccccc3-4)c2)cc1] | 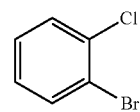 |

| | | |
|---|---|---|
| c10 | 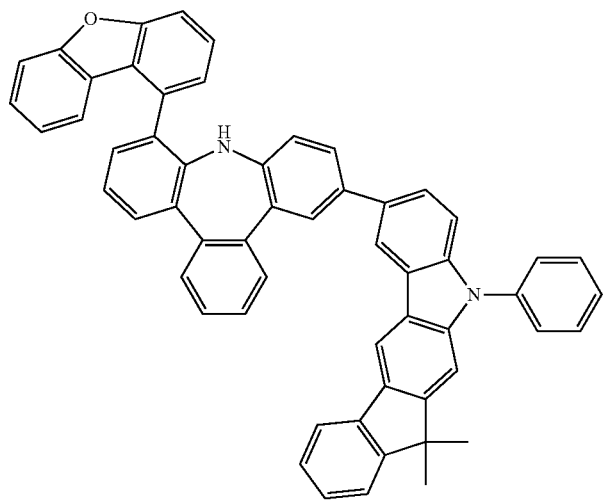 [SMILES: CC1(C)c2ccccc2-c2cc3c4cc(-c5ccc6c(c5)-c5ccccc5-c5cccc(-c7cccc8oc9ccccc9c78)c5N6)ccc4n(-c4ccccc4)c3cc21] | 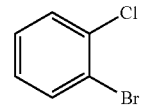 |
| c11 | 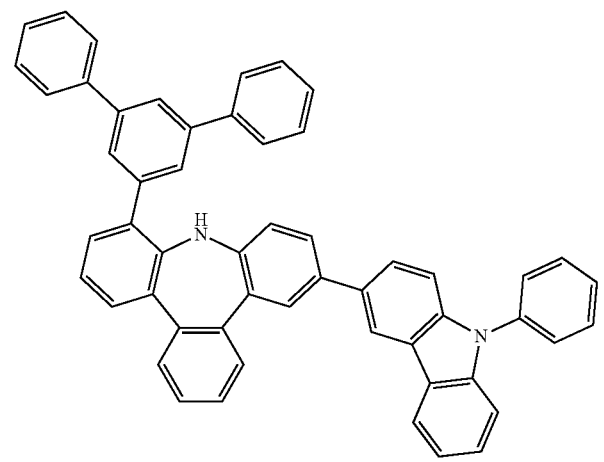 [SMILES: c1ccc(-c2cc(-c3ccccc3)cc(-c3cccc4c3Nc3ccc(-c5ccc6c(c5)c5ccccc5n6-c5ccccc5)cc3-c3ccccc3-4)c2)cc1] | 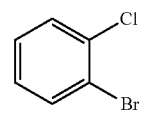 |
| c12 | 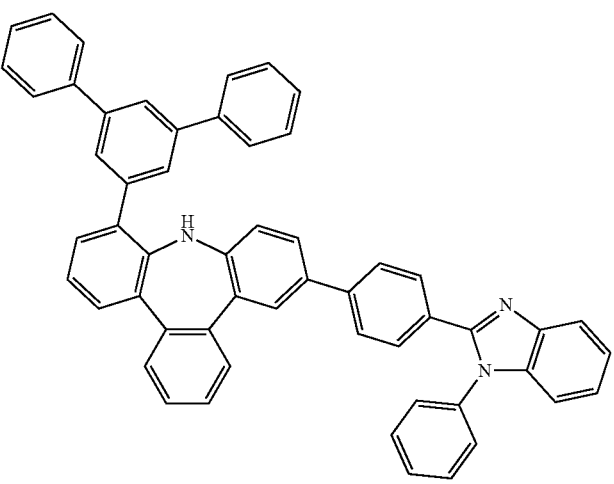 [SMILES: c1ccc(-c2cc(-c3ccccc3)cc(-c3cccc4c3Nc3ccc(-c5ccc(-c6nc7ccccc7n6-c6ccccc6)cc5)cc3-c3ccccc3-4)c2)cc1] | 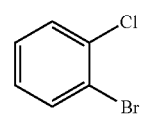 |

-continued
| | | |
|---|---|---|
| c13 | 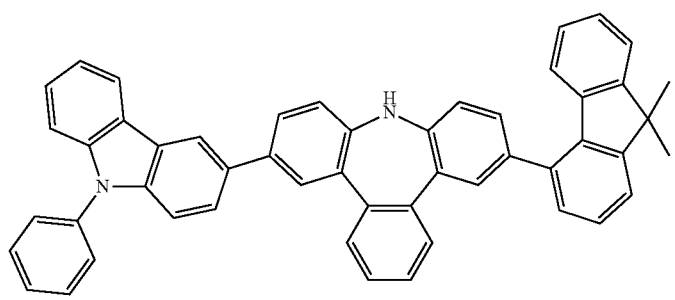 [SMILES: CC1(C)c2ccccc2-c2c(-c3ccc4c(c3)-c3ccccc3-c3cc(-c5ccc6c(c5)c5ccccc5n6-c5ccccc5)ccc3N4)cccc21] | 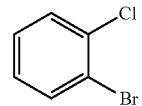 |
| c14 | 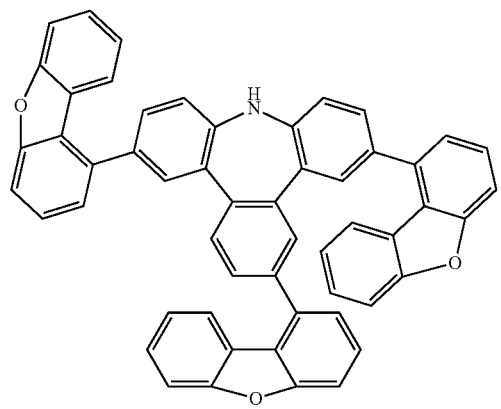 [SMILES: c1ccc2c(c1)oc1cccc(-c3ccc4c(c3)-c3ccc(-c5cccc6oc7ccccc7c56)cc3-c3cc(-c5cccc6oc7ccccc7c56)ccc3N4)c12] | 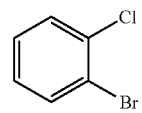 |
| c15 | 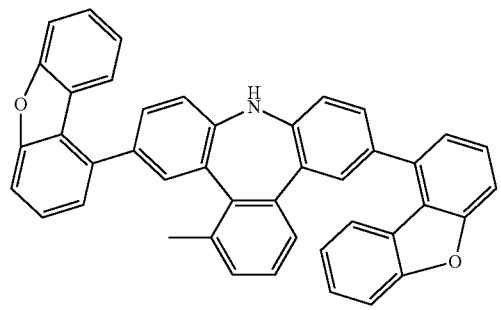 [SMILES: Cc1cccc2c1-c1cc(-c3cccc4oc5ccccc5c34)ccc1Nc1ccc(-c3cccc4oc5ccccc5c34)cc1-2] | 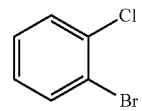 |
| c16 | 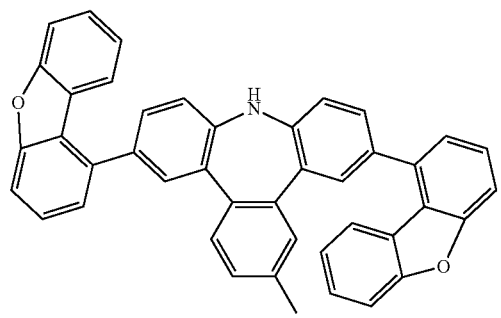 [SMILES: Cc1ccc2c(c1)-c1cc(-c3cccc4oc5ccccc5c34)ccc1Nc1ccc(-c3cccc4oc5ccccc5c34)cc1-2] | 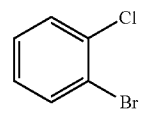 |

-continued
C17 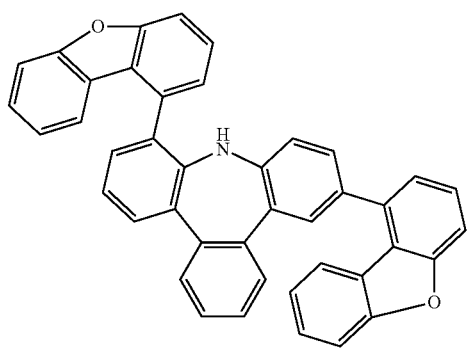 [SMILES: c1ccc2c(c1)-c1cc(-c3cccc4oc5ccccc5c34)ccc1Nc1c-2cccc1-c1cccc2oc3ccccc3c12] 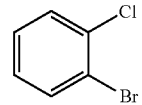
c18 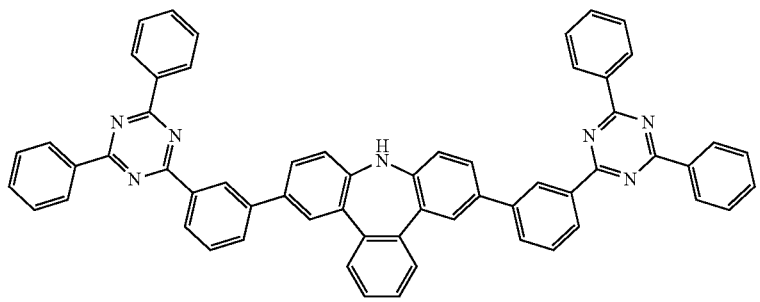 [SMILES: c1ccc(-c2nc(-c3ccccc3)nc(-c3cccc(-c4ccc5c(c4)-c4ccccc4-c4cc(-c6cccc(-c7nc(-c8ccccc8)nc(-c8ccccc8)n7)c6)ccc4N5)c3)n2)cc1] 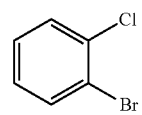
c19 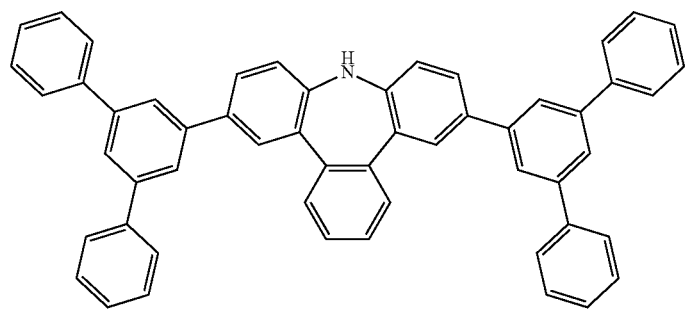 [SMILES: c1ccc(-c2cc(-c3ccccc3)cc(-c3ccc4c(c3)-c3ccccc3-c3cc(-c5cc(-c6ccccc6)cc(-c6ccccc6)c5)ccc3N4)c2)cc1] 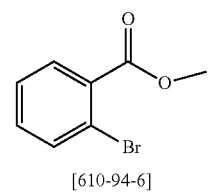
[610-94-6]
c20 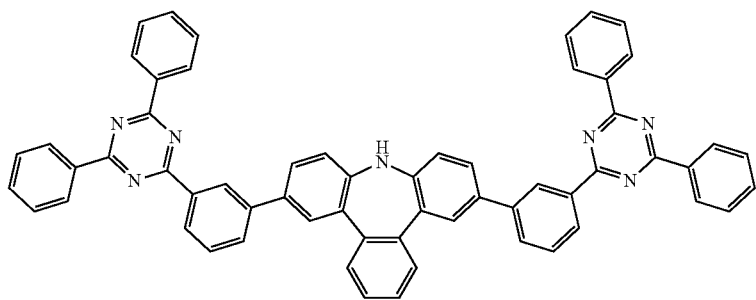 [SMILES: c1ccc(-c2nc(-c3ccccc3)nc(-c3cccc(-c4ccc5c(c4)-c4ccccc4-c4cc(-c6cccc(-c7nc(-c8ccccc8)nc(-c8ccccc8)n7)c6)ccc4N5)c3)n2)cc1] 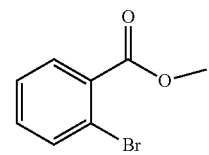

| | | |
|---|---|---|
| c21 | 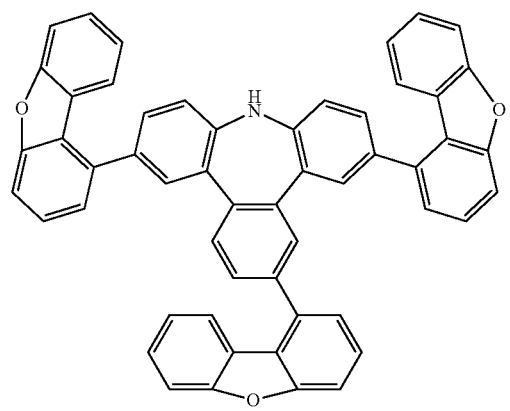 [SMILES: c1ccc2c(c1)oc1cccc(-c3ccc4c(c3)-c3ccc(-c5cccc6oc7ccccc7c56)cc3-c3cc(-c5cccc6oc7ccccc7c56)ccc3N4)c12] | 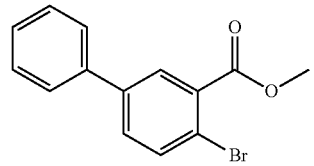
[727408-92-6] |
| c22 | 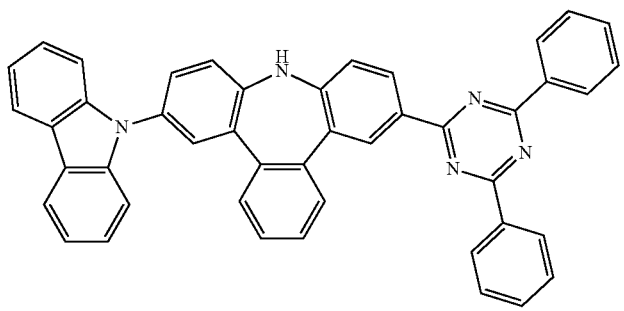 [SMILES: c1ccc(-c2nc(-c3ccccc3)nc(-c3ccc4c(c3)-c3ccccc3-c3cc(-n5c6ccccc6c6ccccc65)ccc3N4)n2)cc1] | 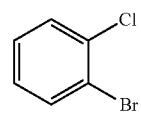 |
| c23 | 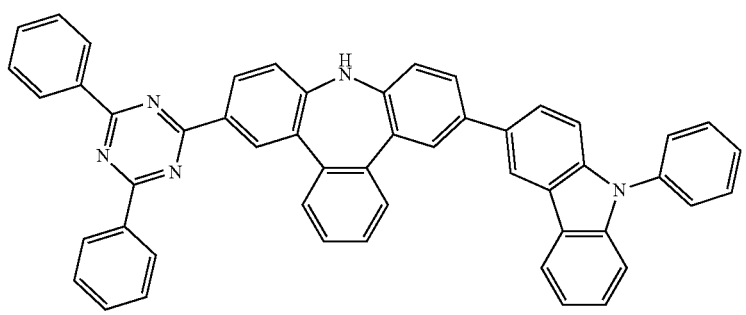 [SMILES: c1ccc(-c2nc(-c3ccccc3)nc(-c3ccc4c(c3)-c3ccccc3-c3cc(-c5ccc6c(c5)c5ccccc5n6-c5ccccc5)ccc3N4)n2)cc1] | 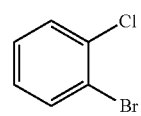 |
| Example | Product | Yield |
|---|---|---|
| c1 | 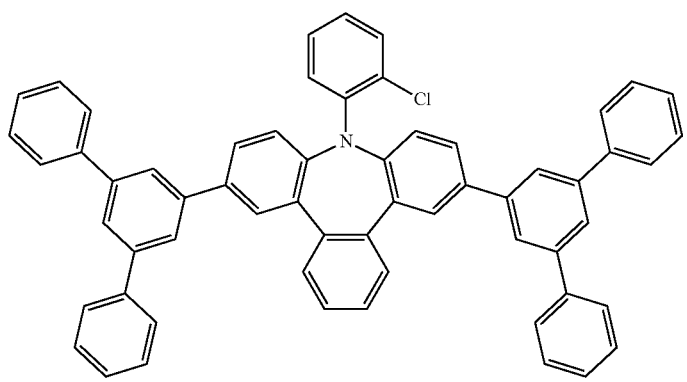 [SMILES: Clc1ccccc1N1c2ccc(-c3cc(-c4ccccc4)cc(-c4ccccc4)c3)cc2-c2ccccc2-c2cc(-c3cc(-c4ccccc4)cc(-c4ccccc4)c3)ccc21] | 64% |

| | | |
|---|---|---|
| c2 | 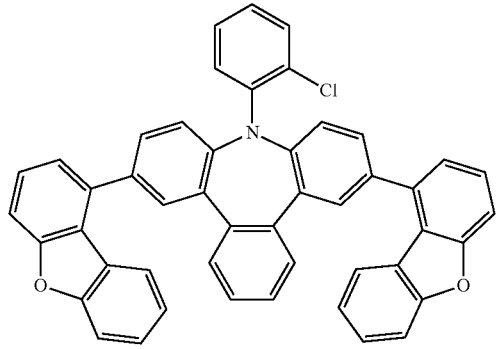 [SMILES: Clc1ccccc1N1c2ccc(-c3cccc4oc5ccccc5c34)cc2-c2ccccc2-c2cc(-c3cccc4oc5ccccc5c34)ccc21] | 78% |
| c3 | 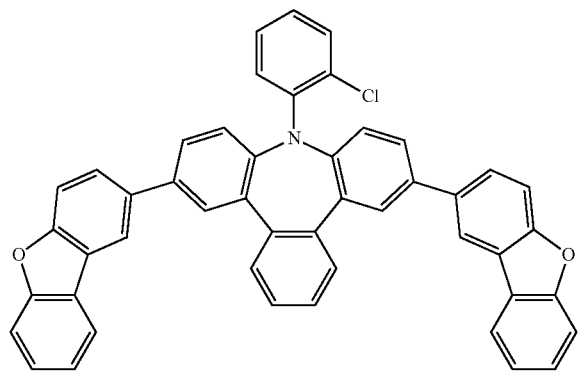 [SMILES: Clc1ccccc1N1c2ccc(-c3ccc4oc5ccccc5c4c3)cc2-c2ccccc2-c2cc(-c3ccc4oc5ccccc5c4c3)ccc21] | 63% |
| c4 | 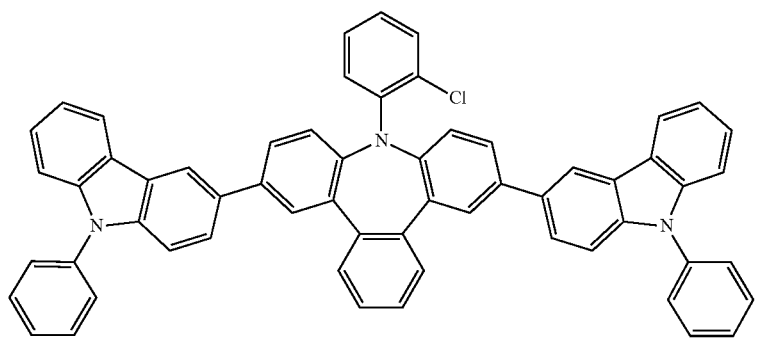 [SMILES: Clc1ccccc1N1c2ccc(-c3ccc4c(c3)c3ccccc3n4-c3ccccc3)cc2-c2ccccc2-c2cc(-c3ccc4c(c3)c3ccccc3n4-c3ccccc3)ccc21] | 78% |
| c5 | 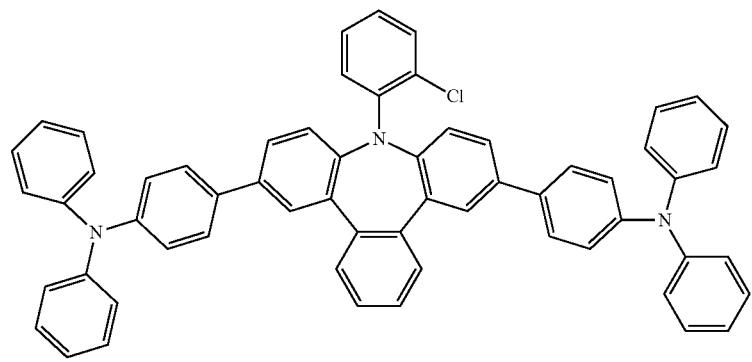 [SMILES: Clc1ccccc1N1c2ccc(-c3ccc(N(c4ccccc4)c4ccccc4)cc3)cc2-c2ccccc2-c2cc(-c3ccc(N(c4ccccc4)c4ccccc4)cc3)ccc21] | 69% |

| | | |
|---|---|---|
| c6 | 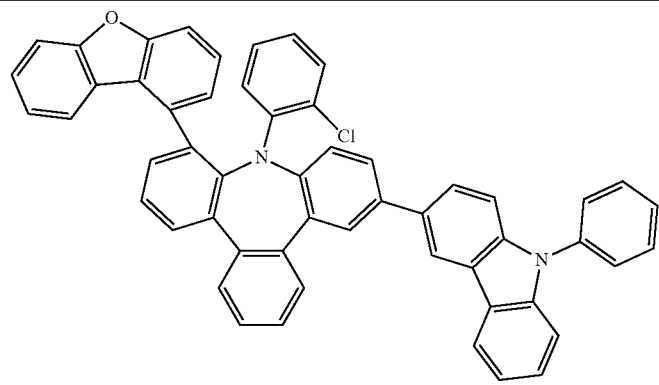 | 61% |
| c7 | 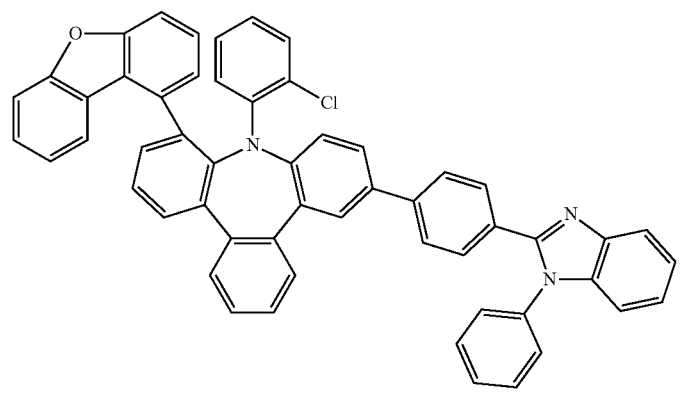 [SMILES: Clc1ccccc1N1c2ccc(-c3ccc(-c4nc5ccccc5n4-c4ccccc4)cc3)cc2-c2ccccc2-c2cccc(-c3cccc4oc5ccccc5c34)c21] | 62% |
| c8 | 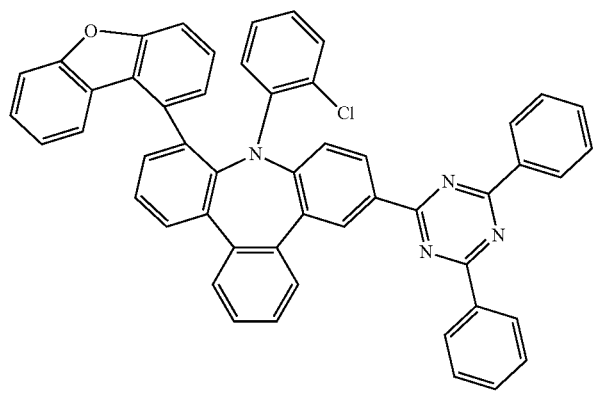 [SMILES: Clc1ccccc1N1c2ccc(-c3nc(-c4ccccc4)nc(-c4ccccc4)n3)cc2-c2ccccc2-c2cccc(-c3cccc4oc5ccccc5c34)c21] | 58% |
| c9 | 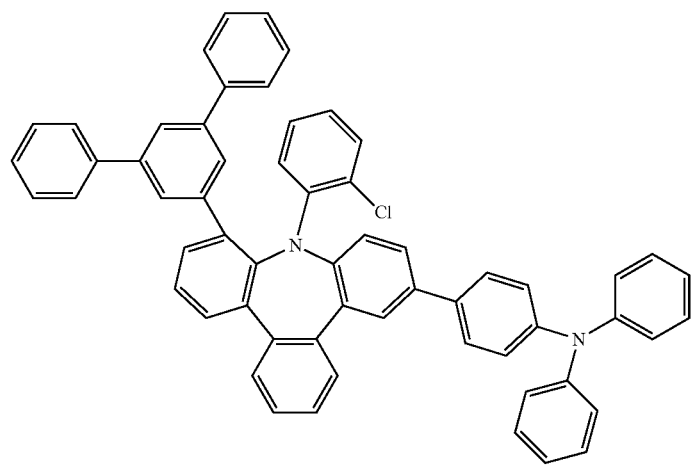 [SMILES: Clc1ccccc1N1c2ccc(-c3ccc(N(c4ccccc4)c4ccccc4)cc3)cc2-c2ccccc2-c2cccc(-c3cc(-c4ccccc4)cc(-c4ccccc4)c3)c21] | 54% |

| | | |
|---|---|---|
| c10 | 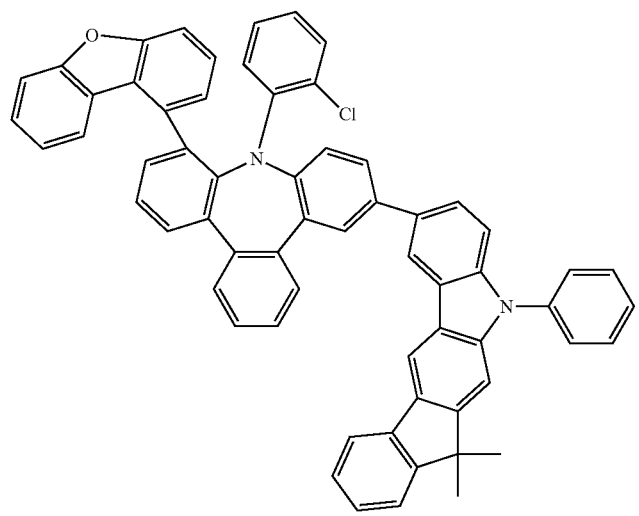 [SMILES: CC1(C)c2ccccc2-c2cc3c4cc(-c5ccc6c(c5)-c5ccccc5-c5cccc(-c7cccc8oc9ccccc9c78)c5N6c5ccccc5Cl)ccc4n(-c4ccccc4)c3cc21] | 59% |
| c11 | 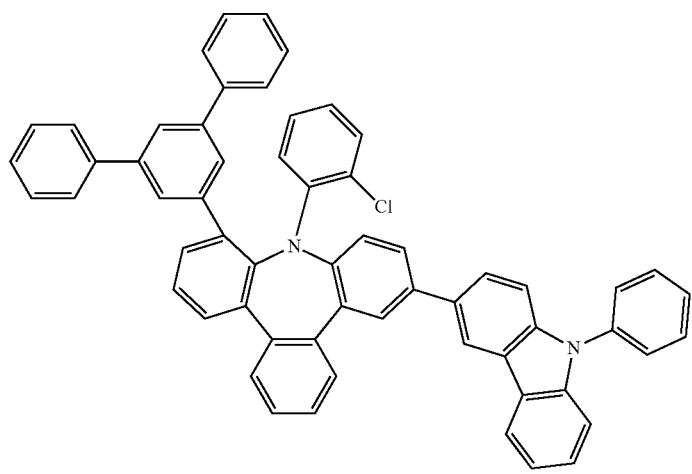 [SMILES: Clc1ccccc1N1c2ccc(-c3ccc4c(c3)c3ccccc3n4-c3ccccc3)cc2-c2ccccc2-c2cccc(-c3cc(-c4ccccc4)cc(-c4ccccc4)c3)c21] | 62% |
| c12 | 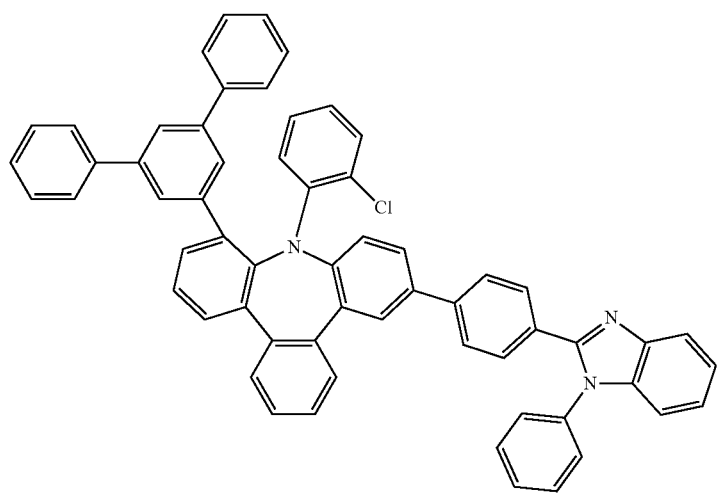 [SMILES: Clc1ccccc1N1c2ccc(-c3ccc(-c4nc5ccccc5n4-c4ccccc4)cc3)cc2-c2ccccc2-c2cccc(-c3cc(-c4ccccc4)cc(-c4ccccc4)c3)c21] | 60% |

| | | |
|---|---|---|
| c13 | 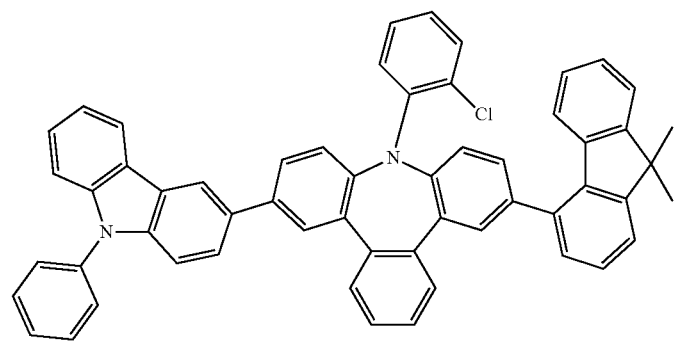 [SMILES: CC1(C)c2ccccc2-c2c(-c3ccc4c(c3)-c3ccccc3-c3cc(-c5ccc6c(c5)c5ccccc5n6-c5ccccc5)ccc3N4c3ccccc3Cl)cccc21] | 81% |
| c14 | 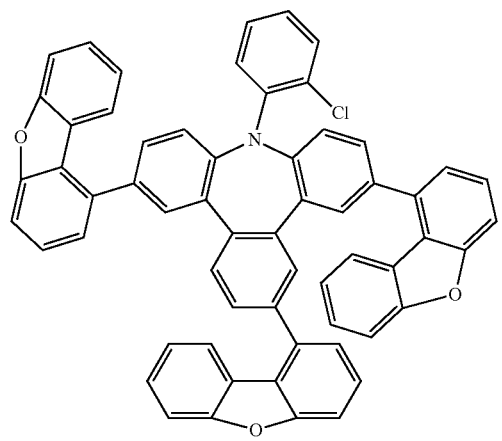 [SMILES: Clc1ccccc1N1c2ccc(-c3cccc4oc5ccccc5c34)cc2-c2ccc(-c3cccc4oc5ccccc5c34)cc2-c2cc(-c3cccc4oc5ccccc5c34)ccc21] | 89% |
| c15 | 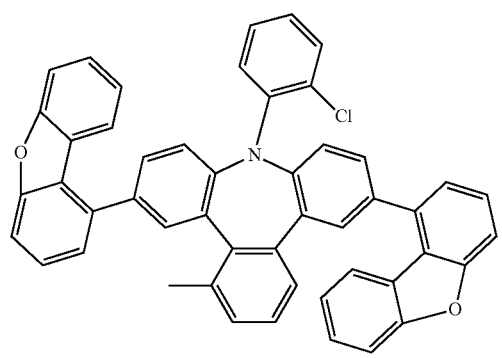 [SMILES: Cc1cccc2c1-c1cc(-c3cccc4oc5ccccc5c34)ccc1N(c1ccccc1Cl)c1ccc(-c3cccc4oc5ccccc5c34)cc1-2] | 87% |
| c16 | 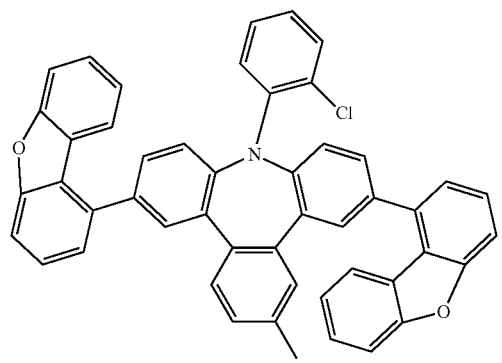 [SMILES: Cc1ccc2c(c1)-c1cc(-c3cccc4oc5ccccc5c34)ccc1N(c1ccccc1Cl)c1ccc(-c3cccc4oc5ccccc5c34)cc1-2] | 88% |

-continued
C17 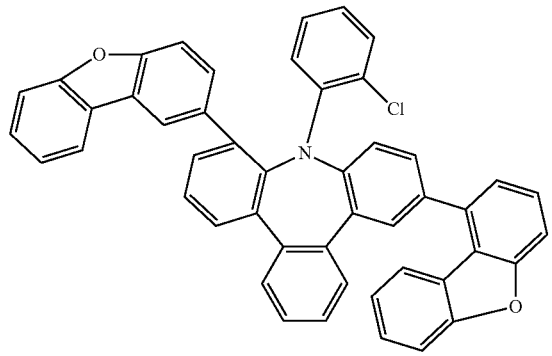 [SMILES: Clc1ccccc1N1c2ccc(-c3cccc4oc5ccccc5c34)cc2-c2ccccc2-c2cccc(-c3ccc4oc5ccccc5c4c3)c21] 86%
c18 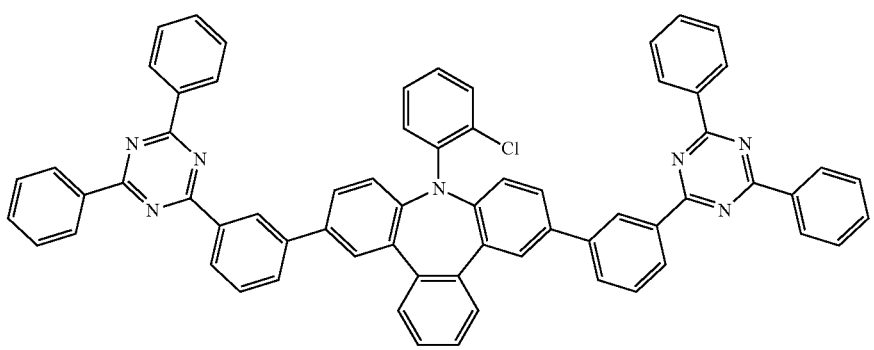 [SMILES: Clc1ccccc1N1c2ccc(-c3cccc(-c4nc(-c5ccccc5)nc(-c5ccccc5)n4)c3)cc2-c2ccccc2-c2cc(-c3cccc(-c4nc(-c5ccccc5)nc(-c5ccccc5)n4)c3)ccc21] 76%
c19 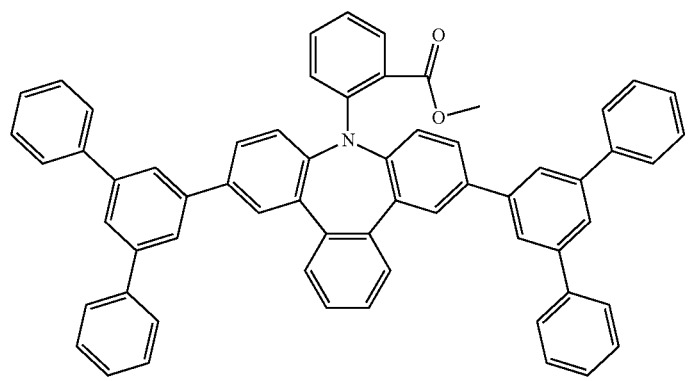 [SMILES: COC(=O)c1ccccc1N1c2ccc(-c3cc(-c4ccccc4)cc(-c4ccccc4)c3)cc2-c2ccccc2-c2cc(-c3cc(-c4ccccc4)cc(-c4ccccc4)c3)ccc21] 74%
c20 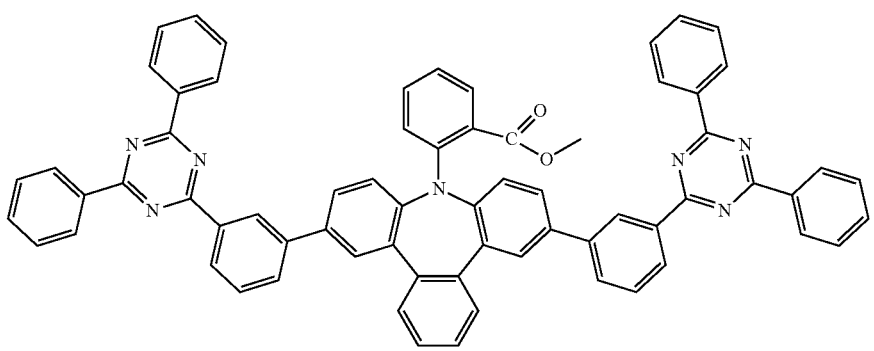 [SMILES: COC(=O)c1ccccc1N1c2ccc(-c3cccc(-c4nc(-c5ccccc5)nc(-c5ccccc5)n4)c3)cc2-c2ccccc2-c2cc(-c3cccc(-c4nc(-c5ccccc5)nc(-c5ccccc5)n4)c3)ccc21] 72%

| | | |
|---|---|---|
| c21 | 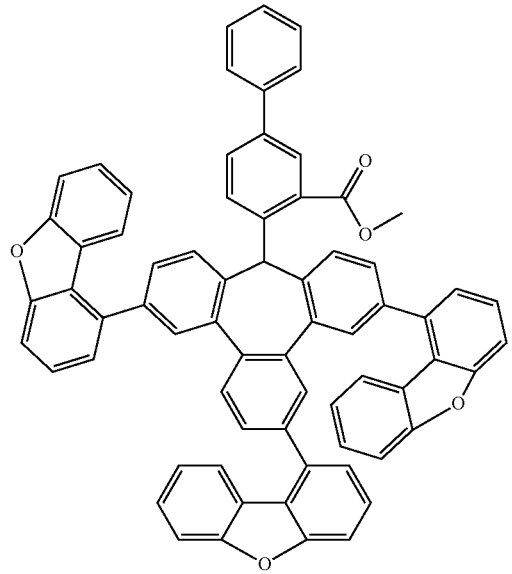 [SMILES: COC(=O)c1cc(-c2ccccc2)ccc1C1c2ccc(-c3cccc4oc5ccccc5c34)cc2-c2ccc(-c3cccc4oc5ccccc5c34)cc2-c2cc(-c3cccc4oc5ccccc5c34)ccc21] | 73% |
| c22 | 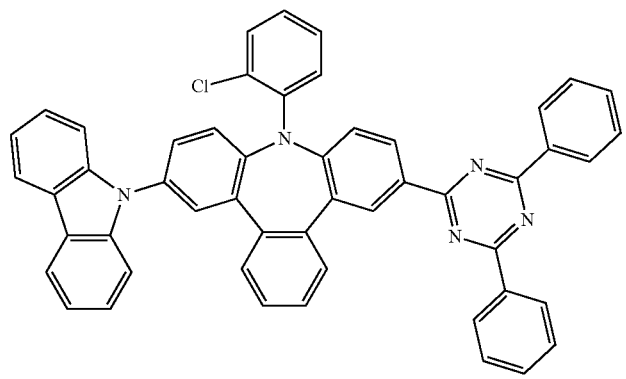 [SMILES: Clc1ccccc1N1c2ccc(-c3nc(-c4ccccc4)nc(-c4ccccc4)n3)cc2-c2ccccc2-c2cc(-n3c4ccccc4c4ccccc43)ccc21] | 74% |
| c23 | 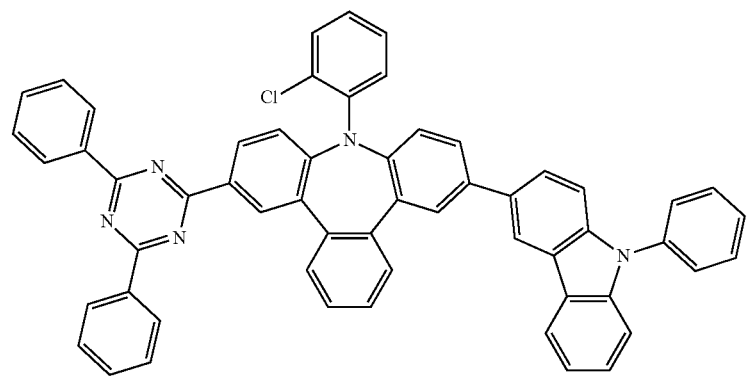 [SMILES: Clc1ccccc1N1c2ccc(-c3ccc4c(c3)c3ccccc3n4-c3ccccc3)cc2-c2ccccc2-c2cc(-c3nc(-c4ccccc4)nc(-c4ccccc4)n3)ccc21] | 73% | d) Cyclization

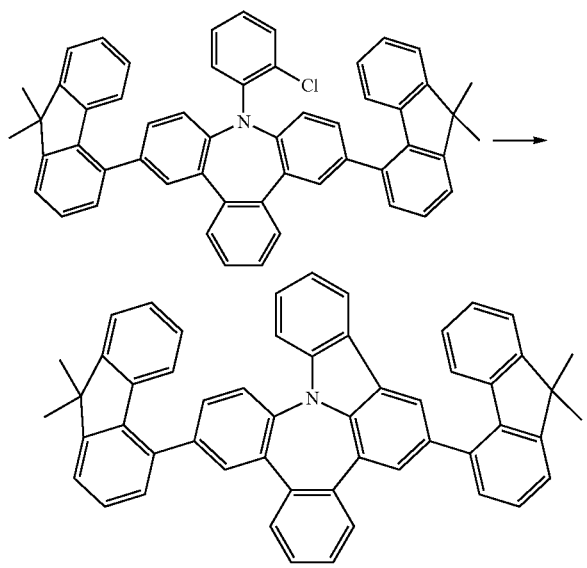

Under protective gas, 45 g (61 mmol) of 9-(2-chlorophenyl)-6,12-bis-(9,9-dimethyl-9H-fluoren-4-yl)-9H-9-azatribenzo[a,c,e]cycloheptene are dissolved in 250 mL of dimethylacetamide. Added to this solution are 21 g (154 mmol) of $K_2CO_3$, 10 ml of tri-tert-butylphosphine (1 mol/L) and 2.7 g (12.5 mmol) of $Pd(OAc)_2$ and 1.8 g (18.5 mmol) of pivalic acid. Then the mixture is stirred at 130° C. for 80 h. After this time, the reaction mixture is cooled to room temperature extracted with dichloromethane. The combined organic phases are dried over $Na_2SO_4$ and concentrated. The residue is subjected to hot extraction with toluene, recrystallized from toluene and finally sublimed under high vacuum. The yield is 37 g (52 mmol), 87% of theory, purity by HPLC about 99.9%.

In an analogous manner, it is possible to obtain the following compounds:

| | Reactant 1 |
|---|---|
| d1 | 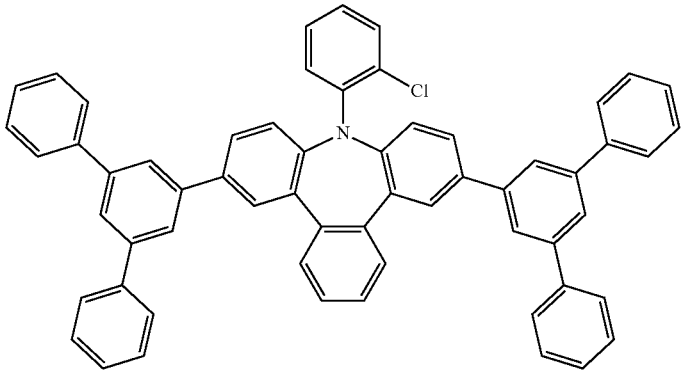 [SMILES: Clc1ccccc1N1c2ccc(-c3cc(-c4ccccc4)cc(-c4ccccc4)c3)cc2-c2ccccc2-c2cc(-c3cc(-c4ccccc4)cc(-c4ccccc4)c3)ccc21] |
| d2 | 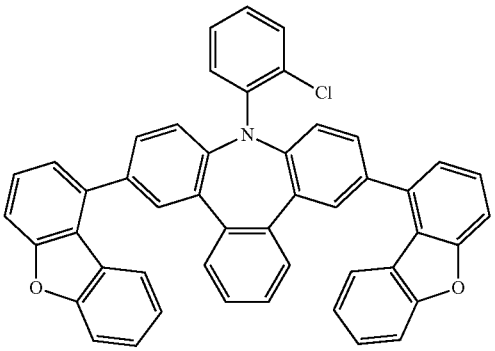 [SMILES: Clc1ccccc1N1c2ccc(-c3cccc4oc5ccccc5c34)cc2-c2ccccc2-c2cc(-c3cccc4oc5ccccc5c34)ccc21] |

-continued
d3
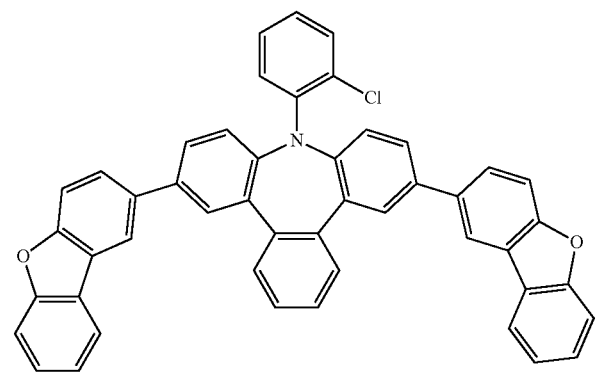 [SMILES: Clc1ccccc1N1c2ccc(-c3ccc4oc5ccccc5c4c3)cc2-c2ccccc2-c2cc(-c3ccc4oc5ccccc5c4c3)ccc21]
d4
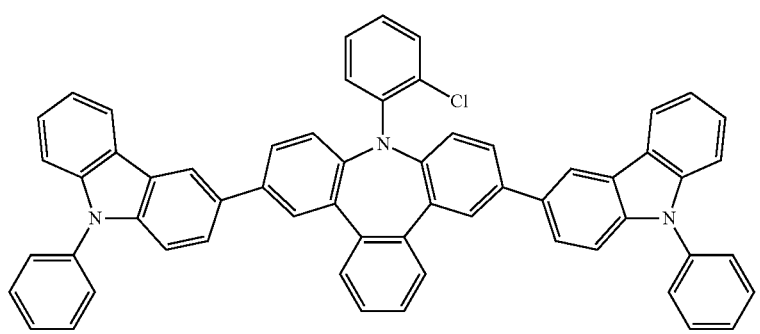 [SMILES: Clc1ccccc1N1c2ccc(-c3ccc4c(c3)c3ccccc3n4-c3ccccc3)cc2-c2ccccc2-c2cc(-c3ccc4c(c3)c3ccccc3n4-c3ccccc3)ccc21]
d5
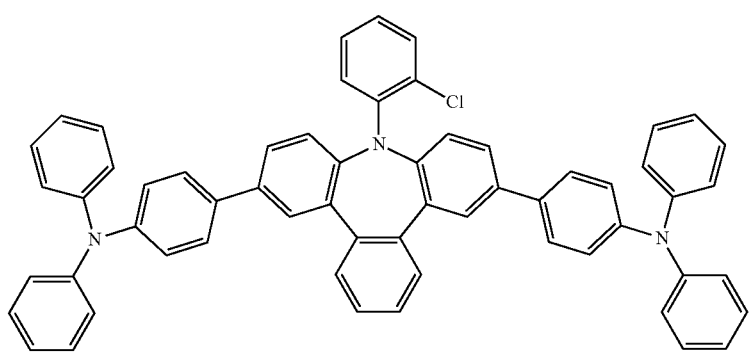 [SMILES: Clc1ccccc1N1c2ccc(-c3ccc(N(c4ccccc4)c4ccccc4)cc3)cc2-c2ccccc2-c2cc(-c3ccc(N(c4ccccc4)c4ccccc4)cc3)ccc21]
d6
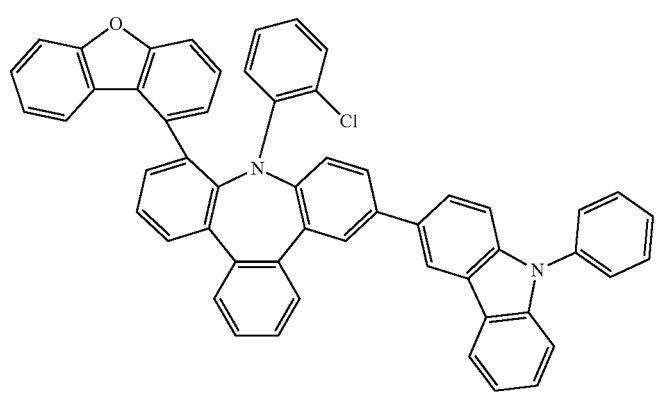 [SMILES: Clc1ccccc1N1c2ccc(-c3ccc4c(c3)c3ccccc3n4-c3ccccc3)cc2-c2ccccc2-c2cccc(-c3cccc4oc5ccccc5c34)c21]

d7
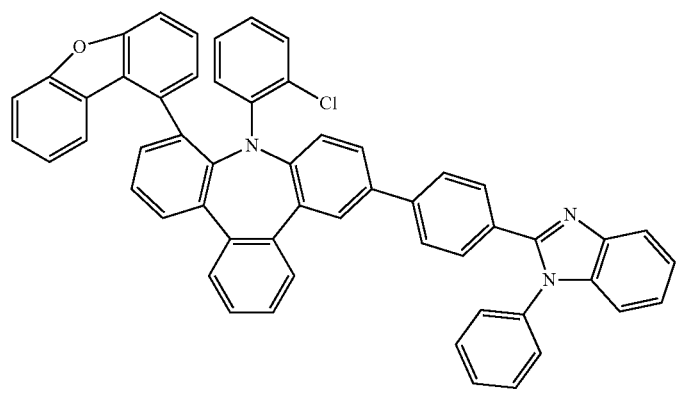 [SMILES: Clc1ccccc1N1c2ccc(-c3ccc(-c4nc5ccccc5n4-c4ccccc4)cc3)cc2-c2ccccc2-c2cccc(-c3cccc4oc5ccccc5c34)c21]
d8
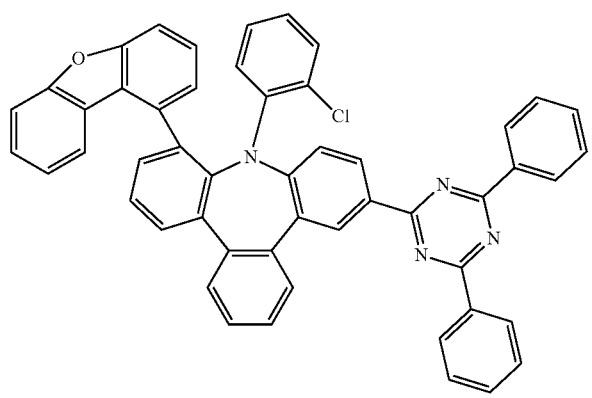 [SMILES: Clc1ccccc1N1c2ccc(-c3nc(-c4ccccc4)nc(-c4ccccc4)n3)cc2-c2ccccc2-c2cccc(-c3cccc4oc5ccccc5c34)c21]
d9
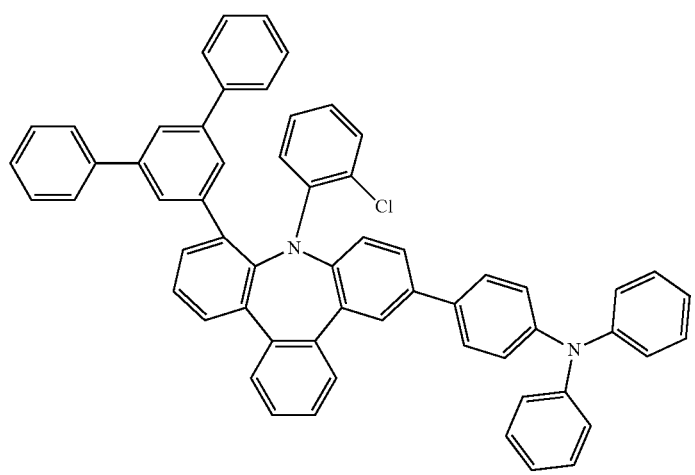 [SMILES: Clc1ccccc1N1c2ccc(-c3ccc(N(c4ccccc4)c4ccccc4)cc3)cc2-c2ccccc2-c2cccc(-c3cc(-c4ccccc4)cc(-c4ccccc4)c3)c21]

-continued
c10
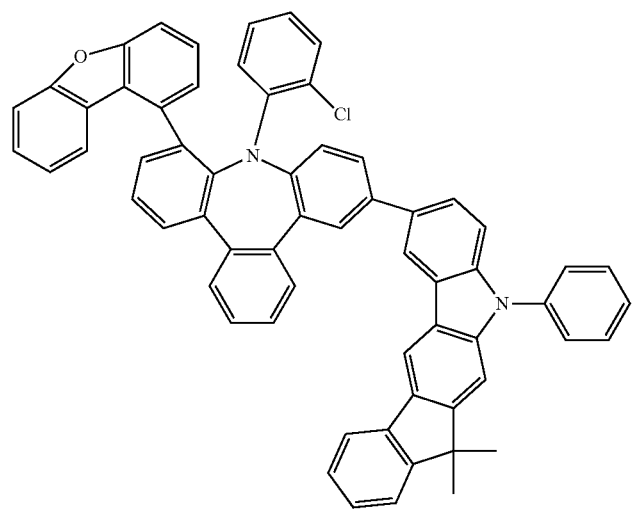 [SMILES: CC1(C)c2ccccc2-c2cc3c4cc(-c5ccc6c(c5)-c5ccccc5-c5cccc(-c7cccc8oc9ccccc9c78)c5N6c5ccccc5Cl)ccc4n(-c4ccccc4)c3cc21]
d11
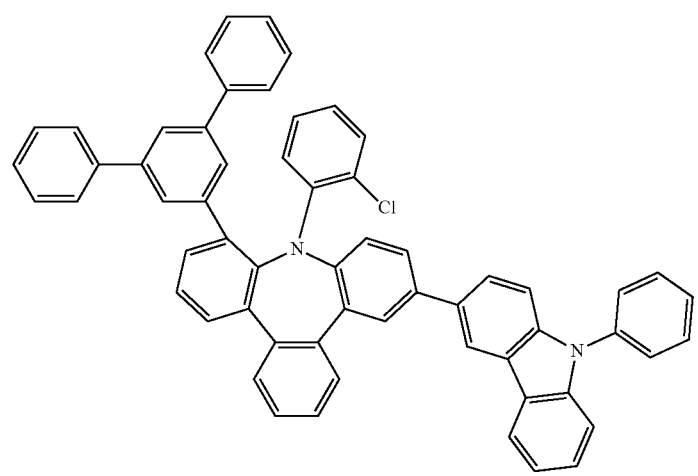 [SMILES: Clc1ccccc1N1c2ccc(-c3ccc4c(c3)c3ccccc3n4-c3ccccc3)cc2-c2ccccc2-c2cccc(-c3cc(-c4ccccc4)cc(-c4ccccc4)c3)c21]
d12
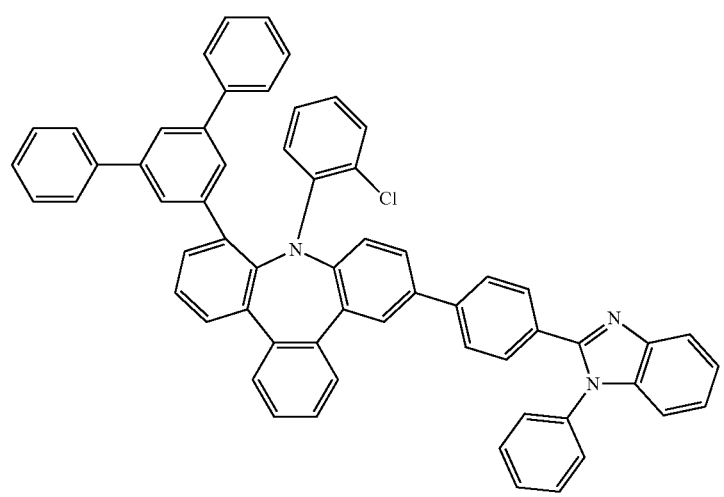 [SMILES: Clc1ccccc1N1c2ccc(-c3ccc(-c4nc5ccccc5n4-c4ccccc4)cc3)cc2-c2ccccc2-c2cccc(-c3cc(-c4ccccc4)cc(-c4ccccc4)c3)c21]

-continued
d13
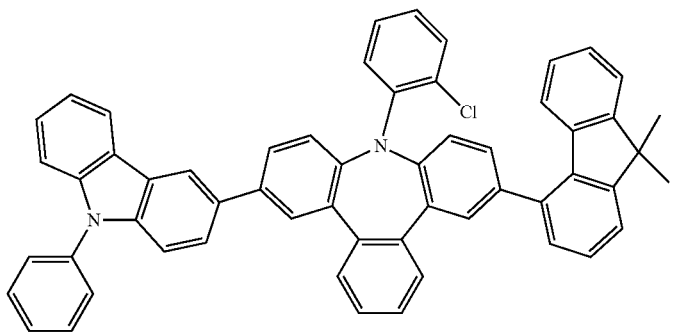 [SMILES: CC1(C)c2ccccc2-c2c(-c3ccc4c(c3)-c3ccccc3-c3cc(-c5ccc6c(c5)c5ccccc5n6-c5ccccc5)ccc3N4c3ccccc3Cl)cccc21]
d14
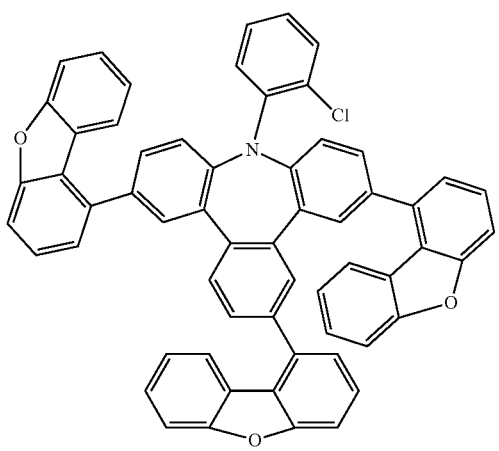 [SMILES: Clc1ccccc1N1c2ccc(-c3cccc4oc5ccccc5c34)cc2-c2ccc(-c3cccc4oc5ccccc5c34)cc2-c2cc(-c3cccc4oc5ccccc5c34)ccc21]
d15
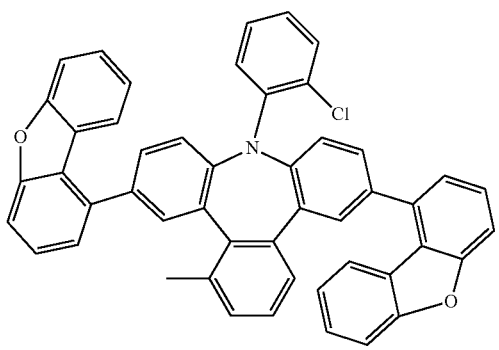 [SMILES: Cc1cccc2c1-c1cc(-c3cccc4oc5ccccc5c34)ccc1N(c1ccccc1Cl)c1ccc(-c3cccc4oc5ccccc5c34)cc1-2]
d16
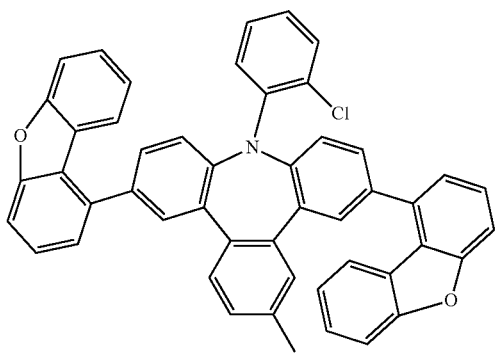 [SMILES: Cc1ccc2c(c1)-c1cc(-c3cccc4oc5ccccc5c34)ccc1N(c1ccccc1Cl)c1ccc(-c3cccc4oc5ccccc5c34)cc1-2]

-continued
d17
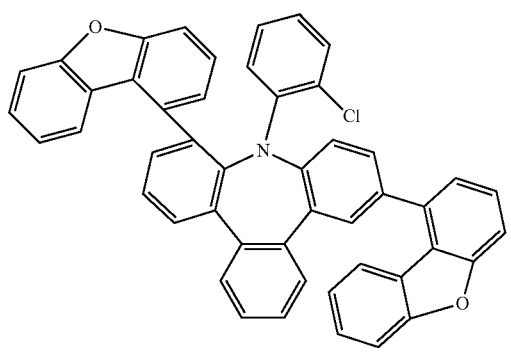 [SMILES: Clc1ccccc1N1c2ccc(-c3cccc4oc5ccccc5c34)cc2-c2ccccc2-c2cccc(-c3cccc4oc5ccccc5c34)c21]
d18
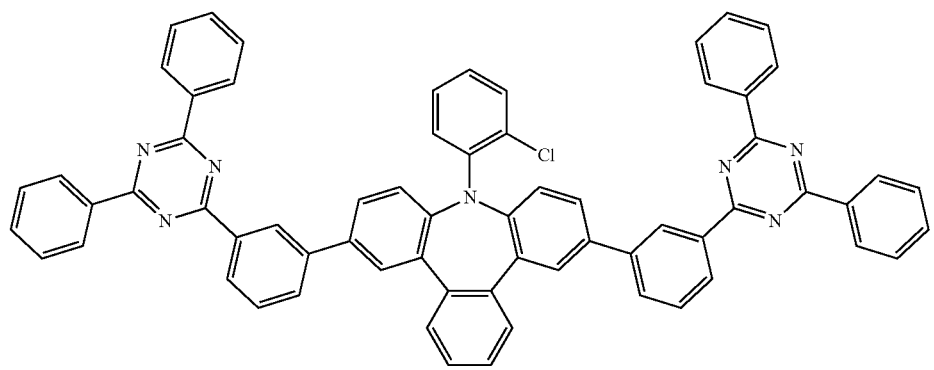 [SMILES: Clc1ccccc1N1c2ccc(-c3cccc(-c4nc(-c5ccccc5)nc(-c5ccccc5)n4)c3)cc2-c2ccccc2-c2cc(-c3cccc(-c4nc(-c5ccccc5)nc(-c5ccccc5)n4)c3)ccc21]
d19-a
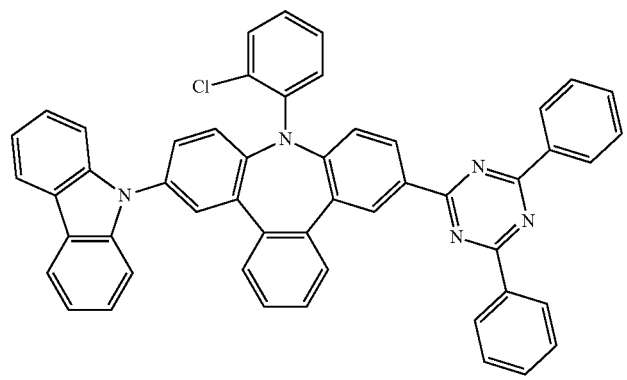 [SMILES: Clc1ccccc1N1c2ccc(-c3nc(-c4ccccc4)nc(-c4ccccc4)n3)cc2-c2ccccc2-c2cc(-n3c4ccccc4c4ccccc43)ccc21]
d19-b
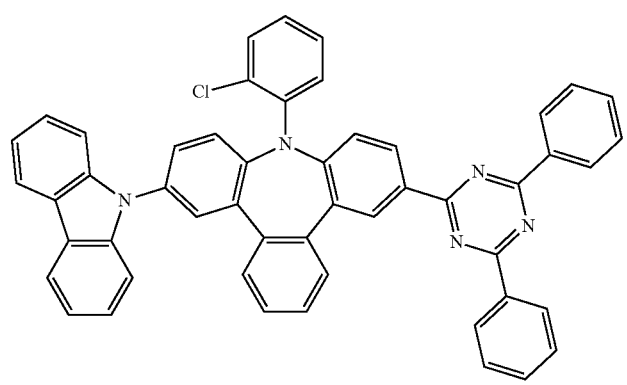 [SMILES: Clc1ccccc1N1c2ccc(-c3nc(-c4ccccc4)nc(-c4ccccc4)n3)cc2-c2ccccc2-c2cc(-n3c4ccccc4c4ccccc43)ccc21]

-continued
d-20a
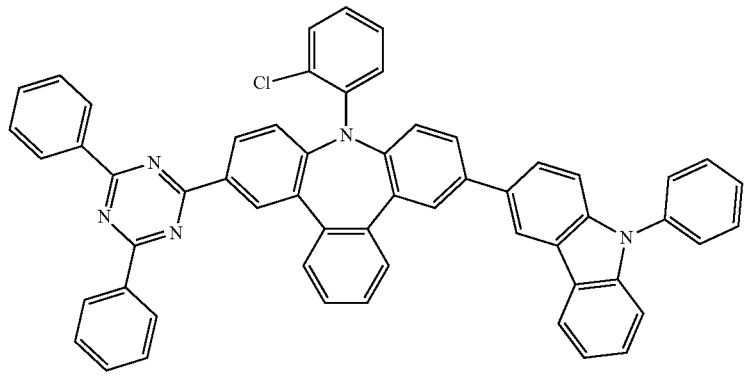 [SMILES: Clc1ccccc1N1c2ccc(-c3ccc4c(c3)c3ccccc3n4-c3ccccc3)cc2-c2ccccc2-c2cc(-c3nc(-c4ccccc4)nc(-c4ccccc4)n3)ccc21]
d20-b
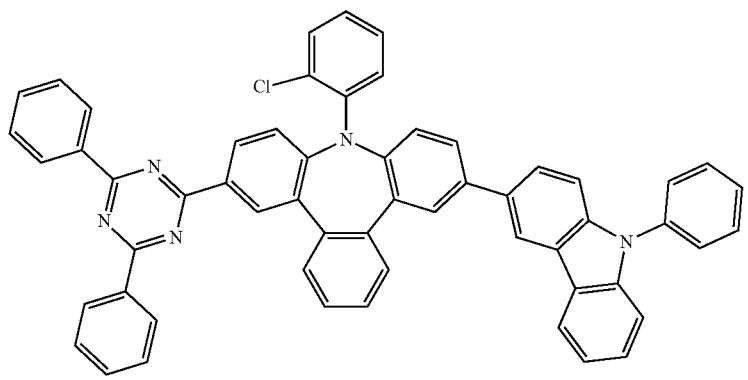 [SMILES: Clc1ccccc1N1c2ccc(-c3ccc4c(c3)c3ccccc3n4-c3ccccc3)cc2-c2ccccc2-c2cc(-c3nc(-c4ccccc4)nc(-c4ccccc4)n3)ccc21]
| | Product | Yield |
|---|---|---|
| d1 | 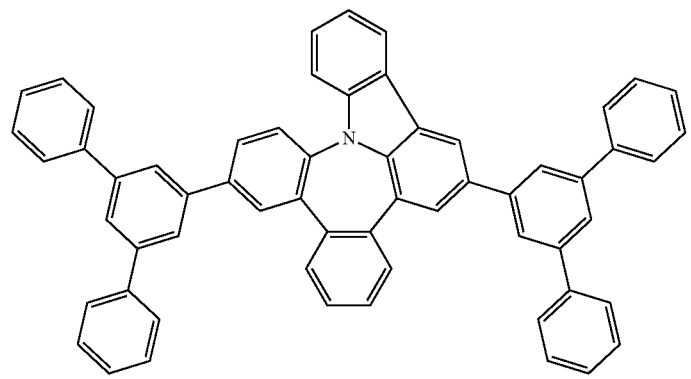 [SMILES: c1ccc(-c2cc(-c3ccccc3)cc(-c3ccc4c(c3)-c3ccccc3-c3cc(-c5cc(-c6ccccc6)cc(-c6ccccc6)c5)cc5c6ccccc6n-4c35)c2)cc1] | 68% |
| d2 | 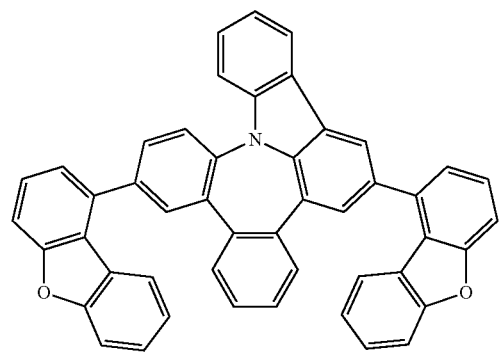 [SMILES: c1ccc2c(c1)-c1cc(-c3cccc4oc5ccccc5c34)ccc1-n1c3ccccc3c3cc(-c4cccc5oc6ccccc6c45)cc-2c31] | 78% |

| | | |
|---|---|---|
| d3 | 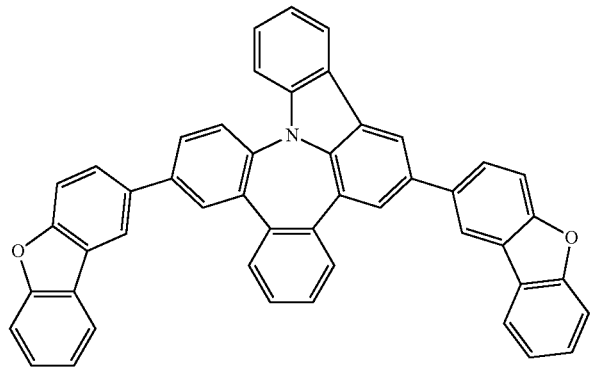 [SMILES: c1ccc2c(c1)-c1cc(-c3ccc4oc5ccccc5c4c3)ccc1-n1c3ccccc3c3cc(-c4ccc5oc6ccccc6c5c4)cc-2c31] | 65% |
| d4 | 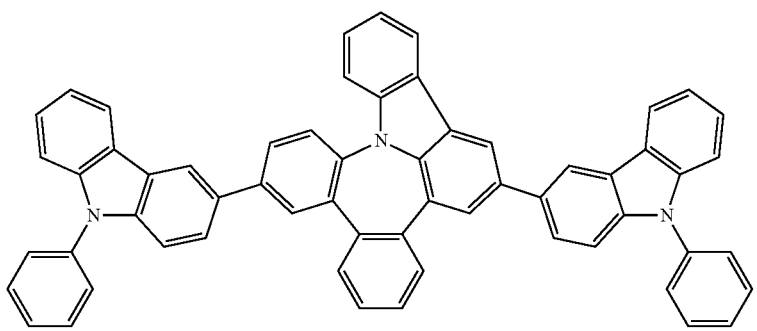 [SMILES: c1ccc(-n2c3ccccc3c3cc(-c4ccc5c(c4)-c4ccccc4-c4cc(-c6ccc7c(c6)c6ccccc6n7-c6ccccc6)cc6c7ccccc7n-5c46)ccc32)cc1] | 69% |
| d5 | 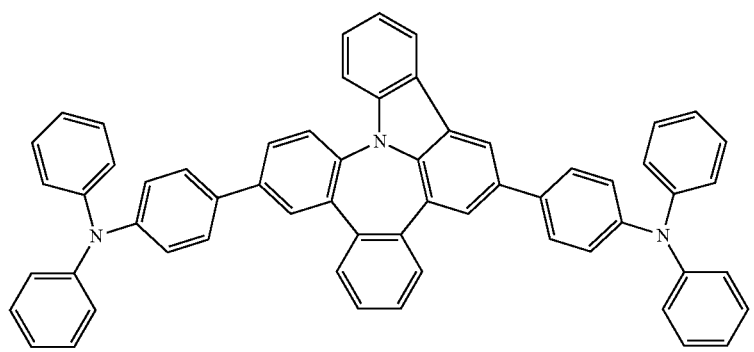 [SMILES: c1ccc(N(c2ccccc2)c2ccc(-c3ccc4c(c3)-c3ccccc3-c3cc(-c5ccc(N(c6ccccc6)c6ccccc6)cc5)cc5c6ccccc6n-4c35)cc2)cc1] | 65% |
| d6 | 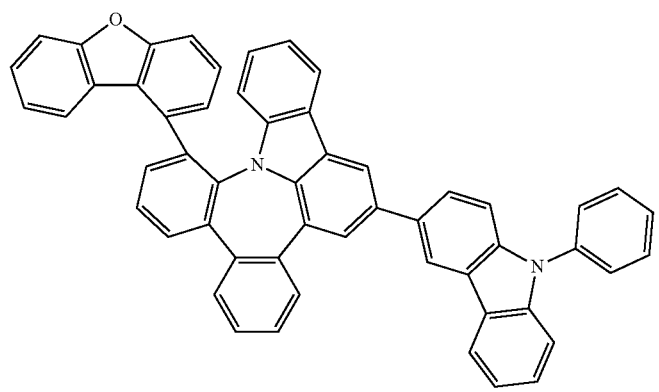 [SMILES: c1ccc(-n2c3ccccc3c3cc(-c4cc5c6c(c4)c4ccccc4n6-c4c(cccc4-c4cccc6oc7ccccc7c46)-c4ccccc4-5)ccc32)cc1] | 61% |

| | | |
|---|---|---|
| d7 | 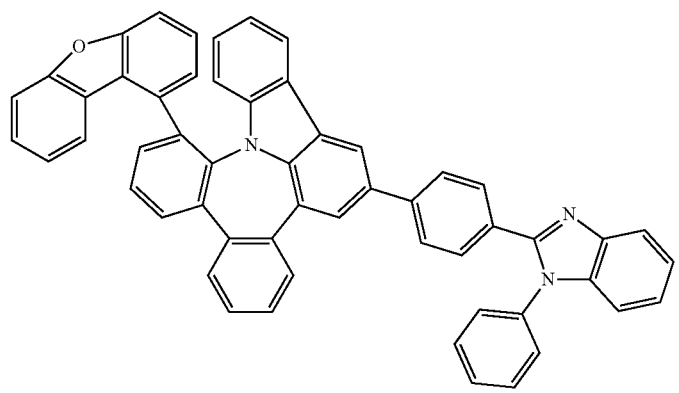 [SMILES: c1ccc(-n2c(-c3ccc(-c4cc5c6c(c4)c4ccccc4n6-c4c(cccc4-c4cccc6oc7ccccc7c46)-c4ccccc4-5)cc3)nc3ccccc32)cc1] | 60% |
| d8 | 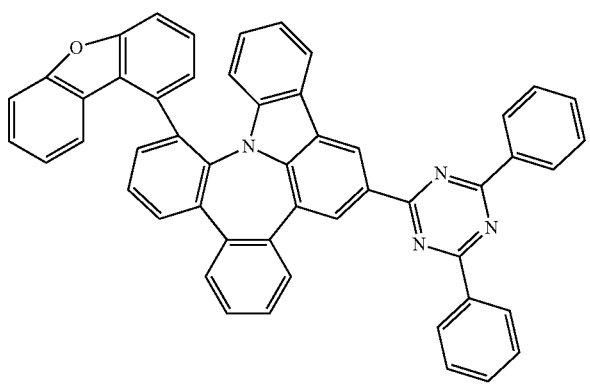 [SMILES: c1ccc(-c2nc(-c3ccccc3)nc(-c3cc4c5c(c3)c3ccccc3n5-c3c(cccc3-c3cccc5oc6ccccc6c35)-c3ccccc3-4)n2)cc1] | 58% |
| d9 | 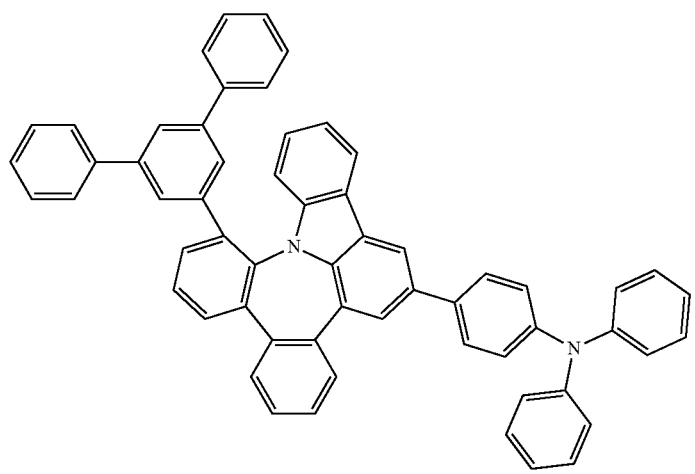 [SMILES: c1ccc(-c2cc(-c3ccccc3)cc(-c3cccc4c3-n3c5ccccc5c5cc(-c6ccc(N(c7ccccc7)c7ccccc7)cc6)cc(c53)-c3ccccc3-4)c2)cc1] | 63% |

-continued
| | | |
|---|---|---|
| c10 | 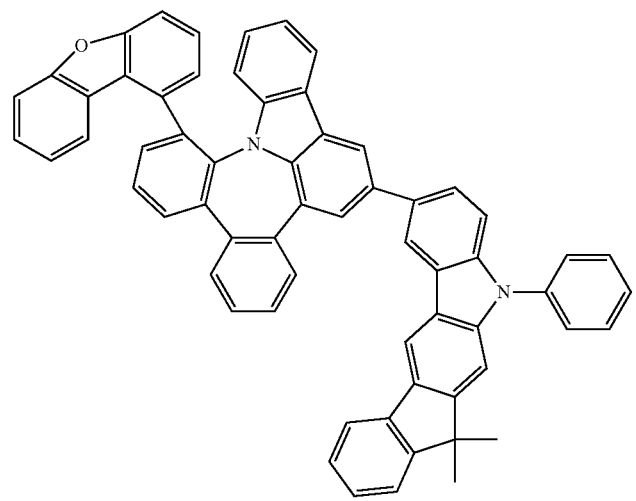 [SMILES: CC1(C)c2ccccc2-c2cc3c4cc(-c5cc6c7c(c5)c5ccccc5n7-c5c(cccc5-c5cccc7oc8ccccc8c57)-c5ccccc5-6)ccc4n(-c4ccccc4)c3cc21] | 60% |
| d11 | 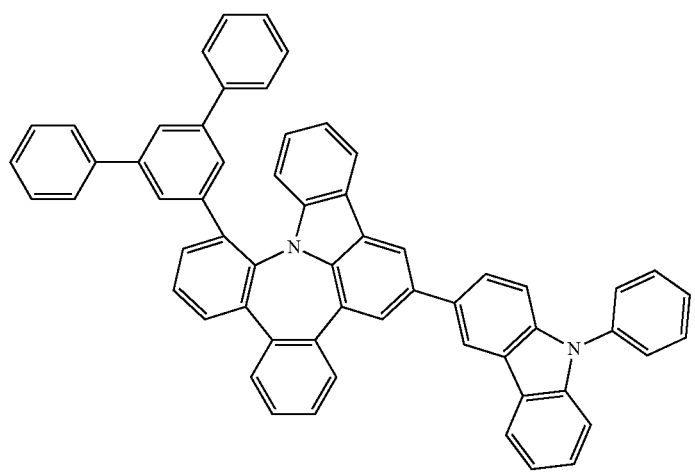 [SMILES: c1ccc(-c2cc(-c3ccccc3)cc(-c3cccc4c3-n3c5ccccc5c5cc(-c6ccc7c(c6)c6ccccc6n7-c6ccccc6)cc(c53)-c3ccccc3-4)c2)cc1] | 62% |
| d12 | 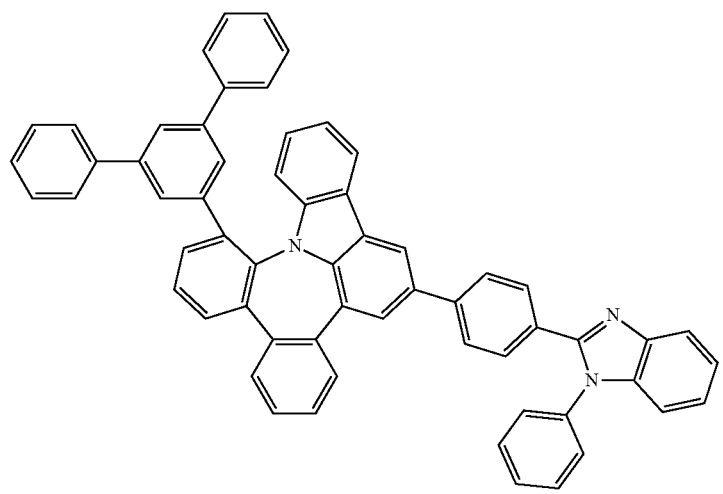 [SMILES: c1ccc(-c2cc(-c3ccccc3)cc(-c3cccc4c3-n3c5ccccc5c5cc(-c6ccc(-c7nc8ccccc8n7-c7ccccc7)cc6)cc(c53)-c3ccccc3-4)c2)cc1] | 64% |

| | | |
|---|---|---|
| d13 | 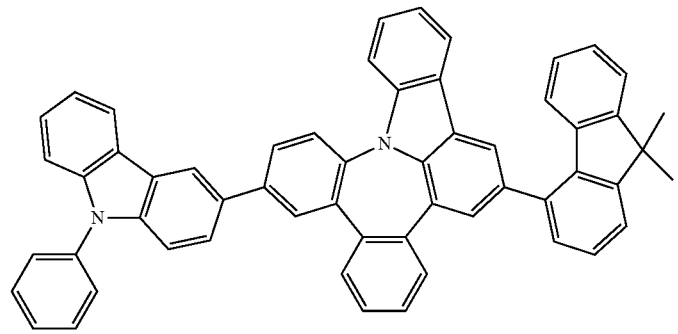 [SMILES: CC1(C)c2ccccc2-c2c(-c3cc4c5c(c3)c3ccccc3n5-c3ccc(-c5ccc6c(c5)c5ccccc5n6-c5ccccc5)cc3-c3ccccc3-4)cccc21] | 61% |
| d14 | 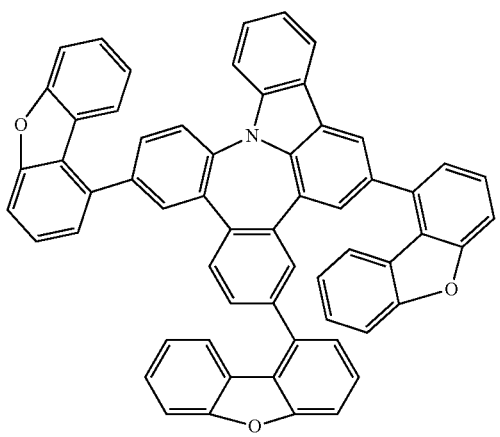 [SMILES: c1ccc2c(c1)oc1cccc(-c3ccc4c(c3)-c3cc(-c5cccc6oc7ccccc7c56)cc5c6ccccc6n(c35)-c3ccc(-c5cccc6oc7ccccc7c56)cc3-4)c12] | 69% |
| d15 | 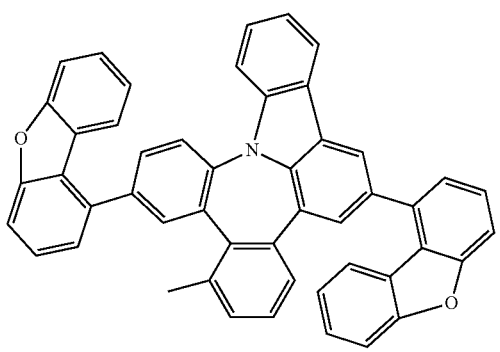 [SMILES: Cc1cccc2c1-c1cc(-c3cccc4oc5ccccc5c34)ccc1-n1c3ccccc3c3cc(-c4cccc5oc6ccccc6c45)cc-2c31] | 66% |
| d16 | 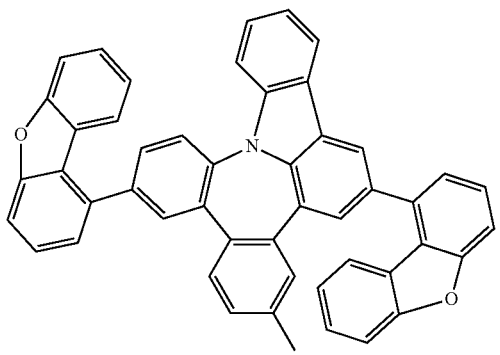 [SMILES: Cc1ccc2c(c1)-c1cc(-c3cccc4oc5ccccc5c34)cc3c4ccccc4n(c13)-c1ccc(-c3cccc4oc5ccccc5c34)cc1-2] | 68% |

-continued
d17 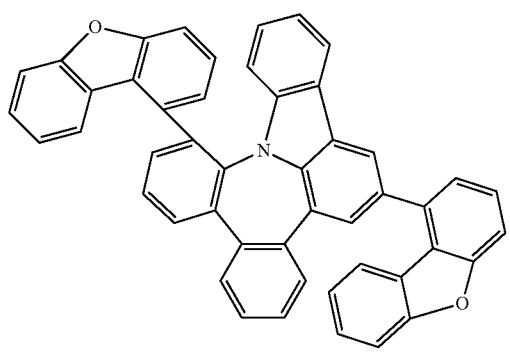 [SMILES: c1ccc2c(c1)-c1cccc(-c3cccc4oc5ccccc5c34)c1-n1c3ccccc3c3cc(-c4cccc5oc6ccccc6c45)cc-2c31] 72%
d18 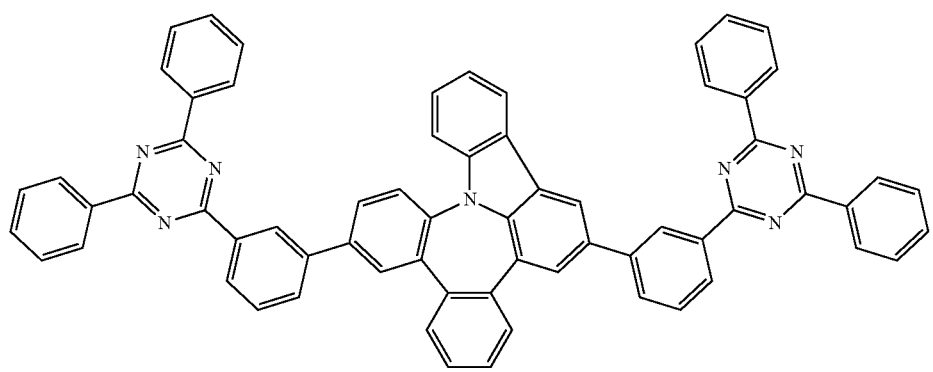 [SMILES: c1ccc(-c2nc(-c3ccccc3)nc(-c3cccc(-c4ccc5c(c4)-c4ccccc4-c4cc(-c6cccc(-c7nc(-c8ccccc8)nc(-c8ccccc8)n7)c6)cc6c7ccccc7n-5c46)c3)n2)cc1] 83%
d19-a 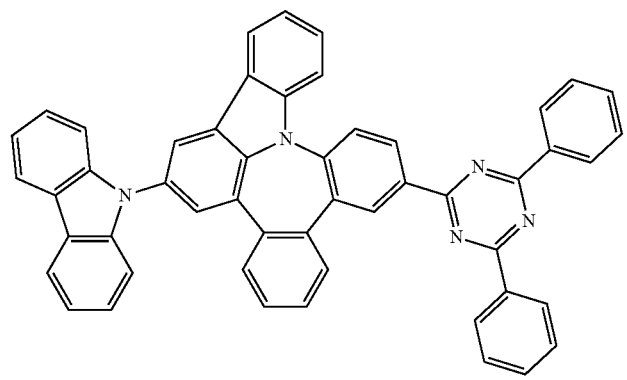 [SMILES: c1ccc(-c2nc(-c3ccccc3)nc(-c3ccc4c(c3)-c3ccccc3-c3cc(-n5c6ccccc6c6ccccc65)cc5c6ccccc6n-4c35)n2)cc1] 35%
d19-b 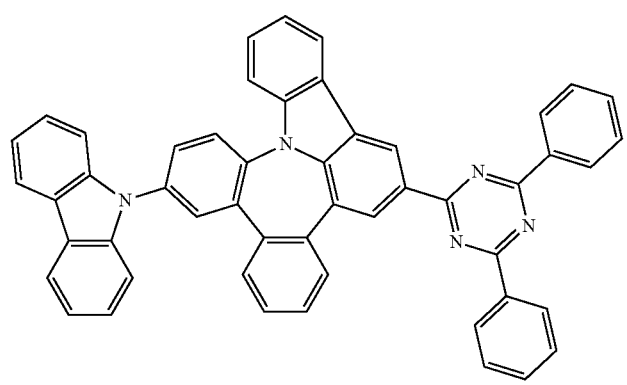 [SMILES: c1ccc(-c2nc(-c3ccccc3)nc(-c3cc4c5c(c3)c3ccccc3n5-c3ccc(-n5c6ccccc6c6ccccc65)cc3-c3ccccc3-4)n2)cc1] 23%

-continued
d20-a 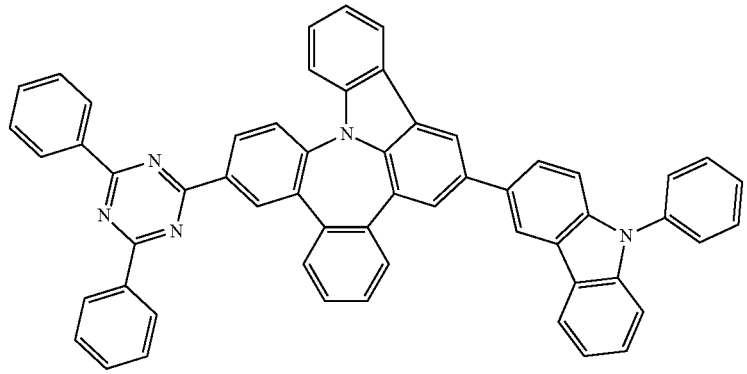 [SMILES: c1ccc(-c2nc(-c3ccccc3)nc(-c3ccc4c(c3)-c3ccccc3-c3cc(-c5ccc6c(c5)c5ccccc5n6-c5ccccc5)cc5c6ccccc6n-4c35)n2)cc1] 37%
d20-b 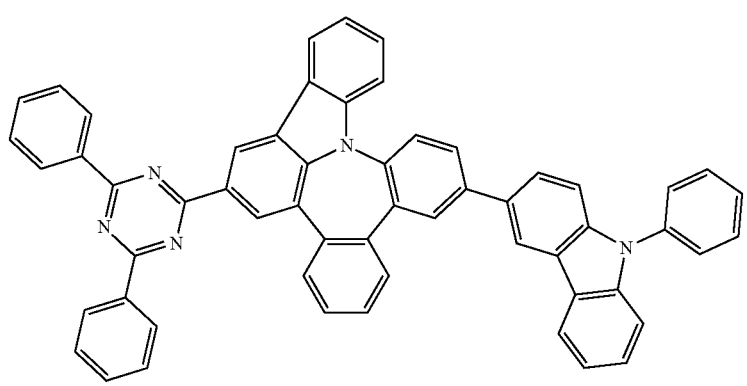 [SMILES: c1ccc(-c2nc(-c3ccccc3)nc(-c3cc4c5c(c3)c3ccccc3n5-c3ccc(-c5ccc6c(c5)c5ccccc5n6-c5ccccc5)cc3-c3ccccc3-4)n2)cc1] 29%
e) 2-[2-(6,12-Bis-[1,1';3',1'']terphenyl-5'-yl-9-aza-tribenzo[a,c,e]cyclohepten-9-yl)phenyl]propan-2-ol
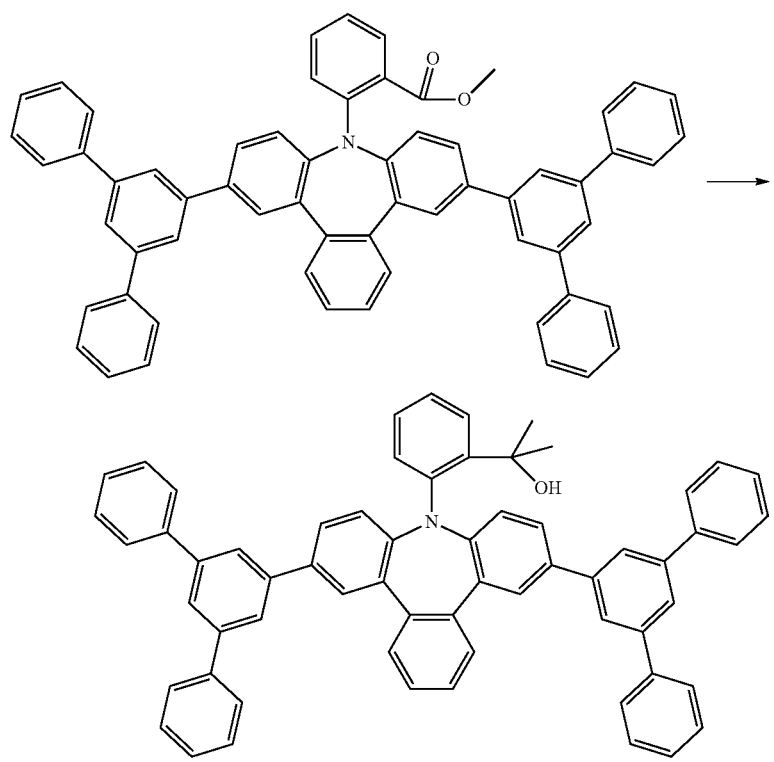

177 g (213 mmol) of methyl 2-(6,12-bis-[1,1';3',1"]ter-phenyl-5'-yl-9-azatribenzo[a,c,e]-cyclohepten-9-yl)benzoate are dissolved in 1500 mL of dried THF and degassed. The mixture is cooled to −78° C., and 569 mL (854 mmol) of methyllithium are added within 40 minutes. The mixture is allowed to warm up to −40° C. within 1 h, and the conversion is monitored via TLC. On completion of conversion, the mixture is quenched cautiously with MeOH at −30° C. The reaction solution is concentrated to 1/3 and 1 L of CH$_2$Cl$_2$ is added, the mixture is washed and the organic phase is dried over MgSO$_4$ and concentrated. The yield is 158 g (189 mmol), 89% of theory.

In an analogous manner, it is possible to prepare the following compound:

| Example | Reactant 1 |
|---------|------------|
| e1 | |
| e2 | |

| Example | Product | Yield |
|---------|---------|-------|
| e1 | | 72% | e2 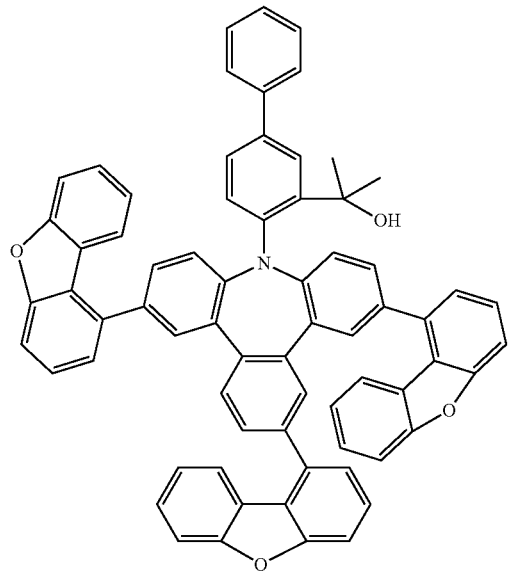 [SMILES: CC(C)(O)c1cc(-c2ccccc2)ccc1N1c2ccc(-c3cccc4oc5ccccc5c34)cc2-c2ccc(-c3cccc4oc5ccccc5c34)cc2-c2cc(-c3cccc4oc5ccccc5c34)ccc21] 74%
f) Cyclization
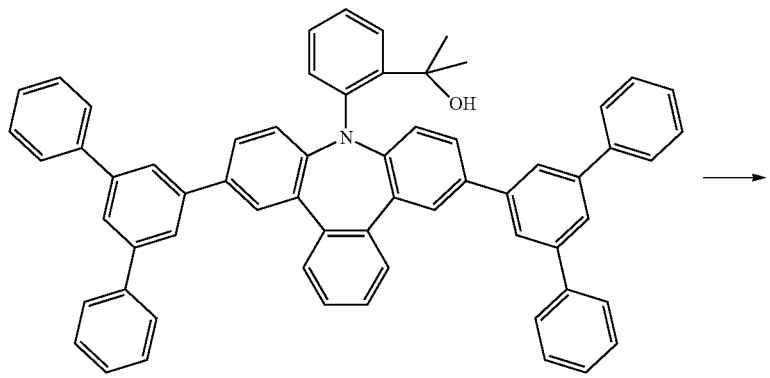
Molecular weight = 834.08
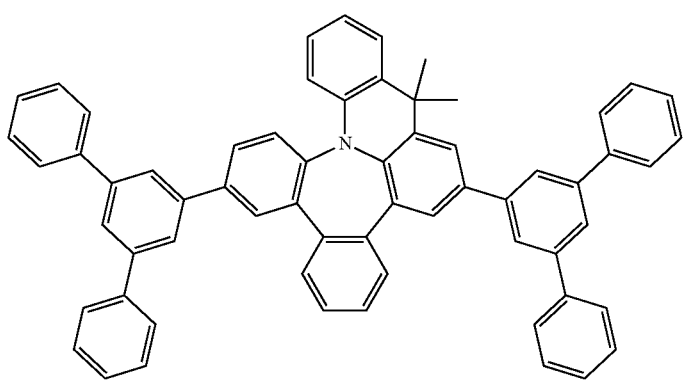
Molecular weight = 816.07

36 g (43.6 mmol) of 2-[2-(6,12-bis-[1,1';3',1'']terphenyl-5''-yl-9-azatribenzo[a,c,e]cyclohepten-9-yl)phenyl]propan-2-ol are dissolved in 1200 mL of degassed toluene, a suspension of 40 g of polyphosphoric acid and 28 mL of methanesulfonic acid is added and the mixture is heated to 60° C. for 1 h. The mixture is cooled down and admixed with water. A solid precipitates out and is dissolved in CH$_2$Cl$_2$/THF (1:1). The solution is cautiously alkalized with 20% NaOH, and the phases are separated and dried over MgSO$_4$. The residue is subjected to hot extraction with toluene, recrystallized from toluene/heptane (1:2) and finally sublimed under high vacuum. The yield is 28 g (35 mmol), 81% of theory.

In an analogous manner, it is possible to obtain the following compounds:

| Example | Reactant 1 |
|---|---|
| f1 | 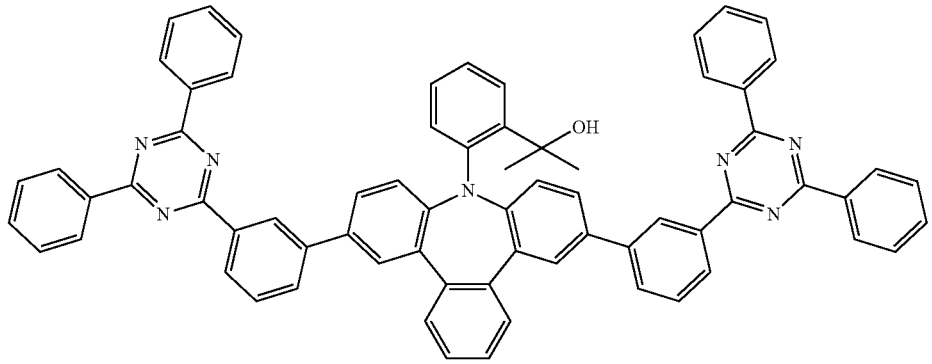 [SMILES: CC(C)(O)c1ccccc1N1c2ccc(-c3cccc(-c4nc(-c5ccccc5)nc(-c5ccccc5)n4)c3)cc2-c2ccccc2-c2cc(-c3cccc(-c4nc(-c5ccccc5)nc(-c5ccccc5)n4)c3)ccc21] |
| f2 | 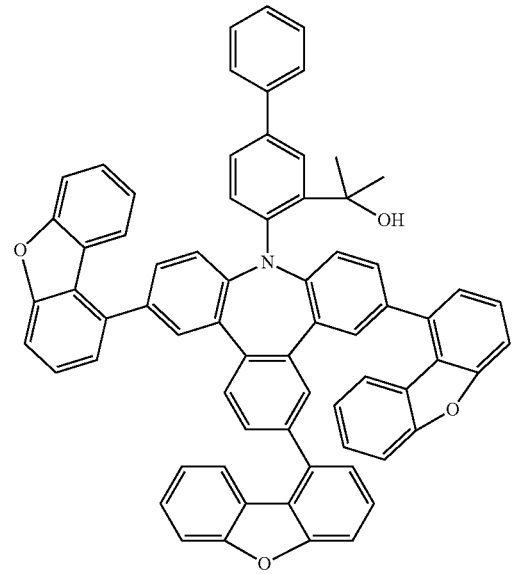 [SMILES: CC(C)(O)c1cc(-c2ccccc2)ccc1N1c2ccc(-c3cccc4oc5ccccc5c34)cc2-c2ccc(-c3cccc4oc5ccccc5c34)cc2-c2cc(-c3cccc4oc5ccccc5c34)ccc21] |

| Example | Product | Yield |
|---|---|---|
| f1 | 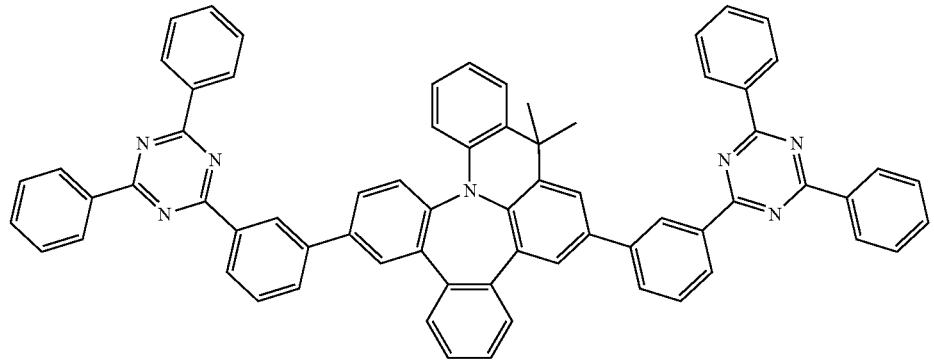 [SMILES: CC1(C)c2ccccc2N2c3ccc(-c4cccc(-c5nc(-c6ccccc6)nc(-c6ccccc6)n5)c4)cc3-c3ccccc3-c3cc(-c4cccc(-c5nc(-c6ccccc6)nc(-c6ccccc6)n5)c4)cc1c32] | 73% |

| | |
|---|---|
| f2 | 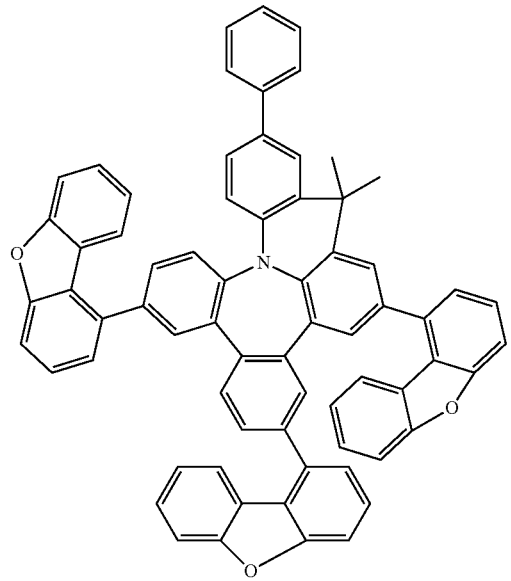 [SMILES: CC1(C)c2cc(-c3ccccc3)ccc2N2c3ccc(-c4cccc5oc6ccccc6c45)cc3-c3ccc(-c4cccc5oc6ccccc6c45)cc3-c3cc(-c4cccc5oc6ccccc6c45)cc1c32] 72% | g) 8-Chloro-9-(2-nitrophenyl)-9H-9-azatribenz[b,d,f]azapine

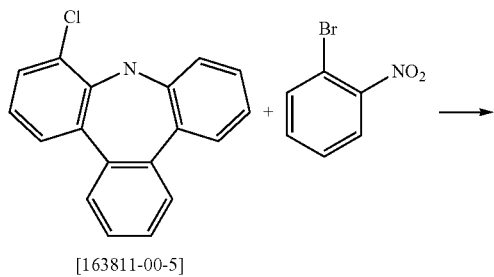

[163811-00-5]

-continued

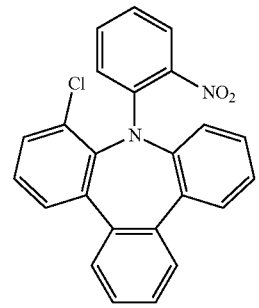

Under protective gas, 24.6 g (89 mmol) of 8-chloro-9H-9-azatribenz[b,d,f]azapine, 17.9 g (89 mmol) of 1,2-bromonitrobenzene and 0.8 g (0.88 mmol) of tris(dibenzylideneacetone)dipalladium, 1.79 g (7.9 mmol) of palladium acetate are suspended in 500 mL of toluene. The reaction mixture is heated under reflux for 8 h. After cooling, the organic phase is removed, washed three times with 200 mL of water and then concentrated to dryness. The purity is 87%. Yield: 25.5 g (63 mmol), 72% of theory.

The following compounds are prepared in an analogous manner:

| | Reactant 1 | Reactant 2 |
|---|---|---|
| g1 | 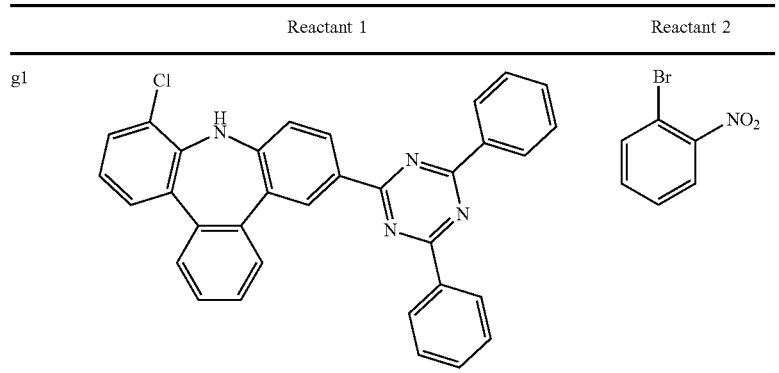 | | g2 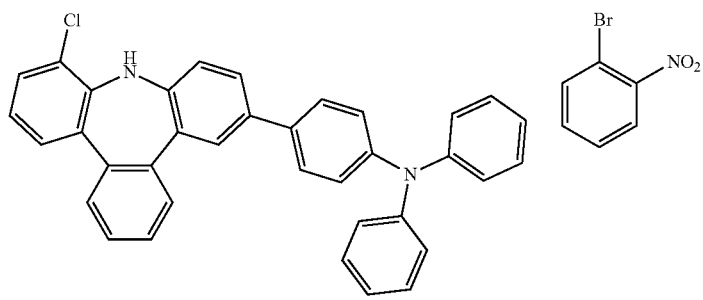
g3 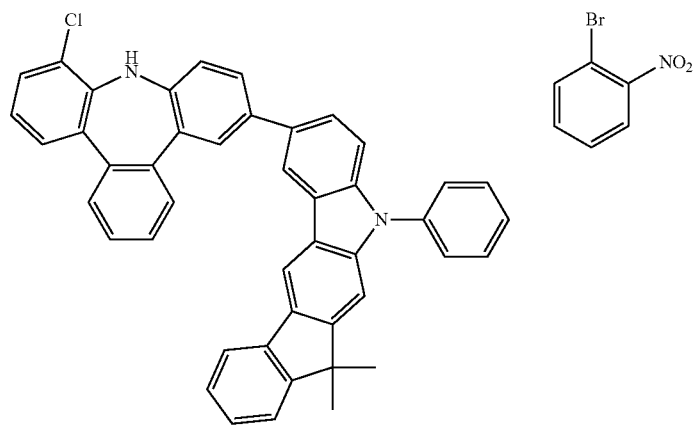
g4 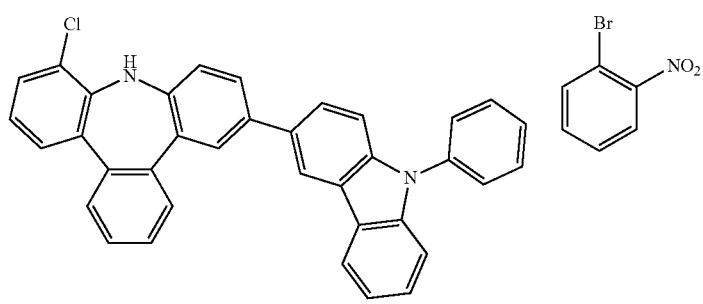
g5 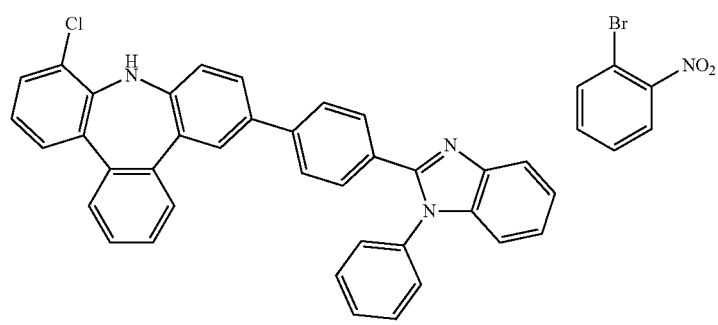

| | | |
|---|---|---|
| g6 | 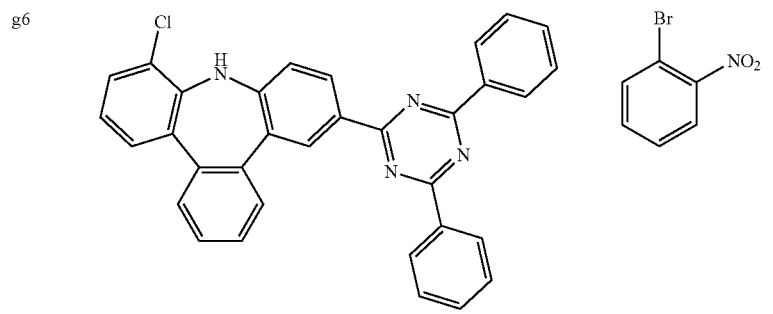 | |
| Product | | Yield |
|---|---|---|
| g1 | 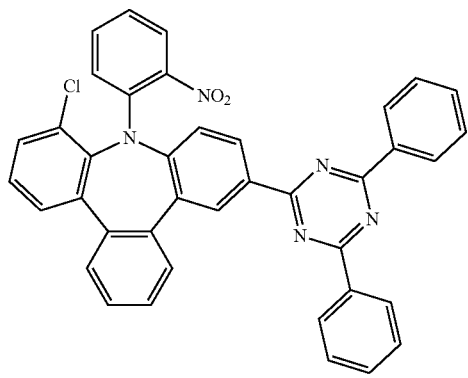 [SMILES: O=[N+]([O-])c1ccccc1N1c2ccc(-c3nc(-c4ccccc4)nc(-c4ccccc4)n3)cc2-c2ccccc2-c2cccc(Cl)c21] | 64% |
| g2 | 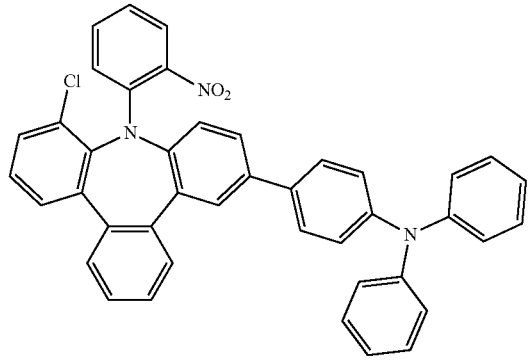 [SMILES: O=[N+]([O-])c1ccccc1N1c2ccc(-c3ccc(N(c4ccccc4)c4ccccc4)cc3)cc2-c2ccccc2-c2cccc(Cl)c21] | 78% |
| g3 | 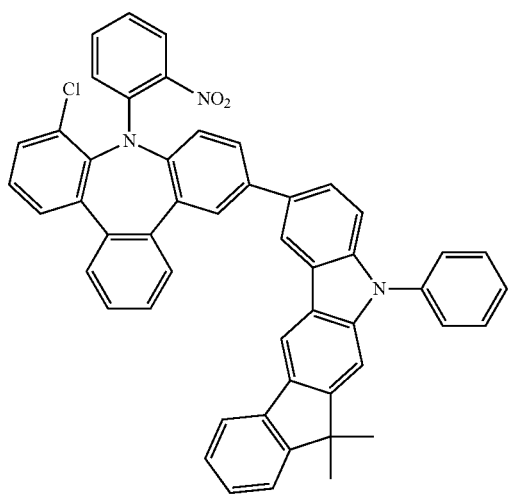 [SMILES: CC1(C)c2ccccc2-c2cc3c4cc(-c5ccc6c(c5)-c5ccccc5-c5cccc(Cl)c5N6c5ccccc5[N+](=O)[O-])ccc4n(-c4ccccc4)c3cc21] | |

| g4 | 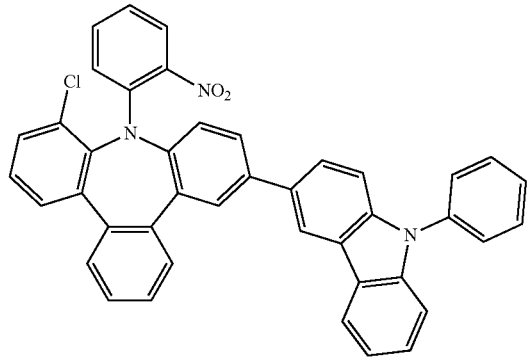 [SMILES: O=[N+]([O-])c1ccccc1N1c2ccc(-c3ccc4c(c3)c3ccccc3n4-c3ccccc3)cc2-c2ccccc2-c2cccc(Cl)c21] |
|---|---|
| g5 | 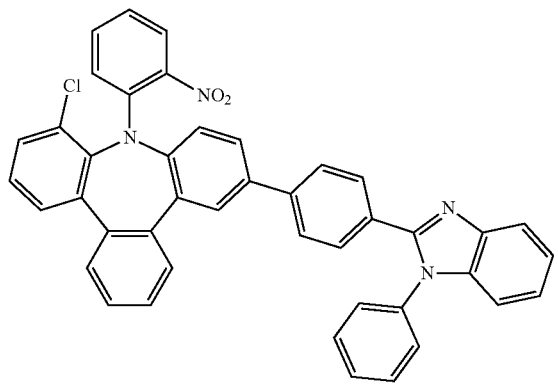 [SMILES: O=[N+]([O-])c1ccccc1N1c2ccc(-c3ccc(-c4nc5ccccc5n4-c4ccccc4)cc3)cc2-c2ccccc2-c2cccc(Cl)c21] |
| g6 | 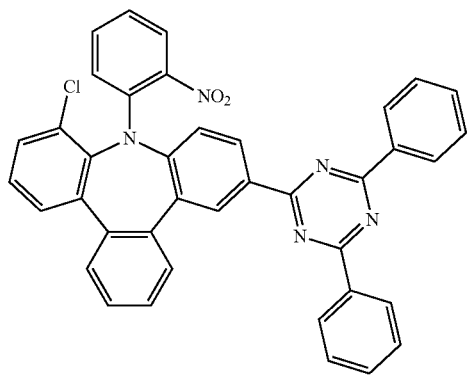 [SMILES: O=[N+]([O-])c1ccccc1N1c2ccc(-c3nc(-c4ccccc4)nc(-c4ccccc4)n3)cc2-c2ccccc2-c2cccc(Cl)c21] |
h) 2-(8-Chloro-9H-9-azatribenz[b,d,f]azapinyl)phenylamine
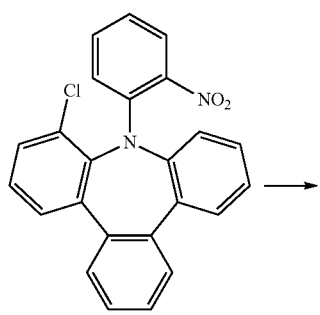 → 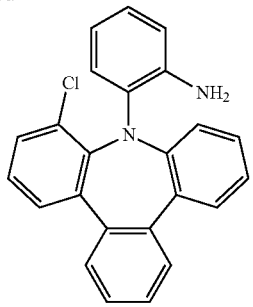
16.7 g (42 mmol) of 8-chloro-9-(2-nitrophenyl)-9H-9-azatribenz[b,d,f]azapine are suspended in 200 mL of ethanol. While stirring at 60° C., 26 g (140 mmol) of SnCl₂ dissolved in 25 mL of concentrated HCl are added in portions and the mixture is boiled under reflux for 8 h. Thereafter, the precipitate is filtered off and dried under reduced pressure. The purity is 90%. Yield: 14.2 g (38 mmol), 92% of theory.

In an analogous manner, it is possible to obtain the following compounds:

| | Reactant 1 | Product | Yield |
|---|---|---|---|
| h1 | | | 71% |
| h2 | | | 73% |
| h3 | | | 70% |

-continued
| | Reactant 1 | Product | Yield |
|---|---|---|---|
| h4 | | | 74% |
| h5 | | | 78% |
| h6 | | | 72% |
i) Cyclization
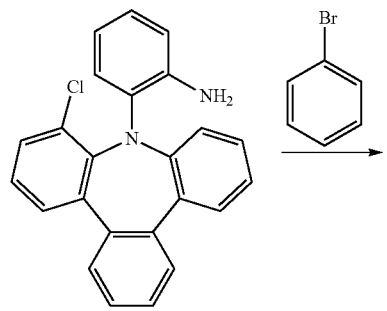
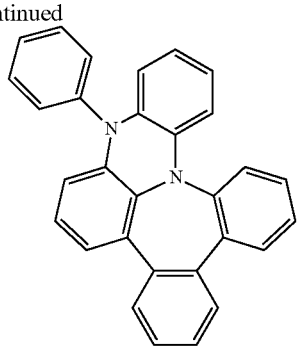
Under protective gas, 9.9 g (27 mmol) of 2-(8-chloro-9H-9-azatribenz[b,d,f]azapinyl)phenylamine, 0.24 g (0.26 mmol) of tris(dibenzylideneacetone)dipalladium, 0.53 g (2.37 mmol) of palladium acetate are suspended in 150 mL of toluene. The reaction mixture is heated under reflux for 8 h. Subsequently, 4 g (26 mmol) of 4-bromobenzene and are added and the mixture is boiled under reflux for a further 8 h. After cooling, the organic phase is removed, washed three times with 80 mL of water and then concentrated to dryness. The residue is subjected to hot extraction with toluene, recrystallized from toluene/heptane (1:2) and finally sublimed under high vacuum. The purity is 99.9% by HPLC. Yield: 7.9 g (19.4 mmol), 72% of theory.

The following compounds: are prepared in an analogous manner:

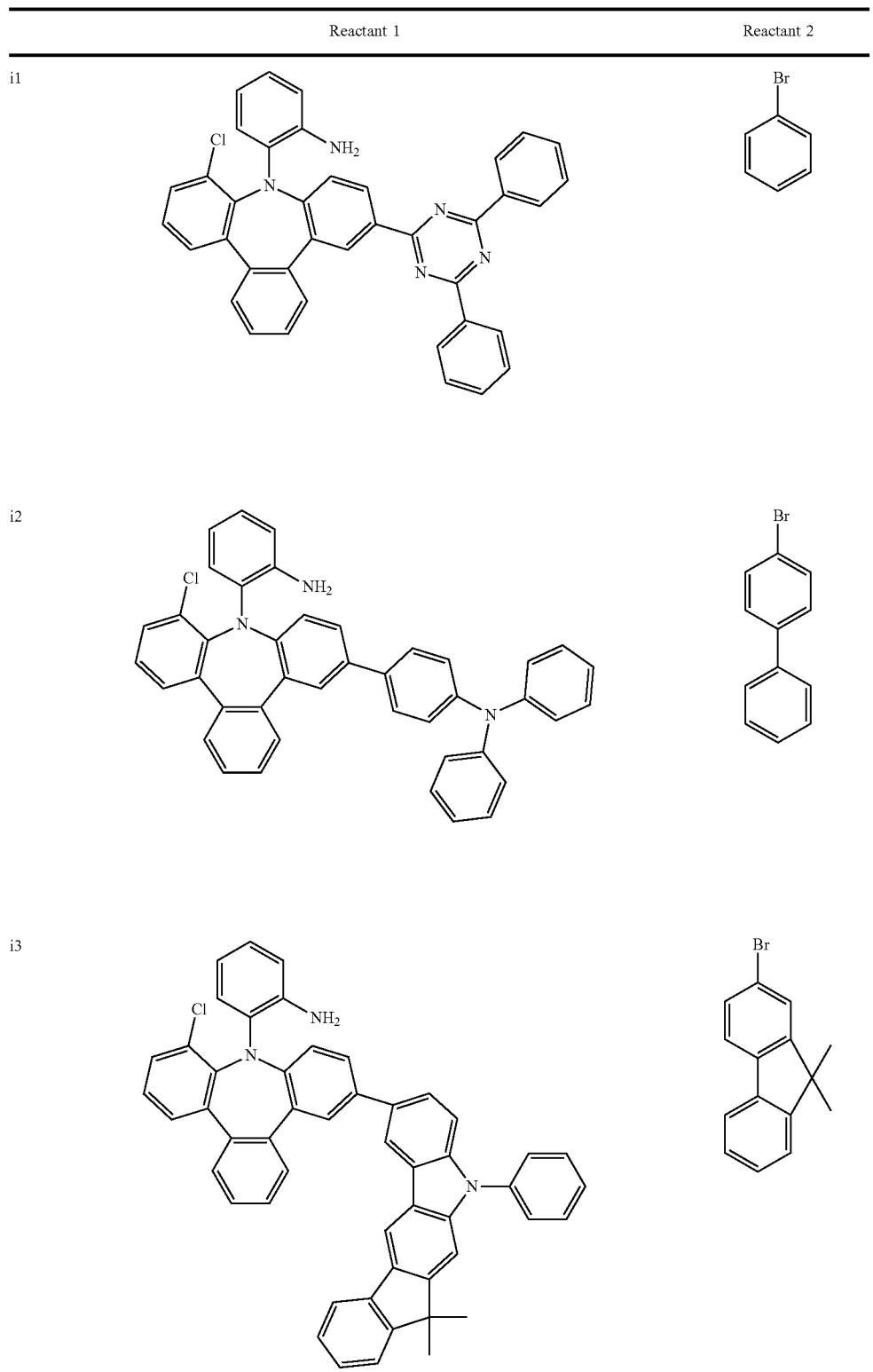

-continued
| | | |
|---|---|---|
| i4 | 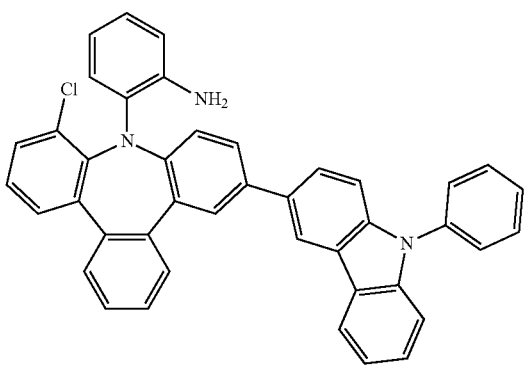 [SMILES: Nc1ccccc1N1c2ccc(-c3ccc4c(c3)c3ccccc3n4-c3ccccc3)cc2-c2ccccc2-c2cccc(Cl)c21] | 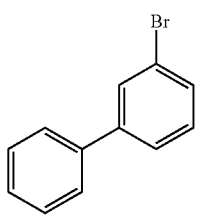 |
| i5 | 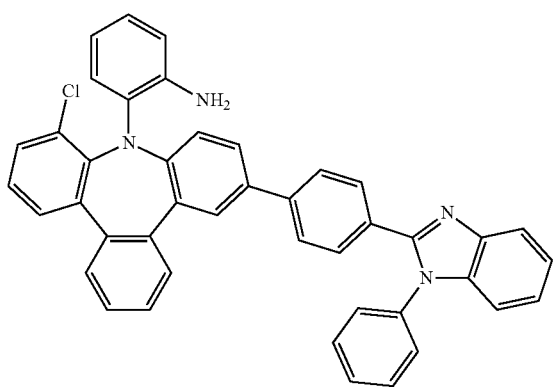 | 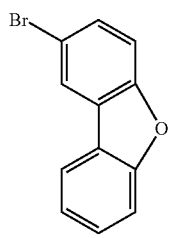 |
| i6 | 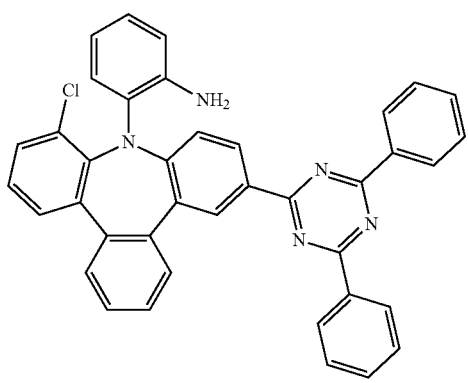 [SMILES: Nc1ccccc1N1c2ccc(-c3nc(-c4ccccc4)nc(-c4ccccc4)n3)cc2-c2ccccc2-c2cccc(Cl)c21] | 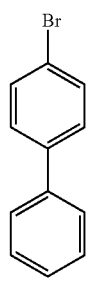 [SMILES: Brc1ccc(-c2ccccc2)cc1] |
| | Product | Yield |
|---|---|---|
| i1 | 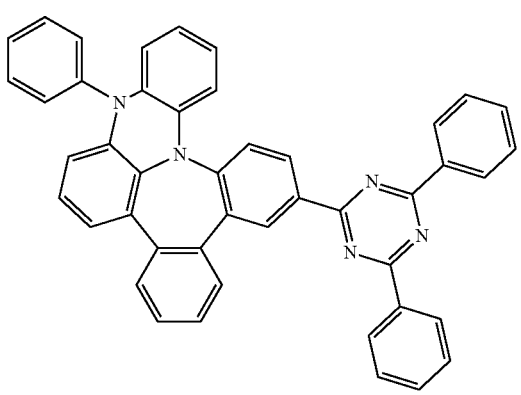 [SMILES: c1ccc(-c2nc(-c3ccccc3)nc(-c3ccc4c(c3)-c3ccccc3-c3cccc5c3N4c3ccccc3N5c3ccccc3)n2)cc1] | 60% | i2 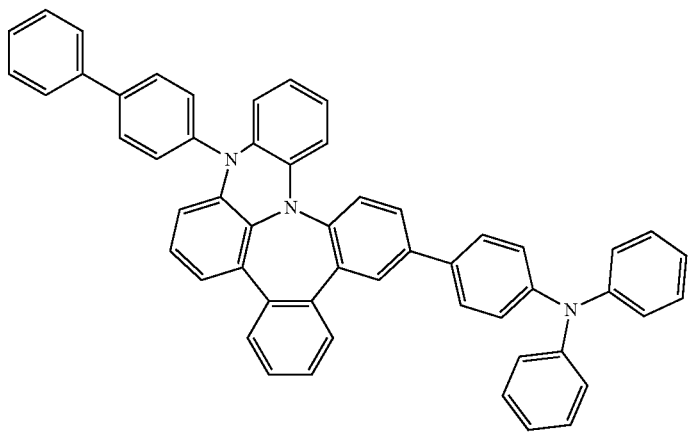 [SMILES: c1ccc(-c2ccc(N3c4ccccc4N4c5ccc(-c6ccc(N(c7ccccc7)c7ccccc7)cc6)cc5-c5ccccc5-c5cccc3c54)cc2)cc1] 67%
i3 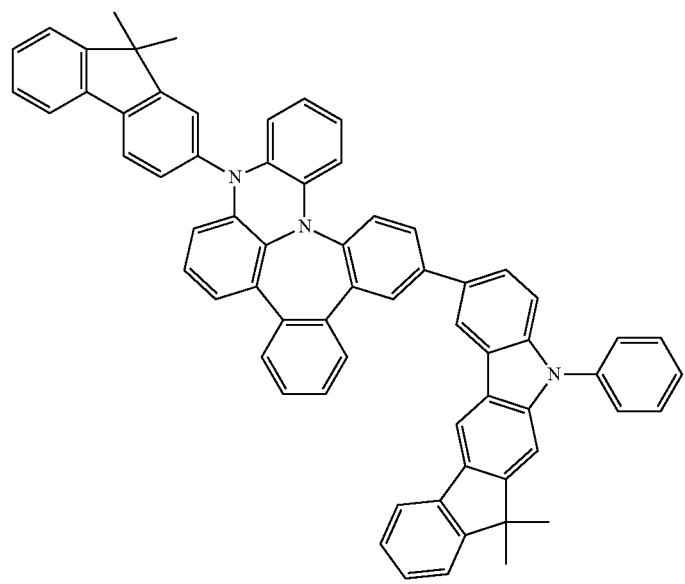 [SMILES: CC1(C)c2ccccc2-c2ccc(N3c4ccccc4N4c5ccc(-c6ccc7c(c6)c6cc8c(cc6n7-c6ccccc6)C(C)(C)c6ccccc6-8)cc5-c5ccccc5-c5cccc3c54)cc21] 69%
i4 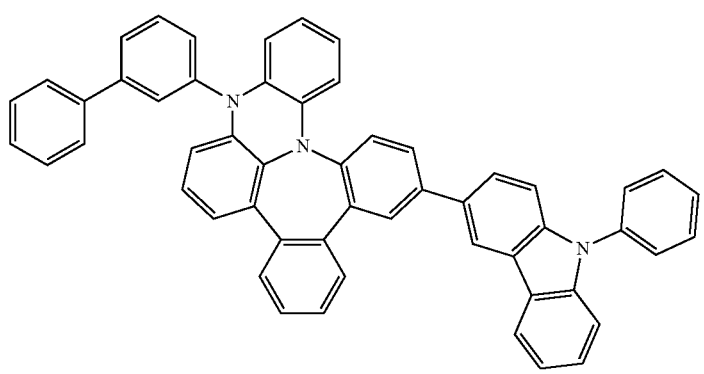 [SMILES: c1ccc(-c2cccc(N3c4ccccc4N4c5ccc(-c6ccc7c(c6)c6ccccc6n7-c6ccccc6)cc5-c5ccccc5-c5cccc3c54)c2)cc1] 68%

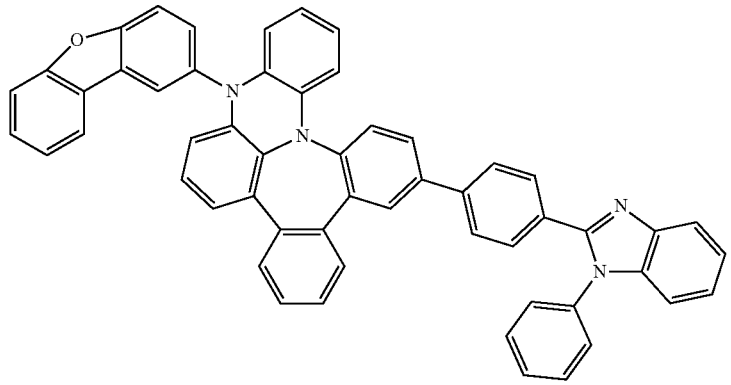 [SMILES: c1ccc(-n2c(-c3ccc(-c4ccc5c(c4)-c4ccccc4-c4cccc6c4N5c4ccccc4N6c4ccc5oc6ccccc6c5c4)cc3)nc3ccccc32)cc1]

i5      65%

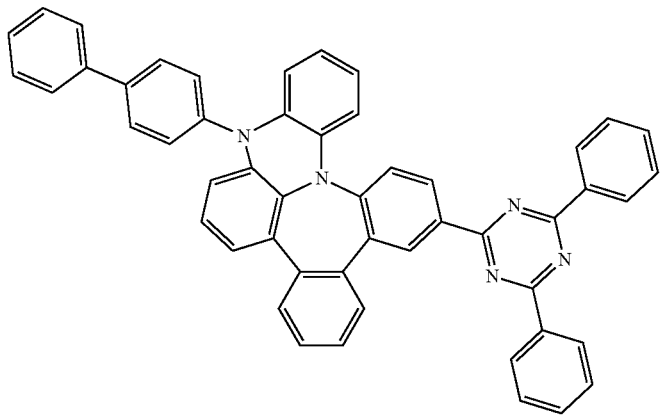 [SMILES: c1ccc(-c2ccc(N3c4ccccc4N4c5ccc(-c6nc(-c7ccccc7)nc(-c7ccccc7)n6)cc5-c5ccccc5-c5cccc3c54)cc2)cc1]

i6      73%

Device Examples

Production of the OLEDs

OLEDs of the invention and OLEDs according to the prior art are produced by a general method according to WO 2004/058911, which is adapted to the circumstances described here (variation in layer thickness, materials).

In examples C1-I6-4 which follow (see tables 1 and 2), the data of various OLEDs are presented. Cleaned glass plaques (cleaning in laboratory glass washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution). These coated glass plaques form the substrates to which the OLEDs are applied.

The OLEDs basically have the following layer structure: substrate/optional hole injection layer (HIL)/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. The materials required for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as ST1:CBP:TER1 (55%:35%:10%) mean here that the material ST1 is present in the layer in a proportion by volume of 55%, CBP in a proportion of 35% and TER1 in a proportion of 10%. Analogously, the electron transport layer may also consist of a mixture of two materials.

The OLEDs are characterized in a standard manner. For this purpose, the electroluminescence spectra, the current efficiency (measured in cd/A) as a function of luminance, calculated from current-voltage-luminance characteristics (IUL characteristics) assuming Lambertian radiation characteristics, and the lifetime are measured. The electroluminescence spectra are determined at a luminance of 1000 cd/m$^2$, and the CIE 1931 x and y color coordinates are calculated therefrom. The parameter U1000 in Table 2 refers to the voltage which is required for a luminance of 1000 cd/m$^2$. CE1000 denotes the current efficiency which is achieved at 1000 cd/m$^2$.

The lifetime LT is defined as the time after which the luminance drops from the starting luminance to a certain proportion L1 in the course of operation with constant current. A figure of L0;j0=4000 cd/m$^2$ and L1=80% in Table X2 means that the lifetime reported in the LT column corresponds to the time after which the starting luminance falls from 4000 cd/m$^2$ to 3200 cd/m$^2$. Analogously, L0;j0=20 mA/cm$^2$, L1=80% means that the starting luminance in the course of operation at 20 mA/cm$^2$ falls to 80% of its starting value after the time LT.

The values for the lifetime can be converted to a figure for other starting luminances with the aid of conversion formulae known to those skilled in the art. In this context, the lifetime for a starting luminance of 1000 cd/m² is a standard figure.

The data for the various OLEDs are collated in Table 2. Examples C1-C5 are comparative examples according to the prior art; examples I1-I6-4 show data of OLEDs comprising inventive materials.

Some of the examples are elucidated in detail hereinafter, in order to illustrate the advantages of the compounds of the invention. However, it should be pointed out that this is merely a selection of the data shown in Table 2. As can be inferred from the table, even when the compounds of the invention that have not been specifically detailed are used, distinct improvements over the prior art are achieved, in some cases in all parameters, but in some cases only an improvements in efficiency or voltage or lifetime is observed. However, improvement in one of the parameters mentioned is already a significant advance because various applications require optimization with regard to different parameters.

The OLEDs C1-C5 are comparative examples according to the prior art.

Use of Compounds of the Invention as Electron Transport Materials

Through the use of compounds of the invention in the electron transport layer of OLEDs, it is possible to achieve distinct increases in terms of operating voltage, external quantum efficiency and hence in particular power efficiency as well. In addition, improved lifetimes are obtained in the case of phosphorescent dopants.

Use of Compounds of the Invention as Hole Blocker Materials

The use of compounds of the invention on the hole blocker side of OLEDs thus gives significant improvements with regard to operating voltage, power efficiency, lifetime and processing complexity.

Use of Compounds of the Invention as Matrix Materials in Phosphorescent OLEDs

The materials of the invention, when used as matrix materials in phosphorescent OLEDs, thus give significant improvements over the prior art in all parameters, particularly with regard to lifetime and in some cases also in power efficiency.

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | PA4:TEG1 (90%:10%) 30 nm | ST2 10 nm | ST2:LiQ (50%:50%) 30 nm | — |
| C2 | SpA1 70 nm | HATCN 5 nm | SpMA1 90 nm | PA2:TEG1 (90%:10%) 30 nm | ST2 10 nm | ST2:LiQ (50%:50%) 30 nm | — |
| C3 | SpA1 70 nm | HATCN 5 nm | SpMA1 90 nm | PA3:TEG1 (90%:10%) 30 nm | ST2 10 nm | ST2:LiQ (50%:50%) 30 nm | — |
| C4 | SpA1 70 nm | HATCN 5 nm | SpMA1 90 nm | PA4:IC1:TEG1 (45%:45%:10%) 30 nm | ST2 10 nm | ST2:LiQ (50%:50%) 30 nm | — |
| C5 | SpA1 70 nm | HATCN 5 nm | SpMA1 90 nm | PA5:IC1:TEG1 (45%:45%:10%) 30 nm | ST2 10 nm | ST2:LiQ (50%:50%) 30 nm | — |
| I1 | SpA1 70 nm | HATCN 5 nm | SpMA1 90 nm | IV1:TEG1 (90%:10%) 30 nm | ST2 10 nm | ST2:LiQ (50%:50%) 30 nm | — |
| I2 | SpA1 70 nm | HATCN 5 nm | SpMA1 90 nm | IV2:TEG1 (90%:10%) 30 nm | ST2 10 nm | ST2:LiQ (50%:50%) 30 nm | — |
| I3 | SpA1 70 nm | HATCN 5 nm | SpMA1 90 nm | IV3:IC1:TEG1 (45%:45%:10%) 30 nm | ST2 10 nm | ST2:LiQ (50%:50%) 30 nm | — |
| I4 | SpA1 70 nm | HATCN 5 nm | SpMA1 90 nm | IV4:IC1:TEG1 (45%:45%:10%) 30 nm | ST2 10 nm | ST2:LiQ (50%:50%) 30 nm | — |
| I1-1 | SpA1 90 nm | HATCN 5 nm | SpMA1 130 nm | IV1:TER1 (92%:8%) 30 nm | — | ST2:LiQ (50%:50%) 40 nm | — |
| I2-1 | SpA1 90 nm | HATCN 5 nm | SpMA1 130 nm | IV2:TER1 (92%:8%) 30 nm | — | ST2:LiQ (50%:50%) 40 nm | — |
| I5 | SpA1 70 nm | HATCN 5 nm | SpMA1 90 nm | IV5:IC1:TEG1 (45%:45%:10%) 30 nm | ST2 10 nm | ST2:LiQ (50%:50%) 30 nm | — |
| I6 | SpA1 70 nm | HATCN 5 nm | SpMA1 90 nm | IV6:TEG1 (90%:10%) 30 nm | ST2 10 nm | ST2:LiQ (50%:50%) 30 nm | — |
| I7 | SpA1 70 nm | HATCN 5 nm | SpMA1 92 nm | IV7:IC1:TEG1 (45%:45%:10%) 30 nm | ST2 10 nm | ST2:LiQ (50%:50%) 30 nm | — |
| I8 | SpA1 70 nm | HATCN 5 nm | SpMA1 90 nm | IV8:TEG1 (90%:10%) 30 nm | ST2 10 nm | ST2:LiQ (50%:50%) 30 nm | — |
| I6-1 | SpA1 70 nm | HATCN 5 nm | SpMA1 90 nm | IC1:TEG1 (90%:10%) 30 nm | — | IV6 40 nm | LiQ 3 nm |
| I6-2 | SpA1 70 nm | HATCN 5 nm | SpMA1 90 nm | IC1:TEG1 (90%:10%) 30 nm | IC1 10 nm | IV6:LiQ (50%:50%) 30 nm | — |
| I6-3 | SpA1 70 nm | HATCN 5 nm | SpMA1 90 nm | IC1:TEG1 (90%:10%) 30 nm | IV6 10 nm | ST2:LiQ (50%:50%) 30 nm | — |
| I6-4 | HATCN 5 nm | SpMA1 70 nm | SpMA2 15 nm | IV6:L1:TEY1 (45%:45%:10%) 25 nm | — | ST1 45 nm | LiQ 3 nm |

TABLE 2

Data of the OLEDs

| Ex. | U1000 (V) | CE1000 (cd/A) | CIE x/y at 1000 cd/m² | $L_0$; $j_0$ | L1 % | LT (h) |
|---|---|---|---|---|---|---|
| C1 | 3.9 | 51 | 0.33/0.63 | 20 mA/cm² | 80 | 90 |
| C2 | 4.3 | 53 | 0.33/0.62 | 20 mA/cm² | 80 | 105 |
| C3 | 4.4 | 54 | 0.33/0.64 | 20 mA/cm² | 80 | 110 |
| C4 | 3.8 | 58 | 0.32/0.64 | 20 mA/cm² | 80 | 190 |
| C5 | 4.0 | 56 | 0.33 0.64 | 20 mA/cm² | 80 | 170 |

TABLE 2-continued
Data of the OLEDs
| Ex. | U1000 (V) | CE1000 (cd/A) | CIE x/y at 1000 cd/m² | $L_0$; $j_0$ | L1 % | LT (h) |
|---|---|---|---|---|---|---|
| I1 | 3.8 | 52 | 0.33/0.62 | 20 mA/cm² | 80 | 110 |
| I2 | 4.2 | 53 | 0.33/0.62 | 20 mA/cm² | 80 | 130 |
| I3 | 3.7 | 59 | 0.33/0.63 | 20 mA/cm² | 80 | 250 |
| I4 | 3.6 | 58 | 0.32/0.63 | 20 mA/cm² | 80 | 210 |
| I1-1 | 4.3 | 12 | 0.66/0.34 | 4000 cd/m² | 80 | 310 |
| I2-1 | 4.5 | 11 | 0.67/0.34 | 4000 cd/m² | 80 | 320 |
| I5 | 4.1 | 48 | 0.33/0.63 | 20 mA/cm² | 80 | 170 |
| I6 | 3.9 | 50 | 0.33/0.62 | 20 mA/cm² | 80 | 80 |
| I7 | 3.4 | 62 | 0.34/0.63 | 20 mA/cm² | 80 | 190 |
| I8 | 3.8 | 49 | 0.33/0.62 | 20 mA/cm² | 80 | 70 |
| I6-1 | 3.9 | 63 | 0.33/0.63 | 20 mA/cm² | 80 | 125 |
| I6-2 | 4.2 | 60 | 0.34/0.63 | 20 mA/cm² | 80 | 165 |
| I6-3 | 3.6 | 59 | 0.34/0.63 | 20 mA/cm² | 80 | 140 |
| I6-4 | 3.0 | 75 | 0.44/0.55 | 50 mA/cm² | 90 | 80 |
TABLE 3
Structural formulae of the materials for the OLEDs
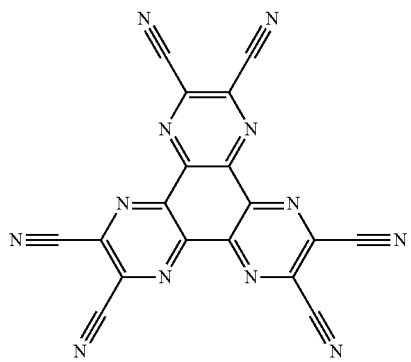 [SMILES: N#Cc1nc2c3nc(C#N)c(C#N)nc3c3nc(C#N)c(C#N)nc3c2nc1C#N]
HATCN
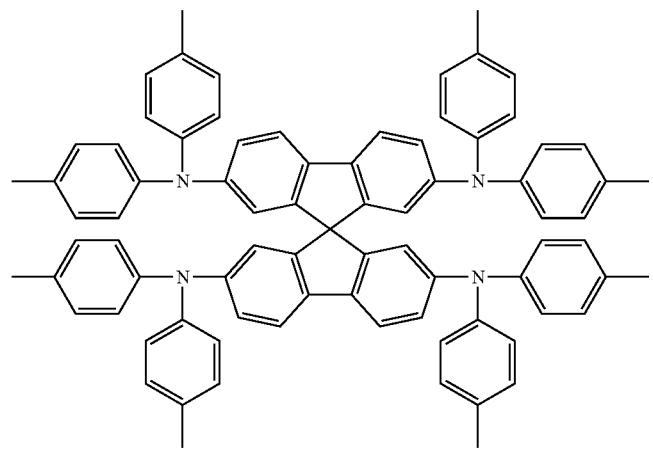
SpA1
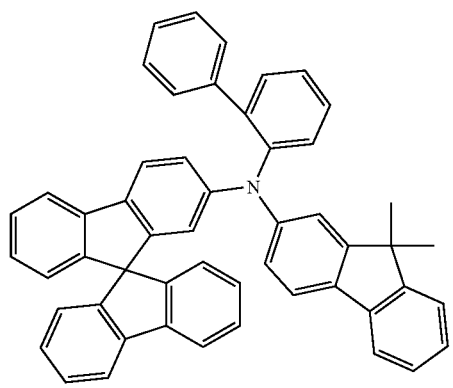 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1

TABLE 3-continued
Structural formulae of the materials for the OLEDs
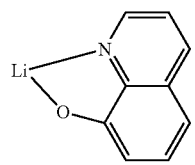
LiQ
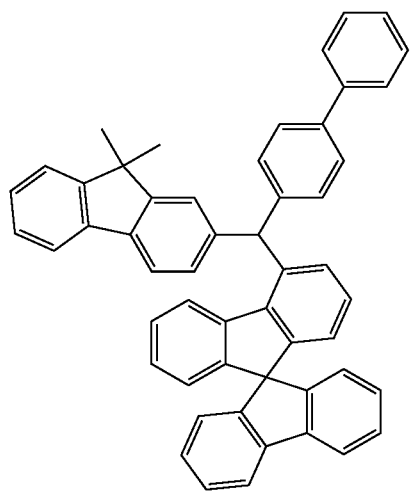 [SMILES: CC1(C)c2ccccc2-c2ccc(C(c3ccc(-c4ccccc4)cc3)c3cccc4c3-c3ccccc3C43c4ccccc4-c4ccccc43)cc21]
SpMA2
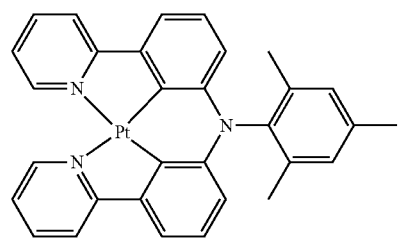
TER1
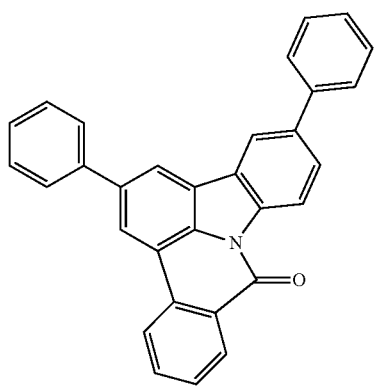 [SMILES: O=c1c2ccccc2c2cc(-c3ccccc3)cc3c4cc(-c5ccccc5)ccc4n1c23]
L1
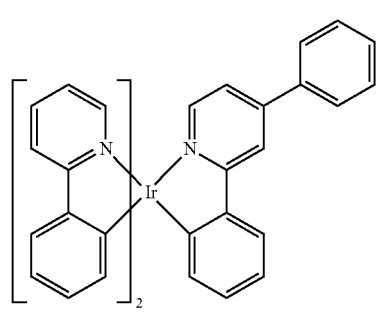
TEY1

TABLE 3-continued
Structural formulae of the materials for the OLEDs
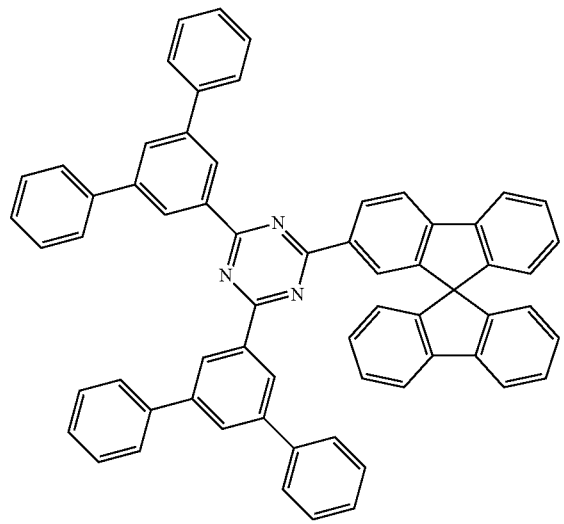 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
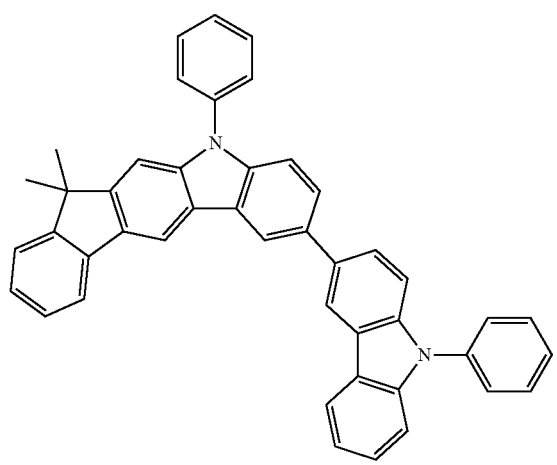 [SMILES: CC1(C)c2ccccc2-c2cc3c4cc(-c5ccc6c(c5)c5ccccc5n6-c5ccccc5)ccc4n(-c4ccccc4)c3cc21]
IC3
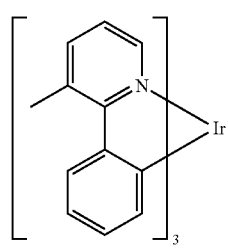
TEG1
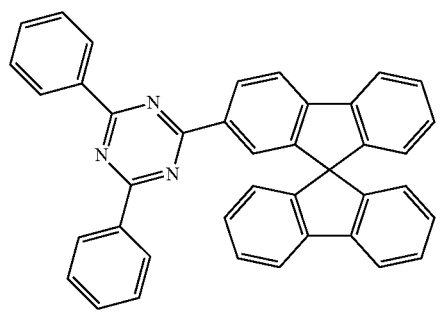 [SMILES: c1ccc(-c2nc(-c3ccccc3)nc(-c3ccc4c(c3)C3(c5ccccc5-c5ccccc53)c3ccccc3-4)n2)cc1]
ST1

TABLE 3-continued
Structural formulae of the materials for the OLEDs
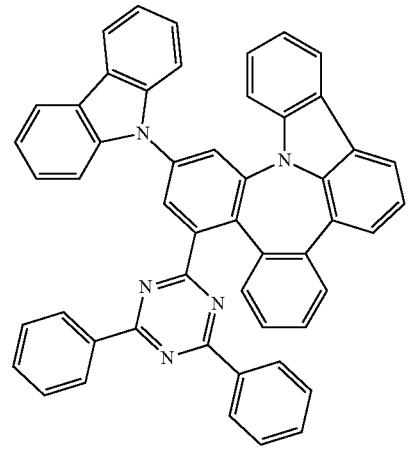 [SMILES: c1ccc(-c2nc(-c3ccccc3)nc(-c3cc(-n4c5ccccc5c5ccccc54)cc4c3-c3ccccc3-c3cccc5c6ccccc6n-4c35)n2)cc1]
PA1
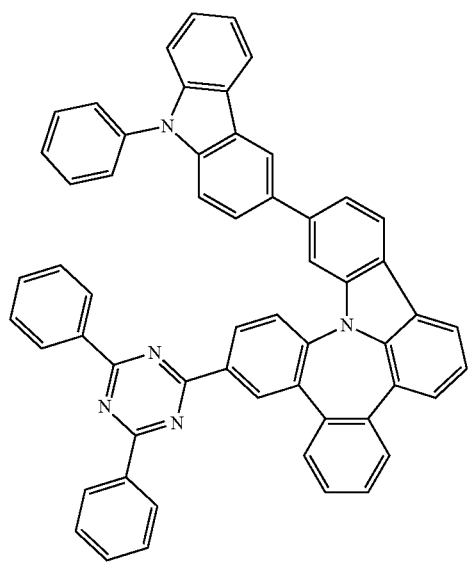 [SMILES: c1ccc(-c2nc(-c3ccccc3)nc(-c3ccc4c(c3)-c3ccccc3-c3cccc5c6ccc(-c7ccc8c(c7)c7ccccc7n8-c7ccccc7)cc6n-4c35)n2)cc1]
PA2
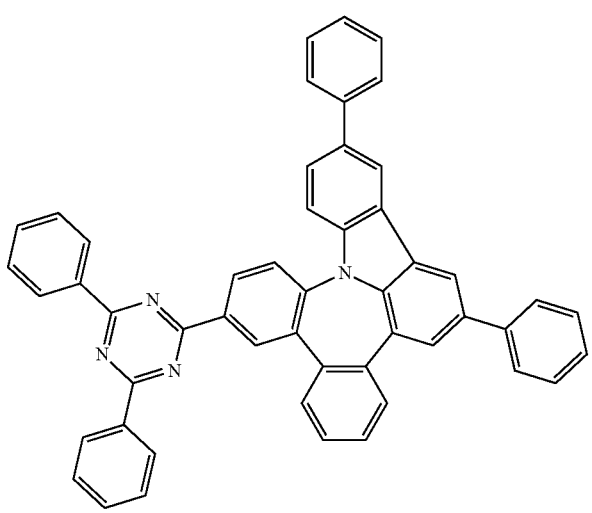 [SMILES: c1ccc(-c2ccc3c(c2)c2cc(-c4ccccc4)cc4c2n3-c2ccc(-c3nc(-c5ccccc5)nc(-c5ccccc5)n3)cc2-c2ccccc2-4)cc1]
PA3

TABLE 3-continued
Structural formulae of the materials for the OLEDs
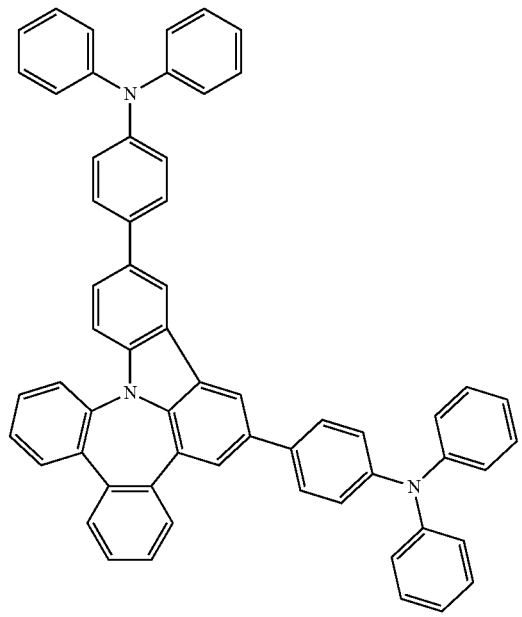 [SMILES: c1ccc(N(c2ccccc2)c2ccc(-c3ccc4c(c3)c3cc(-c5ccc(N(c6ccccc6)c6ccccc6)cc5)cc5c3n4-c3ccccc3-c3ccccc3-5)cc2)cc1]
PA4
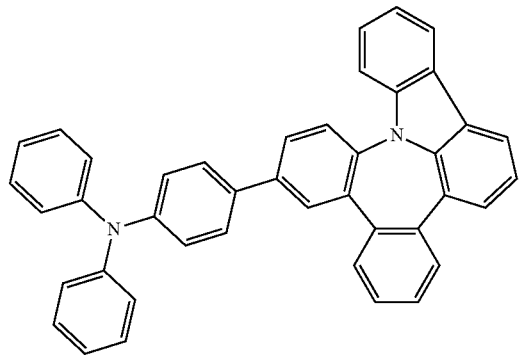 [SMILES: c1ccc(N(c2ccccc2)c2ccc(-c3ccc4c(c3)-c3ccccc3-c3cccc5c6ccccc6n-4c35)cc2)cc1]
PA5
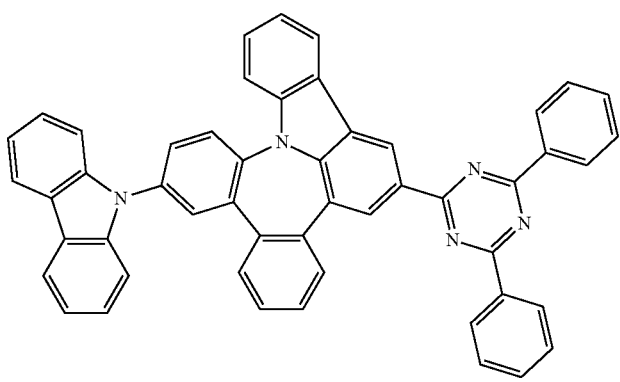 [SMILES: c1ccc(-c2nc(-c3ccccc3)nc(-c3cc4c5c(c3)c3ccccc3n5-c3ccc(-n5c6ccccc6c6ccccc65)cc3-c3ccccc3-4)n2)cc1]
IV1

TABLE 3-continued
Structural formulae of the materials for the OLEDs
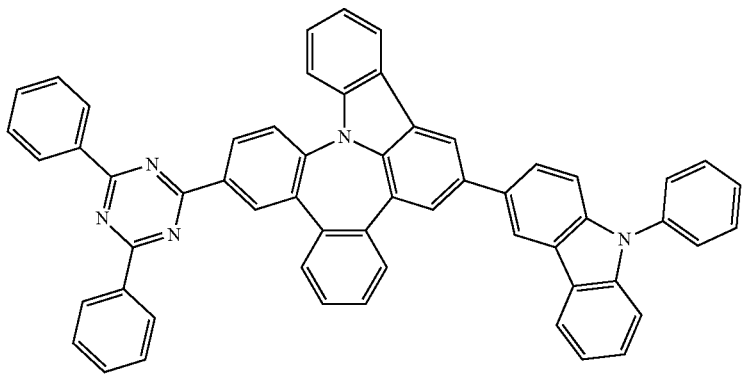 [SMILES: c1ccc(-c2nc(-c3ccccc3)nc(-c3ccc4c(c3)-c3ccccc3-c3cc(-c5ccc6c(c5)c5ccccc5n6-c5ccccc5)cc5c6ccccc6n-4c35)n2)cc1]
IV2
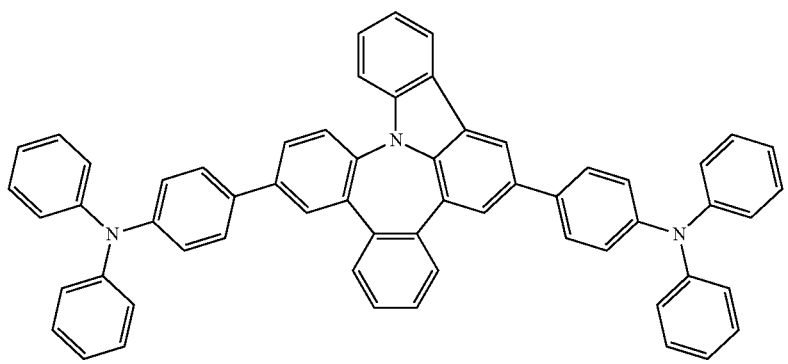 [SMILES: c1ccc(N(c2ccccc2)c2ccc(-c3ccc4c(c3)-c3ccccc3-c3cc(-c5ccc(N(c6ccccc6)c6ccccc6)cc5)cc5c6ccccc6n-4c35)cc2)cc1]
IV3
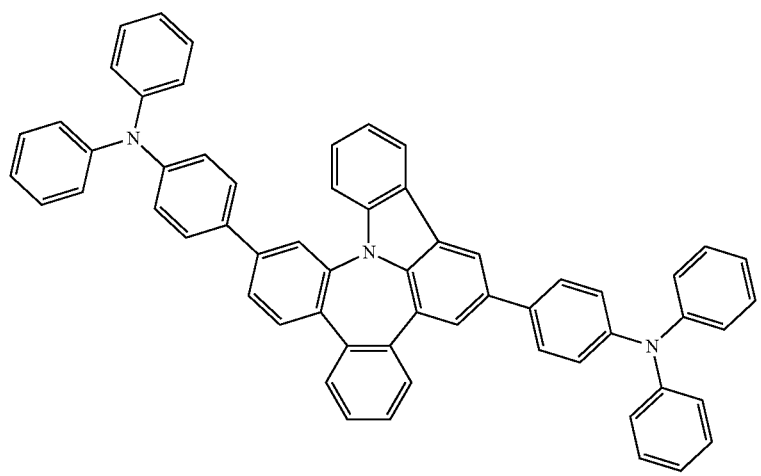 [SMILES: c1ccc(N(c2ccccc2)c2ccc(-c3ccc4c(c3)-n3c5ccccc5c5cc(-c6ccc(N(c7ccccc7)c7ccccc7)cc6)cc(c53)-c3ccccc3-4)cc2)cc1]
IV4
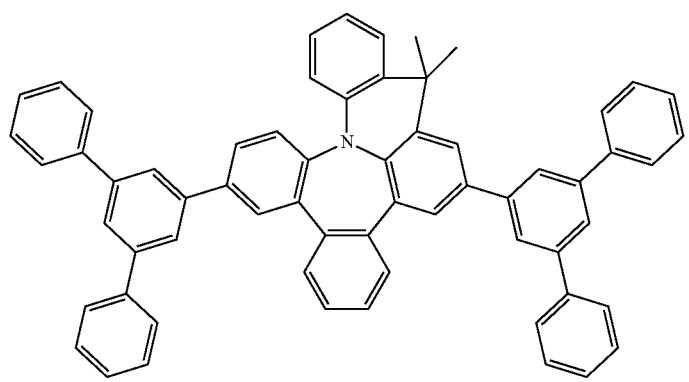 [SMILES: CC1(C)c2ccccc2N2c3ccc(-c4cc(-c5ccccc5)cc(-c5ccccc5)c4)cc3-c3ccccc3-c3cc(-c4cc(-c5ccccc5)cc(-c5ccccc5)c4)cc1c32]
IV5

TABLE 3-continued
Structural formulae of the materials for the OLEDs
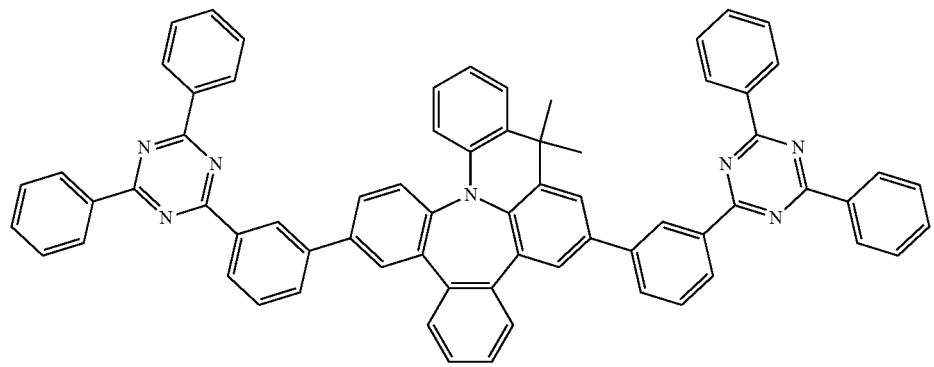 [SMILES: CC1(C)c2ccccc2N2c3ccc(-c4cccc(-c5nc(-c6ccccc6)nc(-c6ccccc6)n5)c4)cc3-c3ccccc3-c3cc(-c4cccc(-c5nc(-c6ccccc6)nc(-c6ccccc6)n5)c4)cc1c32]
IV6
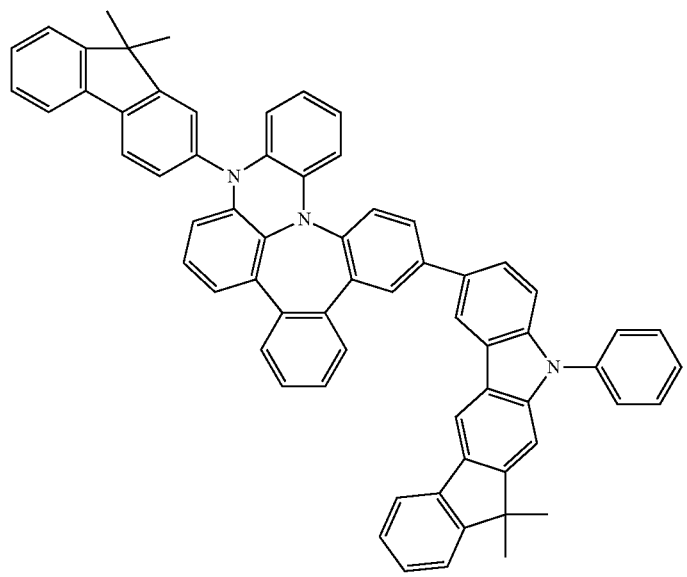 [SMILES: CC1(C)c2ccccc2-c2ccc(N3c4ccccc4N4c5ccc(-c6ccc7c(c6)c6cc8c(cc6n7-c6ccccc6)C(C)(C)c6ccccc6-8)cc5-c5ccccc5-c5cccc3c54)cc21]
IV7
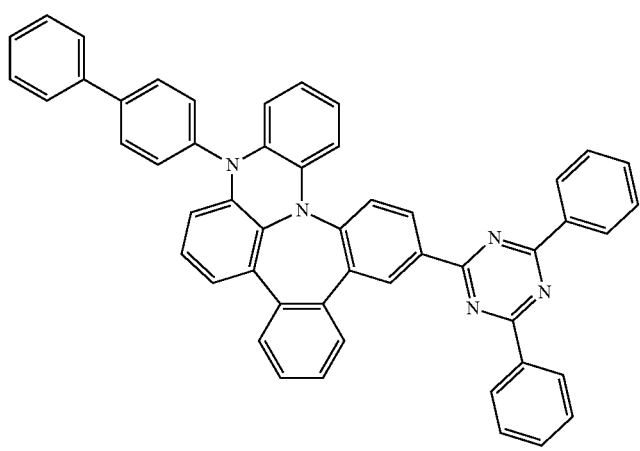 [SMILES: c1ccc(-c2ccc(N3c4ccccc4N4c5ccc(-c6nc(-c7ccccc7)nc(-c7ccccc7)n6)cc5-c5ccccc5-c5cccc3c54)cc2)cc1]
IV8

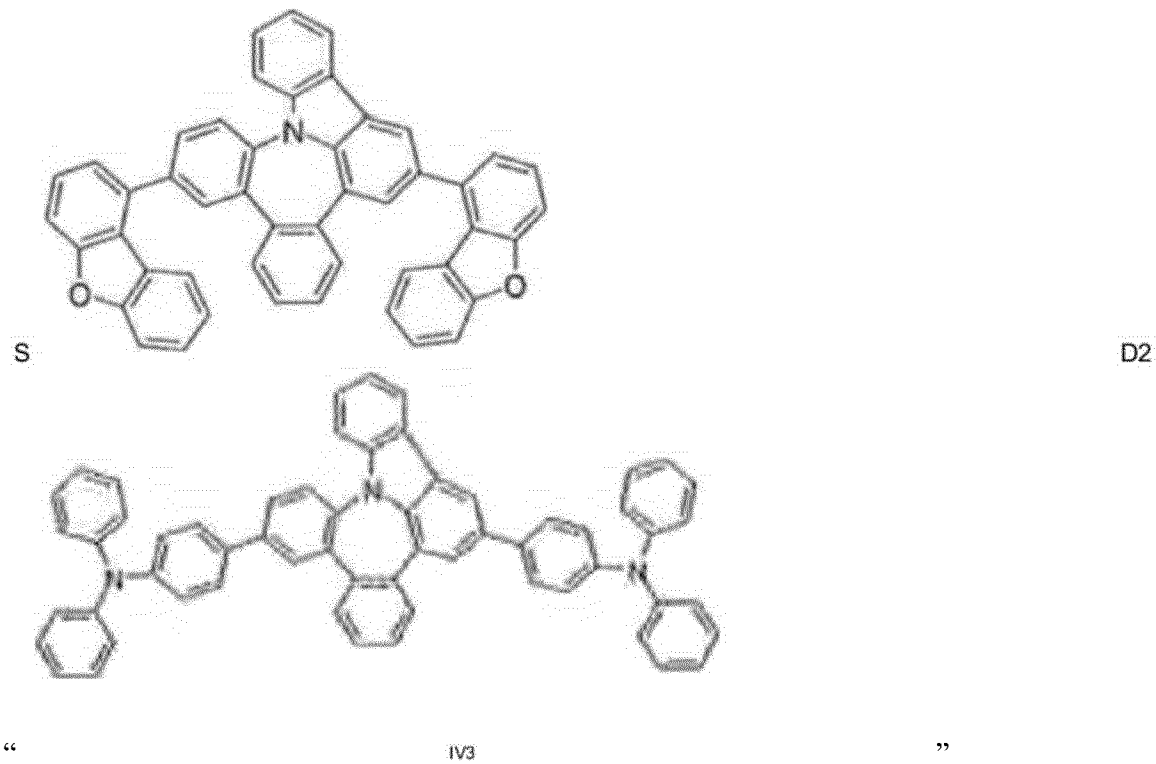

The invention claimed is:
1. A compound of the formula (II)

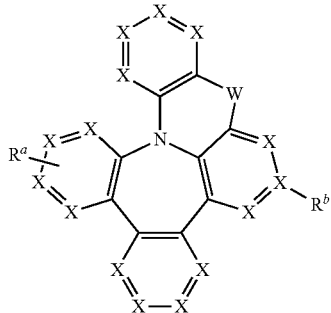

Formula (II)

where the symbols used are as follows:
X is $CR^1$;
W is a bond;
$R^1$ is H;
$R^2$ is the same or different at each instance and is H, D F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $Si(R^3)_2$, $Si(R^2)_2$, $Ge(R^3)_2$, $Sn(R^3)_2$, $C=O$, $C=S$, $C=Se$, $C=NR^3$, $-C(=O)O-$, $-C(=O)NR^3-$, $NR^3$, $P(=O)(R^3)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents together may also form a mono- or polycyclic, aliphatic or aromatic ring system;
$R^3$ is the same or different at each instance and is H, F or an aliphatic, aromatic and/or heteroaromatic hydrocarbyl radical having 1 to 20 carbon atoms, in which hydrogen atoms may also be replaced by F; at the same time, two or more adjacent $R^3$ substituents together may also form a mono- or polycyclic, aliphatic or aromatic ring system;
$R^a$ and $R^b$ are independently an aromatic group having 10 to 40 carbon atoms or a heteroaromatic group having 6 to 40 carbon atoms, where the aromatic and/or heteroaromatic group comprises at least two adjacent aromatic and/or heteroaromatic rings, each of which may be fused or unfused and/or may be substituted by one or more $R^{1'}$ radicals, wherein
$R^{1'}$ is the same or different at each instance and is H, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents together may also form a mono- or polycyclic, aliphatic or aromatic ring system.

2. A compound as claimed in claim 1, wherein the compound is a compound of formula (IV)

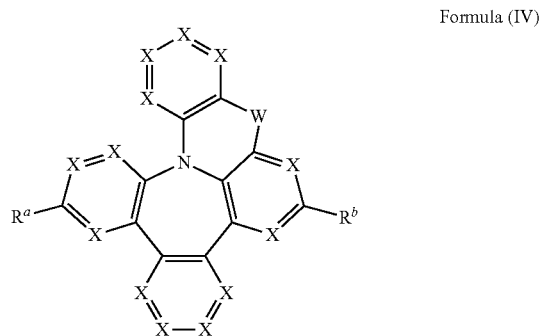

Formula (IV)

where for the symbols used have the definition given in claim 1, and $R^a$ and $R^b$ are selected independently of each other.

3. A compound as claimed in claim 1, wherein at least one of the $R^a$ and/or $R^b$ radicals is a hole transport group or an electron transport group.

4. A compound as claimed in claim 1, wherein the $R^b$ radical in one of the formulae (II), and/or (IV) is a hole transport group and the $R^a$ radical in one of the formulae (II), and/or (IV) is a hole transport group.

5. A compound as claimed in claim 1, wherein the $R^b$ radical in one of the formulae (II), and/or (IV) is an electron transport group and the $R^a$ radical in one of the formulae (II), and/or (IV) is a hole transport group.

6. A compound as claimed in claim 1, wherein the $R^b$ radical in one of the formulae (II), and/or (IV) is a hole transport group and the $R^a$ radical in one of the formulae (II), and/or (IV) is an electron transport group.

7. A compound as claimed in claim 1, wherein the $R^b$ radical in one of the formulae (II), and/or (IV) is an electron transport group and the $R^a$ radical in one of the formulae (II), and/or (IV) is an electron transport group.

8. A compound as claimed in claim 1, wherein, in the structure of formula (I), (II), and/or (IV), at least one $R^a$, and/or $R^b$ radical is a group independently selected from the formulae ($R^1$-2) to ($R^1$-72)

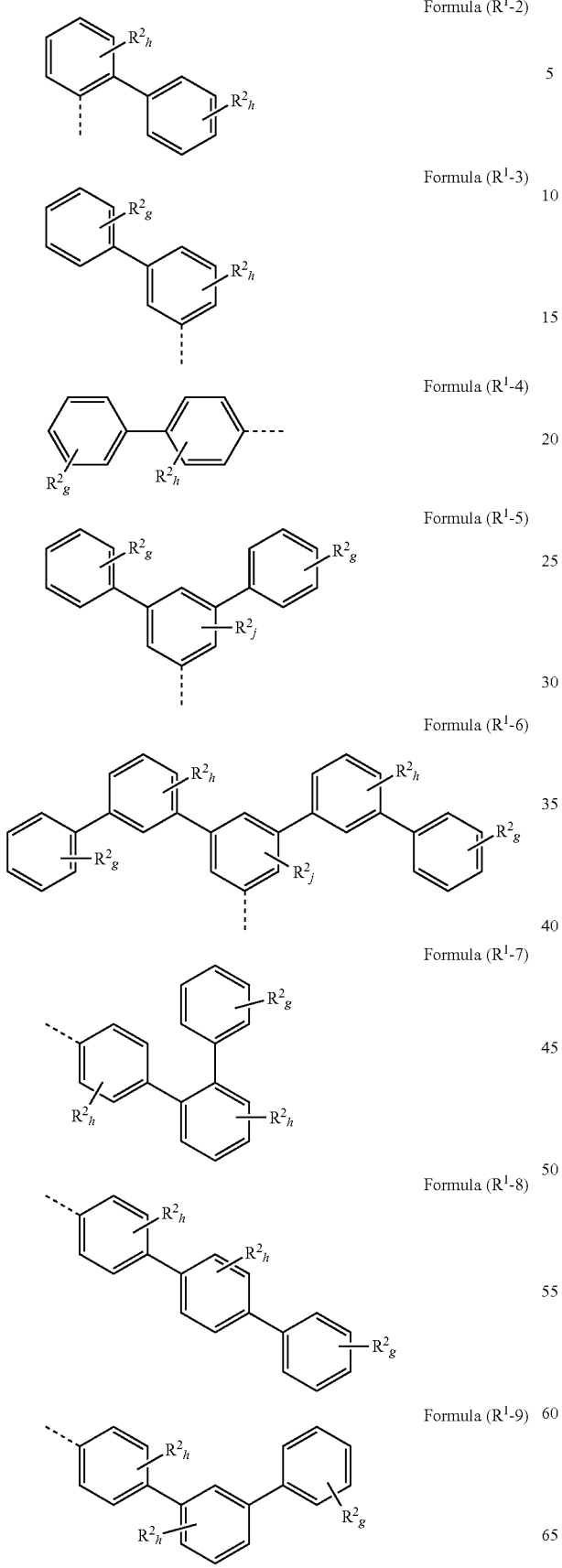
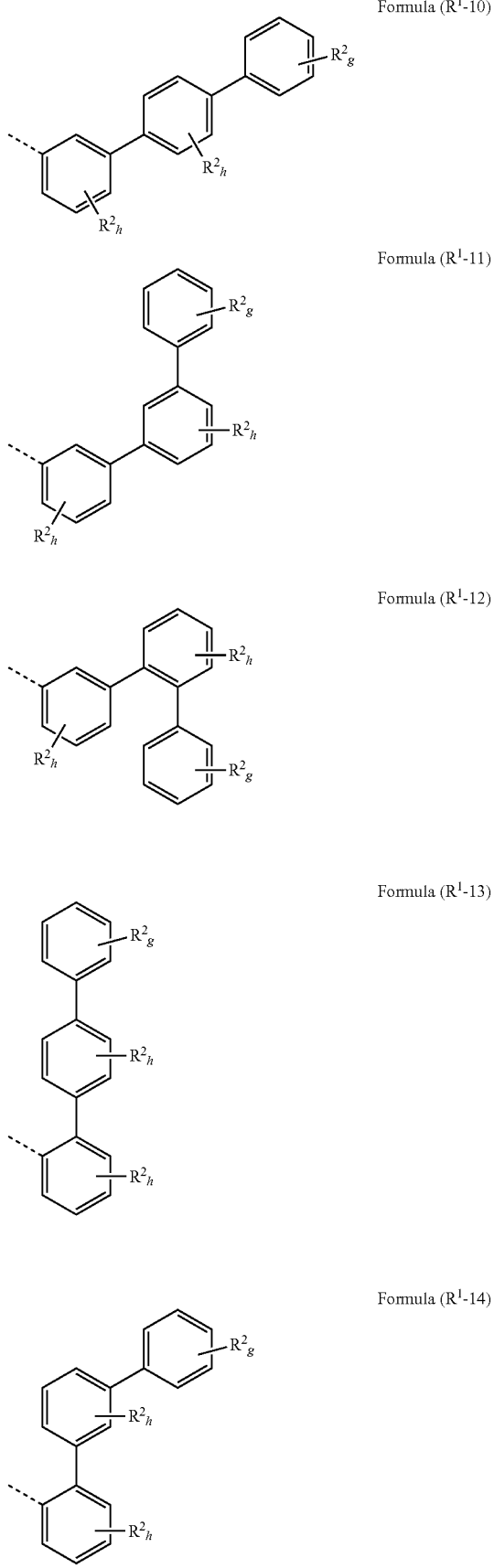

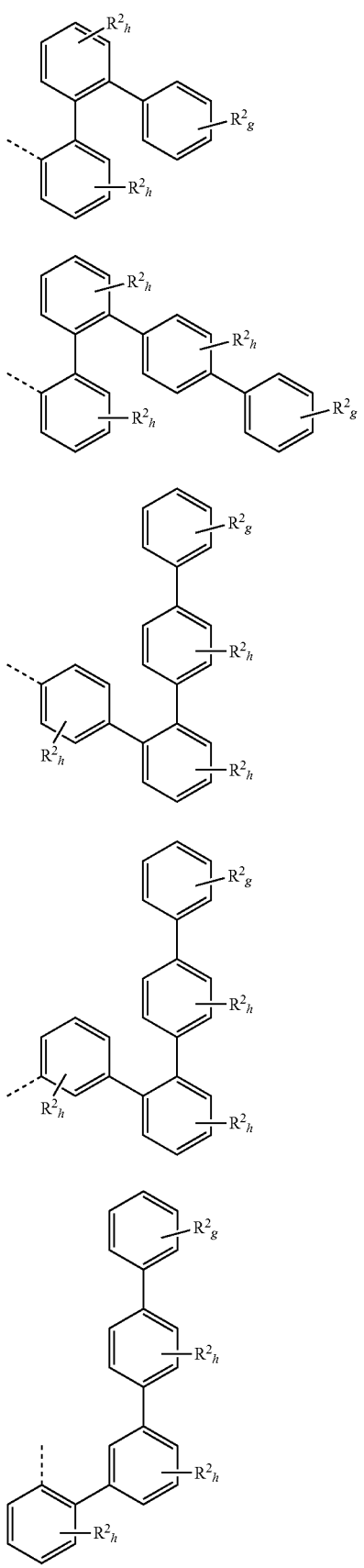
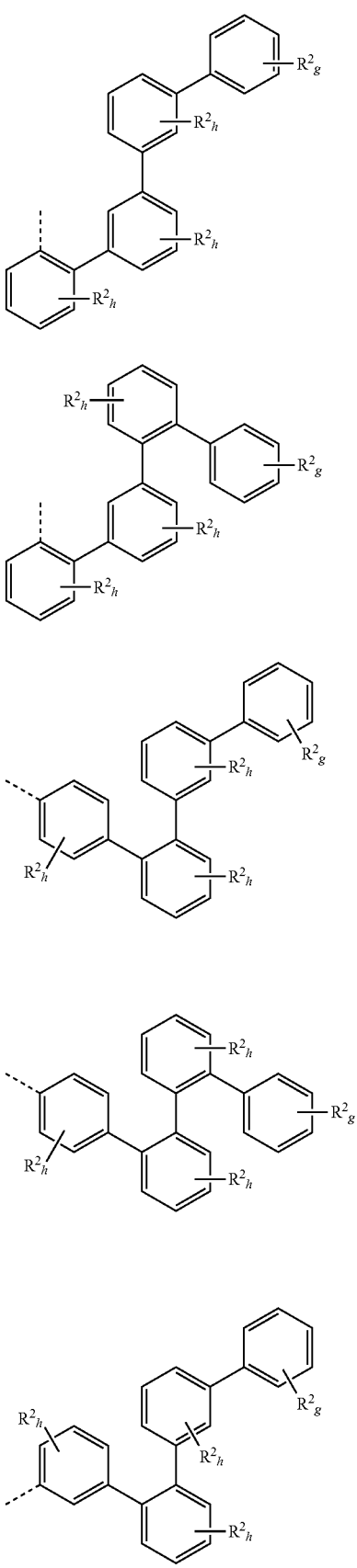

-continued
Formula (R¹-25)
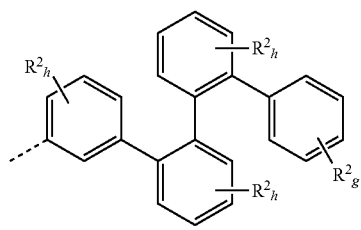
Formula (R¹-26)
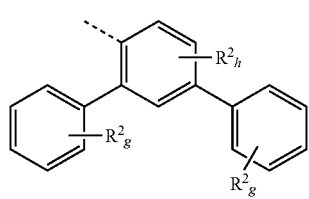
Formula (R¹-27)
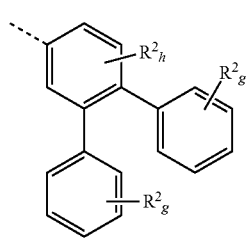
Formula (R¹-28)
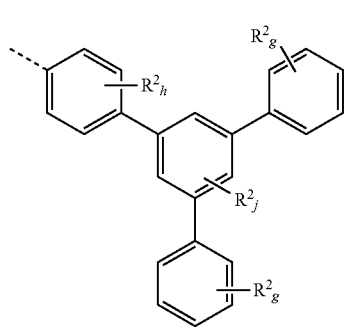
Formula (R¹-29)
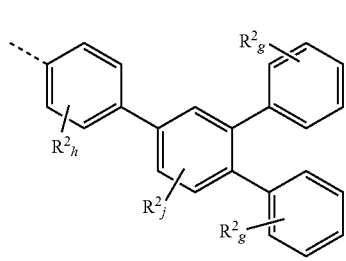
Formula (R¹-30)
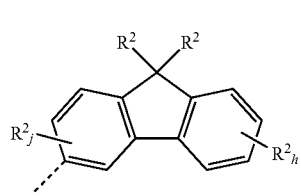
Formula (R¹-31)
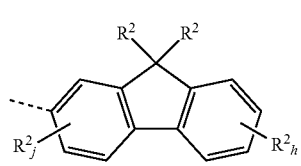
-continued
Formula (R¹-32)
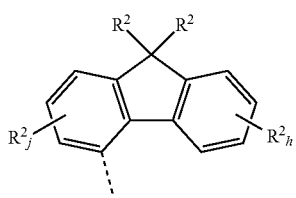
Formula (R¹-33)
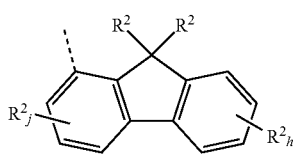
Formula (R¹-34)
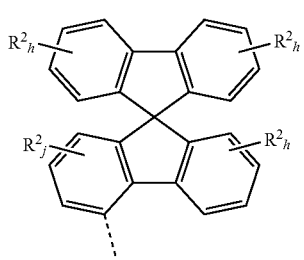
Formula (R¹-35)
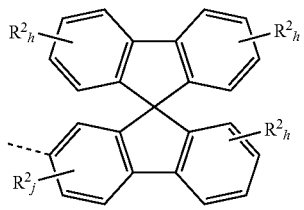
Formula (R¹-36)
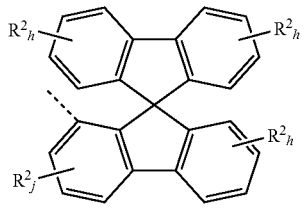
Formula (R¹-37)
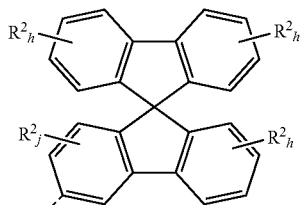
Formula (R¹-38)
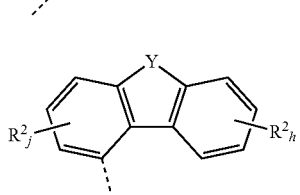
Formula (R¹-39)
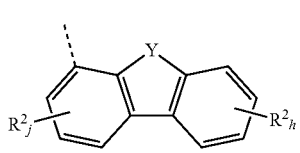

Formula (R¹-40)
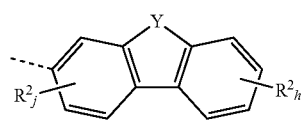
Formula (R¹-41)
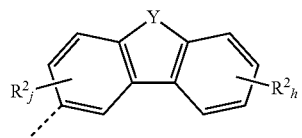
Formula (R¹-42)
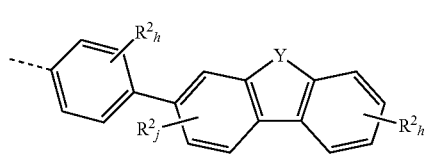
Formula (R¹-43)
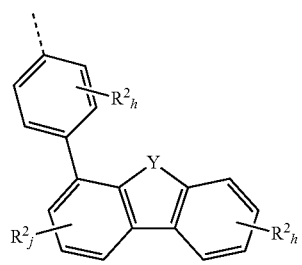
Formula (R¹-44)
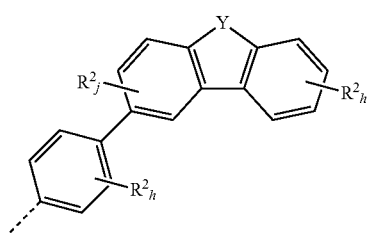
Formula (R¹-45)
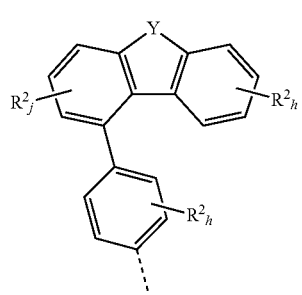
Formula (R¹-46)
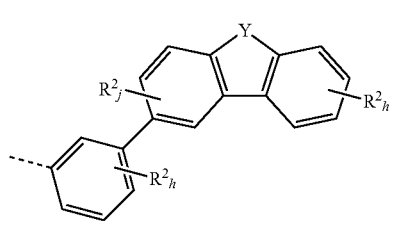
Formula (R¹-47)
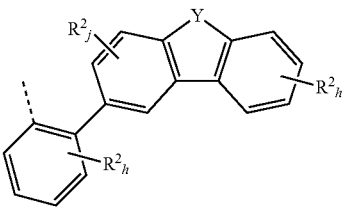
Formula (R¹-48)
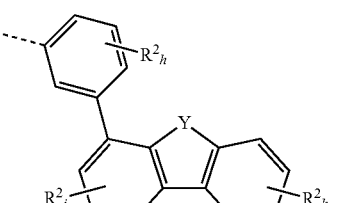
Formula (R¹-49)
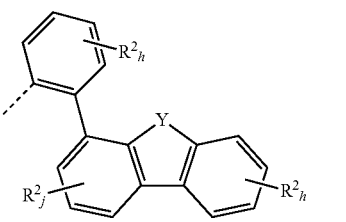
Formula (R¹-50)
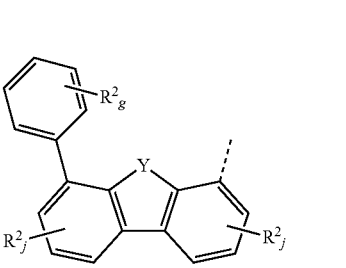
Formula (R¹-51)
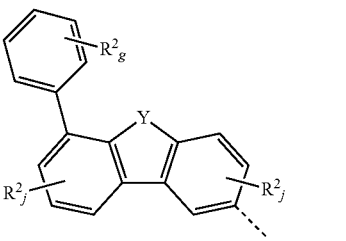
Formula (R¹-52)
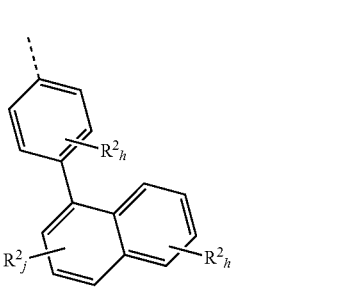

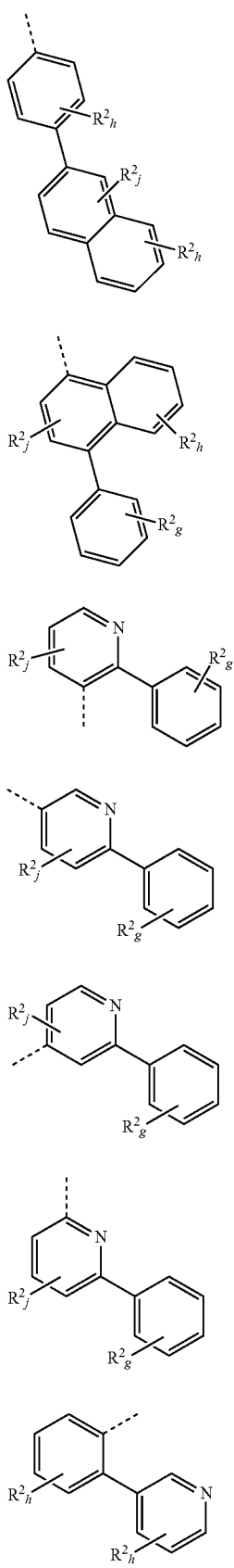

Formula (R¹-68)
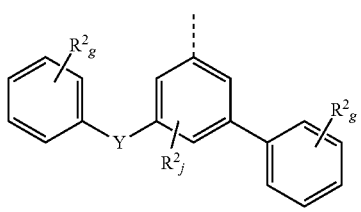

Formula (R¹-69)
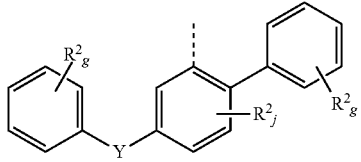

Formula (R¹-70)
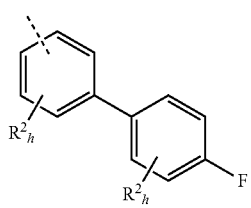

Formula (R¹-71)
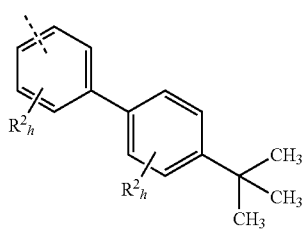

Formula (R¹-72)
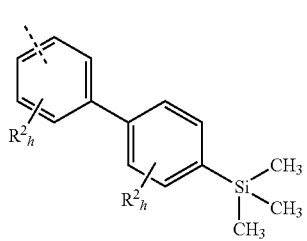

has, where the symbols used are as follows:

Y is O, S or NR²;

j independently at each instance is 0, 1, 2 or 3;

h independently at each instance is 0, 1, 2, 3 or 4;

g independently at each instance is 0, 1, 2, 3, 4 or 5;

the dotted bond marks the attachment position; and

R² is as defined in claim 1.

9. A compound as claimed in claim 8, wherein the sum total of the indices g, h and j in the structures of the formula (R¹-2) to (R¹-72) is at most 3 in each case.

10. A compound as claimed in claim 3, wherein the electron transport group of $R^a$ and/or $R^b$ has independently of each other at least one structure of the formula (E-24) to (E-38)

Formula (E-24)
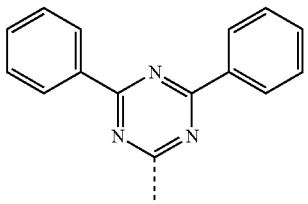

Formula (E-25)
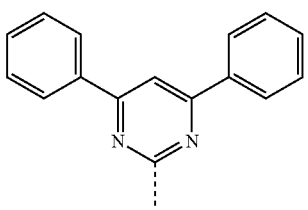

Formula (E-26)
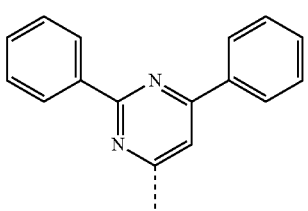

Formula (E-27)
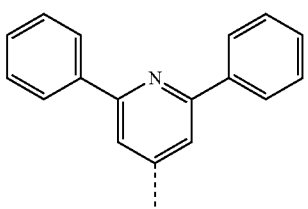

Formula (E-28)
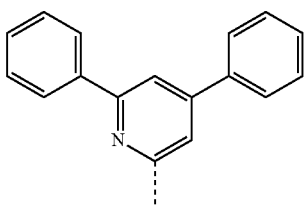

Formula (E-29)
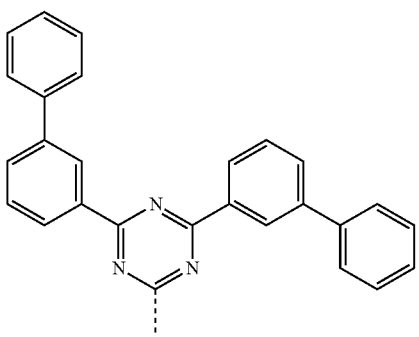

-continued
Formula (E-30)
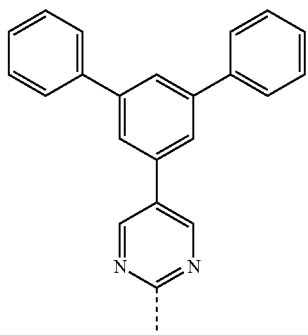
Formula (E-31)
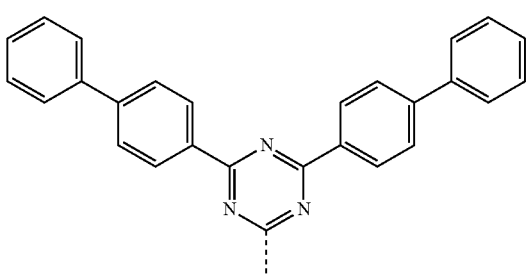
Formula (E-32)
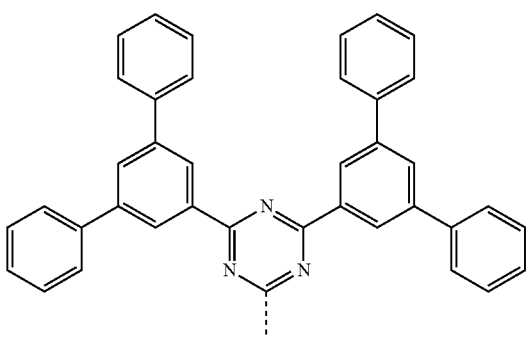
Formula (E-33)
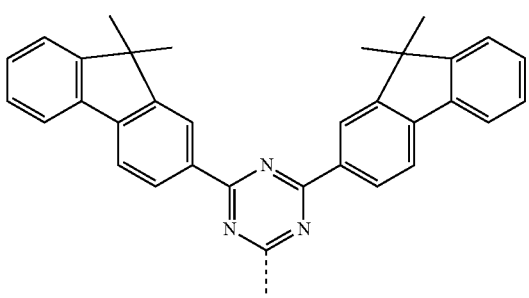
Formula (E-34)
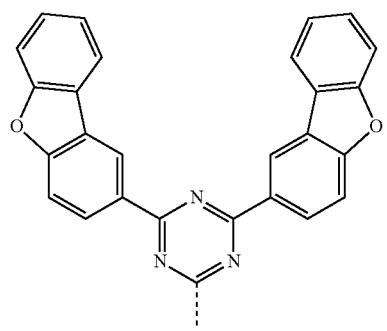
-continued
Formula (E-35)
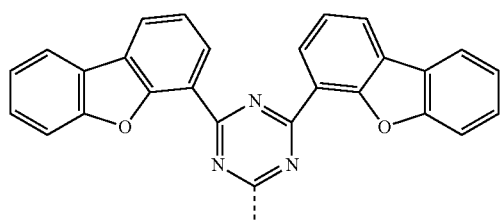
Formula (E-36)
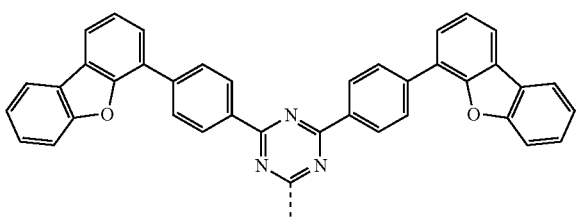
Formula (E-37)
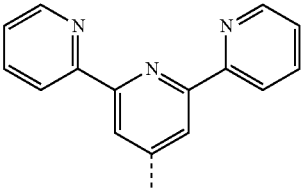
Formula (E-38)
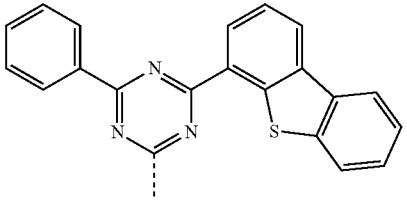
where the dotted bond marks the attachment position.
11. A compound as claimed in claim 3, wherein the electron transport group of $R^a$ and/or $R^b$ has at least one structure of the formula (E-17) to (E-23)
Formula (E-17)
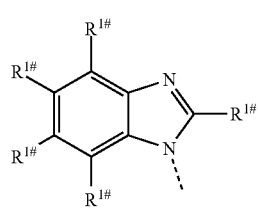
Formula (E-18)
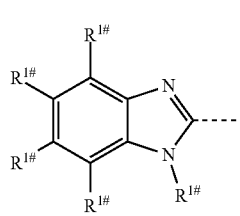

-continued

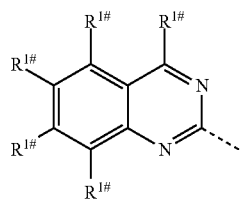
Formula (E-19)

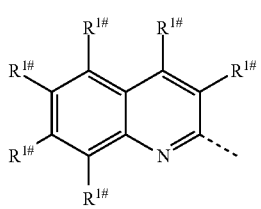
Formula (E-20)

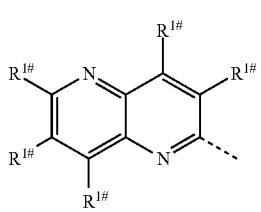
Formula (E-21)

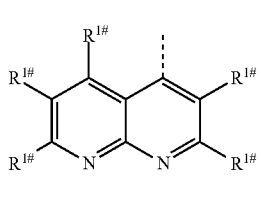
Formula (E-22)

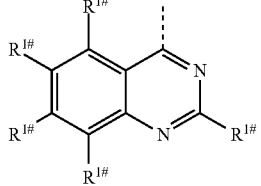
Formula (E-23)

where the dotted bond marks the attachment position and $R^{1\#}$ in the electron-transporting group E are independently of each other selected from the group consisting of H and an aromatic or heteroaromatic ring system which has 5 to 60 aromatic ring atoms and may be substituted in each case by one or more $R^2$ radicals.

12. A compound as claimed in claim 3, wherein the hole transport group of $R^a$ and/or $R^b$ has at least one structure of the formula (L-1) to (L-9)

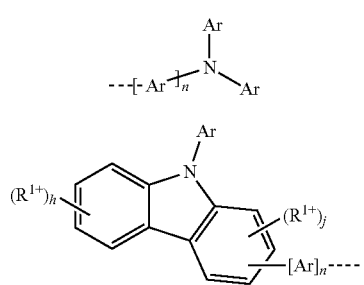
Formula (L-1)

Formula (L-2)

-continued

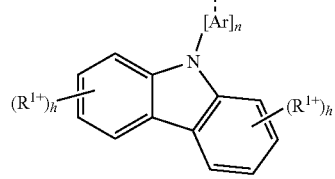
Formula (L-3)

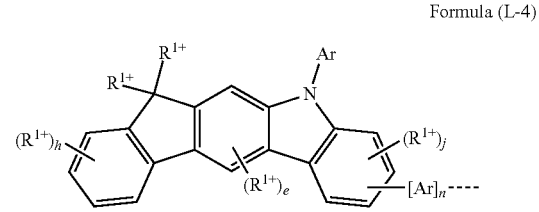
Formula (L-4)

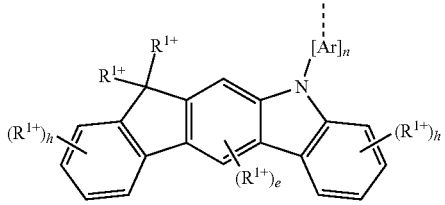
Formula (L-5)

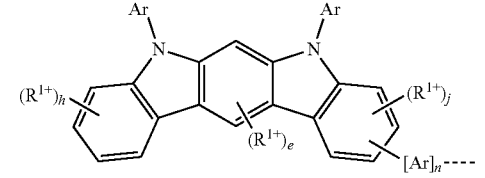
Formula (L-6)

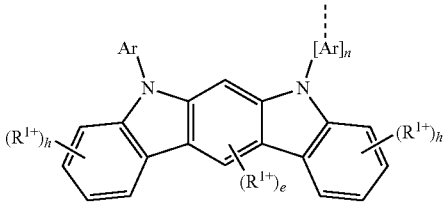
Formula (L-7)

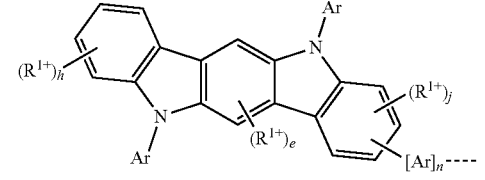
Formula (L-8)

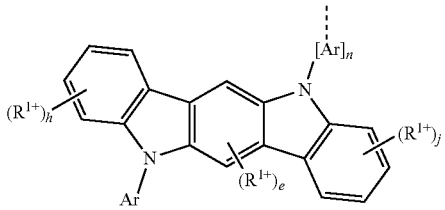
Formula (L-9)

where the dotted bond marks the attachment position, e is 0, 1 or 2, j is 0, 1, 2 or 3, h is 0, 1, 2, 3 or 4, n is 0 or 1, Ar is an aryl group having 6 to 40 carbon atoms or a heteroaryl group having 3 to 40 carbon atoms which may be substituted by one or more $R^{1\pm}$ radicals, and $R^{1+}$ is the same or different at each instance and is H, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, C=O, C=S, C=Se, $C=NR^2$, $-C(=O)O-$, $-C(=O)NR^2-$, $NR^2$, $P(=O)(R^2)$, $-O-$, $-S-$, SO or $SO_2$ and where one or more hydrogen atoms may be replaced by F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents together may also form a mono- or polycyclic, aliphatic or aromatic ring system.

13. An oligomer, polymer or dendrimer containing one or more compounds as claimed in claim 1, wherein one or more bonds of the compound to the polymer, oligomer or dendrimer are present.

14. A composition comprising at least one compound as claimed in claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

15. A formulation comprising at least one compound as claimed in claim 1, and at least one solvent.

16. A method comprising providing the compound as claimed in claim 1, and including the compound in an electronic device as electron blocker material, hole injection material and/or hole transport material.

17. An electronic device comprising at least one compound as claimed in claim 1.

18. The electronic device as claimed in claim 17, wherein the electronic device is preferably selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells and organic laser diodes.

19. A compound according to claim 1, selected from the group consisting of

Formula 1

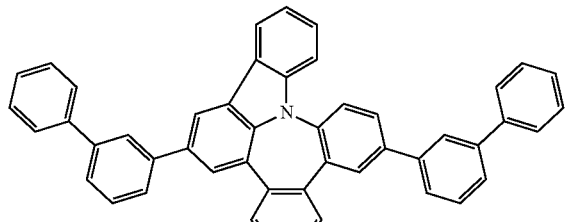

Formula 2

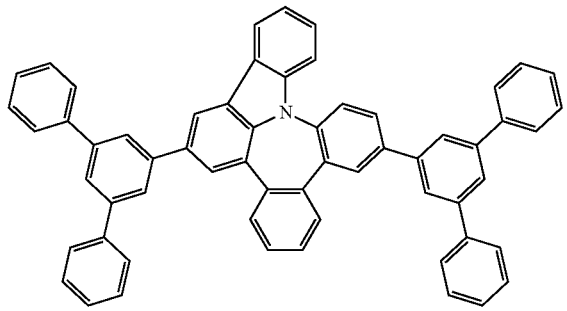

Formula 5

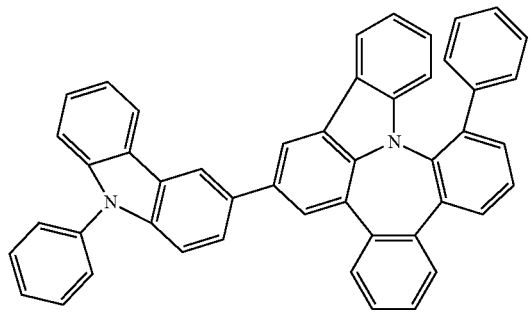

Formula 6

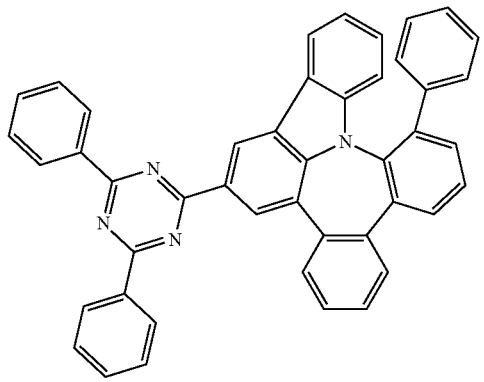

-continued
Formula 7
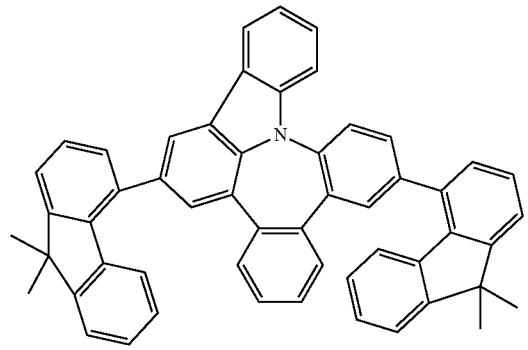
Formula 8
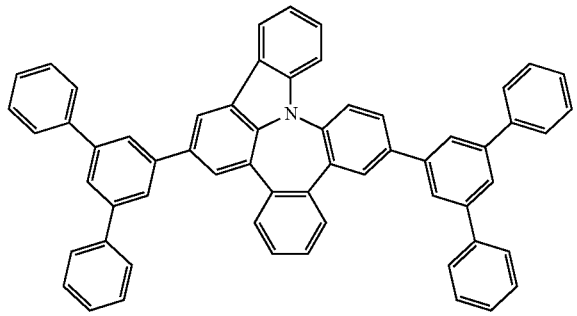
Formula 10
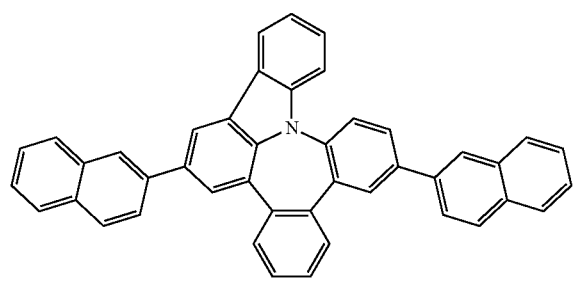
Formula 14
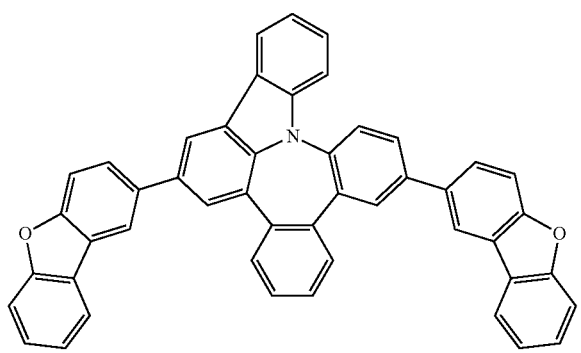
Formula 15
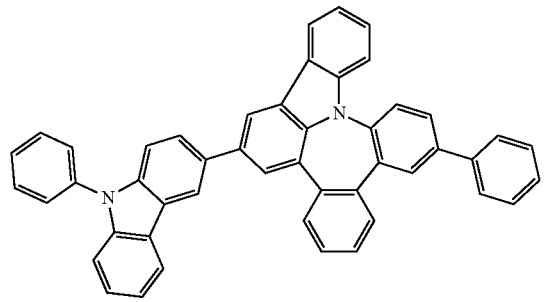
Formula 16
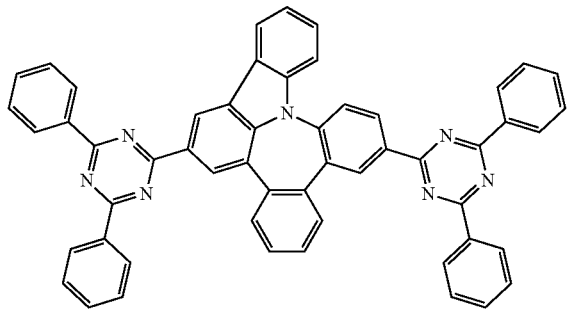
Formula 19
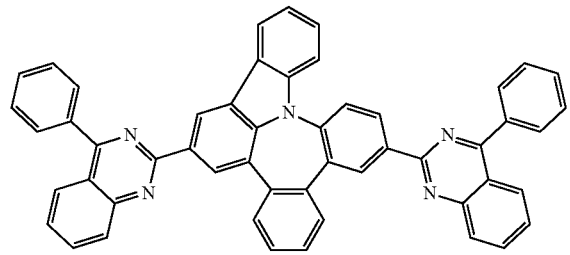
Formula 20
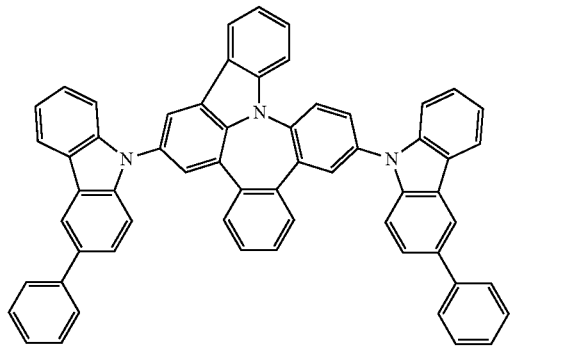

-continued
Formula 21
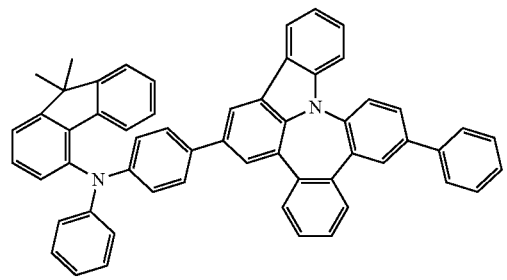
Formula 22
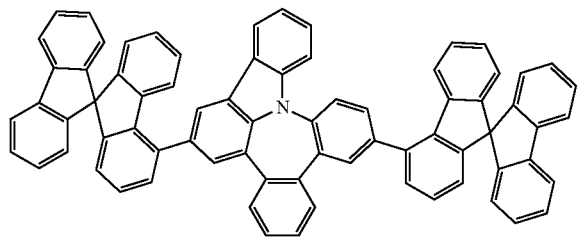
Formula 23
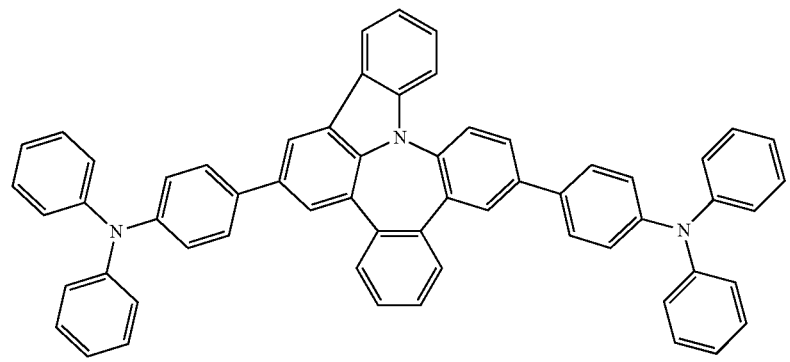
Formula 24
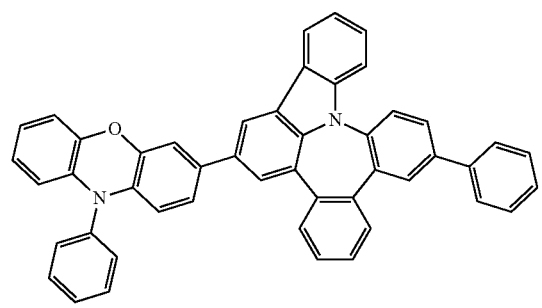
Formula 25
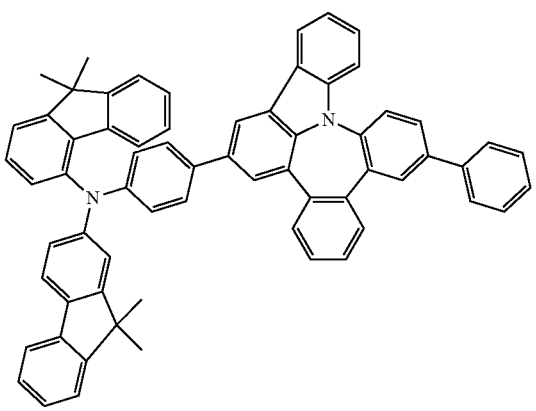
Formula 26
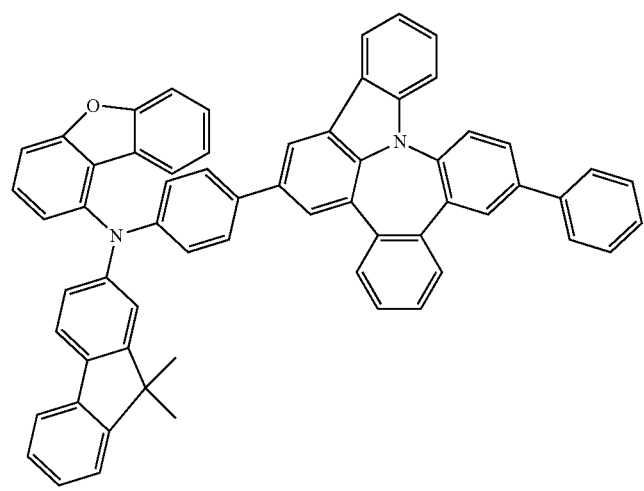

Formula 27
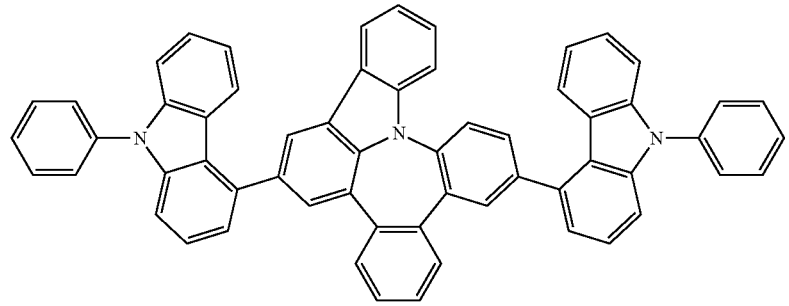
Formula 28
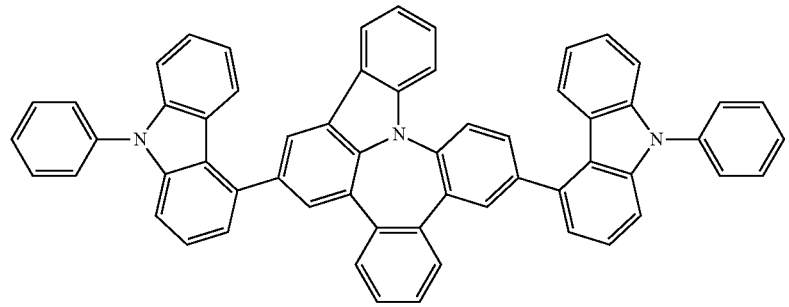
Formula 29
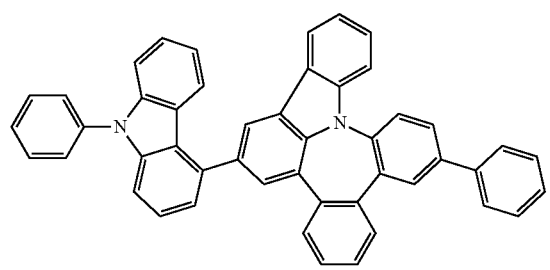
Formula 30
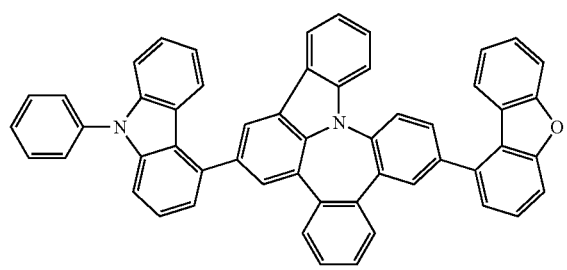
Formula 31
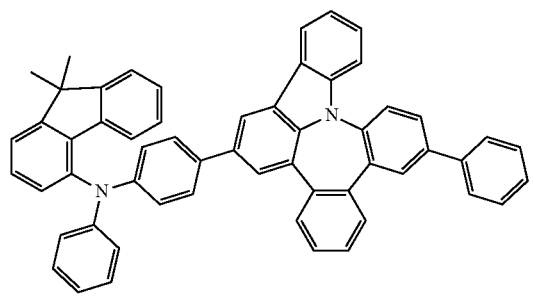
Formula 34
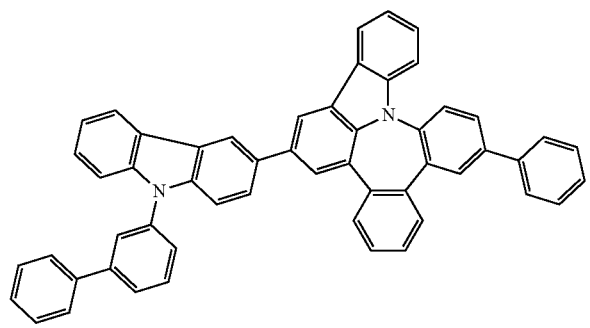
Formula 36
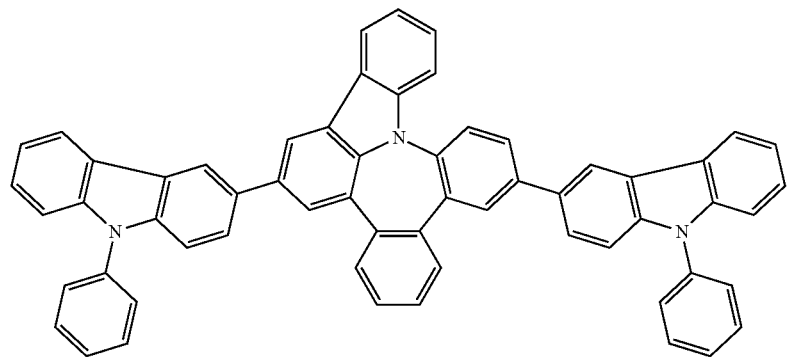

Formula 43
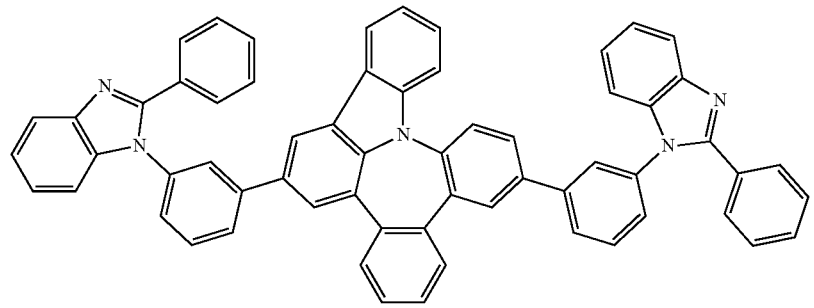
Formula 44
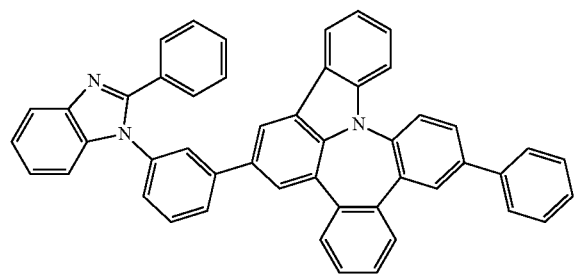
Formula 45
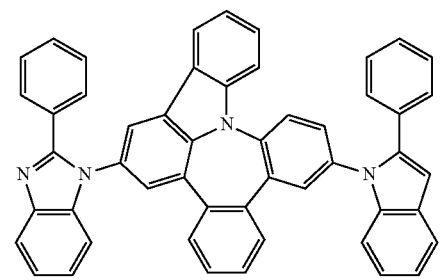
Formula 48
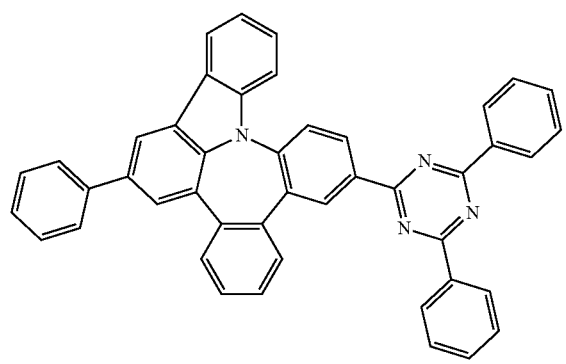
Formula 49
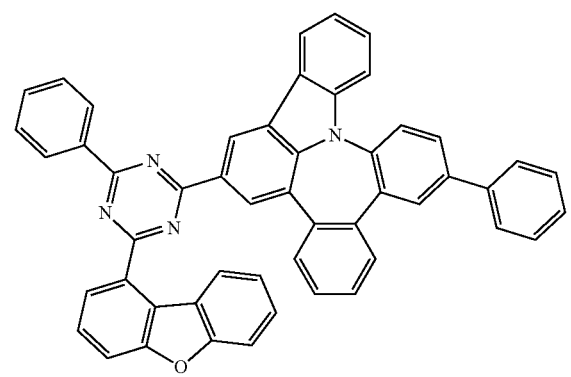
Formula 50
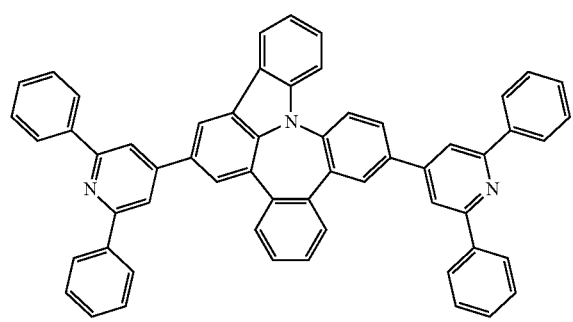
Formula 51
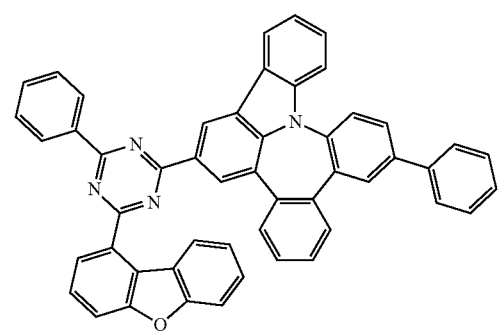
Formula 52
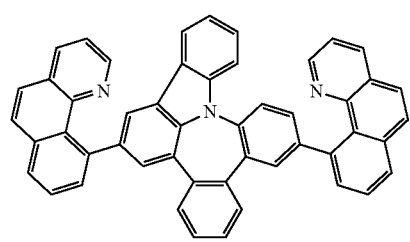
Formula 53
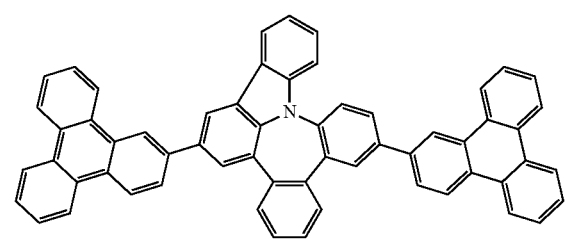

-continued
Formula 54
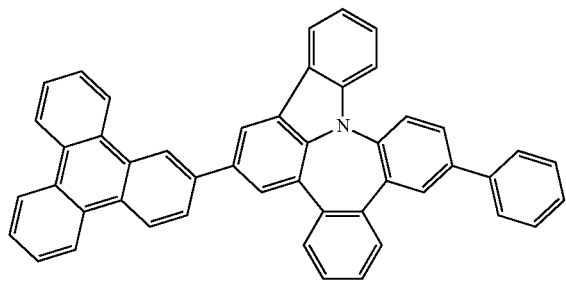
Formula 72
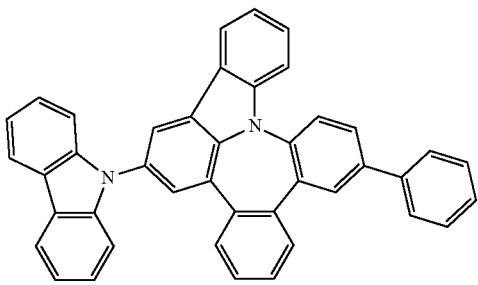
Formula 73
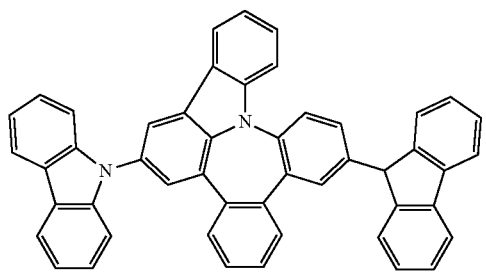
Formula 76
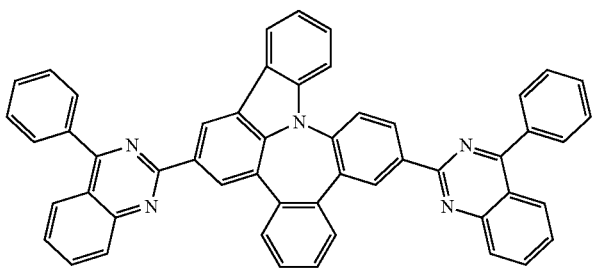
D2
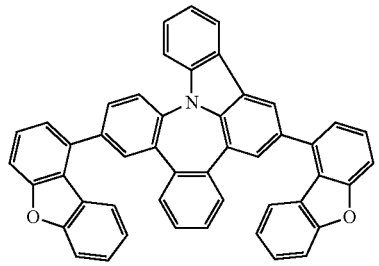
d6
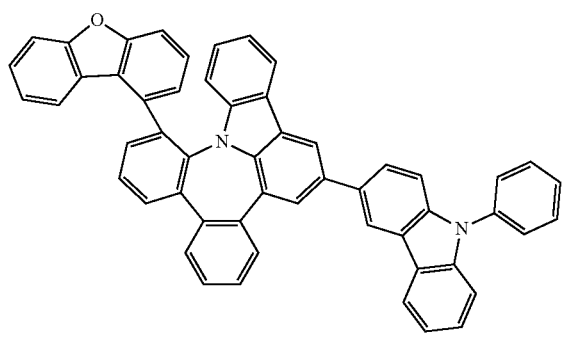
d7
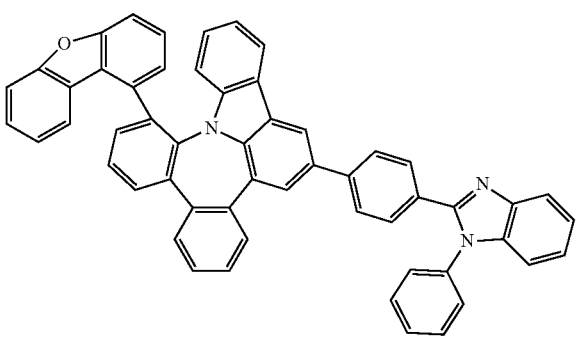
d8
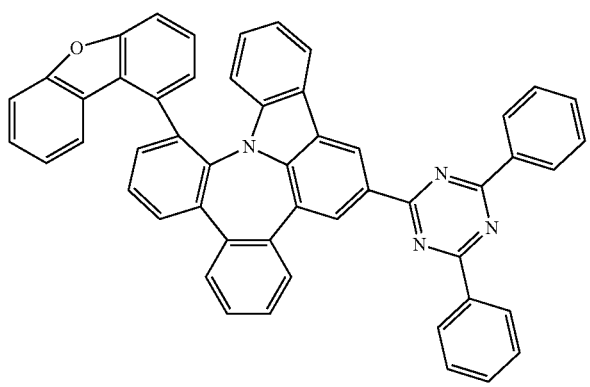

-continued
d9
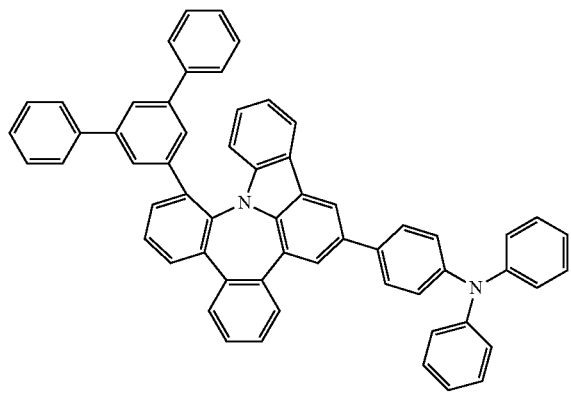
d10 (clerical error)
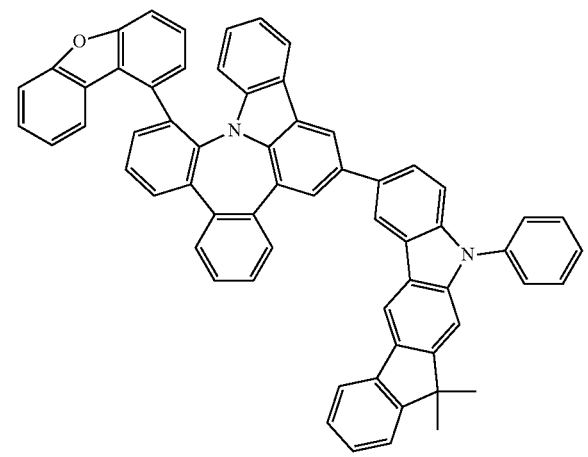
d11
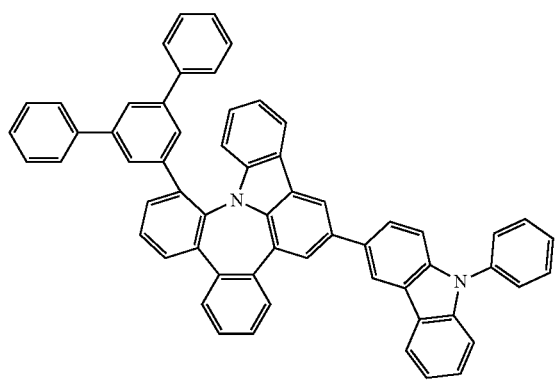
d12
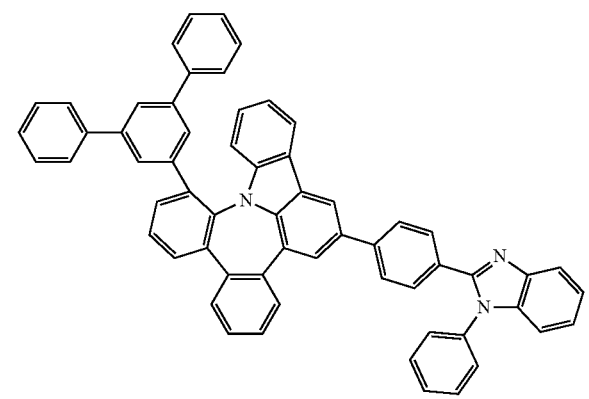
d13
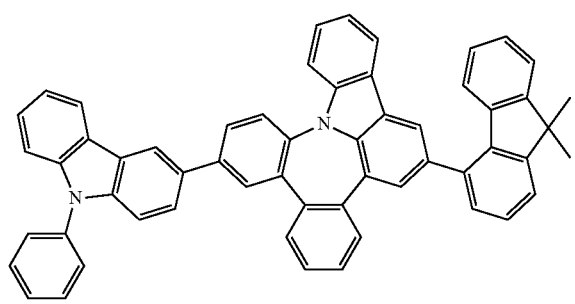
d17
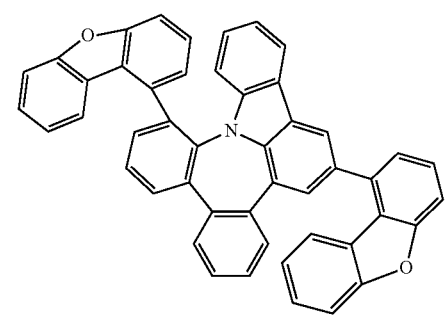
d18
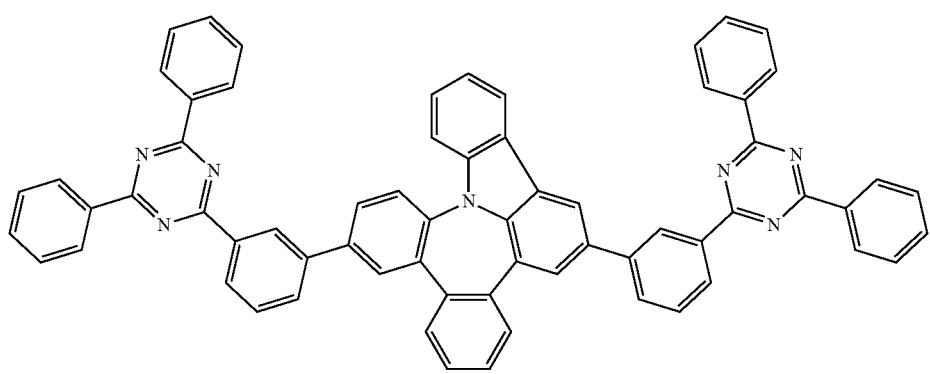

-continued
d19-a
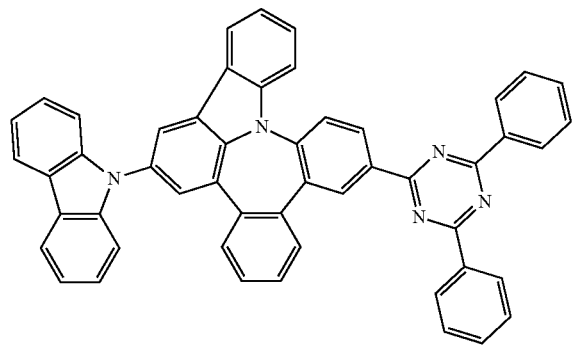
IV1
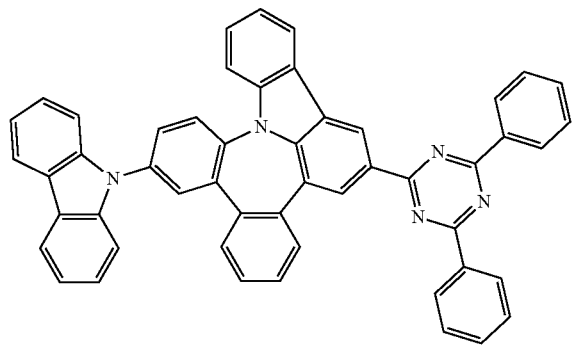
IV2
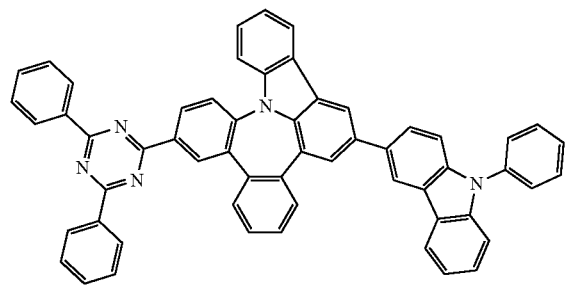
d20-b
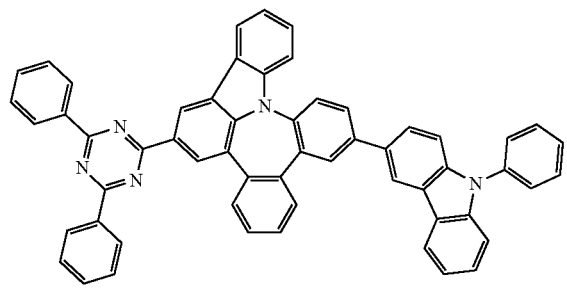
IV4
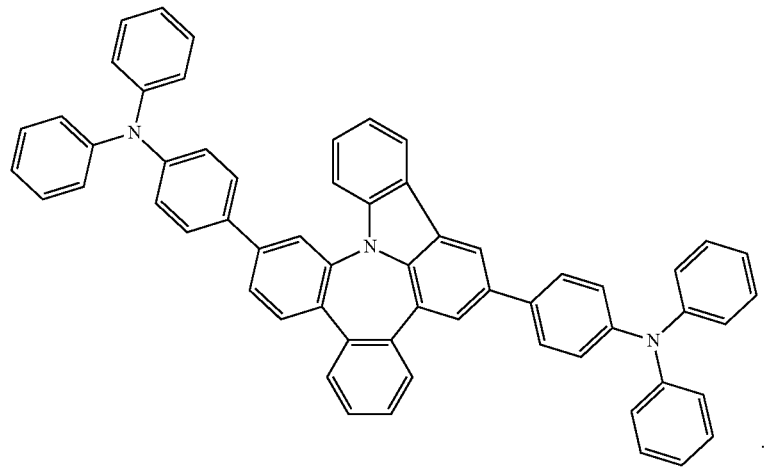
* * * * *

UNITED STATES PATENT AND TRADEMARK OFFICE
CERTIFICATE OF CORRECTION

PATENT NO. : 10,636,979 B2  
APPLICATION NO. : 15/539202  
DATED : April 28, 2020  
INVENTOR(S) : Amir Hossain Parham et al.

Page 1 of 3

It is certified that error appears in the above-identified patent and that said Letters Patent is hereby corrected as shown below:

In the Claims

In Column 219, Claim 1, Line number 12:

"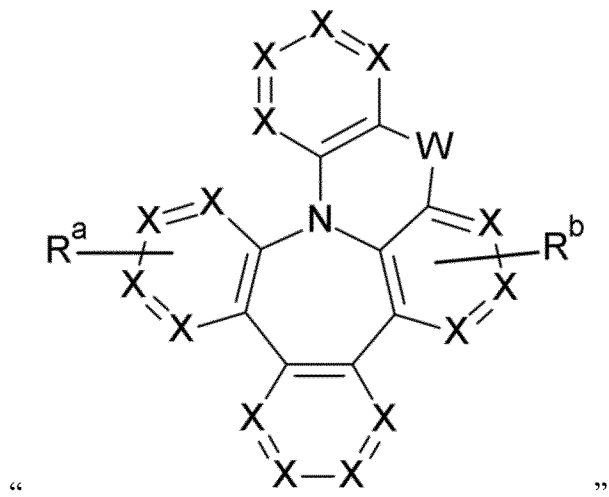"

Should be:

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,636,979 B2

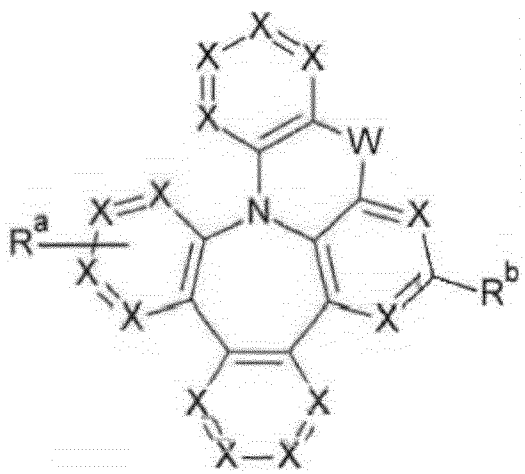

"Formula (II)"

In Column 219, Claim 1, Line number 23:
"is the same or different at each instance and is H, D, F, Cl, Br, I, B(OR3)2, CHO,....."

Should be:
"is the same or different at each instance and is H, F, Cl, Br, I, B(OR3)2, CHO,....."

In Column 237, Claim 12, Line number 12:
"groups may be replaced by –"R2C=CR$^2$-, -C=C-, Si(R$^2$)$_2$, Ge(R$^2$)$_2$, Sn(R$^2$)$_2$, C=O, C=S, C=Se,"

Should be:
"R2C≡CR$^2$-, -C≡C-, Si(R$^2$)$_2$, Ge(R$^2$)$_2$, Sn(R$^2$)$_2$, C=O, C=S, C=Se,"

In Column 248, Claim 19:

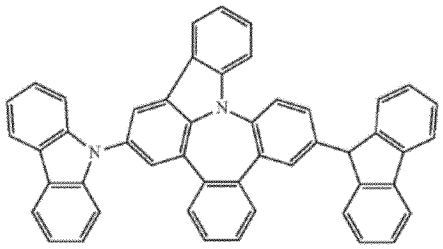 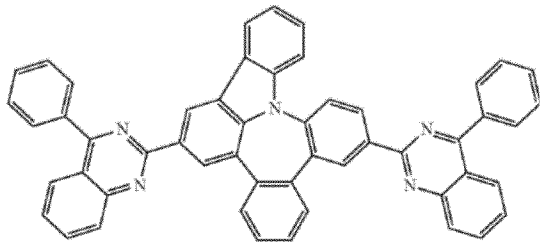

"                                    D2                                        "

Should be:

CERTIFICATE OF CORRECTION (continued)
U.S. Pat. No. 10,636,979 B2